US012747464B2

(12) United States Patent
Pauthenier et al.

(10) Patent No.: US 12,747,464 B2
(45) Date of Patent: Sep. 29, 2026

(54) METHOD FOR THE BIOSYNTHESIS OF DIOSMIN AND/OR HESPERIDIN IN A MICROORGANISM

(71) Applicant: LES LABORATOIRES SERVIER, Suresnes (FR)

(72) Inventors: Cyrille Pauthenier, Juvisy-sur-Orge (FR); André Le Jeune, Draveil (FR); Hélène Scornec, Longjumeau (FR); Célia Roussel, Saintry sur Seine (FR); Laetitia Joubert, Palaiseau (FR)

(73) Assignee: LES LABORATOIRES SERVIER, Suresnes (FR)

( * ) Notice: Subject to any disclaimer, the term of this patent is extended or adjusted under 35 U.S.C. 154(b) by 168 days.

(21) Appl. No.: 18/668,751

(22) Filed: May 20, 2024

(65) Prior Publication Data

US 2024/0409976 A1 Dec. 12, 2024

Related U.S. Application Data

(62) Division of application No. 17/429,459, filed as application No. PCT/EP2020/053503 on Feb. 11, 2020, now Pat. No. 11,987,829.

(30) Foreign Application Priority Data

Feb. 11, 2019 (EP) .................................... 19305163

(51) Int. Cl.

| | |
|---|---|
| ***C12P 19/60*** | (2006.01) |
| ***C12N 9/00*** | (2006.01) |
| ***C12N 9/02*** | (2006.01) |
| ***C12N 9/10*** | (2006.01) |
| ***C12N 9/88*** | (2006.01) |
| ***C12N 9/90*** | (2006.01) |

(52) U.S. Cl.

CPC ............ *C12P 19/60* (2013.01); *C12N 9/0042* (2013.01); *C12N 9/0071* (2013.01); *C12N 9/0073* (2013.01); *C12N 9/1007* (2013.01); *C12N 9/1051* (2013.01); *C12N 9/1085* (2013.01); *C12N 9/88* (2013.01); *C12N 9/90* (2013.01); *C12N 9/93* (2013.01); *C12Y 106/02004* (2013.01); *C12Y 114/11022* (2013.01); *C12Y 114/13011* (2013.01); *C12Y 114/14* (2013.01); *C12Y 204/01* (2013.01); *C12Y 204/01185* (2013.01); *C12Y 205/01006* (2013.01); *C12Y 402/01076* (2013.01); *C12Y 403/01023* (2013.01); *C12Y 403/01024* (2013.01); *C12Y 505/01006* (2013.01); *C12Y 602/01012* (2013.01)

(58) Field of Classification Search

None

See application file for complete search history.

(56) References Cited

U.S. PATENT DOCUMENTS 11,987,829 B2 5/2024 Pauthenier et al.

FOREIGN PATENT DOCUMENTS

| | | |
|---|---|---|
| CN | 108 504 680 | 9/2018 |
| CN | 109 312 375 | 2/2019 |
| EP | 3 321 273 | 5/2018 |
| WO | WO 2018/039923 | 3/2018 |

OTHER PUBLICATIONS

An, D. G. et al. "Biosynthesis of two quercetin O-diglycosides in *Escherichia coli*" *J Ind Microbiol Biotechnol*, 2016, pp. 841-849, vol. 43, No. 6.

Del Bano, M. J. et al. "Flavonoid Distribution during the Development of Leaves, Flowers, Stems, and Roots of *Rosmarinus officinalis*. Postulation of a Biosynthetic Pathway" *J. Agric. Food Chem.*, 2004, pp. 4987-4992, vol. 52, No. 16.

Kim, B. G. et al. "Biosynthesis and production of glycosylated flavonoids in *Escherichia coli*: current state and perspectives" *Appl Microbial Biotechnol.*, 2015, pp. 2979-2988, vol. 99, No. 7.

Ohashi, T. et al. "Substrate preference of citrus naringenin rhamnosyltransferases and their application to flavonoid glycoside production in fission yeast" *Appl Microbial Biotechnol.*, 2016, pp. 687-696, vol. 100, No. 2.

Trantas, E. A. et al. "When plants produce not enough or at all: rnetabolic engineering of flavonoids in microbial hosts" *Frontiers in Plant Science*, Jan. 29, 2015, pp. 1-16, vol. 6, Article 7.

Database Biosis [Online] Accession No. PREV201000250656, "Biotransformation of hesperidin to hesperetin by microorganisms" Jan. 2010, p. 1, XP002793175.

Written Opinion in International Application No. PCT/EP2020/053503, Mar. 19, 2020, pp. 1-8.

*Primary Examiner* — Manjunath N Rao
*Assistant Examiner* — Jae W Lee
(74) *Attorney, Agent, or Firm* — SALIWANCHIK, LLOYD & EISENSCHENK

(57) ABSTRACT

The present invention relates to a recombinant microorganism which is modified to be capable of producing diosmin and hesperidin and to the use thereof for producing diosmin and/or hesperidin.

20 Claims, 35 Drawing Sheets

Specification includes a Sequence Listing.

[Figure 1]
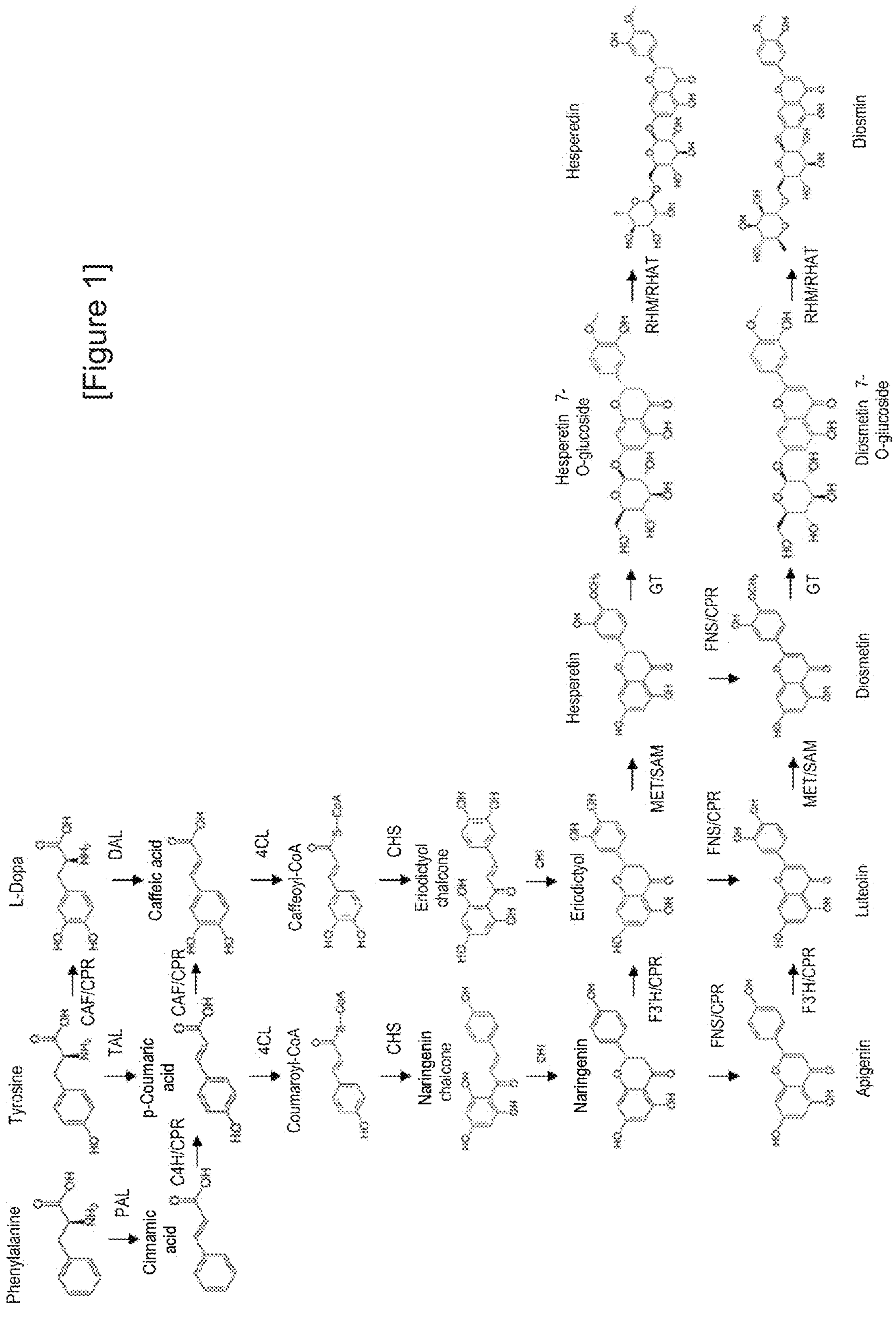

[Figure 2]
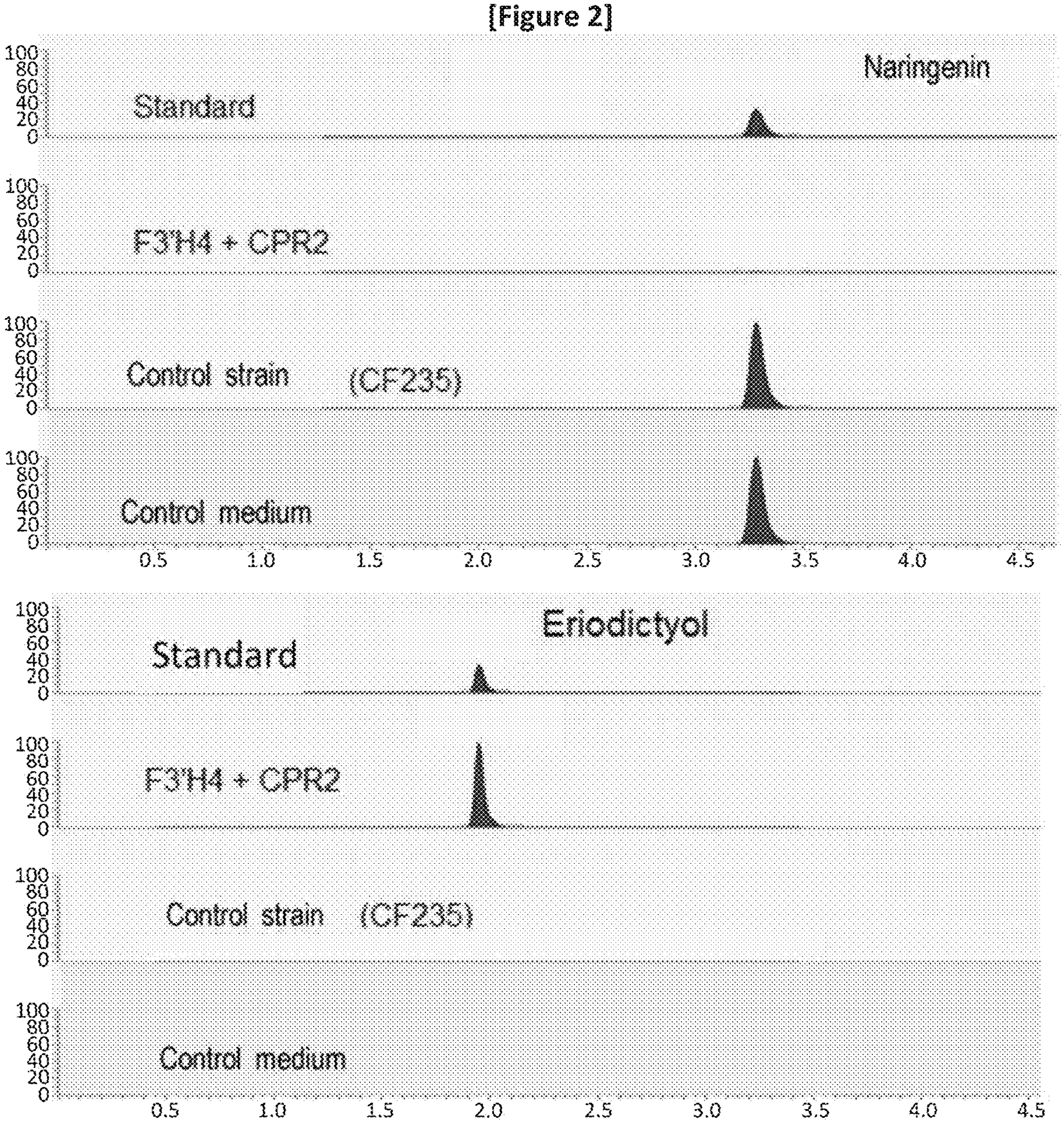

[Figure 3]
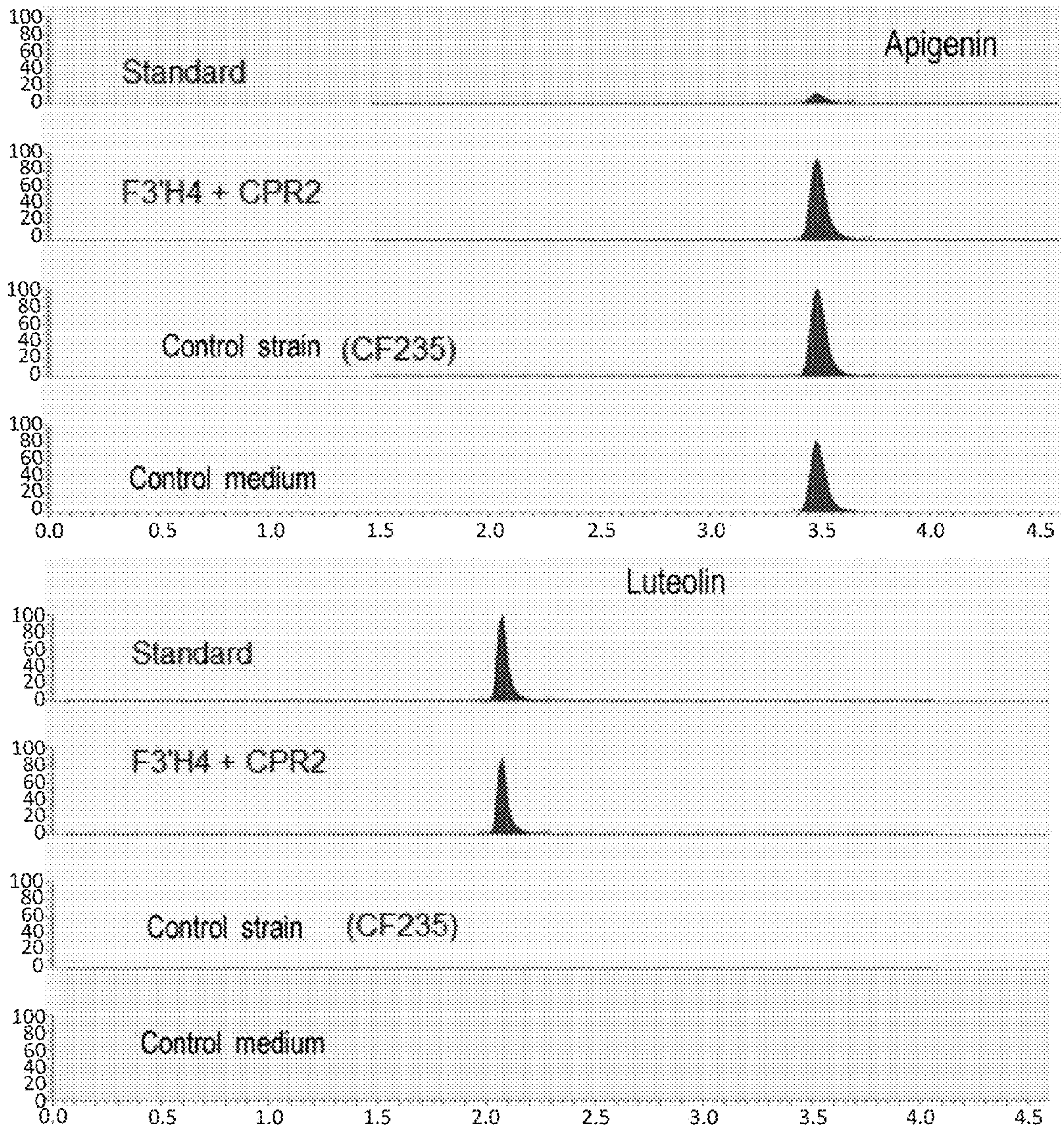

[Figure 4]
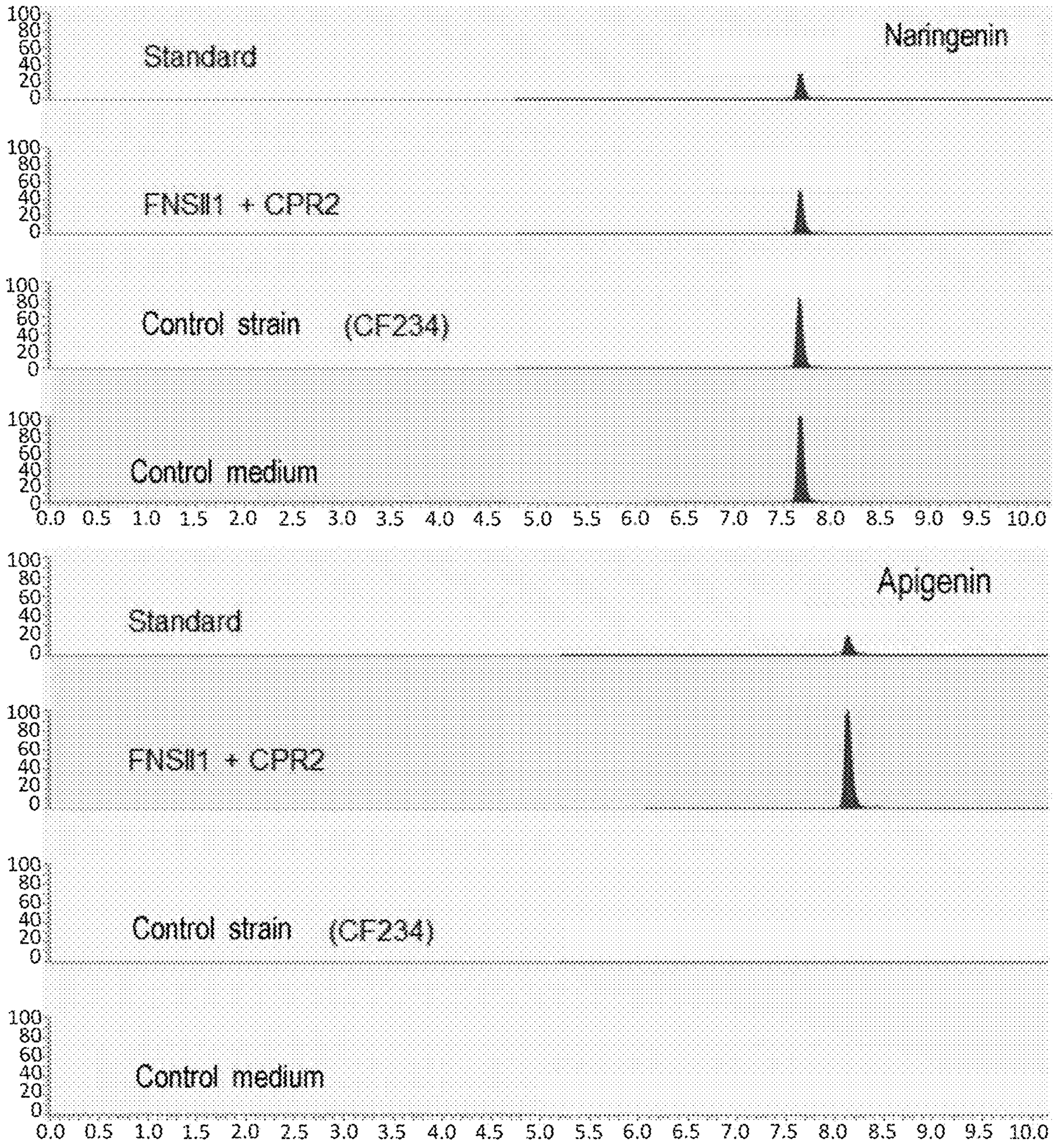

[Figure 5]
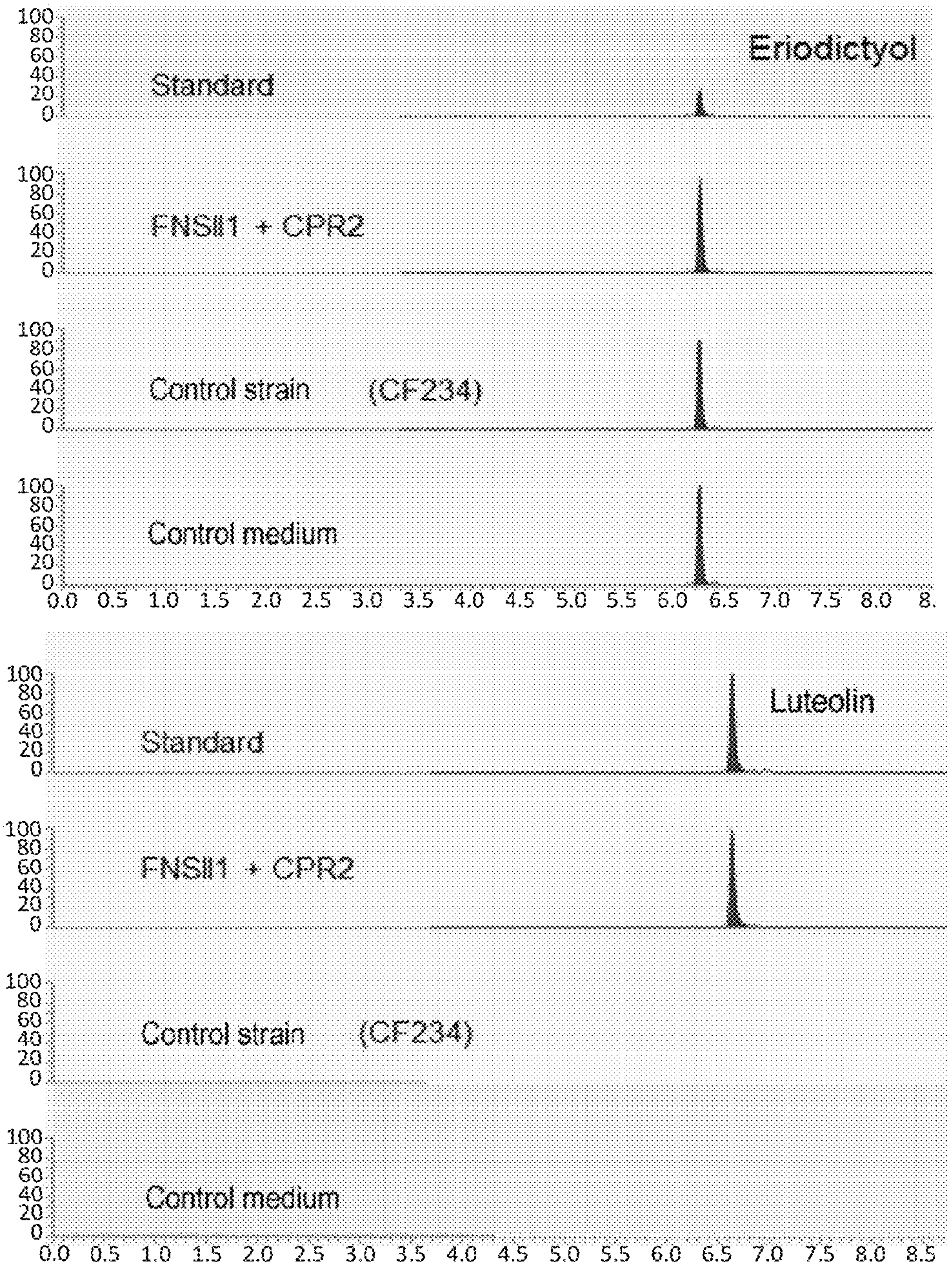

[Figure 6]
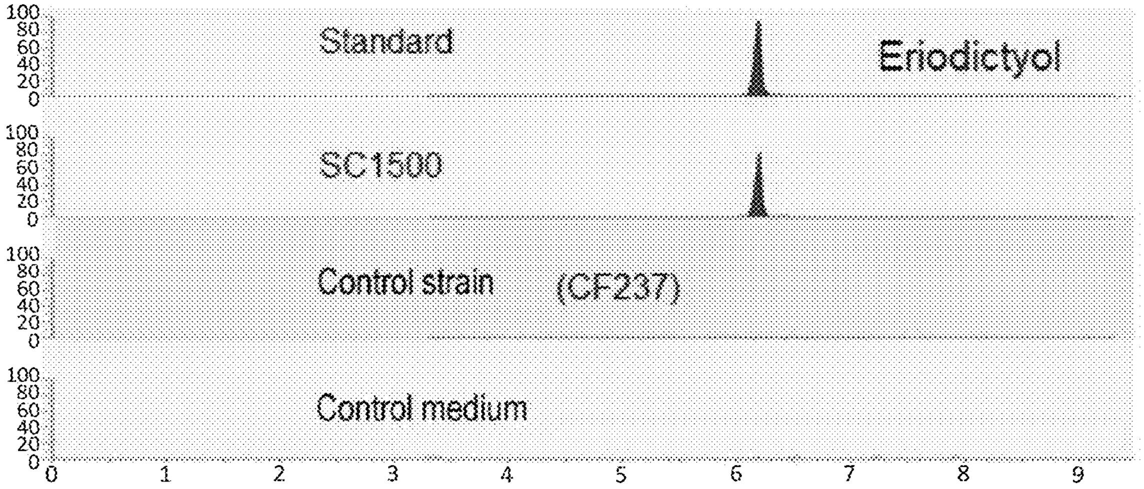
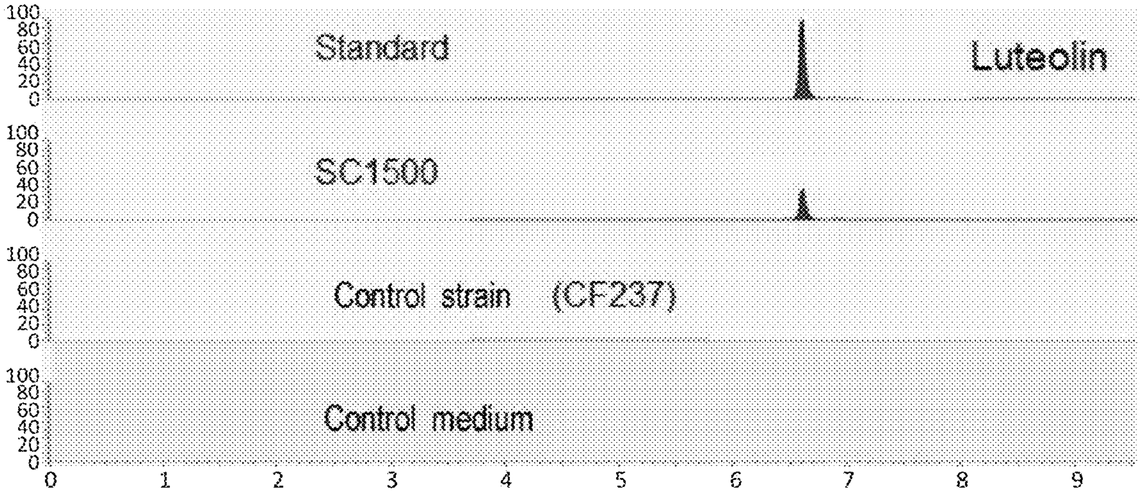

[Figure 7]
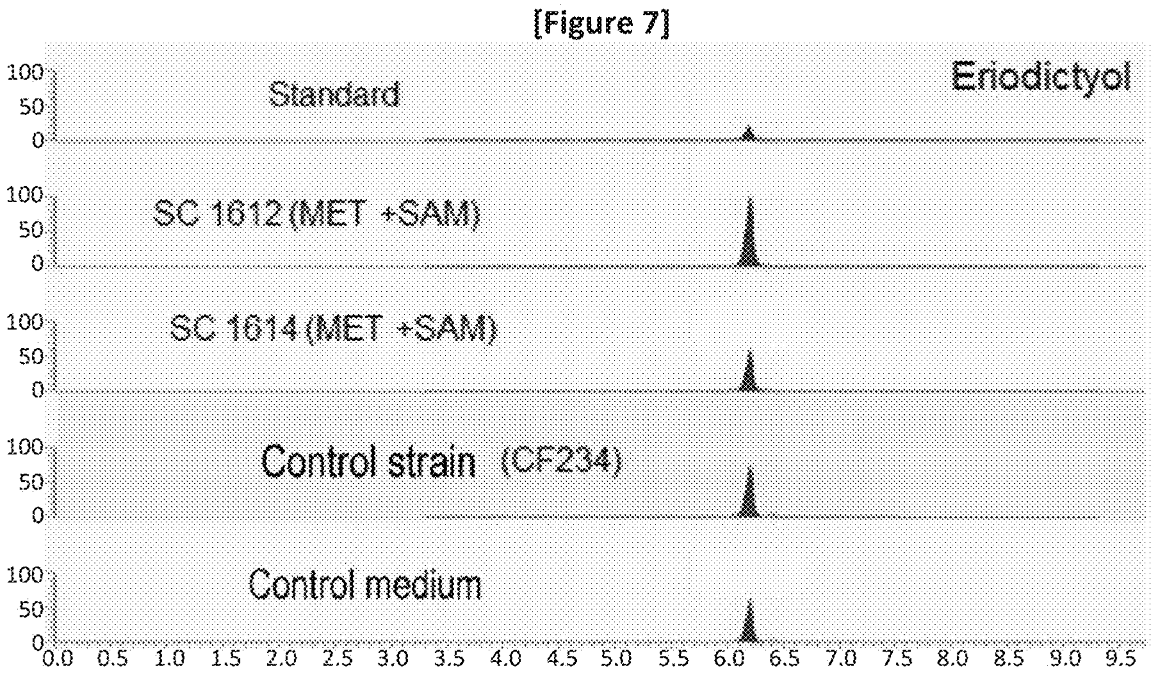
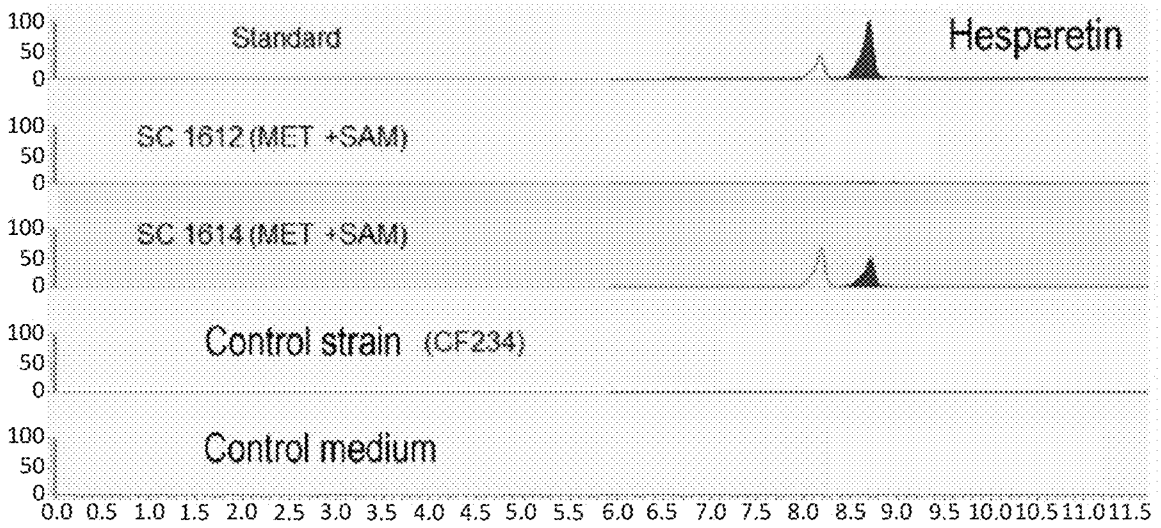

[Figure 8]
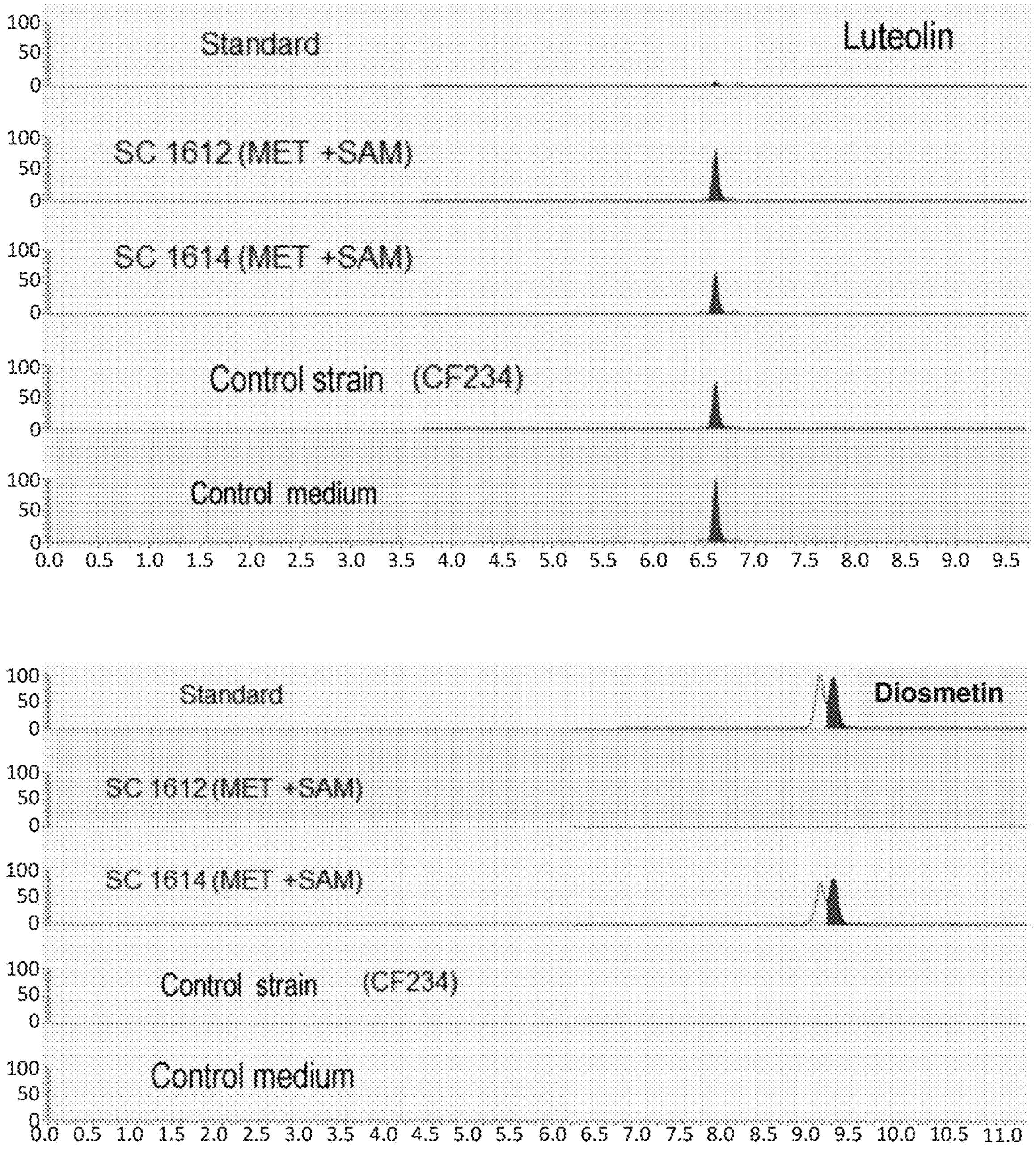

[Figure 9]
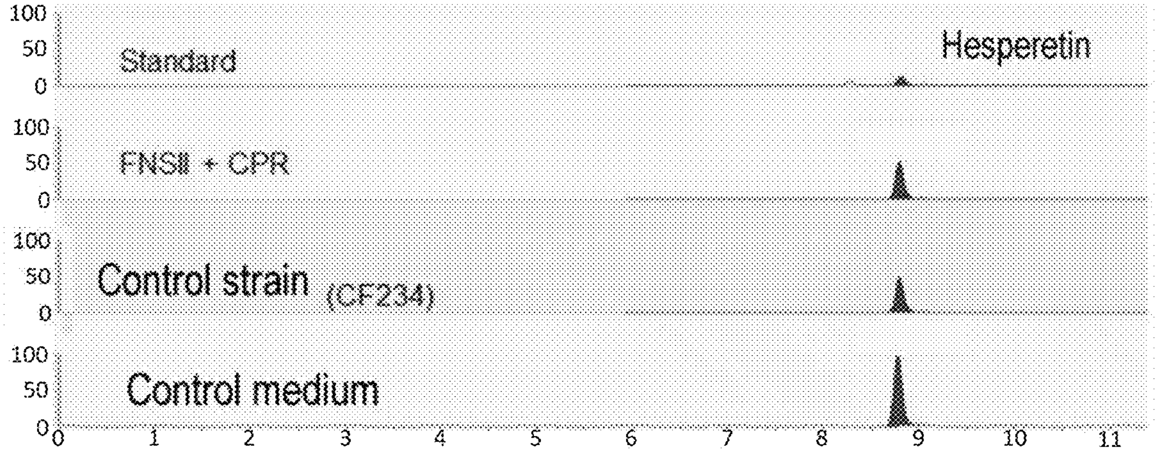
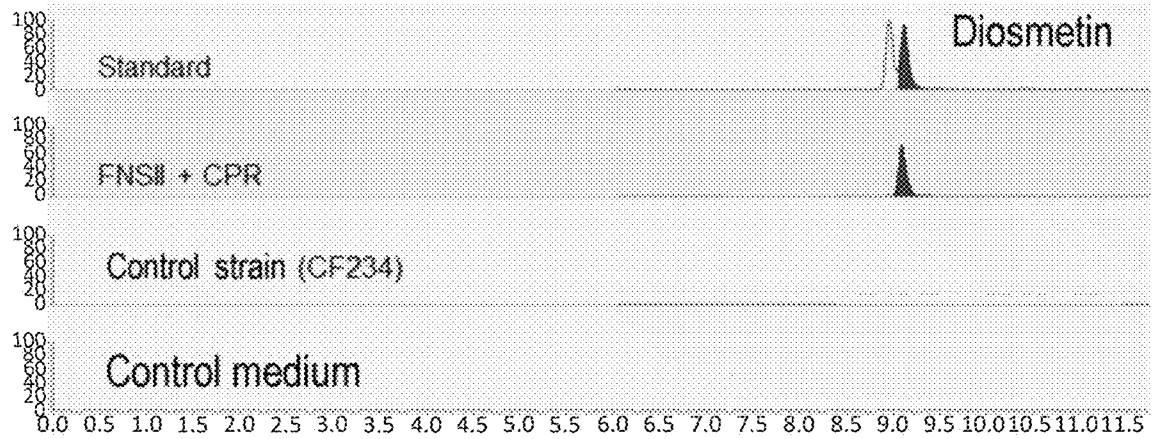

[Figure 10]
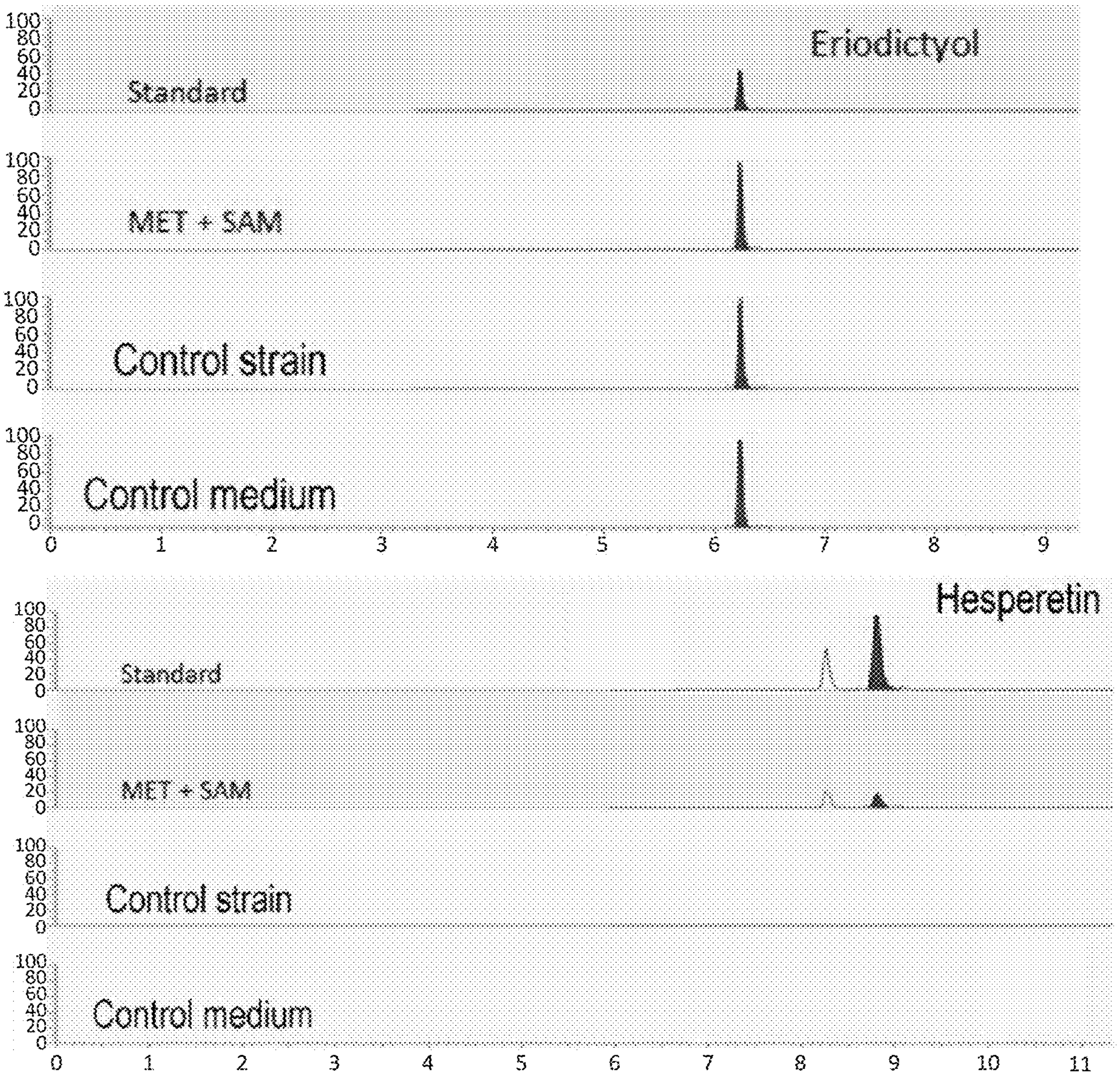

[Figure 11]
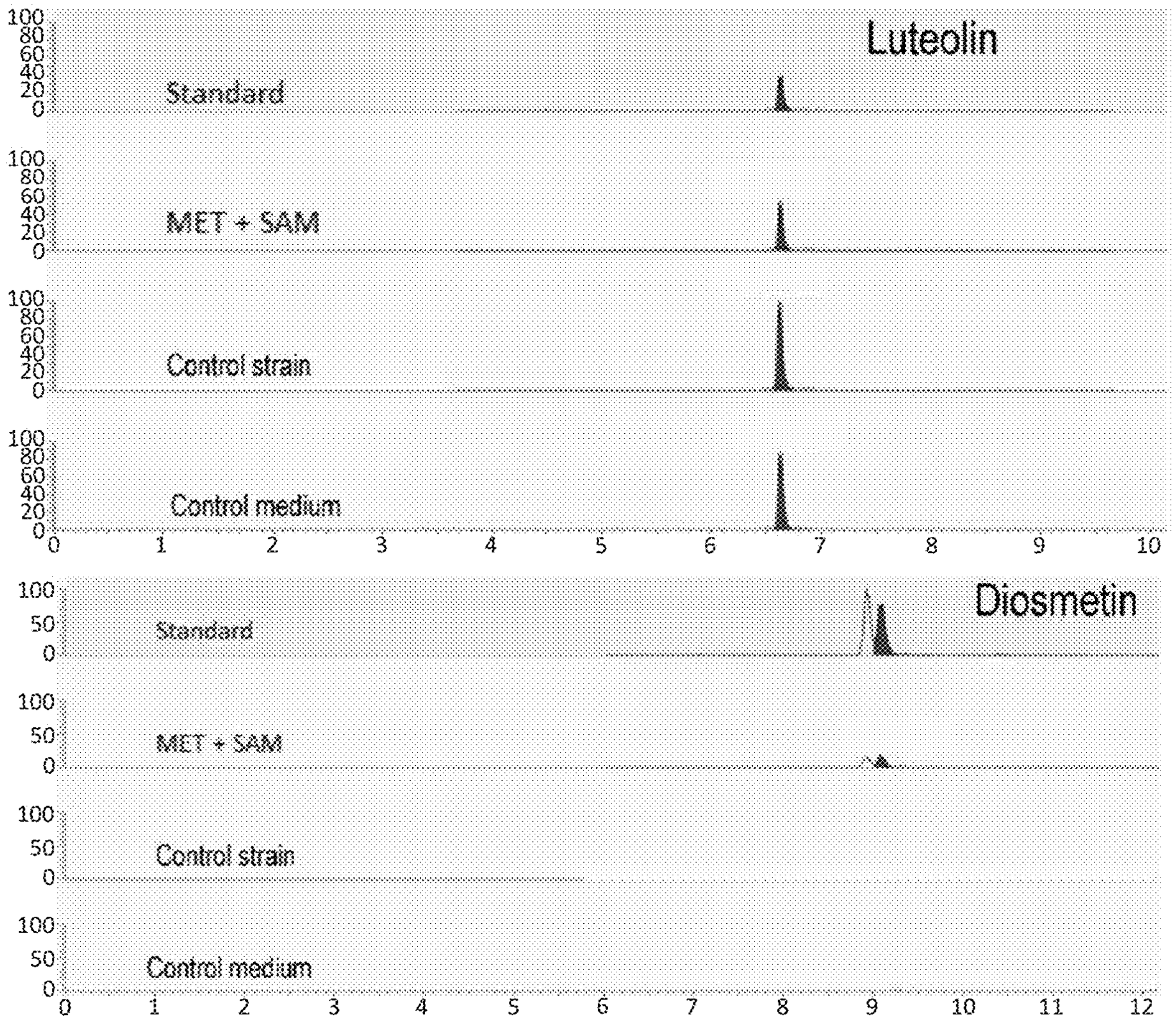

[Figure 12]
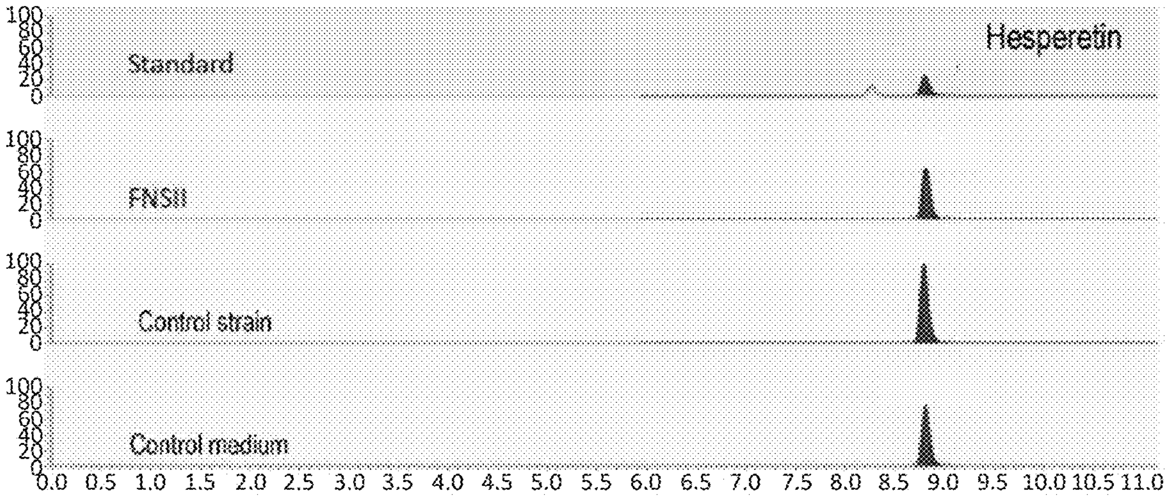
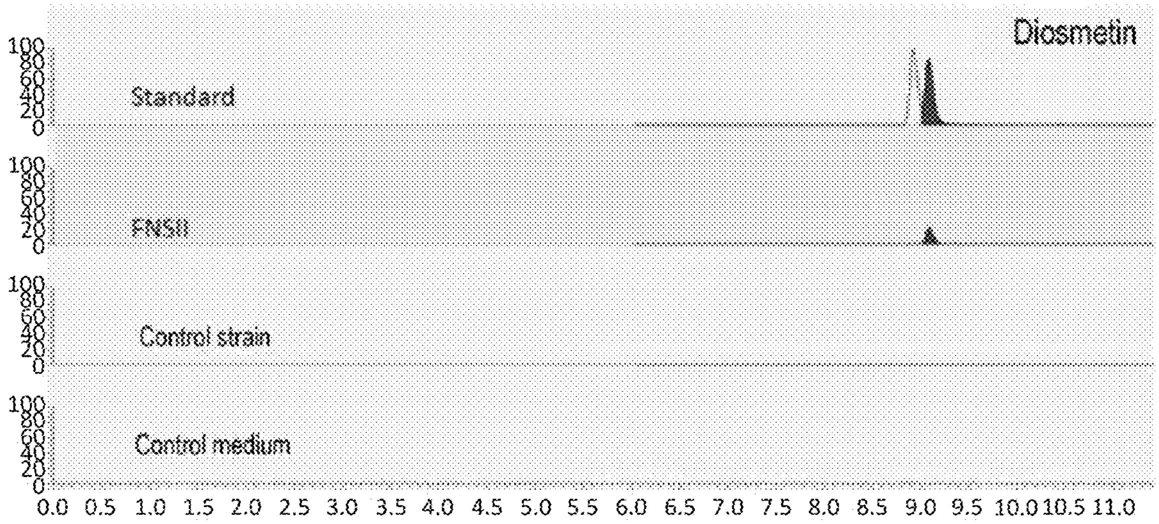

[Figure 13]
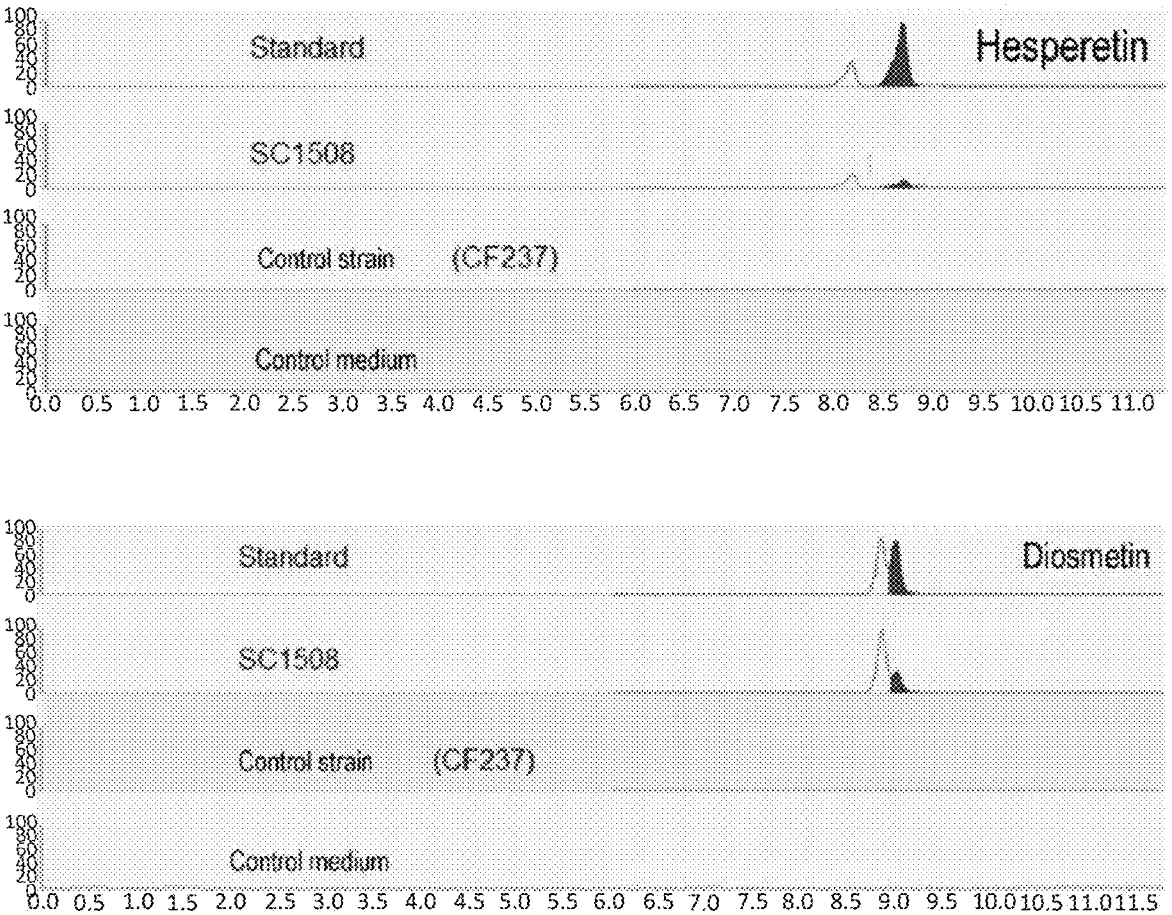

[Figure 14]
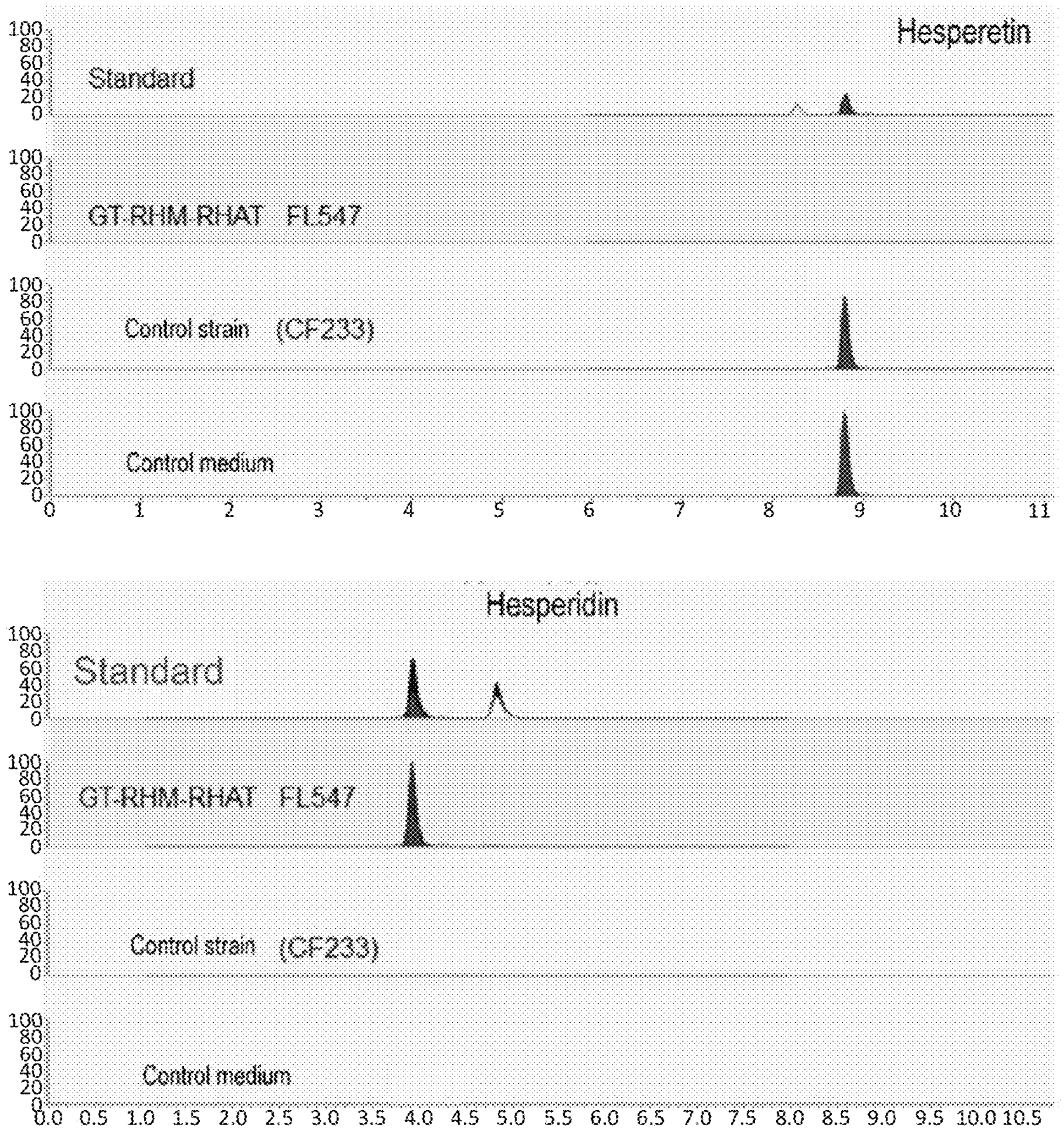

[Figure 15]
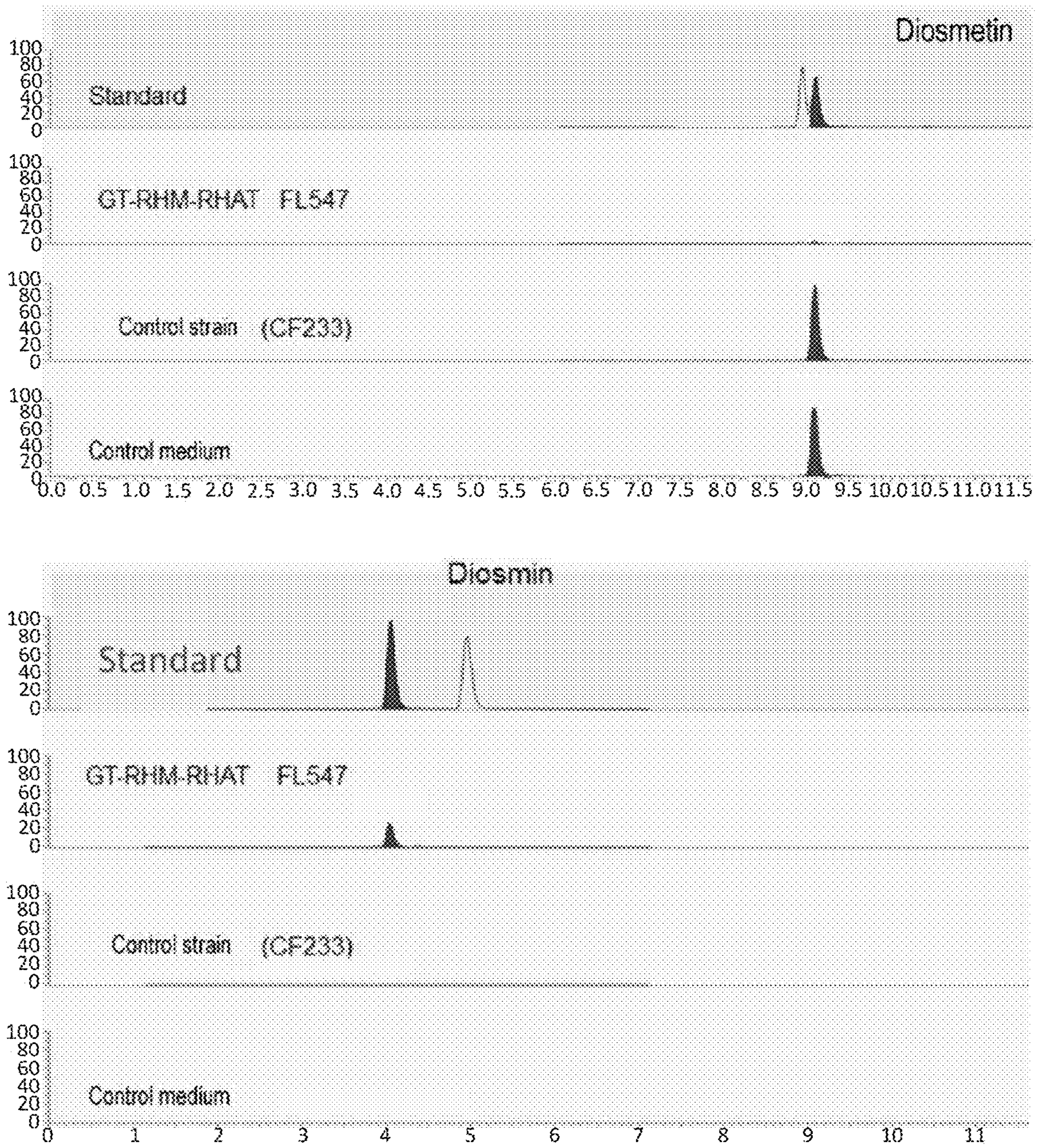

[Figure 16]
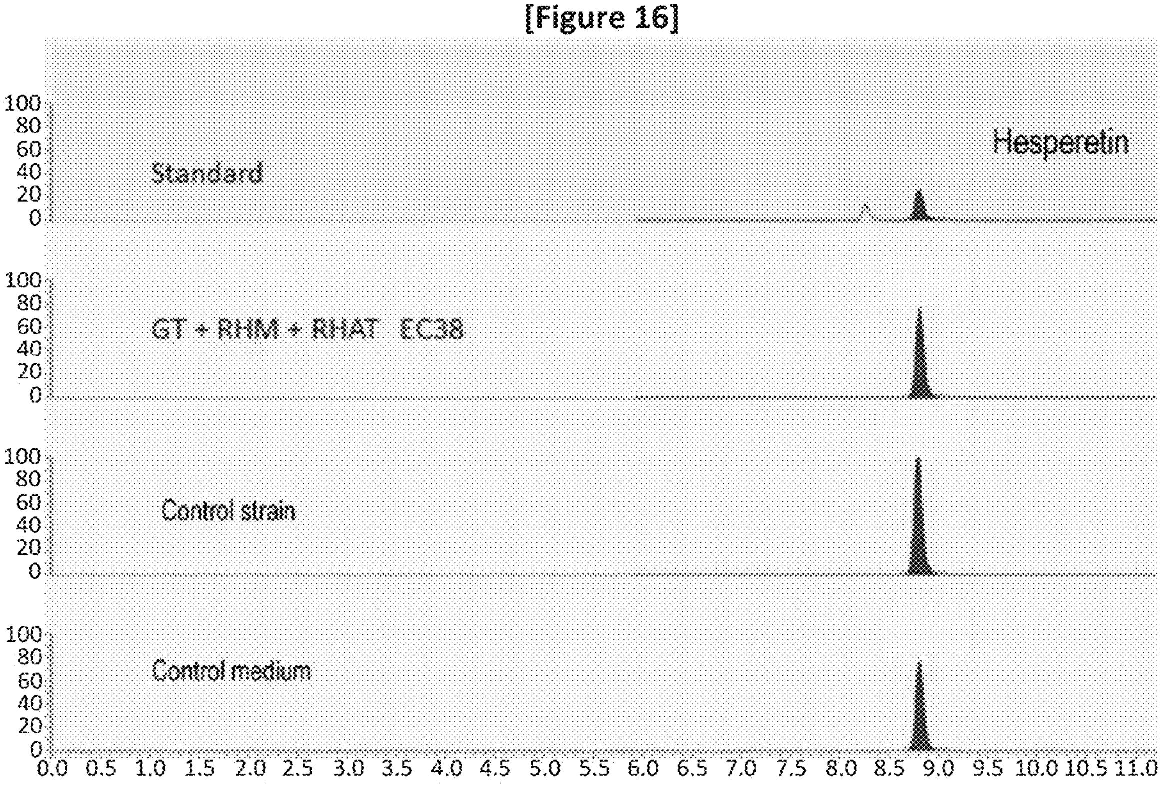
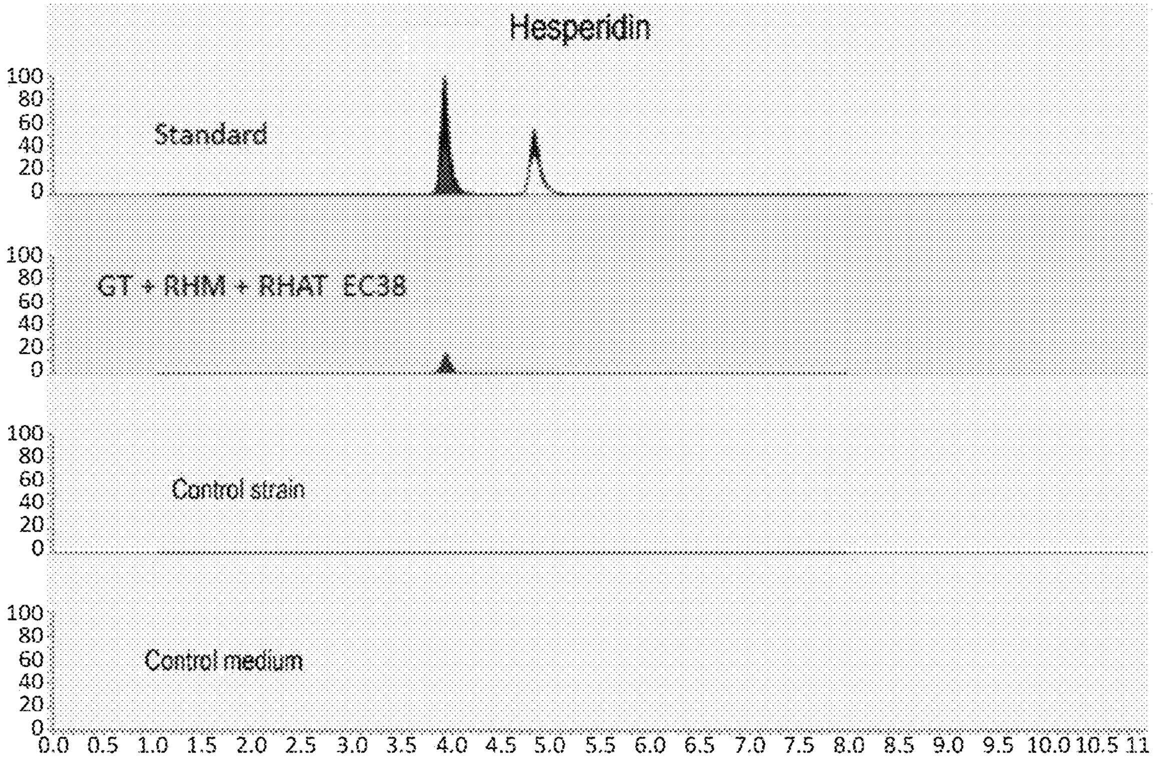

[Figure 16 continued]
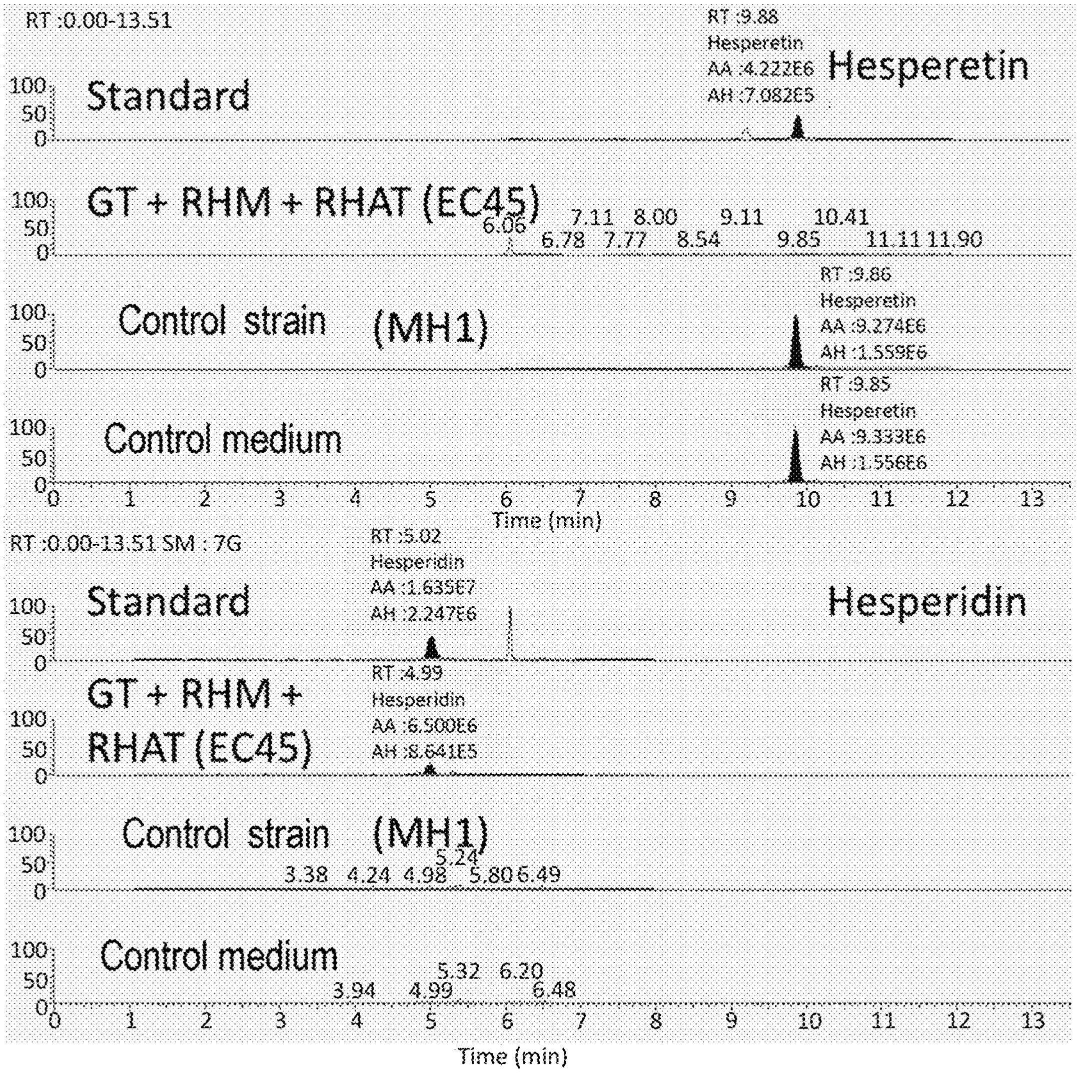

[Figure 16 continued]
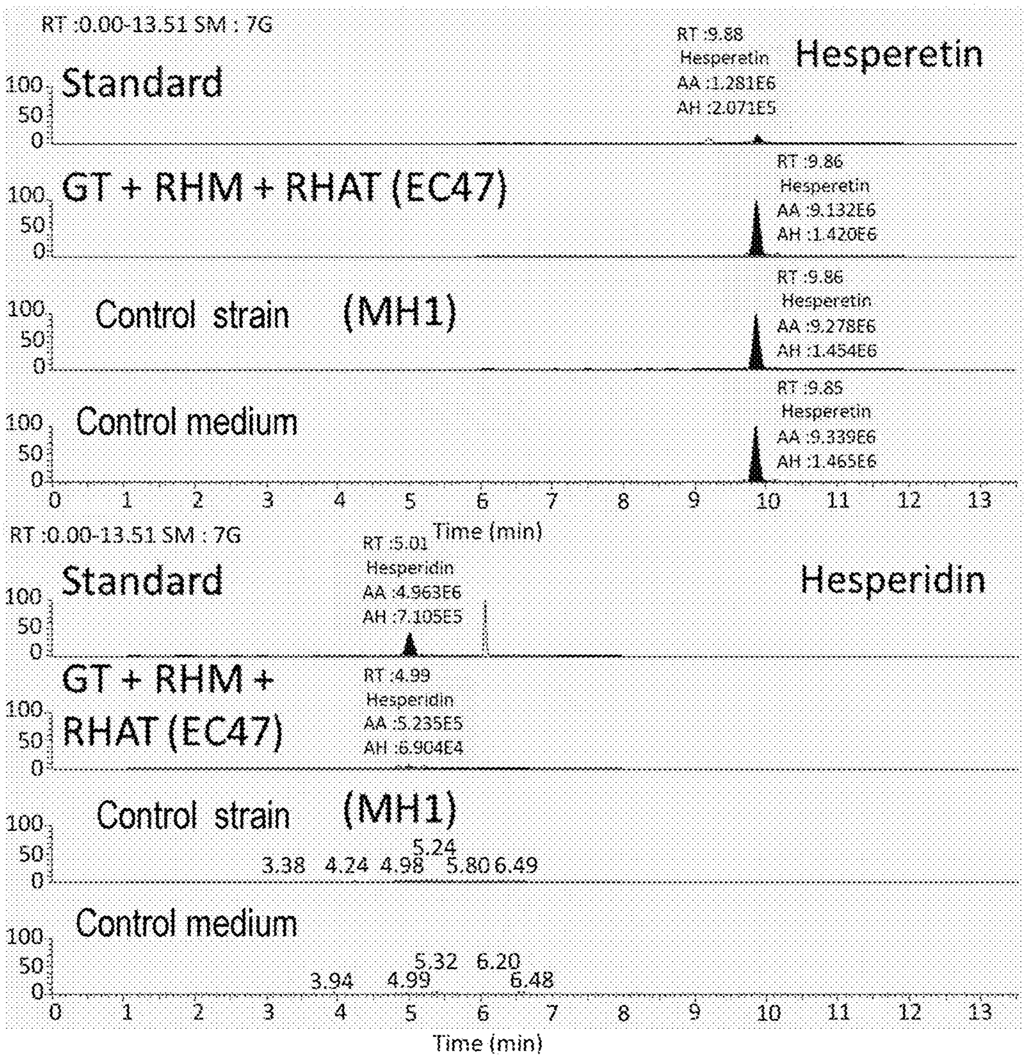

[Figure 17]
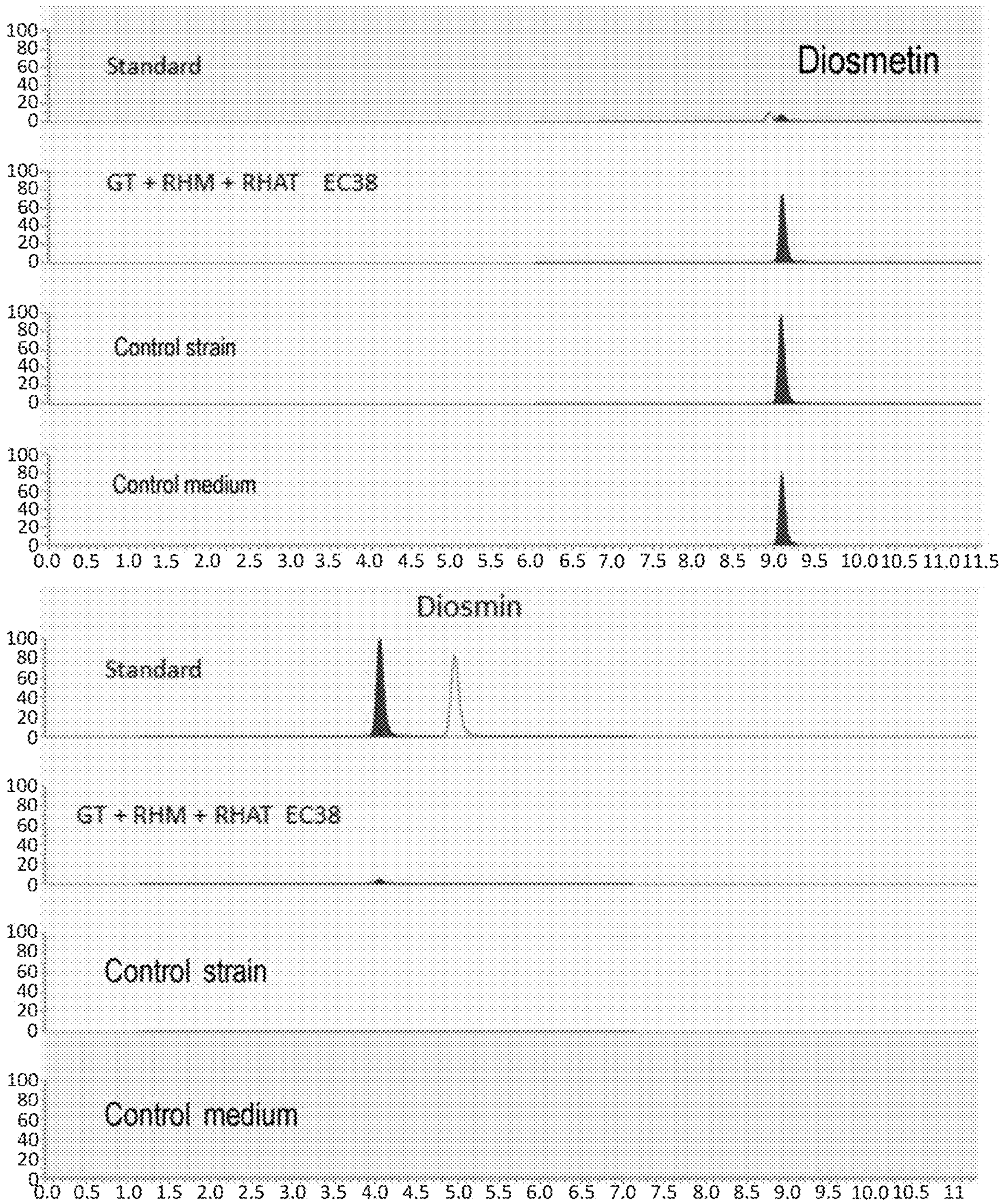

[Figure 17 continued]
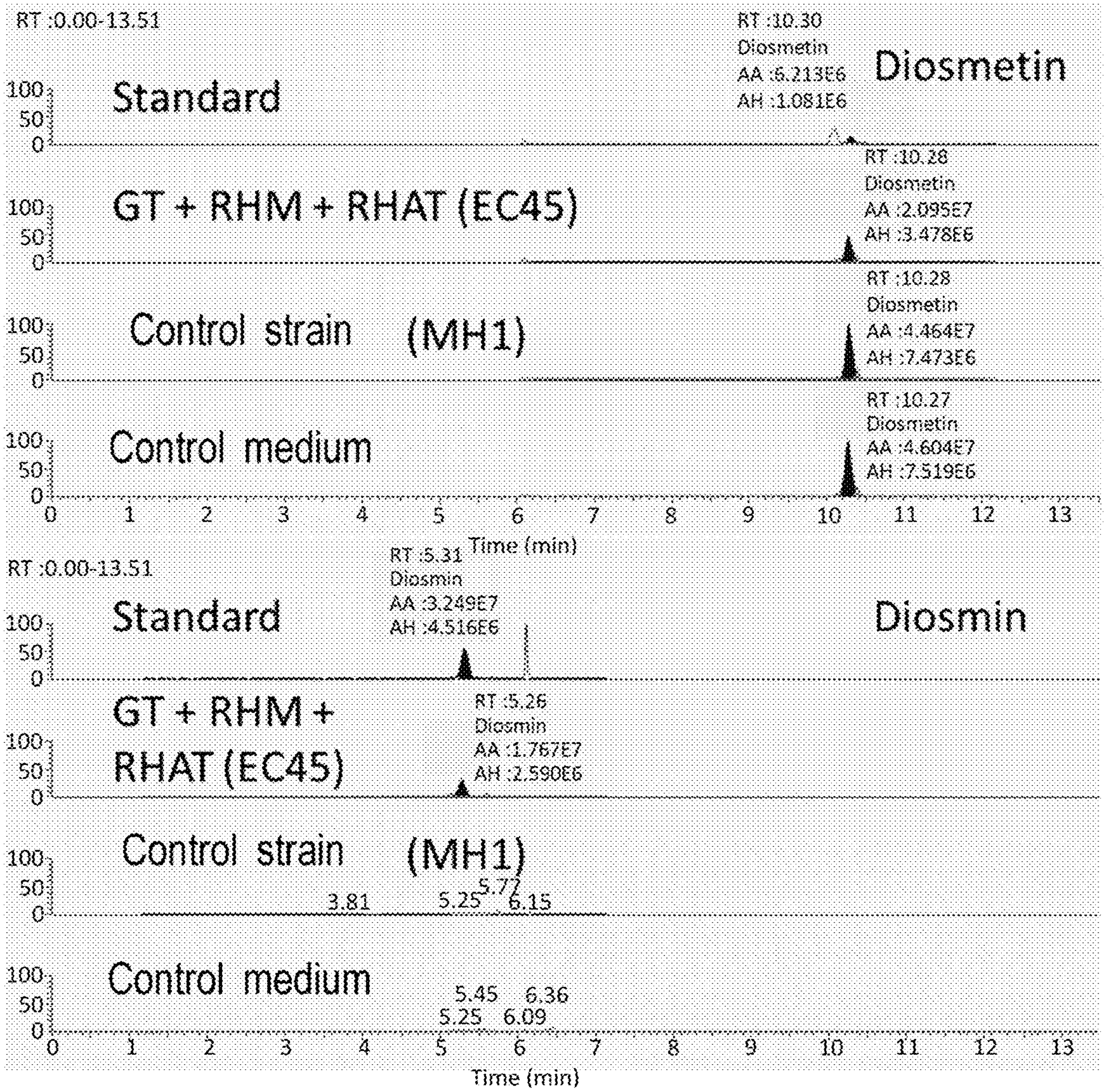

[Figure 17 continued]
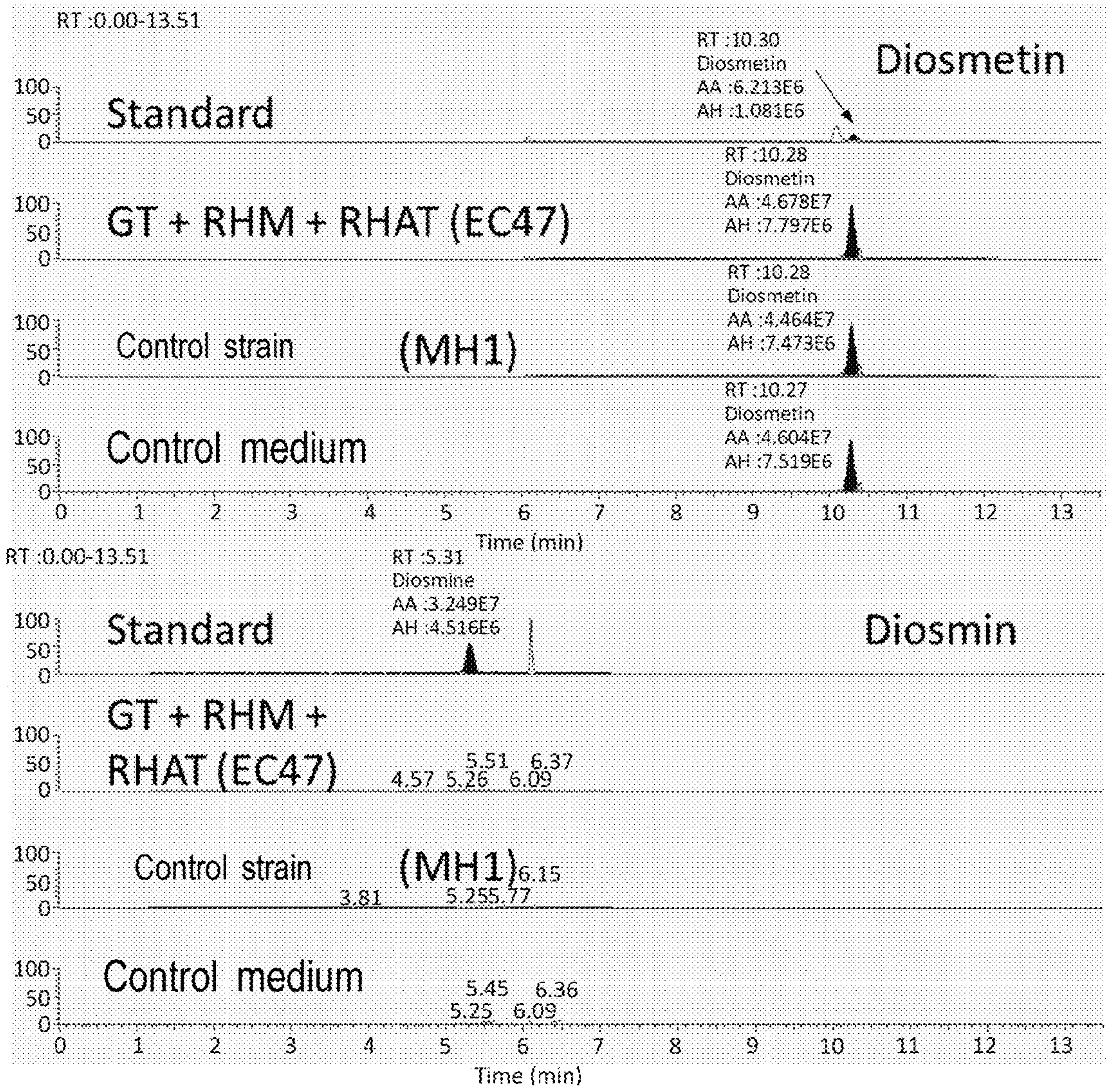

[Figure 18]
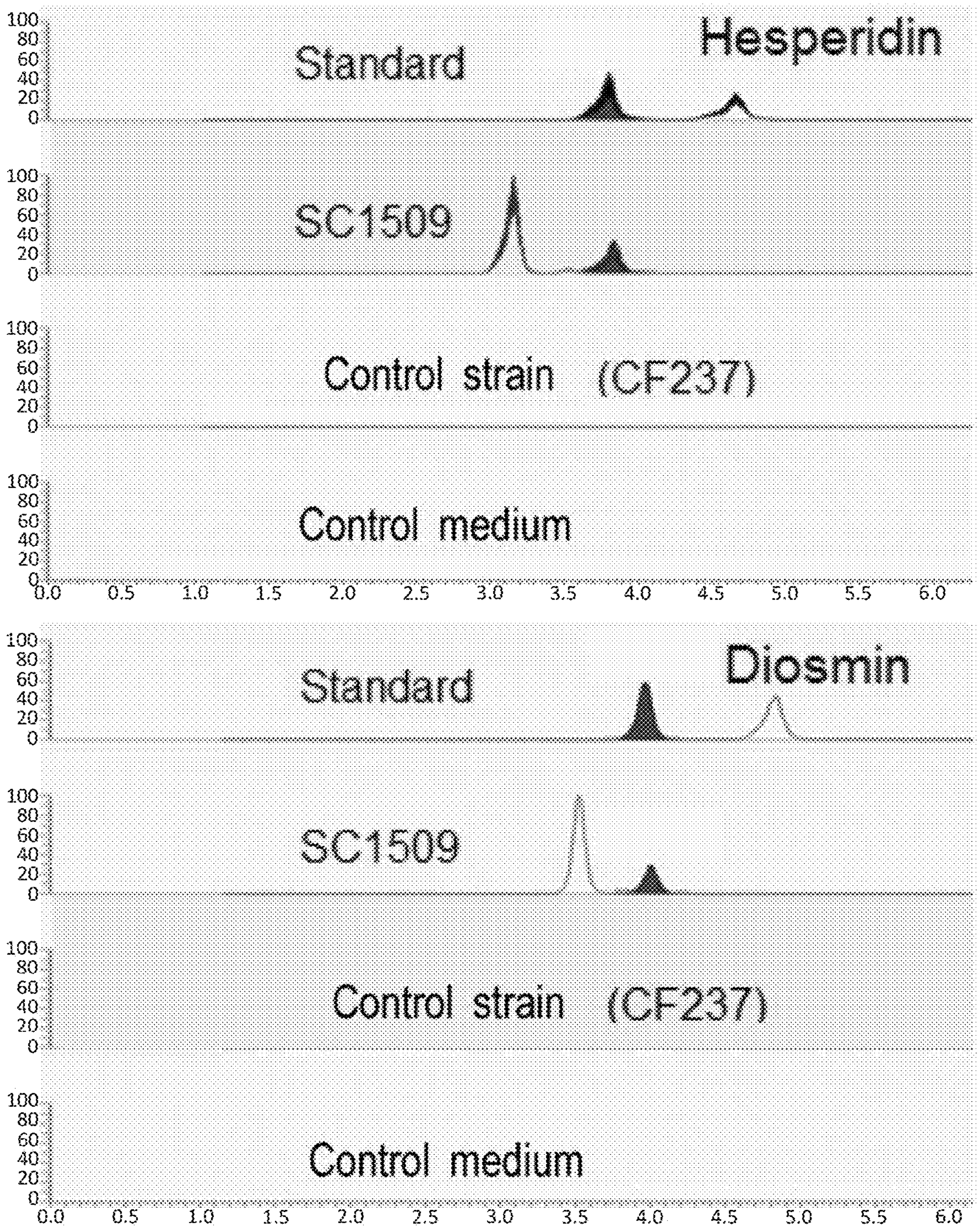

[Figure 18 continued]
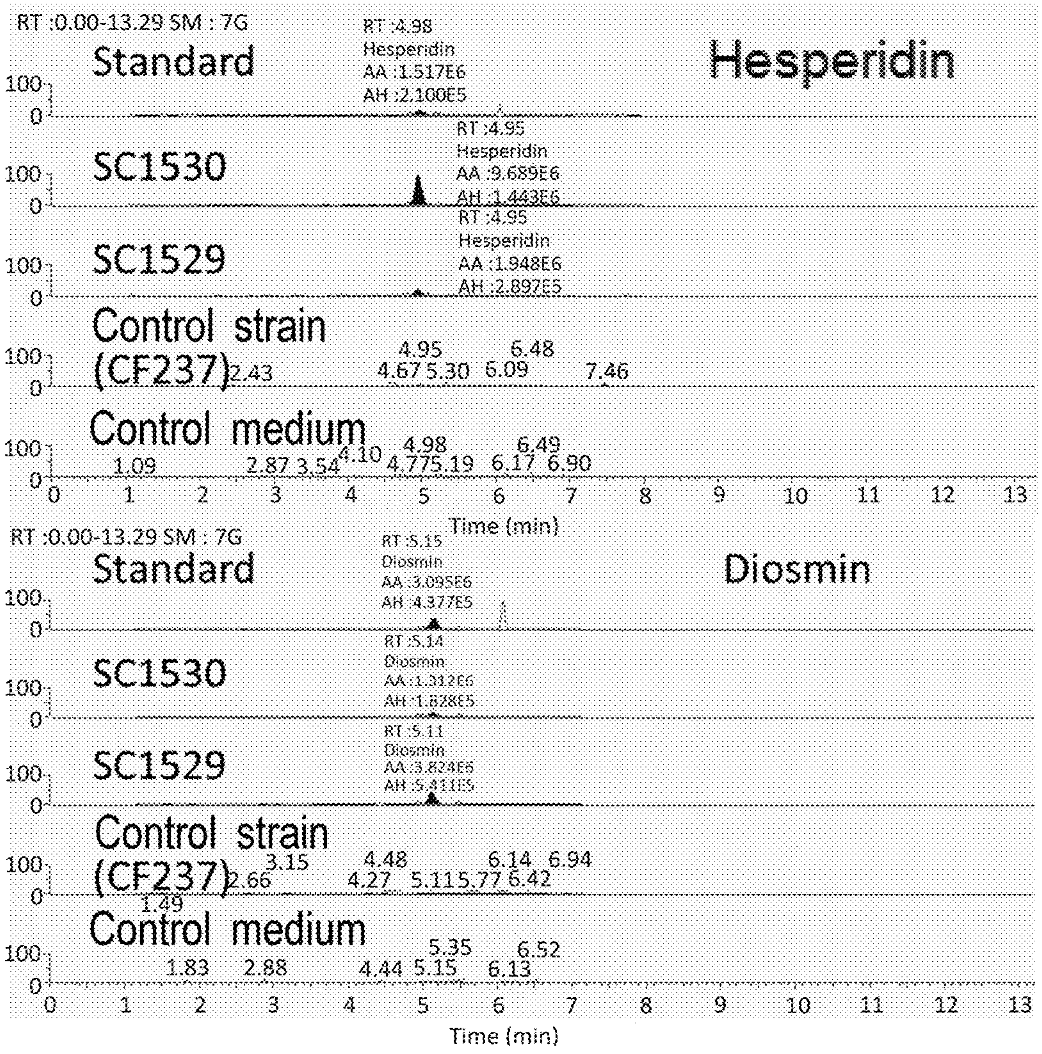

[Figure 18 continued]
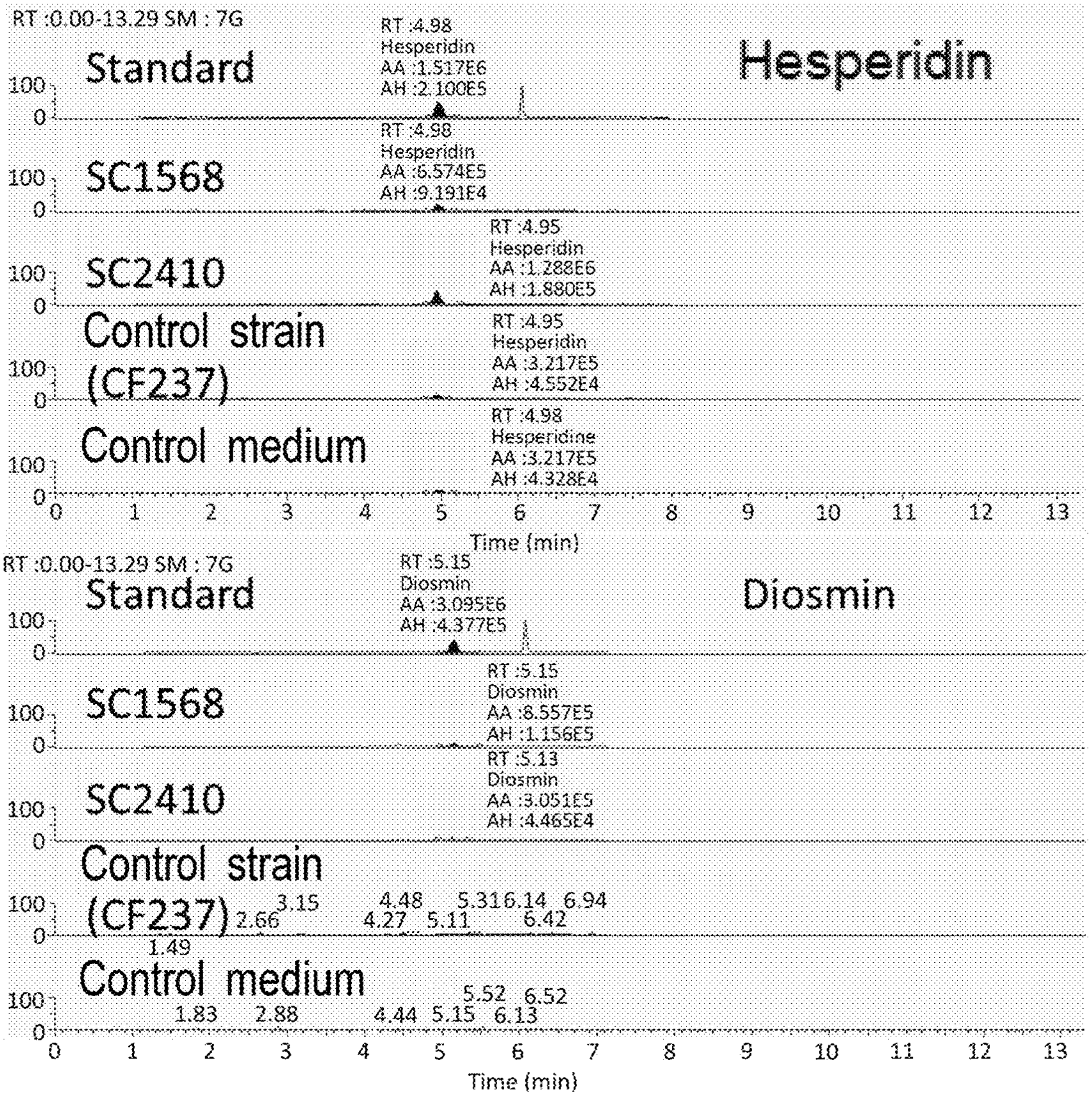

[Figure 19]
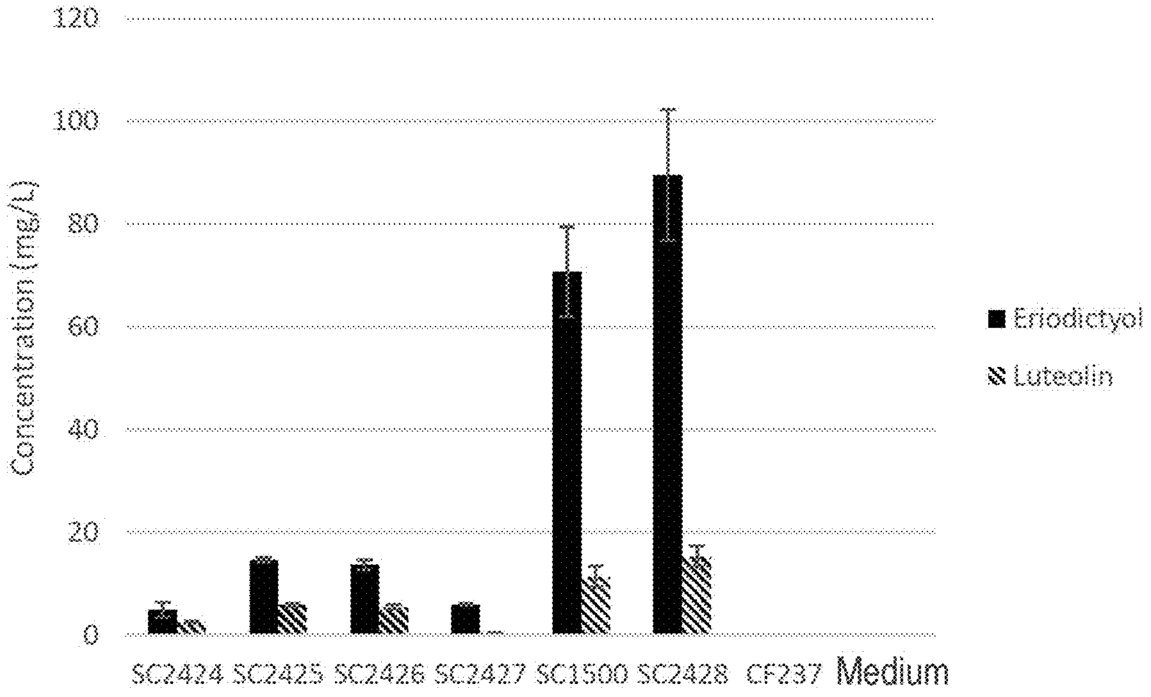

[Figure 20]
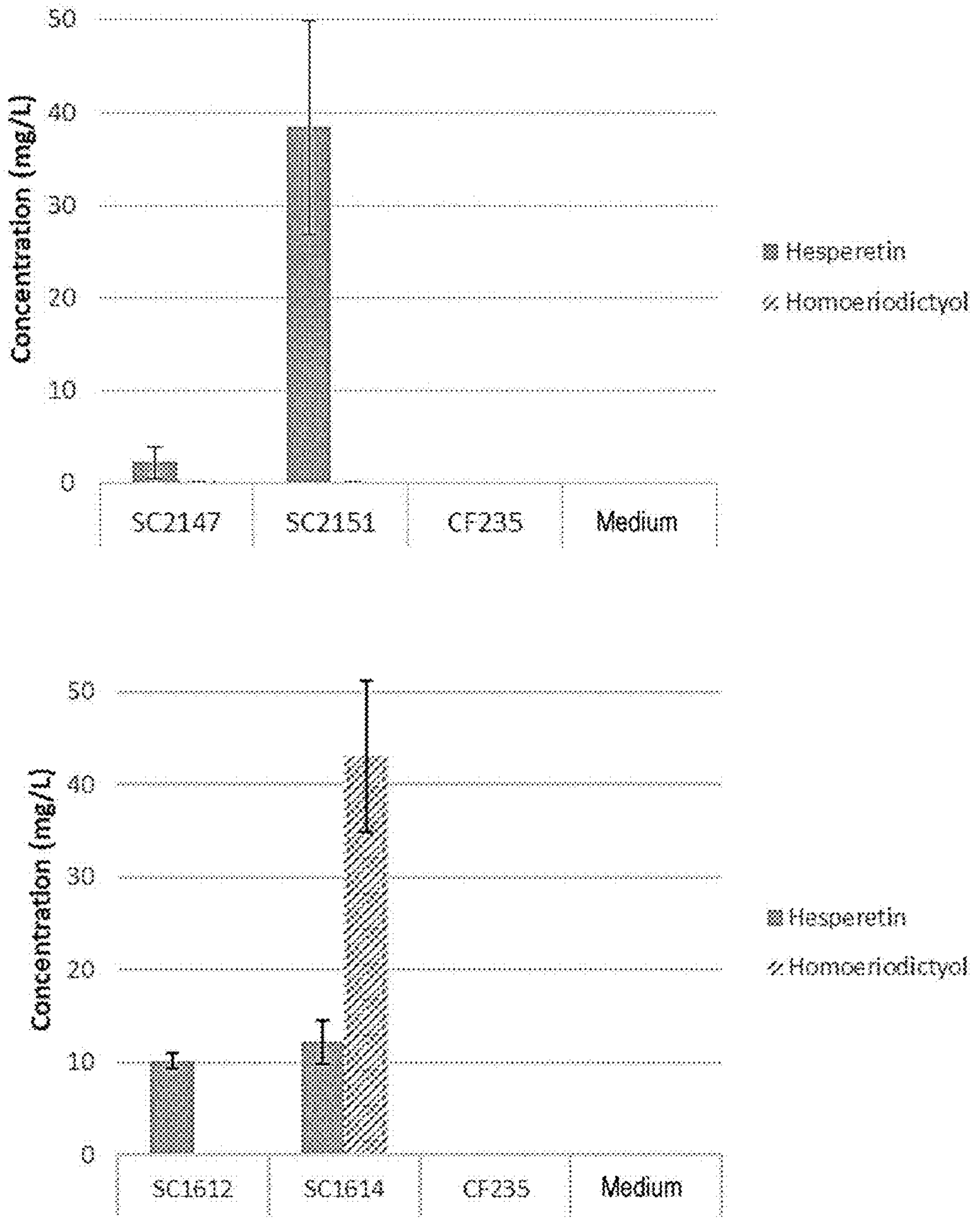

[Figure 21]
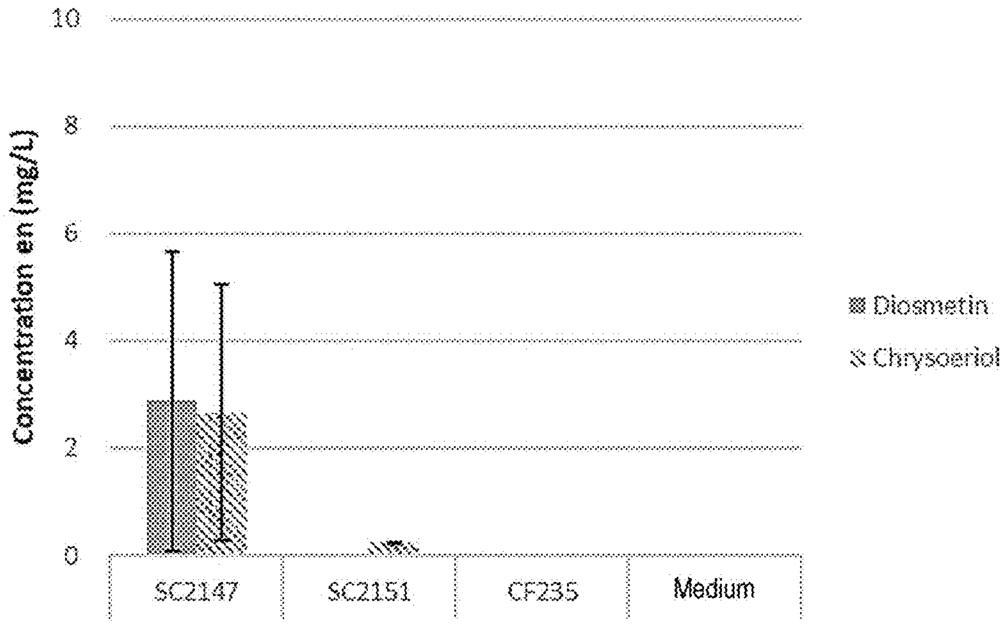
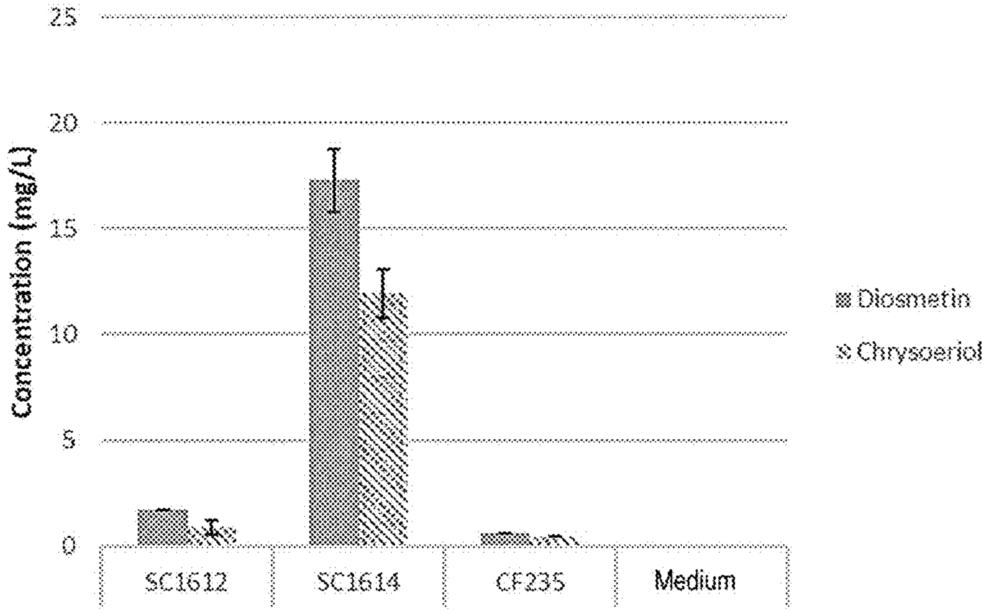

[Figure 22]
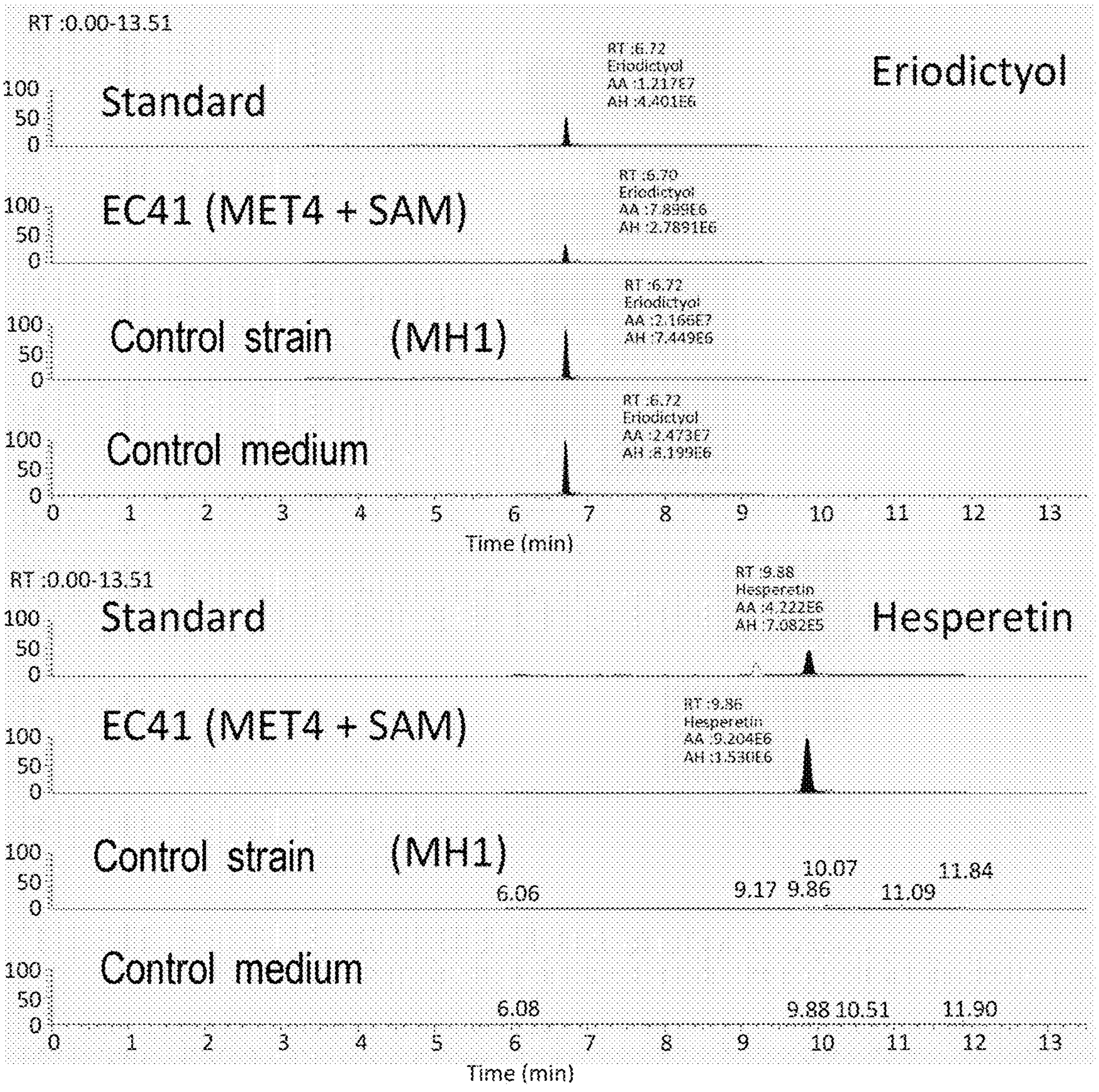

[Figure 23]
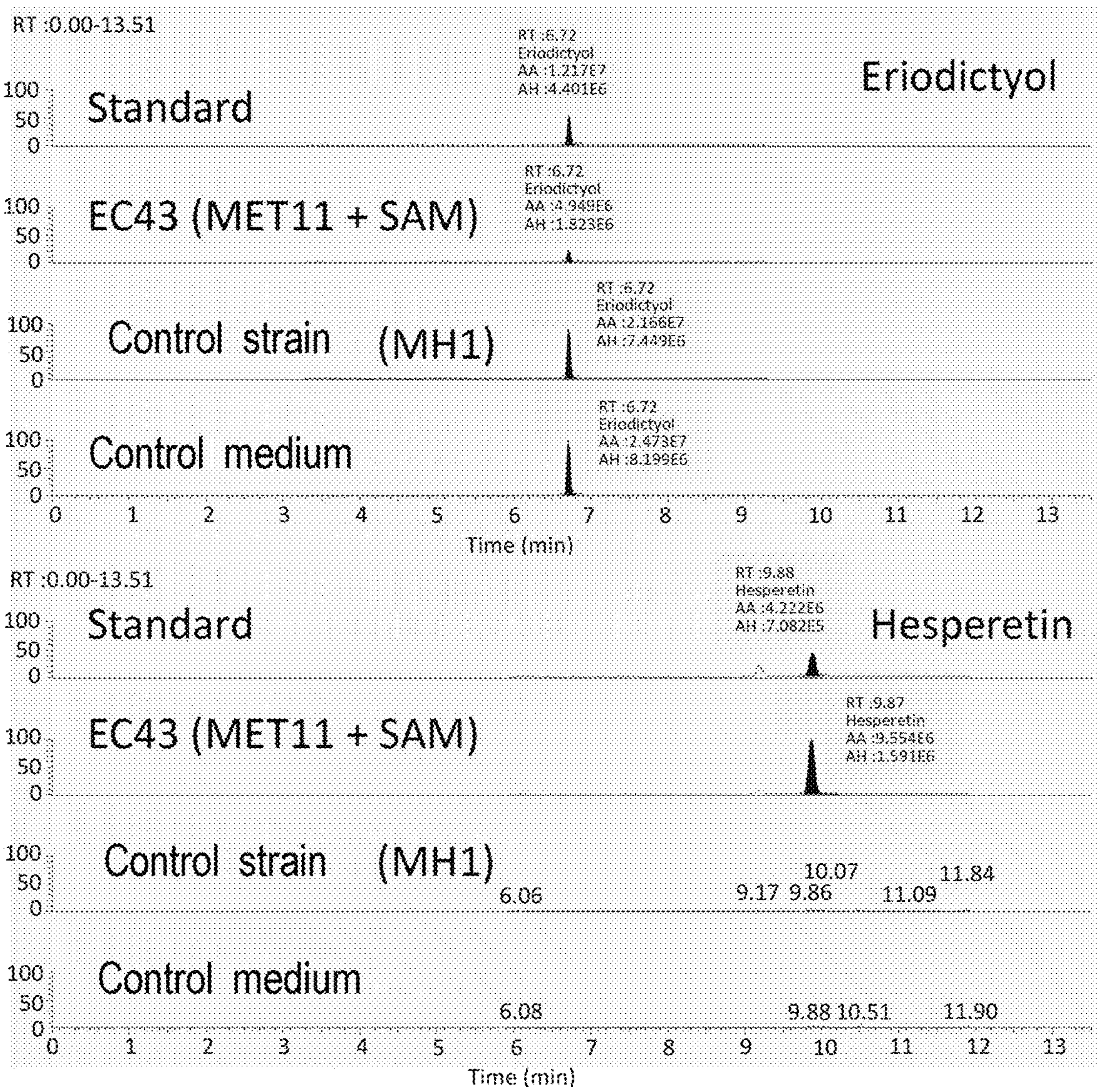

[Figure 24]
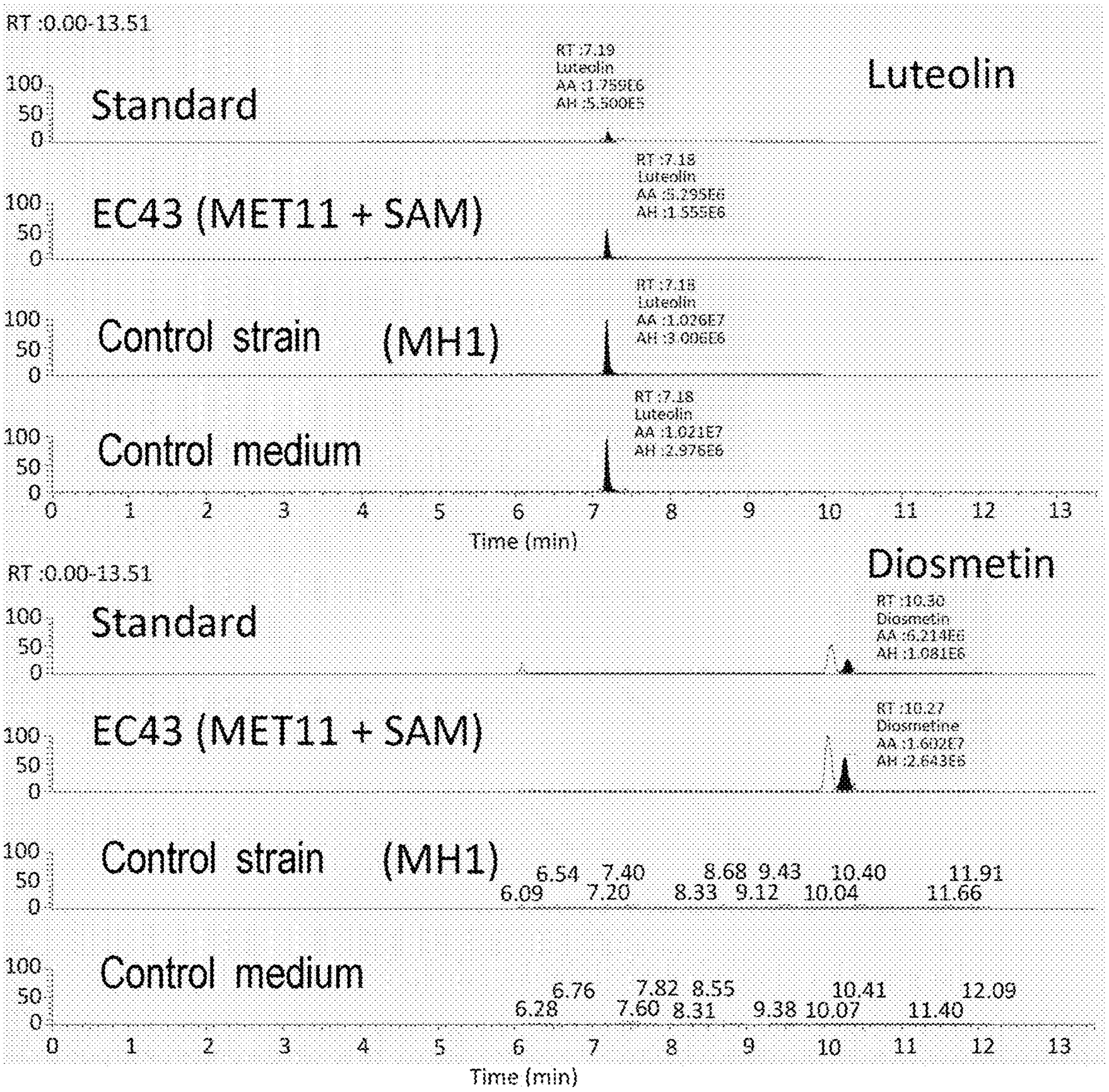

[Figure 25]
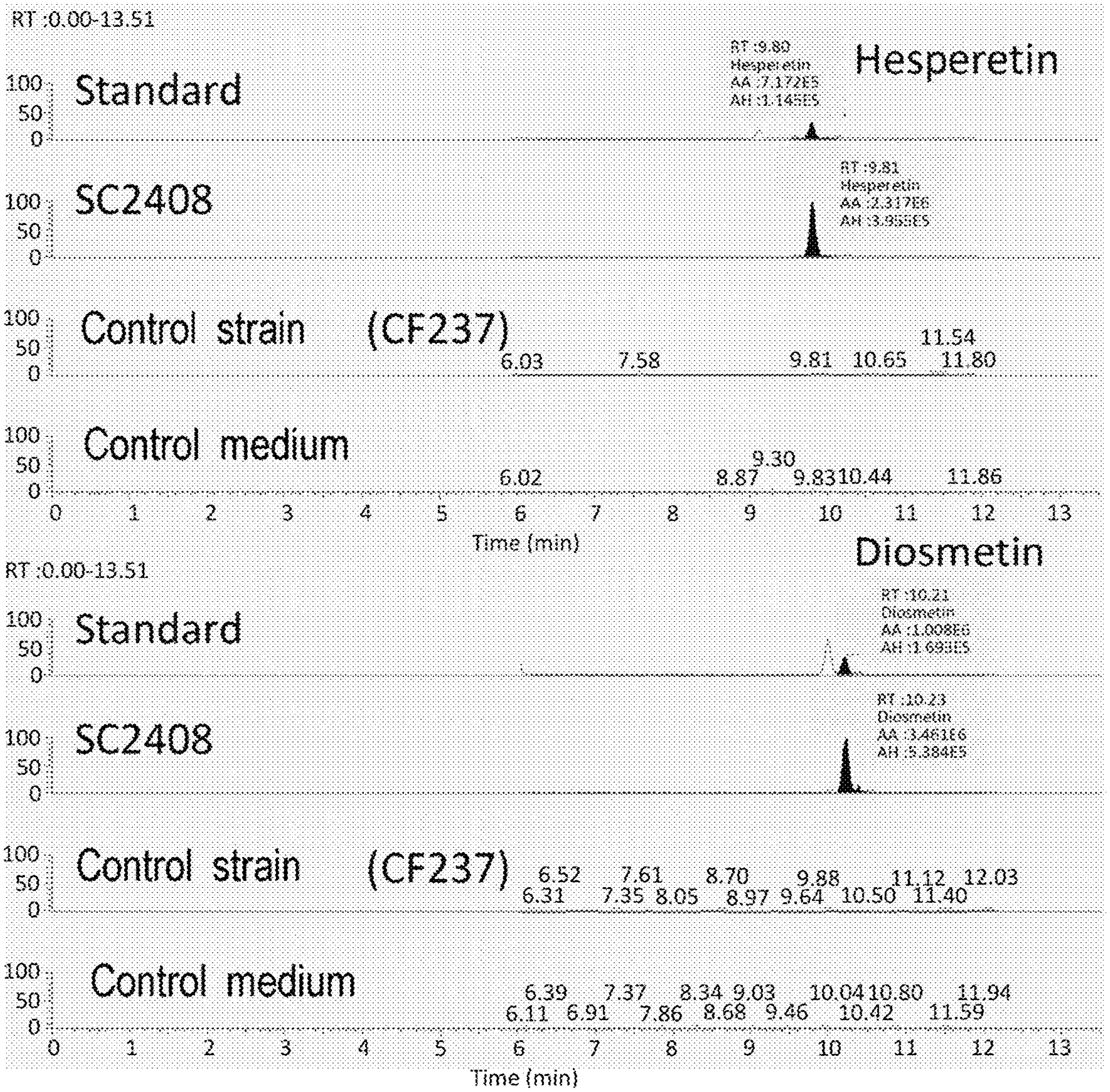

[Figure 26]
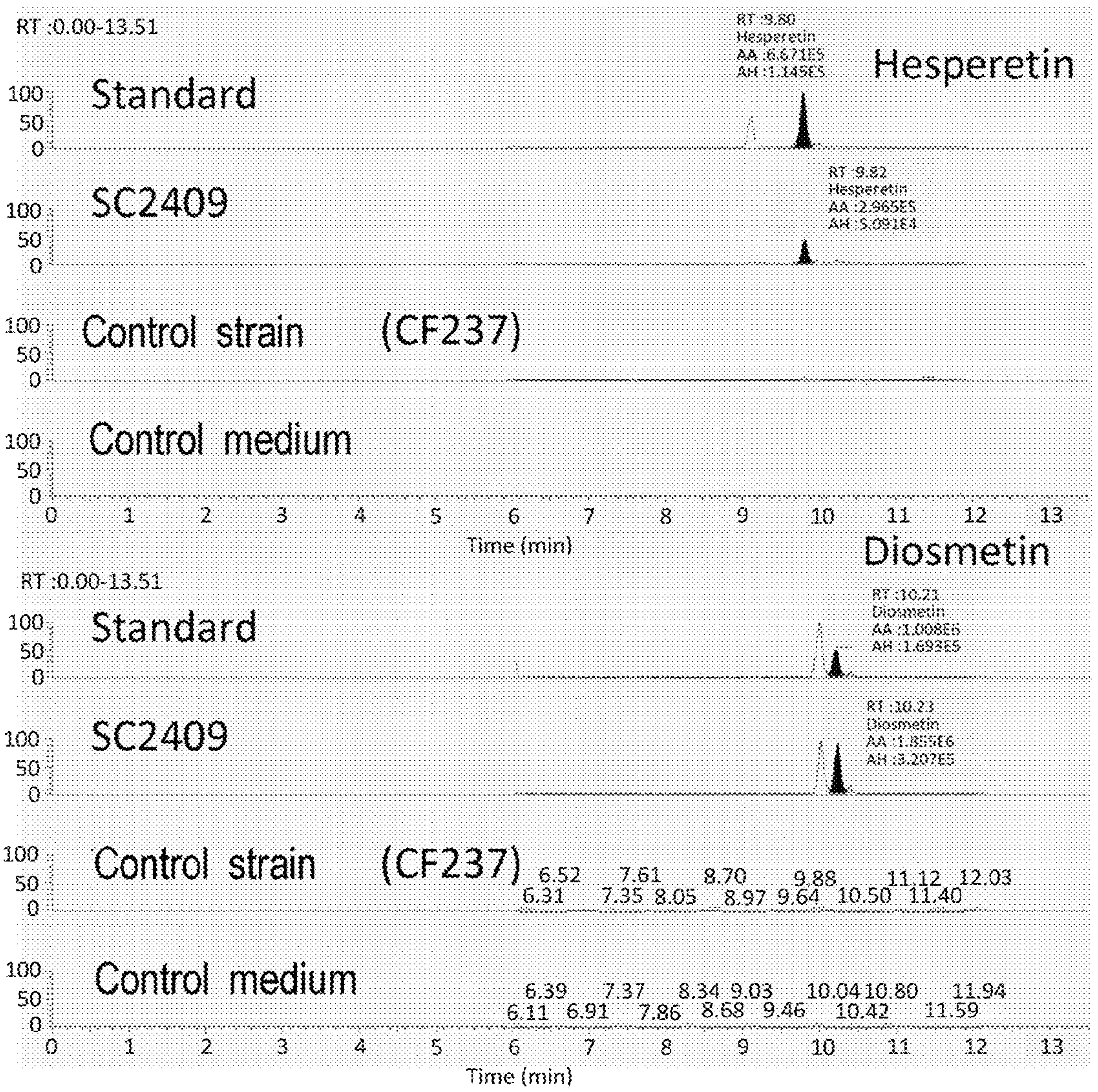

[Figure 27]
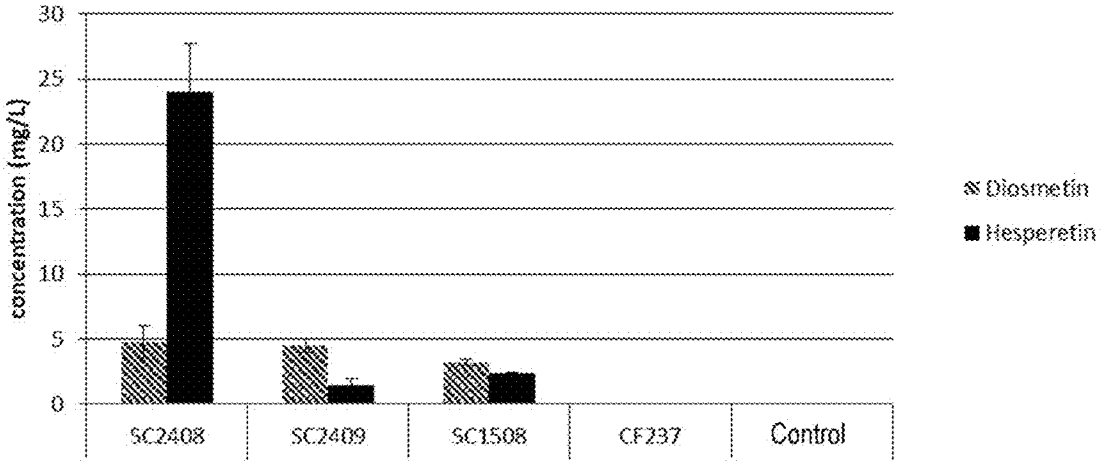
[Figure 28]
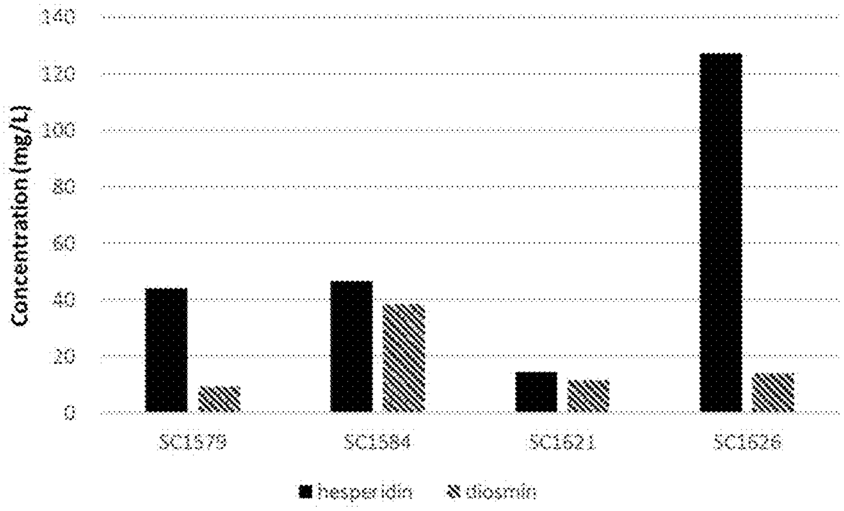

[Figure 29]
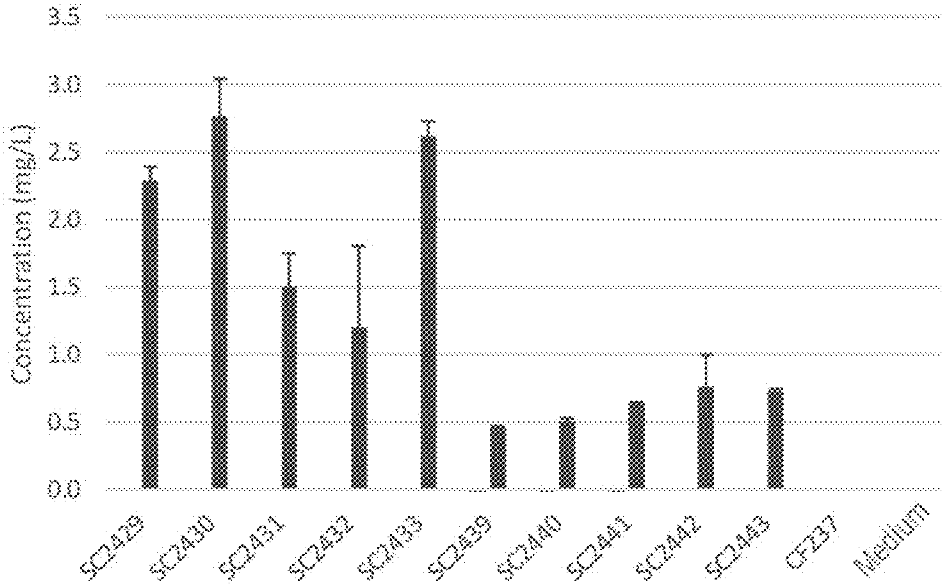
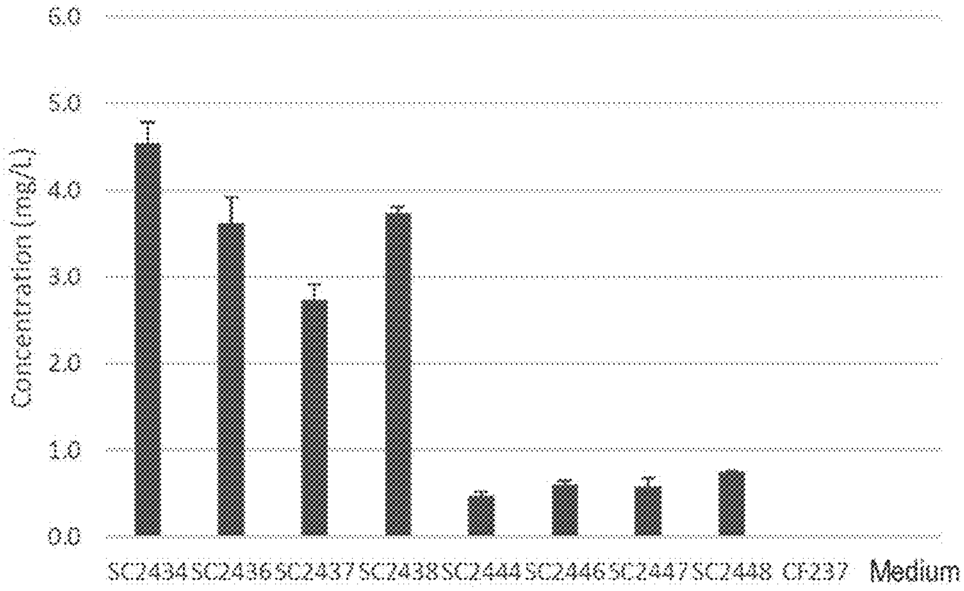

[Figure 29 continued]
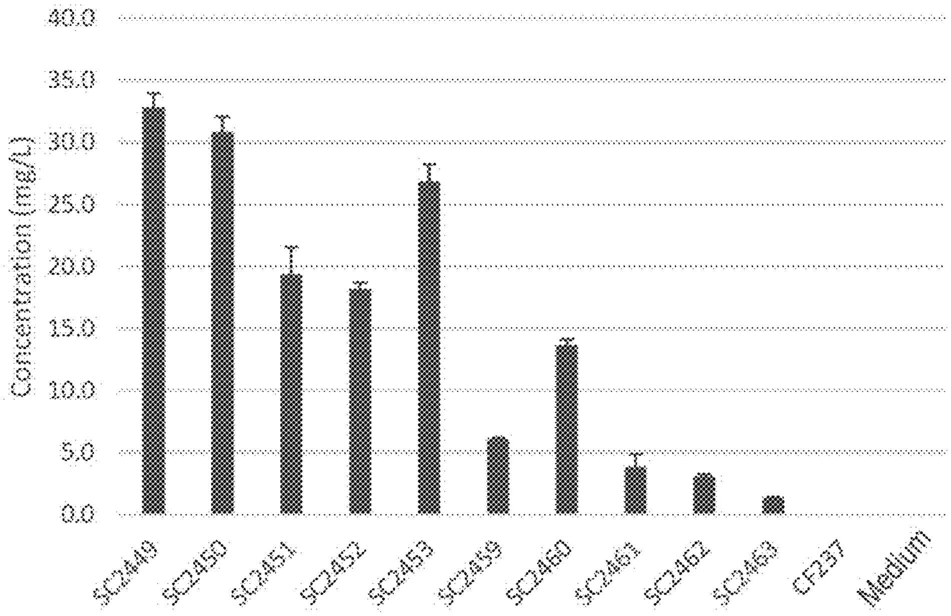
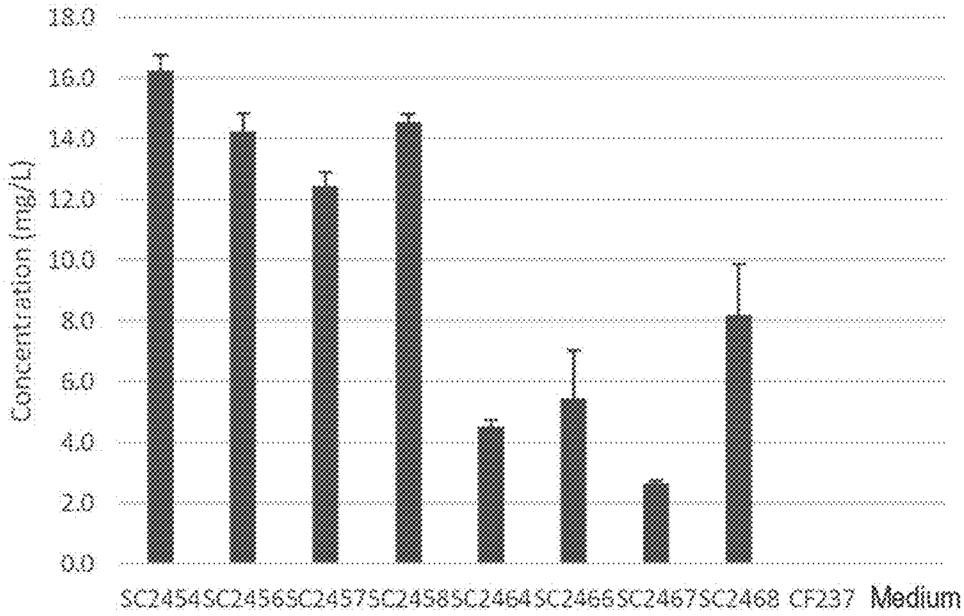

SEQUENCE LISTING

```
Sequence total quantity: 160
SEQ ID NO: 1            moltype = AA  length = 524
FEATURE                 Location/Qualifiers
source                  1..524
                        mol_type = protein
                        organism = Perilla frutescens
SEQUENCE: 1
MSISAAVSLI ICTSILGVLV YFLFLRRGGG SNGRPLPPGP RPWPIVGNLP QLGPKPHQSM  60
AALARVHGPL MHLKMGFVHV VVAASATVAE KFLKVHDTNF LSRPPNSGAE HIAYNYNDLV  120
FAPHGPRWRL LRKICALHLF SSKALDDFRH VREEEVGILI RNLASVGEMP ASIGQMMYVC  180
ATNAISRVML GRHVLGDEHR GAAGGGDTTA EEFKAMVVEL MALAGVFNVG DFIPPLKGLD  240
LQGVVAKMKK LHQRFDAFFS GILHDHKING SNAAEGHVDL LTTLISLKDV DNNGEGGKLT  300
DTEIKALLLN LFTAGTDTTS STVEWAITEL IRNPNILARV RKELDLIVGK DKLVKESDLG  360
QLTYLQAVIK ENFRLHPSTP LSLPRVAQES CEINGYYIPK DSTLLVNVWA IGRDPNVWPD  420
PLEFRPERFL MGGEKPNVDV RGNDFELIPF GSGRRICAGM NLGIRMVQLL IATMVHAFDF  480
ELANGQLAKD LNMEEAYGIT LQRADPLVVH PRPRLARHVY QAQV                  524

SEQ ID NO: 2            moltype = DNA  length = 1575
FEATURE                 Location/Qualifiers
misc_feature            1..1575
                        note = coding sequence for SEQ ID NO: 1
source                  1..1575
                        mol_type = other DNA
                        organism = synthetic construct
SEQUENCE: 2
atgtccatct ctgccgccgt ttctttgatc atctgtactt ccattttggg tgttttggtt  60
tacttcttgt tcttgagaag aggtggtggt tctaacggta gaccattgcc accaggtcca  120
agaccatggc caattgtcgg taacttgcca caattgggtc caaagccaca ccaatctatg  180
gctgccttgg ccagagttca cggtccattg atgcacttga agatgggttt cgttcacgtt  240
gttgttgccg cctccgccac cgttgctgaa aagttcttga aggttcacga caccaacttc  300
ttgtctagac caccaaactc cggtgccgaa cacattgctt acaactacaa cgacttggtt  360
ttcgctccac acggtccaag atggagattg ttgagaaaga tttgtgcctt gcacttgttc  420
tcctccaagg ccttggatga cttcagacac gttagagaag aagaagttgg tatcttgatt  480
agaaacttgg cttctgttgg tgaaatgcca gcttctatcg gtcaaatgat gtacgtttgt  540
gccactaacg ctatctctag agtcatgttg ggtagacacg ttttgggtga cgaacacaga  600
ggtgccgccg gtggtggtga taccactgct gaagaattca aggctatggt tgttgaattg  660
atggctttgg ccggtgtttt caacgttggt gatttcattc caccattgaa gggtttggac  720
ttgcaaggtg ttgttgctaa gatgaagaag ttgcaccaaa gattcgacgc tttcttctct  780
ggtatcttgc acgatcacaa gatcaacggt tctaacgccg ctgaaggtca cgttgacttg  840
ttgactactt tgatttcttt gaaggacgtt gacaacaacg gtgaaggtgg taagttgacc  900
gatactgaaa ttaaggcttt gttgttgaac ttgttcactg ctggtactga cactacttct  960
tctactgttg aatgggccat cactgaattg atcagaaacc caaacatttt ggctagagtt  1020
agaaaggaat tggacttgat cgttggtaag gataagttgg ttaaggaatc cgatttgggt  1080
caattgacct acttgcaagc cgttatcaag gaaaacttca gattgcaccc atctactcca  1140
ttgtctttgc caagagtcgc tcaagaatct tgtgaaatca acggttacta catcccaaag  1200
gattctacct tgttggtcaa cgtttgggcc atcggtagag atccaaacgt ttggccagat  1260
ccattggaat tcagaccaga aagattcttg atgggtggtg aaaagccaaa cgttgatgtt  1320
agaggtaacg atttcgaatt gattccattc ggttctggta gaagaatttg tgctggtatg  1380
aacttgggta ttagaatggt tcaattgttg attgctacta tggttcacgc tttcgatttc  1440
gaattggcta acggtcaatt ggccaaggac ttgaacatgg aagaagctta cggtattact  1500
ttgcaaagag ccgacccatt ggttgtccac ccaagaccaa gattggccag acacgtttac  1560
caagctcaag tttaa                                                  1575

SEQ ID NO: 3            moltype = AA  length = 627
FEATURE                 Location/Qualifiers
source                  1..627
                        mol_type = protein
                        organism = Phanerochaete chrysosporium
SEQUENCE: 3
MSPLLSAVPA AALPLLAAAM YVLWTFLALL VRQARSPLRH LRGPPSPSFL VGNLREMHDQ  60
ENTALFARWE HRYGSTFVYH GFLGGARLLT TDPVAVAHIL AHGYDFPKPE FIRDALASMA  120
AGHEGLLVVE GDGHRRQRKI LSPAFATPHI KSLSPIIWSK ATQLRDVWID LASSPSLTPA  180
ATPSDPLAHA EEQPARASGF LPNPFSSFLS SKAHPRSALP RAEAHPEDRM SSPGTKVDVL  240
AWLARATLDV IGEAGFGYAF NSVRAAACPG DAAEDELARA FAVIFSTARK FRLITVLQVW  300
```

```
FPFLRRFRRN SAAEDHARAT MRRIGLALIA ERRQEVLDDK AHASQEAMDG KDLLTVMIKS  360
SLSSDPSQQL STNEMLCQIA TFLAAGHETS ASALSWALYA LARAPACQHT LRRELRALTL  420
PADPSAADLQ AVLALPYLDA VVRETLRVHA PVTSTMRVAA HDAAVPVGTP FRDAHGAQHA  480
AIRLRAGDVV TLPLQAMNKA RALWGADAAC FRPERWLAHG DAPREPRGLW GGVMTFGTGV  540
VANGNRSCIG YRFAVNEIKL FLYALVRDIE FTIDPWIEIE KRVNVVTRPC VKSEPHLGNQ  600
MPLRLRRVAV EETVGDSSGD GAPRTVS                                     627

SEQ ID NO: 4            moltype = DNA  length = 1884
FEATURE                 Location/Qualifiers
misc_feature            1..1884
                        note = coding sequence for SEQ ID NO: 3
source                  1..1884
                        mol_type = other DNA
                        organism = synthetic construct
SEQUENCE: 4
atgtccccat tgttgtctgc cgttccagcc gccgctttgc cattgttggc cgccgctatg  60
tacgttttgt ggactttctt ggctttgttg gttagacaag ccagatcccc attgagacac  120
ttgagaggtc caccatctcc atctttcttg gtcggtaact tgagagaaat gcacgaccaa  180
gaaaacaccg ctttgttcgc tagatgggaa cacagatacg gttctacctt cgtctaccac  240
ggtttcttgg gtggtgccag attgttgacc accgacccag tcgccgtcgc ccacatcttg  300
gcccacggtt acgacttccc aaagccagaa ttcatcagag atgccttggc ttctatggcc  360
gccggtcacg aaggtttgtt ggtcgtcgaa ggtgacggtc acaggagaca aagaaagatc  420
ttgtccccag ctttcgccac tccacacatc aagtctttgt ctccaatcat ctggtctaag  480
gctactcaat tgagagatgt ttggattgac ttggcctctt ctccatcctt gactccagct  540
gctaccccat ccgacccatt ggctcacgct gaagaacaac cagctagagc ttctggtttc  600
ttgccaaacc cattctcttc tttcttgtca tctaaggctc acccaagatc cgctttgcca  660
agagctgaag ctcacccaga agatagaatg tcctctccag gtaccaaggt cgacgttttg  720
gcttggtttgg ctagagccac tttggacgtc atcggtgaag ccggtttcgg ttacgctttc  780
aactctgtca gagccgctgc ttgtccaggt gacgccgctg aagatgaatt ggctagagct  840
ttcgctgtca tcttctctac tgctagaaag ttcagattga tcactgtctt gcaagtttgg  900
ttcccattct tgagaagatt cagaagaaac tctgctgctg aagatcacgc tagagctact  960
atgagaagaa tcggtttggc tttgatcgct gaaaggagac aagaagtctt ggacgacaag  1020
gctcacgcct ctcaagaagc tatggatggt aaggacttgt tgactgtcat gatcaagtca  1080
tctttgtcat ccgatccatc tcaacaattg tctactaacg aaatgttgtg tcaaatcgct  1140
actttcttgg ctgctggtca cgaaacctct gcttctgctt tgtcttgggc cttgtacgcc  1200
ttggctagag ctccagcttg tcaacacact ttgagaagag aattgagagc tttgactttg  1260
ccagctgacc catctgccgc tgacttgcaa gctgttttgg ctttgccata cttggacgcc  1320
gtcgttagag aaactttgag agttcacgct ccagttactt ctactatgag agtcgctgct  1380
cacgacgccg ctgttccagt cggtactcca ttcagagatg ctcacggtgc tcaacacgcc  1440
gctatcagat tgagagctgg tgacgtcgtc actttgccat tgcaagctat gaacaaggcc  1500
agagctttgt ggggtgccga cgccgcttgt ttcagaccag aaagatggtt ggctcacggt  1560
gacgccccaa gagaaccaag aggtttgtgg ggtggtgtca tgactttcgg taccggtgtc  1620
gtcgctaacg gtaacagatc ttgtattggt tacagattcg ctgttaacga aatcaagttg  1680
ttcttgtacg ccttggttag agacatcgaa ttcactatcg acccatggat cgaaatcgaa  1740
aagagagtta acgtcgtcac cagaccatgt gtcaagtccg aaccacactt gggtaaccaa  1800
atgccattga gattgagaag agtcgctgtt gaagaaactg ttggtgattc ttctggtgac  1860
ggtgctccaa gaactgtttc ttaa                                        1884

SEQ ID NO: 5            moltype = AA  length = 513
FEATURE                 Location/Qualifiers
source                  1..513
                        mol_type = protein
                        organism = Petunia x hybrida
SEQUENCE: 5
MSEILSLILY TVIFSFLLQF ILRSFFRKRY PLPLPPGPKP WPIIGNLVHL GPKPHQSTAA  60
MAQTYGPLMY LKMGFVDVVV AASASVAAQF LKTHDANFSS RPPNSGAEHM AYNYQDLVFA  120
PYGPRWRMLR KICSVHLFST KALDDFRHVR QDEVKTLTRA LASAGQKPVK LGQLLNVCTT  180
NALARVMLGK RVFADGSGDV DPQAAEFKSM VVEMMVVAGV FNIGDFIPQL NWLDIQGVAA  240
KMKKLHARFD AFLTDILEEH KGKIFGEMKD LLSTLISLKN DDADNDGGKL TDTEIKALLL  300
NLFVAGTDTS SSTVEWAIAE LIRNPKILAQ AQQEIDKVVG RDRLVGELDL AQLTYLEAIV  360
KETFRLHPST PLSLPRIASE SCEINGYFIP KGSTLLLNVW AIARDPNAWA DPLEFRPERF  420
LPGGEKPKVD VRGNDFEVIP FGAGRRICAG MNLGIRMVQL MIATLIHAFN WDLVSGQLPE  480
MLNMEEAYGL TLQRADPLVV HPRPRLEAQA YIG                               513

SEQ ID NO: 6            moltype = DNA  length = 1542
FEATURE                 Location/Qualifiers
misc_feature            1..1542
                        note = coding sequence for SEQ ID NO: 5
source                  1..1542
                        mol_type = other DNA
                        organism = synthetic construct
SEQUENCE: 6
atgtccgaaa tcttgtcttt gattttgtac accgtcattt tctctttctt gttgcaattc  60
attttgagat ctttcttcag aaagagatac ccattgccat tgccaccagg tccaaagcca  120
tggccaatta tcggtaactt ggtccacttg ggtccaaagc cacaccaatc tactgctgcc  180
atggctcaaa cttacggtcc attgatgtac ttgaagatgg gtttcgttga cgttgttgtt  240
gctgcctctg cttctgttgc tgctcaattc ttaaagactc acgatgctaa cttctcttct  300
agaccaccaa actctggtgc tgaacacatg gcttacaact accaagattt ggttttcgct  360
ccatacggtc caagatggag aatgttgaga aagatttgtt ctgttcactt gttctctacc  420
```

```
aaggctttgg atgacttcag acacgtcaga caagatgaag ttaagacttt gactagagct  480
ttggcttctg ctggtcaaaa gccagtcaag ttgggtcaat tgttgaacgt ttgtactact  540
aacgctttgg ctagagttat gttgggtaag agagttttcg ccgacggttc tggtgatgtt  600
gatccacaag ctgctgaatt caagtctatg gttgttgaaa tgatggttgt cgccggtgtt  660
ttcaacattg gtgatttcat tccacaattg aactggttgg atattcaagg tgttgccgct  720
aagatgaaga agttgcacgc tagattcgac gctttcttga ctgatatctt ggaagaacac  780
aagggtaaga ttttcggtga aatgaaggat ttgttgtcta ctttgatctc tttgaagaac  840
gatgatgctg ataacgatgg tggtaagttg actgatactg aaattaaggc tttgttgttg  900
aacttgttcg ttgctggtac tgacacttct tcttctactg ttgaatgggc cattgctgaa  960
ttgattagaa acccaaagat cttggcccaa gcccaacaag aaatcgacaa ggtcgttggt  1020
agagacagat tggttggtga attggacttg gcccaattga cttacttgga agctatcgtc  1080
aaggaaacct tcagattgca cccatctacc ccattgtctt tgccaagaat tgcttctgaa  1140
tcttgtgaaa tcaacggtta cttcattcca aagggttcta ctttgttgtt gaacgtttgg  1200
gccattgcta gagatccaaa cgcttgggct gatccattgg aattcagacc agaaagattc  1260
ttgccaggtg gtgaaaagcc aaaggttgat gtcagaggta acgacttcga agtcatccca  1320
ttcggtgctg gtagaagaat ttgtgctggt atgaacttgg gtatcagaat ggtccaattg  1380
atgattgcta ctttgatcca cgctttcaac tgggatttgg tatctggtca attgccagaa  1440
atgttgaaca tggaagaagc ttacggtttg accttgcaaa gagctgatcc attggttgtt  1500
cacccaagac caagattgga agcccaagct tacattggtt aa                    1542

SEQ ID NO: 7           moltype = AA  length = 519
FEATURE                Location/Qualifiers
source                 1..519
                       mol_type = protein
                       organism = Callistephus chinensis
SEQUENCE: 7
MSTILPFIFY TCITALVLYV LLNLLTRNPN RLPPGPTPWP IVGNLPHLGM IPHHSLAALA  60
QKYGPLMHLR LGFVDVVVAA SASVAAQFLK THDANFASRP PNSGAKHIAY NYQDLVFAPY  120
GPRWRMLRKI CSVHLFSTKA LDDFRHVREE EVAILTRVLV HAGESAVKLG QLLNVCTTNA  180
LARVMLGRRV FADGSEGRGV DPKADEFKDM VVELMELAGE FNIGDFIPPL DCLDLQGITK  240
KMKKLHARFD KFLNIILDDH KIEKGAAGRR HSDLLTTLIS LKDVDAADDD EEGKLSDIEI  300
KALLLNLFAA GTDTSSSTVE WAVAELIRHP ELLKQAREEM DIVVGRDRLV TELDLSRLTF  360
LQAIVKETFR LHPSTPLSLP RMASESCEVD GYYIPKGSTL LVNVWAIARD PKMWTNPLEF  420
RPSRFLPGGE KPDADIKGND FEVIPFGAGR RICAGMSLGM RMVQLLIATL VQTFDWELAN  480
GLDPEKLNME EAYGLTLQRA EPLMVHPRPR LSPHVYESR                        519

SEQ ID NO: 8           moltype = DNA  length = 1560
FEATURE                Location/Qualifiers
misc_feature           1..1560
                       note = coding sequence for SEQ ID NO: 7
source                 1..1560
                       mol_type = other DNA
                       organism = synthetic construct
SEQUENCE: 8
atgtccacca ttttgccatt cattttctac acttgtatca ctgccttggt tttgtacgtt  60
ttgttgaact tgttgaccag aaacccaaac agattgccac caggtccaac cccatggcca  120
atcgttggta acttgccaca cttgggtatg atcccacacc actctttggc tgccttggcc  180
caaaagtacg gtccattgat gcacttgaga ttgggtttcg ttgacgttgt cgttgccgct  240
tctgcttccg ttgctgctca attcttaaag actcacgacg ctaacttcgc ttctagacca  300
ccaaactctg gtgccaagca cattgcctac aactaccaag atttggtttt cgctccatac  360
ggtccaagat ggagaatgtt gagaaagatt tgttctgttc acttgttctc cactaaggct  420
ttggacgact tcagacacgt tagagaagaa gaagttgcta tcttgactag agttttggtc  480
cacgctggtg aatctgctgt taagttgggt caattgttga acgtttgtac cactaacgct  540
ttggctagag ttatgttggg tagaagagtt ttcgctgacg gttctgaagg tagaggtgtc  600
gacccaaagg ctgatgaatt caaggacatg gttgttgaat tgatggaatt ggccggtgaa  660
ttcaacatcg gtgacttcat cccaccattg gactgtttgg atttgcaagg tatcaccaag  720
aagatgaaga agttgcacgc tagattcgac aagttcttga acatcatctt ggacgaccac  780
aagatcgaaa agggtgctgc cggtagaagg cactctgact tgttgaccac tttgatttct  840
ttgaaggatg ttgatgctgc tgatgatgat gaagaaggta agttgtctga cattgaaatc  900
aaggctttgt tgttgaactt gttcgctgct ggtactgaca cttcttcttc taccgttgaa  960
tgggctgttg ccgaattgat tagacaccca gaattgttga agcaagctag agaagaaatg  1020
gatatcgttg ttggtagaga cagattggtt accgaattgg acttgtctag attgactttc  1080
ttgcaagcca ttgttaagga aaccttcaga ttgcacccat ctactccatt gtccttgcca  1140
agaatggctt ctgaatcttg tgaagttgat ggttactaca ttccaaaggg ttccactttg  1200
ttggttaacg tttgggccat cgccagagat ccaaagatgt ggactaaccc attggaattc  1260
agaccatcta gattcttgcc aggtggtgaa aagccagatg ctgatatcaa gggtaacgat  1320
ttcgaagtca tcccattcgg tgccggtaga agaatctgtg ctggtatgtc tttgggtatg  1380
agaatggtcc aattgttgat tgctactttg gtccaaacct tcgattggga attggctaac  1440
ggtttggacc cagaaaagtt gaacatggaa gaagcttacg gtttgacctt gcaaagagct  1500
gaaccattga tggttcaccc aagaccaaga ttgtctccac acgtttacga atctagataa  1560

SEQ ID NO: 9           moltype = AA  length = 511
FEATURE                Location/Qualifiers
source                 1..511
                       mol_type = protein
                       organism = Callistephus chinensis
SEQUENCE: 9
MSSILSLLVY FCISLLVIIA LVNMFITRHT NRLPPGPAPW PVVGNLPHLG AIPHHTLAAL  60
ATKYGPLVYL RLGFVHVVVA SSPSVAAQFL KVHDLKFASR PPNSGAKHIA YNYQDMVFAP  120
```

```
YGPQWTMFRK ICKDHLFSSK ALDDFRHVRQ EEVAILARGL AGAGRSKVNL GQQLNMCTAN  180
TLARMMLDKR VFGNESGGDD PKANEFKEMA TELMFLAGQF NIGDYIPVLD WLDLQGIVKK  240
MKKLHTRFDK FLDVILDEHK VIASGHIDML STLISLKDDT SVDGRKPSDI EIKALLLELF  300
VAGTDTSSNT VEWAIAELIR QPHLLKRAQE EMDSVVGQNR LVTEMDLSQL TFLQAIVKEA  360
FRLHPSTPLS LPRIASESCE VDGYYIPKGS TLLVNIWAIG RHPEVWTDPL EFRPTRFLPG  420
GEKPGIVVKV NDFEVLPFGA GRRICAGMSL ALRTVQLLMG TLVQAFDWEL ANGIKPEKLN  480
MDEAFGLSVQ RAEPLVVHPR PRLPPHVYKS G                                511

SEQ ID NO: 10          moltype = DNA  length = 1536
FEATURE                Location/Qualifiers
misc_feature           1..1536
                       note = coding sequence for SEQ ID NO: 9
source                 1..1536
                       mol_type = other DNA
                       organism = synthetic construct
SEQUENCE: 10
atgtcctcta ttttgtcttt gttggtctac ttctgtatct ctttgttggt tatcattgct  60
ttggttaaca tgttcatcac cagacacacc aacagattgc caccaggtcc agccccatgg  120
ccagtcgtcg gtaacttgcc acacttgggt gctattccac accacacttt ggctgctttg  180
gctactaagt acggtccatt ggtttacttg agattgggtt tcgttcacgt tgttgttgcc  240
tcttctccat ccgttgctgc tcaattcttg aaggttcacg acttgaagtt cgcctctaga  300
ccaccaaact ctggtgctaa gcacatcgct tacaactacc aagatatggt tttcgctcca  360
tacggtccac aatggactat gttcagaaag atttgtaagg atcacttgtt ctcttctaag  420
gctttggatg atttcagaca cgttagacaa gaagaagttg ctatcttggc tagaggtttg  480
gctggtgctg gtagatctaa ggttaacttg ggtcaacaat tgaacatgtg taccgctaac  540
actttggcta gaatgatgtt ggacaagaga gttttcggta acgaatctgg tggtgatgat  600
ccaaaggcta acgaattcaa ggaaatggct actgaattga tgttcttggc tggtcaattc  660
aacattggtg actacatccc agttttggac tggttggact tgcaaggtat tgttaagaag  720
atgaagaagt tgcacactag attcgataag ttcttggacg ttatcttgga tgaacacaag  780
gttatcgctt ctggtcacat cgacatgttg tctactttga tttctttgaa ggatgatacc  840
tctgttgacg gtagaaagcc atccgacatc gaaatcaagg ctttgttgtt ggaattgttc  900
gttgctggta ctgacacttc ttctaacacc gttgaatggg ctatcgctga attgattaga  960
caaccacact tgttgaagag agcccaagaa gaaatggact ctgttgttgg tcaaaacaga  1020
ttggttaccg aaatggactt gtctcaattg actttcttgc aagccattgt taaggaagcc  1080
ttcagattgc acccatctac tccattgtcc ttgccaagaa ttgcttccga atcttgtgaa  1140
gttgatggtt actacatccc aaagggttcc actttgttgg ttaacatctg ggccattggt  1200
agacacccag aagtttggac cgacccattg gaattcagac caactagatt cttgccaggt  1260
ggtgaaaagc caggtattgt cgtcaaggtt aacgatttcg aagtcttgcc attcggtgcc  1320
ggtagaagaa tctgtgctgg tatgtctttg gccttgagaa ctgtccaatt gttgatgggt  1380
actttggtcc aagccttcga ttgggaattg gctaacggta tcaagccaga aaagttgaac  1440
atggacgaag ccttcggttt gtctgttcaa agagctgaac cattggttgt tcacccaaga  1500
ccaagattgc caccacacgt ttacaagtct ggttaa                           1536

SEQ ID NO: 11          moltype = AA  length = 513
FEATURE                Location/Qualifiers
source                 1..513
                       mol_type = protein
                       organism = Gerbera hybrida
SEQUENCE: 11
MSTPLTLLIG TCVTGLFLYV LLNRCTRNPN RLPPGPTPWP VVGNLPHLGT IPHHSLAAMA  60
KKYGPLMHLR LGFVDVVVAA SASVAAQFLK THDANFADRP PNSGAKHIAY NYQDLVFAPY  120
GPRWRMLRKI CSVHLFSTKA LDDFRHVRQE EVAILARALV GAGKSPVKLG QLLNVCTTNA  180
LARVMLGRRV FDSGDAQADE FKDMVVELMV LAGEFNIGDF IPVLDWLDLQ GVTKKMKKLH  240
AKFDSFLNTI LEEHKTGAGD GVASGKVDLL STLISLKDDA DGEGGKLSDI EIKALLLNLF  300
TAGTDTSSST IEWAIAELIR NPQLLNQARK EMDTIVGQDR LVTESDLGQL TFLQAIIKET  360
FRLHPSTPLS LPRMALESCE VGGYYIPKGS TLLVNVWAIS RDPKIWADPL EFQPTRFLPG  420
GEKPNTDIKG NDFEVIPFGA GRRICVGMSL GLRMVQLLTA TLIHAFDWEL ADGLNPKKLN  480
MEEAYGLTLQ RAAPLVVHPR PRLAPHVYET TKV                              513

SEQ ID NO: 12          moltype = DNA  length = 1542
FEATURE                Location/Qualifiers
misc_feature           1..1542
                       note = coding sequence for SEQ ID NO:11
source                 1..1542
                       mol_type = other DNA
                       organism = synthetic construct
SEQUENCE: 12
atgtccactc cattgacttt gttgatcggt acctgtgtca ctggtttgtt cttgtacgtt  60
ttgttgaaca gatgtaccag aaacccaaac agattgccac caggtccaac tccatggcca  120
gtcgtcggta acttgccaca cttgggtact atcccacacc actctttggc tgctatggct  180
aagaagtacg gtccattgat gcacttgaga ttgggtttcg tcgacgtcgt tgttgccgcc  240
tccgcctccg tcgccgctca attcttaaag actcacgacg ctaacttcgc cgatagacca  300
ccaaactccg gtgccaagca catcgcttac aactaccaag atttggtttt cgctccatac  360
ggtccaagat ggagaatgtt gagaaagatt tgttctgttc acttgttctc caccaaggct  420
ttggatgatt tcagacacgt cagacaagaa gaagttgcta tcttggctag agctttggtc  480
ggtgccggta agtctccagt taagttgggt caattgttga acgtttgtac cactaacgct  540
ttggctagag ttatgttggg tagaagagtt ttcgactccg gtgatgctca agctgatgaa  600
ttcaaggaca tggttgttga attgatggtt ttggccggtg aattcaacat cggtgacttc  660
atcccagttt tggactggtt ggacttgcaa ggtgttacta agaagatgaa gaagttgcac  720
```

```
gctaagttcg actctttctt gaacactatc ttggaagaac acaagaccgg tgccggtgac  780
ggtgtcgctt ctggtaaggt tgacttgttg tctactttga tttctttgaa ggatgacgct  840
gatggtgaag gtggtaagtt gtctgacatt gaaatcaagg ctttgttgtt gaacttgttc  900
actgctggta ctgacacttc ttcttctact attgaatggg ctatcgctga attgattaga  960
aacccacaat tgttgaacca agccagaaag gaaatggaca ccatcgttgg tcaagacaga  1020
ttggttaccg aatctgactt gggtcaattg actttcttgc aagccattat caaggaaact  1080
ttcagattgc acccatctac cccattgtct ttgccaagaa tggctttgga atcttgtgaa  1140
gttggtggtt actacatccc aaagggttcc actttgttgg ttaacgtttg ggccatttct  1200
agagatccaa agatttgggc cgatccattg gaattccaac caactagatt cttgccaggt  1260
ggtgaaaagc caaacactga tatcaagggt aacgatttcg aagtcatccc attcggtgcc  1320
ggtagaagaa tttgtgtcgg tatgtctttg ggtttgagaa tggtccaatt gttgactgct  1380
accttgatcc acgccttcga ttgggaattg gctgatggtt tgaacccaaa gaagttgaac  1440
atggaagaag cttacggttt gaccttgcaa agagccgctc cattggttgt tcacccaaga  1500
ccaagattgg ccccacacgt ttacgaaact actaaggtct aa                     1542

SEQ ID NO: 13          moltype = AA  length = 515
FEATURE                Location/Qualifiers
source                 1..515
                       mol_type = protein
                       organism = Osteospermum hybrid cultivar
SEQUENCE: 13
MSTILPLVLY SCITGLVIYV LLNLRTRHSN RLPPGPTPWP IVGNLPHLGV VPHHSLAAMA  60
EKYGPLMHLR LGFVDVVVAA SAAVAAQFLK VHDANFASRP PNSGAKHIAY NYQDLVFAPY  120
YGPRWRMLRK ICSVHLFSSK ALDDFRHVRQ EEVAILTRAL IGAGDSPVKL GQLLNVCTTN  180
ALARVMLGKR VFGDRSGGGD PKADEFKDMV VEVMELAGEF NIGDFIPVLD SLDLQGIAKK  240
MKELHVRFDS FLGKILEEHK TGNGGASSQH TDLLTTLISL KDDTDEEGGK LSDIEIKALL  300
LNLFTAGTDT SSSTVEWAIA ELIRHPQLLK QAQEEIDNVV GRDHLVTELD LTQLPFLQAI  360
VKETFRLHPS TPLSLPRIAS ESCEVNGYHI PKGSTLLVNV WAIARDPKMW SEPLEFRPAR  420
FLPGGEKPDA DVKGNDFEVI PFGAGRRSCA GMSLGLRMVQ LLVATLVQTF DWELANGLKP  480
EKLNMEEAYG LTLQRAAPLL VHPKPRLAPH VYGSN                             515

SEQ ID NO: 14          moltype = DNA  length = 1548
FEATURE                Location/Qualifiers
misc_feature           1..1548
                       note = coding sequence for SEQ ID NO: 13
source                 1..1548
                       mol_type = other DNA
                       organism = synthetic construct
SEQUENCE: 14
atgtccacca ttttgccatt ggttttgtac tcttgtatca ctggtttggt tatctacgtt  60
ttgttgaact tgagaaccag acactctaac agattgccac caggtccaac tccatggcca  120
atcgtcggta acttgccaca cttgggtgtt gttccacacc actctttggc tgctatggct  180
gaaaagtacg gtccattgat gcacttgaga ttgggtttcg ttgacgttgt tgttgctgct  240
tctgctgccg ttgctgctca attcttgaag gttcacgatg ctaacttcgc ttctagacca  300
ccaaactccg gtgctaagca catcgcttac aactaccaag acttggtttt cgctccatac  360
tacggtccaa gatggagaat gttgagaaag atttgttccg ttcacttgtt ctcttctaag  420
gctttggatg atttcagaca cgtcagacaa gaagaagttg ctatcttgac tagagctttg  480
atcggtgccg gtgactctcc agttaagttg ggtcaattgt tgaacgtttg tactactaac  540
gctttggcta gagttatgtt gggtaagaga gttttcggtg acagatctgg tggtggtgat  600
ccaaaggctg atgaattcaa ggatatggtt gttgaagtta tggaattggc cggtgaattc  660
aacatcggtg atttcatccc agttttggat tctttggatt tgcaaggtat cgctaagaag  720
atgaaggaat tgcacgttag attcgattct ttcttgggta agatcttgga agaacacaag  780
accggtaacg gtggtgcttc ttctcaacac actgacttgt tgactacctt gatttctttg  840
aaggatgata ctgatgaaga aggtggtaag ttgtctgaca ttgaaatcaa ggctttgttg  900
ttgaacttgt tcactgctgg tactgacact tcttcttcta ccgttgaatg ggctatcgcc  960
gaattgatta gacacccaca attgttgaag caagcccaag aagaaatcga caacgttgtt  1020
ggtagagatc acttggttac cgaattggac ttgacccaat tgccattctt gcaagccatt  1080
gttaaggaaa ccttcagatt gcacccatct actccattgt ctttgccaag aattgcttcc  1140
gaatcttgtg aagtcaacgg ttaccacatc ccaaagggtt ccactttgtt ggttaacgtt  1200
tgggccatcg ccagagatcc aaagatgtgg tccgaaccat tggaattcag accagccaga  1260
ttcttgccag gtggtgaaaa gccagatgct gatgttaagg gtaacgattt cgaagtcatc  1320
ccattcggtg ccggtagaag atcttgtgct ggtatgtctt tgggtttgag aatggttcaa  1380
ttgttggttg ctactttggt tcaaaccttc gactgggaat tggctaacgg tttgaagcca  1440
gaaaagttga acatggaaga agcttacggt ttgactttgc aaagagctgc tccattgttg  1500
gttcacccaa agccaagatt ggctccacac gtttacggtt ctaactaa               1548

SEQ ID NO: 15          moltype = AA  length = 539
FEATURE                Location/Qualifiers
source                 1..539
                       mol_type = protein
                       organism = Citrus clementina
SEQUENCE: 15
MSQPLVRLLV PFLRFLWETK QRAMSTLPLL ILYTSLLAIV ISFLFSLLRN RRRHSSHRLP  60
PGPKPWPIVG NLPHLGPMPH QSIAGLARTH GPLMYLRLGF VDVVVAASAS VAAQFLKIHD  120
SNFSNRPPNS GAKHIAYNYQ DIVFRPYGPR WRMLRKISSV HLFSGKALDD YRHVRQEEMA  180
VLTRALASAG TEPVNLAQRL NLCVVNALGR VMLGFRVFGD GTGGSDPRAD EFKSMVVELM  240
VLAGVFNVGD FVPALERLDL QGVARKMKKL HKRFDVFLSD ILEERKMNGR DGGNKLTDLL  300
GTLISLMDDA NGEEKLTETE IKALLLNMFT AGTDTSSSTI EWAIAELIRH PKVWAQVQQE  360
LDSVVGRDRL VTELDLPQLT YLQAVIKEIF RLHPSTPLSL PRAASESCKI NGYDIPKGST  420
```

```
LLVNIWAIAR DPNEWADPLE FRPERFLPGG EKYNVDVKGN DYELIPFGAG RRICAGLSWG  480
LRMVQLGTAT LAHAFNWELP GGLKPEKLNM DEAYGLTLQR AAPLVVHPRP RLSPNAYQA   539

SEQ ID NO: 16          moltype = DNA  length = 1620
FEATURE                Location/Qualifiers
misc_feature           1..1620
                       note = coding sequence for SEQ ID NO: 15
source                 1..1620
                       mol_type = other DNA
                       organism = synthetic construct
SEQUENCE: 16
atgtcccaac cattggttag attgttggtt ccattcttga gattcttgtg ggaaactaag  60
caaagagcta tgtctacttt gccattgttg atcttgtaca cttctttgtt ggctattgtc  120
atttctttct tgttctcttt gttgagaaac agaaggagac actcctccca cagattgcca  180
ccaggtccaa agccatggcc aatcgtcggt aacttgccac acttgggtcc aatgccacac  240
caatccatcg ctggtttggc cagaacccac ggtccattga tgtacttgag attgggtttc  300
gttgacgtcg tcgttgccgc ttccgcttcc gttgctgccc aattcttgaa gatccacgat  360
tccaacttct ccaacagacc accaaactcc ggtgccaagc acatcgctta caactaccaa  420
gacatcgttt tcagaccata cggtccaaga tggagaatgt tgagaaagat ctcttccgtt  480
cacttgttct ccggtaaggc cttggatgac tacagacacg ttagacaaga agaaatggct  540
gttttgacta gagctttggc ttctgctggt actgaaccag ttaacttggc tcaaagattg  600
aacttgtgtg ttgttaacgc cttgggtaga gttatgttgg gtttcagagt tttcggtgac  660
ggtaccggtg gttctgaccc aagagctgac gaattcaagt ctatggttgt tgaattgatg  720
gttttggctg gtgttttcaa cgtcggtgat ttcgtcccag ccttggaaag attggacttg  780
caaggtgttg ctagaaagat gaagaagttg cacaagagat tcgatgtttt cttgtctgat  840
atcttggaag aaagaaagat gaacggtaga gatggtggta acaagttgac tgacttgttg  900
ggtaccttga tttctttgat ggatgatgct aacggtgaag aaaagttgac tgaaactgaa  960
atcaaggctt tgttgttgaa catgttcact gctggtaccg acacttcttc ttctactatc  1020
gaatgggcca ttgctgaatt gatcagacac ccaaaggtct gggcccaagt ccaacaagaa  1080
ttggattctg ttgttggtag agatagattg gtcaccgaat tggacttgcc acaattgact  1140
tacttgcaag ccgttatcaa ggaaatcttc agattgcacc catctactcc attgtctttg  1200
ccaagagctg cttccgaatc ttgtaagatc aacggttacg atattccaaa gggttccact  1260
ttgttggtca acatctgggc cattgctaga gatccaaacg aatgggccga cccattggaa  1320
ttcagaccag aaagattctt gccaggtggt gaaaagtaca acgttgatgt taagggtaac  1380
gattacgaat tgatcccatt cggtgccggt agaagaattt gtgctggttt gtcttggggt  1440
ttgagaatgg ttcaattggg tactgctact ttggcccacg ctttcaactg ggaattgcca  1500
ggtggtttga agccagaaaa gttgaacatg gacgaagctt acggtttgac cttgcaaaga  1560
gctgctccat tggttgttca cccaagacca agattgtctc caaacgctta ccaagcttaa  1620

SEQ ID NO: 17          moltype = AA  length = 517
FEATURE                Location/Qualifiers
source                 1..517
                       mol_type = protein
                       organism = Citrus sinensis
SEQUENCE: 17
MSSTLPLLIL YTSLLAIVIS FLFSLLRNRR RHSSHRLPPG PKPWPIVGNL PHLGPMPHQS  60
IAGLARTHGP LMYLRLGFVD VVVAASASVA AQFLKIHDSN FSNRPPNSGA KHIAYNYQDI  120
VFRPYGPRWR MLRKISSVHL FSGKALDDYR HVRQEEMAVL ARALASAGTE PVNLAQRLNL  180
CVVNALGRVM LGFRVFGDGT GGSDPRADEF KSMVVELMVL AGVFNVGDFV PALERLDLQG  240
VARKMKKLHK RFDVFLSDIL EERKMNGRDG GNKHTDLLGT LISLMDDANG EEKLTETEIK  300
ALLLNMFTAG TDTSSSTIEW AIAELIRHPK VRAQVQQELD SVVGRDRLVT ELDLPQLTYL  360
QAVIKEIFRL HPSTPLSLPR AASESCKING YDIPKGSTLL VNIWAIARDP NEWADPLEFR  420
PERFLPGGEK YNVDVKGNDY ELIPFGAGRR ICAGLSWGLR MVQLGTATLA HAFNWELPGG  480
LKPEKLSMDE AYGLTLQRAA PLVVHPRPRL SPNAYQA                         517

SEQ ID NO: 18          moltype = DNA  length = 1554
FEATURE                Location/Qualifiers
misc_feature           1..1554
                       note = coding sequence for SEQ ID NO: 17
source                 1..1554
                       mol_type = other DNA
                       organism = synthetic construct
SEQUENCE: 18
atgtcctcta ctttgccatt gttgatcttg tacacttctt tgttggctat tgtcatttct  60
ttcttgttct ctttgttgag aaacagaagg agacactcct cccacagatt gccaccaggt  120
ccaaagccat ggccaatcgt cggtaacttg ccacacttgg gtccaatgcc acaccaatcc  180
atcgctggtt tggccagaac ccacggtcca ttgatgtact tgagattggg tttcgttgac  240
gtcgtcgttg ccgcttctgc ttccgttgct gcccaattct tgaagatcca cgattccaac  300
ttctccaaca gaccaccaaa ctccggtgcc aagcacatcg cttacaacta ccaagacatc  360
gttttcagac catacggtcc aagatggaga atgttgagaa agatctcttc cgttcacttg  420
ttctccggta aggccttgga tgactacaga cacgttagac aagaagaaat ggctgttttg  480
gctagagctt tggcttctgc tggtactgaa ccagttaact tggctcaaag attgaacttg  540
tgtgttgtta acgccttggg tagagttatg ttgggtttca gagttttcgg tgacggtacc  600
ggtggttctg acccaagagc tgacgaattc aagtctatgg ttgttgaatt gatggttttg  660
gctggtgttt tcaacgtcgg tgacttcgtc ccagccttgg aaagattgga cttgcaaggt  720
gttgctagaa agatgaagaa gttgcacaag agattcgatg ttttcttgtc tgatatcttg  780
gaagaaagaa agatgaacgg tagagatggt ggtaacaagc acactgactt gttgggtacc  840
ttgatttctt tgatggatga tgctaacggt gaagaaaagt tgactgaaac tgaaatcaag  900
gctttgttgt tgaacatgtt cactgctggt accgacactt cttcttctac tatcgaatgg  960
```

```
gccattgctg aattgatcag acacccaaag gtcagagccc aagtccaaca agaattggat  1020
tctgttgttg gtagagatag attggtcacc gaattggact tgccacaatt gacttacttg  1080
caagccgtta tcaaggaaat cttcagattg cacccatcta ctccattgtc tttgccaaga  1140
gctgcttccg aatcttgtaa gatcaacggt tacgatattc caaagggttc cactttgttg  1200
gtcaacatct gggccattgc tagagatcca aacgaatggg ccgacccatt ggaattcaga  1260
ccagaaagat tcttgccagg tggtgaaaag tacaacgttg atgttaaggg taacgattac  1320
gaattgatcc cattcggtgc cggtagaaga atttgtgctg gtttgtcttg ggtttgaga   1380
atggttcaat tgggtactgc tactttggcc cacgctttca actgggaatt gccaggtggt  1440
ttgaagccag aaaagttgtc tatggacgaa gcttacggtt tgaccttgca aagagctgct  1500
ccattggttg ttcacccaag accaagattg tctccaaacg cttaccaagc ttaa        1554

SEQ ID NO: 19          moltype = AA  length = 513
FEATURE                Location/Qualifiers
source                 1..513
                       mol_type = protein
                       organism = Pilosella officinarum
SEQUENCE: 19
MSTLLSLIIY LCITGVTAYV LVNLRTRRAN RLPPGPTPWP IVGNLPHLGT IPHHSLADLA  60
TRYGPLMHLR LGFVDVVVAA SASVAAQFLK THDANFASRP PNSGAKHMAY NYQDLVFAPY  120
GPRWRMLRKI CSVHLFSAKS LDDFRHVRQE EVAILTRALV GAGKSTVKLG QLLHVCTTNA  180
LVRVMLGRRV FGDGSGGGDP KADEFKNMVI EMMVLAGEFN LGDFIPVLDL LDLQGVTKKM  240
KKLHTRFDSF LNSILEEHRT SSGGASGHVD LLSTLISLKD EADGEGGKLT DTEIKALLLN  300
LFVAGTDTSS STVEWAIAEL IRNPQLLKQA QQELDTVVGQ GRLVNESDLS QLTFLQAIVK  360
ETFRLHPSTP LSLPRIASES CEINGYNIPK GSTLLVNVWA IARDPKMWTE PLEFRPSRFL  420
PDGEKPNADV KGNDFEVIPF GAGRRICAGM SLGLRMVQLL TATLIQAFDW ELANGLEPRN  480
LNMEEAYGLT LQRAQPLMVH PRPRLAPHVY GTG                               513

SEQ ID NO: 20          moltype = DNA  length = 1542
FEATURE                Location/Qualifiers
misc_feature           1..1542
                       note = coding sequence for SEQ ID NO: 19
source                 1..1542
                       mol_type = other DNA
                       organism = synthetic construct
SEQUENCE: 20
atgtccacct tgttgtcctt gatcatctac ttgtgtatca ctggtgttac tgcctacgtt  60
ttggttaact tgagaactag aagagctaac agattgccac caggtccaac cccatggcca  120
atcgtcggta acttgccaca cttgggtact attccacacc actctttggc tgatttggct  180
actagatacg gtccattgat gcacttgaga ttgggtttcg ttgacgttgt tgttgccgcc  240
tctgcttccg tcgctgctca attcttaaag actcacgacg ctaacttcgc ttctagacca  300
ccaaactctg gtgctaagca catggcttac aactaccaag atttggtttt cgctccatac  360
ggtccaagat ggagaatgtt gagaaagatt tgttccgttc acttgttctc tgccaagtct  420
ttggatgatt tcagacacgt tagacaagaa gaagttgcta tcttgactag agctttggtc  480
ggtgccggta agtctactgt taagttgggt caattgttgc acgtttgtac cactaacgct  540
ttggttagag ttatgttggg tagaagagtt ttcggtgatg gttctggtgg tggtgatcca  600
aaggctgatg aattcaagaa catggttatt gaaatgatgg ttttggccgg tgaattcaac  660
ttgggtgatt tcatcccagt tttggatttg ttggacttgc aaggtgttac taagaagatg  720
aagaagttgc acactagatt cgattctttc ttgaactcta tcttggaaga acacagaact  780
tcttctggtg gtgcttctgg tcacgtcgat ttgttgtcta ctttgatttc tttgaaggat  840
gaagccgatg gtgaaggtgg taagttgact gacactgaaa ttaaggcttt gttgttgaac  900
ttgttcgttg ctggtactga cacttcttct tctaccgttg aatgggctat cgctgaattg  960
attagaaacc cacaattgtt gaagcaagcc caacaagaat tggacactgt tgttggtcaa  1020
ggtagattgg ttaacgaatc tgacttgtct caattgacct tcttgcaagc cattgttaag  1080
gaaactttca gattgcaccc atctactcca ttgtccttgc caagaatcgc ttccgaatct  1140
tgtgaaatca acggttacaa cattccaaag ggttccactt tgttggttaa cgtttgggcc  1200
atcgctagag atccaaagat gtggaccgaa ccattggaat tcagaccatc cagattcttg  1260
ccagacggtg aaaagccaaa cgctgatgtt aagggtaacg atttcgaagt catcccattc  1320
ggtgctggta gaagaatttg tgctggtatg tctttgggtt tgagaatggt ccaattgttg  1380
accgctactt tgattcaagc cttcgattgg gaattggcta acggtttgga accaagaaac  1440
ttgaacatgg aagaagccta cggtttgacc ttgcaaagag ctcaaccatt gatggttcac  1500
ccaagaccaa gattggcccc acacgtttac ggtactggtt aa                     1542

SEQ ID NO: 21          moltype = AA  length = 406
FEATURE                Location/Qualifiers
source                 1..406
                       mol_type = protein
                       organism = Streptomyces avermitilis
SEQUENCE: 21
MSAAAFDLAF DPWDPAFLAD PYPAYADLRA KGRVHYYEPT NQWLVPHHAD VSALLRDRRL  60
GRAYQHRYTH EDFGRTAPPA EHEPFHTLND HGMLDLEPPD HTRIRRLVSK AFTPRTVEQL  120
KPYVAKLAGE LVDRLVAAGG GDLLADVAEP LPVAVIAEML GIPESDRAPL RPWSADICGM  180
YELNPPKDVA AKAVRASVEF SDYLRELIAE RRKEPGDDLI SGLIAAHDEG DRLTEQEMIS  240
TCVLLLNAGH EATVNATVNG WYALFRNPDQ LAALRADHSL VPAAVEELMR YDTPLQLFER  300
WVLDEIEIDG TTVPRGAEIA MLFGSANHDP EVFRNPEKLD LTREDNPHIS FSAGIHYCIG  360
APLARIELAA SMTALLEKAP TLGLVAEPKR KPNFVIRGLE GLSVAV                 406

SEQ ID NO: 22          moltype = DNA  length = 1221
FEATURE                Location/Qualifiers
misc_feature           1..1221
```

```
                         note = coding sequence for SEQ ID NO: 21
source                   1..1221
                         mol_type = other DNA
                         organism = synthetic construct
SEQUENCE: 22
atgtccgctg ctgctttcga cttggccttc gacccatggg acccagcttt cttggccgac  60
ccatacccag cctacgccga tttgagagcc aagggtagag ttcactacta cgaaccaact  120
aaccaatggt tggttccaca ccacgctgac gtttctgctt tgttgagaga cagaagattg  180
ggtagagctt accaacacag atacactcac gaagatttcg gtagaaccgc tccaccagct  240
gaacacgaac cattccacac cttgaacgac cacggtatgt tggacttgga accaccagac  300
cacaccagaa tcagaagatt ggtttctaag gctttcactc caagaaccgt tgaacaattg  360
aagccatacg ttgccaagtt ggccggtgaa ttggttgaca gattggtcgc tgctggtggt  420
ggtgatttgt tggctgatgt cgccgaacca ttgccagttg ccgtcatcgc cgaaatgttg  480
ggtatcccag aatccgacag agccccatta agaccatggt ctgctgacat ctgtggtatg  540
tacgaattga acccaccaaa ggacgttgct gctaaggctg ttagagcttc tgttgaattc  600
tccgactact tgagagaatt gatcgccgaa agaagaaagg aaccaggtga cgatttgatc  660
tctggtttga tcgccgccca cgacgaaggt gacagattga ccgaacaaga aatgatctcc  720
acctgtgtct tgttgttgaa cgctggtcac gaagccaccg tcaacgccac tgtcaacggt  780
tggtacgcct tgttcagaaa cccagaccaa ttggccgcct tgagagccga ccactctttg  840
gttccagccg ccgttgaaga attgatgaga tacgacactc cattgcaatt gttcgaaaga  900
tgggtcttgg acgaaatcga aatcgacggt actactgtcc caagaggtgc tgaaatcgcc  960
atgttgttcg gttccgccaa ccacgaccca gaagttttca gaaacccaga aaagttggac  1020
ttgaccagag aagataaccc acacatttcc ttctctgctg gtatccacta ctgtatcggt  1080
gctccattgg ctagaatcga attggctgct tctatgactg ccttgttgga aaaggcccca  1140
actttgggtt tggttgctga accaaagaga aagccaaact tcgttatcag aggtttggaa  1200
ggtttgtctg tcgctgtcta a                                          1221

SEQ ID NO: 23            moltype = AA  length = 715
FEATURE                  Location/Qualifiers
source                   1..715
                         mol_type = protein
                         organism = Catharanthus roseus
SEQUENCE: 23
MSDSSSEKLS PFELMSAILK GAKLDGSNSS DSGVAVSPAV MAMLLENKEL VMILTTSVAV  60
LIGCVVVLIW RRSSGSGKKV VEPPKLIVPK SVVEPEEIDE GKKKFTIFFG TQTGTAEGFA  120
KALAEEAKAR YEKAVIKVID IDDYAADDEE YEEKFRKETL AFFILATYGD GEPTDNAARF  180
YKWFVEGNDR GDWLKNLQYG VFGLGNRQYE HFNKIAKVVD EKVAEQGGKR IVPLVLGDDD  240
QCIEDDFAAW RENVWPELDN LLRDEDDTTV STTYTAAIPE YRVVFPDKSD SLISEANGHA  300
NGYANGNTVY DAQHPCRSNV AVRKELHTPA SDRSCTHLDF DIAGTGLSYG TGDHVGVYCD  360
NLSETVEEAE RLLNLPPETY FSLHADKEDG TPLAGSSLPP PFPPCTLRTA LTRYADLLNT  420
PKKSALLALA AYASDPNEAD RLKYLASPAG KDEYAQSLVA NQRSLLEVMA EFPSAKPPLG  480
VFFAAIAPRL QPRFYSISSS PRMAPSRIHV TCALVYEKTP GGRIHKGVCS TWMKNAIPLE  540
ESRDCSWAPI FVRQSNFKLP ADPKVPVIMI GPGTGLAPFR GFLQERLALK EEGAELGTAV  600
FFFGCRNRKM DYIYEDELNH FLEIGALSEL LVAFSREGPT KQYVQHKMAE KASDIWRMIS  660
DGAYVYVCGD AKGMARDVHR TLHTIAQEQG SMDSTQAEGF VKNLQMTGRY LRDVW        715

SEQ ID NO: 24            moltype = DNA  length = 2148
FEATURE                  Location/Qualifiers
misc_feature             1..2148
                         note = coding sequence for SEQ ID NO: 23
source                   1..2148
                         mol_type = other DNA
                         organism = synthetic construct
SEQUENCE: 24
atgtccgatt cttcttctga aaagttgtct ccattcgaat tgatgtctgc tatcttgaag  60
ggtgctaagt tggatggttc taactcttct gattctggtg ttgctgtttc tccagctgtt  120
atggctatgt tgttggaaaa caaggaattg gttatgattt tgactacttc tgttgctgtt  180
ttgatcggtt gtgtcgttgt tttgatctgg agaagatctt ccggttctgg taagaaggtc  240
gttgaaccac caaagttgat cgttccaaag tctgttgttg aaccagaaga aattgatgaa  300
ggtaagaaga agttcaccat cttcttcggt actcaaactg gtactgctga aggtttcgct  360
aaggctttgg ctgaagaagc caaggctaga tacgaaaagg ctgttatcaa ggttattgat  420
atcgatgatt acgctgctga tgatgaagaa tacgaagaaa agttcagaaa ggaaaccttg  480
gctttcttca tcttggccac ttacggtgat ggtgaaccaa ccgacaacgc tgctagattc  540
tacaagtggt tcgttgaagg taacgataga ggtgactggt tgaagaactt gcaatacggt  600
gttttcggtt tgggtaacag acaatacgaa cacttcaaca agattgctaa ggttgttgat  660
gaaaaggttg ctgaacaagg tggtaagaga attgttccat tggttttggg tgacgatgac  720
caatgtattg aagatgactt cgctgcttgg agagaaaacg tttggccaga attggataac  780
ttgttgagag atgaagatga tactactgtt tctactacct acactgctgc tattccagaa  840
tacagagttg ttttcccaga caagtctgat tctttgattt ctgaagctaa cggtcacgcc  900
aacggttacg ctaacggtaa caccgtttac gatgcccaac acccatgtag atctaacgtt  960
gctgttagaa aggaattgca cactccagct tctgatagat cttgtaccca cttggatttc  1020
gacattgctg gtactggttt gtcttacggt actggtgatc acgttggtgt ttactgtgat  1080
aacttgtctg aaaccgttga agaagctgaa agattgttga acttgccacc agaaacttac  1140
ttctctttgc acgctgataa ggaagatggt accccattgg ctggttcttc tttgccacca  1200
ccattcccac catgtacttt gagaaccgcc ttgactagat acgctgattt gttgaacact  1260
ccaaagaagt ctgctttgtt ggctttggct gcttacgctt ctgatccaaa cgaagccgat  1320
agattgaagt acttggcttc tccagccggt aaggatgaat acgctcaatc tttggttgct  1380
aaccaaagat ctttgttgga agtcatggct gaattcccat ctgctaagcc accattgggt  1440
gttttcttcg ctgctattgc tccaagattg caaccaagat tctactctat ctcttcttct  1500
```

```
ccaagaatgg ctccatctag aattcacgtc acttgtgctt tggtttacga aaagactcca  1560
ggtggtagaa ttcacaaggg tgtttgttct acttggatga agaacgccat tccattggaa  1620
gaatctagag actgttcttg ggctccaatc ttcgtcagac aatctaactt caagttgcca  1680
gccgatccaa aggttccagt tatcatgatc ggtccaggta ctggtttggc tccattcaga  1740
ggtttcttgc aagaaagatt ggctttgaag gaagaaggtg ctgaattggg tactgctgtt  1800
ttcttcttcg gttgtagaaa cagaaagatg gattacatct acgaagatga attgaaccac  1860
ttcttggaaa ttggtgcttt gtccgaattg ttggttgctt tctctagaga aggtccaact  1920
aagcaatacg ttcaacacaa gatggctgaa aaggcttctg atatttggag aatgatttct  1980
gatggtgctt acgtttacgt ctgtggtgat gccaagggta tggccagaga tgtccacaga  2040
actttgcaca ccattgctca agaacaaggt tctatggatt ctactcaagc tgaaggtttc  2100
gttaagaact tgcaaatgac cggtagatac ttgagagatg tctggtaa               2148

SEQ ID NO: 25           moltype = AA  length = 692
FEATURE                 Location/Qualifiers
source                  1..692
                        mol_type = protein
                        organism = Saccharomyces cerevisiae
SEQUENCE: 25
MSPFGIDNTD FTVLAGLVLA VLLYVKRNSI KELLMSDDGD ITAVSSGNRD IAQVVTENNK  60
NYLVLYASQT GTAEDYAKKF SKELVAKFNL NVMCADVENY DFESLNDVPV IVSIFISTYG  120
EGDFPDGAVN FEDFICNAEA GALSNLRYNM FGLGNSTYEF FNGAAKKAEK HLSAAGAIRL  180
GKLGEADDGA GTTDEDYMAW KDSILEVLKD ELHLDEQEAK FTSQFQYTVL NEITDSMSLG  240
EPSAHYLPSH QLNRNADGIQ LGPFDLSQPY IAPIVKSREL FSSNDRNCIH SEFDLSGSNI  300
KYSTGDHLAV WPSNPLEKVE QFLSIFNLDP ETIFDLKPLD PTVKVPFPTP TTIGAAIKHY  360
LEITGPVSRQ LFSSLIQFAP NADVKEKLTL LSKDKDQFAV EITSKYFNIA DALKYLSDGA  420
KWDTVPMQFL VESVPQMTPR YYSISSSSLS EKQTVHVTSI VENFPNPELP DAPPVVGVTT  480
NLLRNIQLAQ NNVNIAETNL PVHYDLNGPR KLFANYKLPV HVRRSNFRLP SNPSTPVIMI  540
GPGTGVAPFR GFIRERVAFL ESQKKGGNNV SLGKHILFYG SRNTDDFLYQ DEWPEYAKKL  600
DGSFEMVVAH SRLPNTKKVY VQDKLKDYED QVFEMINNGA FIYVCGDAKG MAKGVSTALV  660
GILSRGKSIT TDEATELIKM LKTSGRYQED VW                                692

SEQ ID NO: 26           moltype = DNA  length = 2079
FEATURE                 Location/Qualifiers
misc_feature            1..2079
                        note = coding sequence for SEQ ID NO: 25
source                  1..2079
                        mol_type = other DNA
                        organism = synthetic construct
SEQUENCE: 26
atgtccccgt ttggaataga caacaccgac ttcactgtcc tggcggggct agtgcttgcc  60
gtgctactgt acgtaaagag aaactccatc aaggaactgc tgatgtccga tgacggagat  120
atcacagctg tcagctcggg caacagagac attgctcagg tggtgaccga aaacaacaag  180
aactacttgg tgttgtatgc gtcgcagact gggactgccg aggattacgc caaaaagttt  240
tccaaggagc tggtggccaa gttcaaccta aacgtgatgt gcgcagatgt tgagaactac  300
gactttgagt cgctaaacga tgtgcccgtc atagtctcga tttttatctc tacatatggt  360
gaaggagact tccccgacgg ggcggtcaac tttgaggact ttatttgtaa tgcggaagcg  420
ggtgcactat cgaacctgag gtataaatatg tttggtctgg gaaattctac ttatgaattc  480
tttaatggtg ccgccaagaa ggccgagaag catctctccg ccgcgggcgc tatcagacta  540
ggcaagctcg gtgaagctga tgatggtgca ggaactacag acgaagatta catggcctgg  600
aaggactcca tcctggaggt tttgaaagac gaactgcatt tggacgaaca ggaagccaag  660
ttcacctctc aattccagta cactgtgttg aacgaaatca ctgactccat gtcgcttggt  720
gaaccctctg ctcactattt gccctcgcat cagttgaacc gcaacgcaga cggcatccaa  780
ttgggtccct tcgatttgtc tcaaccgtat attgcaccca tcgtgaaatc tcgcgaactg  840
ttctcttcca atgaccgtaa ttgcatccac tctgaatttg acttgtccgg ctctaacatc  900
aagtactcca ctggtgacca tcttgctgtt tggccttcca acccattgga aaaggtcgaa  960
cagttcttat ccatattcaa cctggaccct gaaaccattt ttgacttgaa gcccctggat  1020
cccaccgtca aagtgccctt cccaacgcca actactattg gcgctgctat taaacactat  1080
ttggaaatta caggacctgt ctccagacaa ttgttttcat ctttgattca gttcgccccc  1140
aacgctgacg tcaaggaaaa attgactctg ctttcgaaag acaaggacca attcgccgtc  1200
gagataacct ccaaatattt caacatcgca gatgctctga aatatttgtc tgatggcgcc  1260
aaatgggaca ccgtacccat gcaattcttg gtcgaatcag ttccccaaat gactcctcgt  1320
tactactcta tctcttcctc ttctctgtct gaaaagcaaa ccgtccatgt cacctccatt  1380
gtggaaaact ttcctaaccc agaattgcct gatgctcctc cagttgttgg tgttacgact  1440
aacttgttaa gaaacattca attggctcaa aacaatgtta acattgccga aactaaccta  1500
cctgttcact acgatttaaa tggcccacgt aaacttttcg ccaattacaa attgcccgtc  1560
cacgttcgtc gttctaactt cagattgcct tccaaccctt ccaccccagt tatcatgatc  1620
ggtccaggta ccggtgttgc cccattccgt gggtttatca gagagcgtgt cgcgttcctc  1680
gaatcacaaa agaagggcgg taacaacgtt tcgctaggta agcatatact gttttatgga  1740
tcccgtaaca ctgatgattt cttgtaccag gacgaatggc cagaatacgc caaaaaattg  1800
gatggttcgt tcgaaatggt cgtggcccat tccaggttgc caaacaccaa aaaagtttat  1860
gttcaagata aattaaagga ttacgaggac caagtatttg aaatgattaa caacggtgca  1920
tttatctacg tctgtggtga tgcaaagggt atggccaagg gtgtgtcaac cgcattggtt  1980
ggcatcttat cccgtggtaa atccattacc actgatgaag caacagagct aatcaagatg  2040
ctcaagactt caggtagata ccaagaagat gtctggtaa                        2079

SEQ ID NO: 27           moltype = AA  length = 658
FEATURE                 Location/Qualifiers
REGION                  1..658
                        note = chimeric cytochrome P450 reductase
```

```
source                  1..658
                        mol_type = protein
                        organism = synthetic construct
SEQUENCE: 27
MSPFGIDNTD FTVLAGLVLA VLLYVKRNSI KELLMSDDGD ITAVSSGNRD IAQVVTENNK  60
NYLVLYASQT GTAEDYAKKF SKELVAKFNL NVMCADVENY DFESLNDVPV IVSIFISTYG  120
EGDFPDGAVN FEDFICNAEA GALSNLRYNM FGLGNSTYEF FNGAAKKAEK HLSAAGAIRL  180
GKLGEADDGA GTTDEDYMAW KDSILEVLKD ELGVEATGEE SSIRQYELVV HTDIDAAKVY  240
MGEMGRLKSY ENQKPPFDAK NPFLAAVTTN RKLNQGTERH LMHLELDISD SKIRYESGDH  300
VAVYPANDSA LVNQLGKILG ADLDVVMSLN NLDEESNKKH PFPCPTSYRT ALTYYLDITN  360
PPRTNVLYEL AQYASEPSEQ ELLRKMASSS GEGKELYLSW VVEARRHILA ILQDCPSLRP  420
PIDHLCELLP RLQARYYSIA SSSKVHPNSV HICAVVVEYE TKAGRINKGV ATNWLRAKEP  480
AGENGGRALV PMFVRKSQFR LPFKATTPVI MVGPGTGVAP FIGFIQERAW LRQQGKEVGE  540
TLLYYGCRRS DEDYLYREEL AQFHRDGALT QLNVAFSREQ SHKVYVQHLL KQDREHLWKL  600
IEGGAHIYVC GDARNMARDV QNTFYDIVAE LGAMEHAQAV DYIKKLMTKG RYSLDVWS    658

SEQ ID NO: 28           moltype = DNA  length = 1977
FEATURE                 Location/Qualifiers
misc_feature            1..1977
                        note = coding sequence for SEQ ID NO: 27
source                  1..1977
                        mol_type = other DNA
                        organism = synthetic construct
SEQUENCE: 28
atgtccccat tcggtatcga caacaccgac ttcactgtct tggctggttt ggttttggcc  60
gttttgttgt acgttaagag aaactccatc aaggaattgt tgatgtccga tgacggtgat  120
atcactgctg tctcttctgg taacagagac attgctcaag ttgttaccga aaacaacaag  180
aactacttgg ttttgtacgc ttctcaaact ggtactgccg aagattacgc caagaagttc  240
tccaaggaat tggttgccaa gttcaacttg aacgttatgt gtgctgatgt tgaaaactac  300
gacttcgaat ctttgaacga tgttccagtc atcgtatcta ttttcatctc tacttacggt  360
gaaggtgact tcccagacgg tgctgtcaac ttcgaagatt tcatttgtaa cgctgaagct  420
ggtgctttgt ctaacttgag atacaacatg ttcggtttgg gtaactctac ttacgaattc  480
ttcaacggtg ccgccaagaa ggccgaaaag cacttgtccg ccgctggtgc tatcagattg  540
ggtaagttgg gtgaagctga tgatggtgct ggtactactg acgaagatta catggcctgg  600
aaggactcca tcttggaagt tttgaaggac gaattgggtg ttgaagccac tggtgaagaa  660
tcctctatta gacaatacga attggttgtc cacaccgaca tcgatgctgc caaggtttac  720
atgggtgaaa tgggtagatt gaagtcttac gaaaaccaaa agccaccatt cgatgccaag  780
aacccattct tggctgctgt caccaccaac agaaagttga accaaggtac cgaaagacac  840
ttgatgcact tggaattgga catctctgac tccaagatca gatacgaatc tggtgaccac  900
gttgctgttt acccagccaa cgactctgct ttggtcaacc aattgggtaa gatcttgggt  960
gccgacttgg acgtcgtcat gtccttgaac aacttggatg aagaatccaa caagaagcac  1020
ccattcccat gtccaacttc ctacagaact gccttgacct actacttgga catcaccaac  1080
ccaccaagaa ccaacgtttt gtacgaattg gctcaatacg cctctgaacc atctgaacaa  1140
gaattgttga gaaagatggc ctcctcctcc ggtgaaggta aggaattgta cttgtcttgg  1200
gttgttgaag ccaggagaca catcttggcc atcttgcaag actgtccatc cttaagacca  1260
ccaatcgacc acttgtgtga attgttgcca agattgcaag ccagatacta ctccatcgcc  1320
tcttcctcca aggtccaccc aaactctgtt cacatctgtg ctgttgttgt tgaatacgaa  1380
accaaggctg gtagaatcaa caagggtgtt gccaccaact ggttgagagc caaggaacca  1440
gccggtgaaa acggtggtag agctttggtt ccaatgttcg ttagaaagtc ccaattcaga  1500
ttgccattca aggccaccac tccagtcatc atggttggtc caggtaccgg tgttgctcca  1560
ttcatcggtt tcatccaaga aagagcctgg ttgagacaac aaggtaagga agttggtgaa  1620
actttgttgt actacggttg tagaagatct gatgaagatt acttgtacag agaagaattg  1680
gctcaattcc acagagatgg tgctttgacc caattgaacg ttgccttctc cagagaacaa  1740
tcccacaagg tctacgtcca acacttgttg aagcaagaca gagaacactt gtggaagttg  1800
atcgaaggtg gtgcccacat ctacgtctgt ggtgatgcta gaaacatggc cagagatgtt  1860
caaaacacct tctacgacat cgttgctgaa ttgggtgcca tggaacacgc tcaagctgtt  1920
gactacatca agaagttgat gaccaagggt agatactcct tggacgtttg gtcttaa     1977

SEQ ID NO: 29           moltype = AA  length = 693
FEATURE                 Location/Qualifiers
source                  1..693
                        mol_type = protein
                        organism = Arabidopsis thaliana
SEQUENCE: 29
MSTSALYASD LFKQLKSIMG TDSLSDDVVL VIATTSLALV AGFVVLLWKK TTADRSGELK  60
PLMIPKSLMA KDEDDDLDLG SGKTRVSIFF GTQTGTAEGF AKALSEEIKA RYEKAAVKVI  120
DLDDYAADDD QYEEKLKKET LAFFCVATYG DGEPTDNAAR FYKWFTEENE RDIKLQQLAY  180
GVFALGNRQY EHFNKIGIVL DEELCKKGAK RLIEVGLGDD DQSIEDDFNA WKESLWSELD  240
KLLKDEDDKS VATPYTAVIP EYRVVTHDPR FTTQKSMESN VANGNTTIDI HHPCRVDVAV  300
QKELHTHESD RSCIHLEFDI SRTGITYETG DHVGVYAENH VEIVEEAGKL LGHSLDLVFS  360
IHADKEDGSP LESAVPPPFP GPCTLGTGLA RYADLLNPPR KSALVALAAY ATEPSEAEKL  420
KHLTSPDGKD EYSQWIVASQ RSLLEVMAAF PSAKPPLGVF FAAIAPRLQP RYYSISSSPR  480
LAPSRVHVTS ALVYGPTPTG RIHKGVCSTW MKNAVPAEKS HECSGAPIFI RASNFKLPSN  540
PSTPIVMVGP GTGLAPFRGF LQERMALKED GEELGSSLLF FGCRNRQMDF IYEDELNNFV  600
DQGVISELIM AFSREGAQKE YVQHKMMEKA AQVWDLIKEE GYLYVCGDAK GMARDVHRTL  660
HTIVQEQEGV SSSEAEAIVK KLQTEGRYLR DVW                               693

SEQ ID NO: 30           moltype = DNA  length = 2082
FEATURE                 Location/Qualifiers
```

```
misc_feature          1..2082
                      note = coding sequence for SEQ ID NO: 29
source                1..2082
                      mol_type = other DNA
                      organism = synthetic construct
SEQUENCE: 30
atgtccactt ctgctttgta cgcttccgat ttgttcaagc aattgaagtc tattatgggt  60
actgattctt tgtccgacga tgttgttttg gttattgcta ctacttcttt ggctttggtt  120
gctggtttcg ttgttttgtt gtggaagaaa actactgctg atagatctgg tgaattgaag  180
ccattgatga tcccaaagtc tttgatggct aaggacgaag atgatgattt ggatttgggt  240
tccggtaaga ctagagtctc tatcttcttc ggtactcaaa ctggtactgc tgaaggtttc  300
gctaaggctt tgtccgaaga aatcaaggct agatacgaaa aggctgctgt caaggtcatt  360
gacttggatg actacgctgc cgatgatgac caatacgaag aaaagttgaa gaaggaaact  420
ttggctttct tctgtgttgc tacttacggt gatggtgaac caactgacaa cgctgccaga  480
ttctacaagt ggttcactga agaaaacgaa agagatatca agttgcaaca attggcttac  540
ggtgttttcg ctttgggtaa cagacaatac gaacacttca acaagatcgg tatcgttttg  600
gatgaagaat tgtgtaagaa gggtgctaag agattgattg aagtcggttt gggtgatgat  660
gatcaatcta ttgaagatga tttcaacgcc tggaaggaat ctttgtggtc tgaattggac  720
aagttgttga aggacgaaga tgataagtct gttgctactc catacactgc tgttattcca  780
gaatacagag ttgttactca cgatccaaga ttcactactc aaaagtctat ggaatctaac  840
gttgccaacg gtaacactac tattgacatt caccacccat gtagagttga tgttgctgtt  900
caaaaggaat tgcacactca cgaatctgat agatcttgta ttcacttgga attcgacatc  960
tccagaactg gtattactta cgaaactggt gaccacgttg gtgtttacgc tgaaaaccac  1020
gttgaaatcg ttgaagaagc tggtaagttg ttgggtcact ctttggattt ggttttctcc  1080
atccacgctg acaaggaaga tggttcccca ttggaatctg ctgttccacc accattccca  1140
ggtccatgta ctttgggtac tggtttggct agatacgctg acttgttgaa cccaccaaga  1200
aagtctgctt tggttgcctt ggctgcctac gccactgaac catctgaagc cgaaaagttg  1260
aagcacttga cttctccaga tggtaaggat gaatactctc aatggattgt tgcttctcaa  1320
agatctttgt tggaagttat ggctgctttc ccatctgcta agccaccatt gggtgttttc  1380
ttcgctgcta tcgctccaag attgcaacca agatactact ccatctcttc ctctccaaga  1440
ttggctccat ctagagttca cgttacttcc gctttggttt acggtccaac tccaactggt  1500
agaatccaca agggtgtttg ttctacttgg atgaagaacg ctgttccagc tgaaaagtct  1560
cacgaatgtt ctggtgcccc aatcttcatt agagcttcta acttcaagtt gccatccaac  1620
ccatctactc caatcgttat ggttggtcca ggtactggtt tggctccatt cagaggtttc  1680
ttgcaagaaa gaatggcttt gaaggaagat ggtgaagaat tgggttcttc tttgttgttc  1740
ttcggttgta gaaacagaca aatggacttc atctacgaag atgaattgaa caacttcgtt  1800
gatcaaggtg ttatctctga attgatcatg gctttctcca gagaaggtgc tcaaaaggaa  1860
tacgttcaac acaagatgat ggaaaaggct gctcaagttt gggatttgat caaggaagaa  1920
ggttacttgt acgtttgtgg tgatgctaag ggtatggcta gagatgtcca cagaactttg  1980
cacaccattg ttcaagaaca agaaggtgtt tcttcttctg aagctgaagc tatcgttaag  2040
aagttgcaaa ccgaaggtag atacttgaga gatgtctggt aa                    2082

SEQ ID NO: 31         moltype = AA  length = 712
FEATURE               Location/Qualifiers
source                1..712
                      mol_type = protein
                      organism = Arabidopsis thaliana
SEQUENCE: 31
MSSSSSSSTS MIDLMAAIIK GEPVIVSDPA NASAYESVAA ELSSMLIENR QFAMIVTTSI  60
AVLIGCIVML VWRRSGSGNS KRVEPLKPLV IKPREEEIDD GRKKVTIFFG TQTGTAEGFA  120
KALGEEAKAR YEKTRFKIVD LDDYAADDDE YEEKLKKEDV AFFFLATYGD GEPTDNAARF  180
YKWFTEGNDR GEWLKNLKYG VFGLGNRQYE HFNKVAKVVD DILVEQGAQR LVQVGLGDDD  240
QCIEDDFTAW REALWPELDT ILREEGDTAV ATPYTAAVLE YRVSIHDSED AKFNDINMAN  300
GNGYTVFDAQ HPYKANVAVK RELHTPESDR SCIHLEFDIA GSGLTYETGD HVGVLCDNLS  360
ETVDEALRLL DMSPDTYFSL HAEKEDGTPI SSSLPPPFPP CNLRTALTRY ACLLSSPKKS  420
ALVALAAHAS DPTEAERLKH LASPAGKVDE YSKWVVESQR SLLEVMAEFP SAKPPLGVFF  480
AGVAPRLQPR FYSISSSPKI AETRIHVTCA LVYEKMPTGR IHKGVCSTWM KNAVPYEKSE  540
NCSSAPIFVR QSNFKLPSDS KVPIIMIGPG TGLAPFRGFL QERLALVESG VELGPSVLFF  600
GCRNRRMDFI YEEELQRFVE SGALAELSVA FSREGPTKEY VQHKMMDKAS DIWNMISQGA  660
YLYVCGDAKG MARDVHRSLH TIAQEQGSMD STKAEGFVKN LQTSGRYLRD VW          712

SEQ ID NO: 32         moltype = DNA  length = 2139
FEATURE               Location/Qualifiers
misc_feature          1..2139
                      note = coding sequence for SEQ ID NO: 31
source                1..2139
                      mol_type = other DNA
                      organism = synthetic construct
SEQUENCE: 32
atgtcctctt cttcttcttc ttctacctcc atgatcgatt tgatggctgc tatcatcaag  60
ggtgaaccag ttattgtctc cgacccagct aacgcctccg cttacgaatc cgttgctgct  120
gaattgtcct ctatgttgat cgaaaacaga caattcgcca tgattgttac cacttccatt  180
gctgttttga ttggttgtat cgttatgttg gtttggagaa gatccggttc tggtaactct  240
aagagagtcg aaccattgaa gccattggtt attaagccaa gagaagaaga aattgatgat  300
ggtagaaaga aggttaccat cttcttcggt actcaaactg gtactgctga aggtttcgct  360
aaggctttgg gtgaagaagc taaggctaga tacgaaaaga ccagattcaa gatcgttgat  420
ttggatgatt acgctgctga tgatgatgaa tacgaagaaa agttgaagaa ggaagatgtt  480
gctttcttct tcttggccac ttacggtgat ggtgaaccaa ccgacaacgc tgctagattc  540
tacaagtggt tcaccgaagg taacgacaga ggtgaatggt tgaagaactt gaagtacggt  600
```

```
gttttcggtt tgggtaacag acaatacgaa cacttcaaca aggttgccaa ggttgttgat  660
gacattttgg tcgaacaagg tgctcaaaga ttggttcaag ttggtttggg tgatgatgac  720
caatgtattg aagatgactt caccgcttgg agagaagctt tgtggccaga attggatact  780
atcttgagag aagaaggtga tactgctgtt gccactccat acactgctgc tgttttggaa  840
tacagagttt ctattcacga ctctgaagat gccaagttca acgatatcaa catggctaac  900
ggtaacggtt acactgtttt cgatgctcaa cacccataca aggctaacgt cgctgttaag  960
agagaattgc acactccaga atctgataga tcttgtatcc acttggaatt cgacattgct  1020
ggttctggtt tgacttacga aactggtgat cacgttggtg ttttgtgtga taacttgtct  1080
gaaactgttg atgaagcttt gagattgttg gatatgtctc cagatactta cttctctttg  1140
cacgctgaaa aggaagatgg tactccaatc tcttcttctt tgccaccacc attcccacca  1200
tgtaacttga gaactgcttt gactagatac gcttgtttgt tgtcatctcc aaagaagtct  1260
gctttggttg ctttggctgc tcacgcttct gatccaaccg aagctgaaag attgaagcac  1320
ttggcttctc cagctggtaa ggttgatgaa tactctaagt gggttgttga atctcaaaga  1380
tctttgttgg aagttatggc cgaattccca tctgccaagc caccattggg tgttttcttc  1440
gctggtgttg ctccaagatt gcaaccaaga ttctactcta tctcttcttc tccaaagatt  1500
gctgaaacta gaattcacgt cacttgtgct ttggtttacg aaaagatgcc aactggtaga  1560
attcacaagg gtgtttgttc cacttggatg aagaacgctg ttccatacga aaagtctgaa  1620
aactgttcct ctgctccaat cttcgttaga caatccaact tcaagttgcc atctgattct  1680
aaggttccaa tcatcatgat cggtccaggt actggtttgg ctccattcag aggtttcttg  1740
caagaaagat tggctttggt tgaatctggt gttgaattgg gtccatctgt tttgttcttc  1800
ggttgtagaa acagaagaat ggatttcatc tacgaagaag aattgcaaag attcgttgaa  1860
tctggtgctt tggctgaatt gtctgtcgcc ttctctagag aaggtccaac caaggaatac  1920
gttcaacaca agatgatgga caaggcttct gatatctgga acatgatctc tcaaggtgct  1980
tacttgtacg tttgtggtga cgccaagggt atggctagag atgttcacag atctttgcac  2040
actatcgctc aagaacaagg ttctatggat tctactaagg ctgaaggttt cgttaagaac  2100
ttgcaaactt ctggtagata cttgagagat gtttggtaa                         2139

SEQ ID NO: 33          moltype = AA  length = 522
FEATURE                Location/Qualifiers
source                 1..522
                       mol_type = protein
                       organism = Lonicera japonica
SEQUENCE: 33
MSWIFDLTIS FTTLLFLIFT TALLLLLKVF KKNHKLRPPP SPFTLPIIGH LHLLGPLIHQ  60
SFHRLSTLYG PLIQLKIGYI PCVVASTPEL AKEFLKTHEL AFSSRKHSAA IKLLTYDVSF  120
AFSPYGPYWK FIKKTCTFEL LGTRNMNHFL PIRTNEIRRF LQVMLEKAKA SEGVNVTEEL  180
IKLTNNVISQ MMFSTRSSGT EGEAEEMRTL VREVTQIFGE FNVSDFIKLC KNIDIGGFKK  240
RSKDIQKRYD ALLEKIISER ESERARRGKN RETLGEEGGK DFLDMMLDTM EDGKCEVEIT  300
RDHIKALVLD FLTAATDTTA IAVEWTLAEL ISNPEVFDKA REEIDKVVGK HRLVTELDTP  360
NLPYIHAIIK ESFRLHPPIP LLIRKSVQDC TVGGYHISAN TILFVNIWAI GRNPKYWESP  420
MKFWPERFLE SNGPGPVGSM DIKGHHYELL PFGSGRRGCP GMALAMQELP VVLAAMIQCF  480
NWKPVTLDGE ELDMSERPGL TAPRAHDLVC VPSARINSFD NF                     522

SEQ ID NO: 34          moltype = DNA  length = 1569
FEATURE                Location/Qualifiers
misc_feature           1..1569
                       note = coding sequence for SEQ ID NO: 33
source                 1..1569
                       mol_type = other DNA
                       organism = synthetic construct
SEQUENCE: 34
atgtcctgga tcttcgactt gactatctct ttcaccactt tgttgttctt gatcttcacc  60
accgccttgt tgttgttgtt gaaggttttc aagaagaacc acaagttaag accaccacca  120
tctccattca ccttgccaat catcggtcac ttgcacttgt tgggtccatt gatccaccaa  180
tccttccaca gattgtccac cttgtacggt ccattgatcc aattgaagat cggttacatc  240
ccatgtgttg ttgcctctac tccagaattg gctaaggaat tcttaaagac tcacgaattg  300
gctttctcct ctagaaagca ctccgctgcc attaagttgt tgacctacga tgtttctttc  360
gctttctctc catacggtcc atactggaag ttcatcaaaa agacttgtac cttcgaattg  420
ttgggtacta gaaacatgaa ccacttcttg ccaattagaa ccaacgaaat tagaagattc  480
ttgcaagtta tgttggaaaa ggccaaggct tctgaaggtg ttaacgttac tgaagaattg  540
atcaagttga ctaacaacgt tatctctcaa atgatgttct ctactagatc ttctggtacc  600
gaaggtgaag ctgaagaaat gagaactttg gttagagaag ttactcaaat cttcggtgaa  660
ttcaacgttt ctgatttcat caagttgtgt aagaacattg atattggtgg tttcaagaag  720
agatctaagg atatccaaaa gagatacgat gctttgttgg aaaagatcat ctctgaaaga  780
gaatctgaaa gagctagaag aggtaagaac agagaaactt tgggtgaaga aggtggtaag  840
gatttcttgg atatgatgtt ggatactatg gaagatggta agtgtgaagt tgaaatcact  900
agagatcaca ttaaggcctt ggttttggat ttcttgactg ctgccactga tactactgct  960
attgctgttg aatggacttt ggccgaattg atctctaacc cagaagtttt cgataaggct  1020
agagaagaaa tcgataaggt cgttggtaag cacagattgg tcactgaatt ggacactcca  1080
aacttgccat acatccacgc tatcatcaag gaatctttca gattgcaccc accaattcca  1140
ttgttgatca gaaagtctgt ccaagattgt actgttggtg gttaccacat ctctgctaac  1200
accatcttgt tcgtcaacat ttgggccatc ggtagaaacc caaagtactg ggaatctcca  1260
atgaagttct ggccagaaag attcttggaa tccaacggtc caggtccagt tggttctatg  1320
gatattaagg gtcaccacta cgaattgttg ccattcggtt ctggtagaag aggttgtcca  1380
ggtatggctt tggccatgca agaattgcca gttgttttgg ccgccatgat ccaatgtttc  1440
aactggaagc cagttacttt ggacggtgaa gaattggata tgtctgaaag accaggtttg  1500
actgctccaa gagcccacga tttggtttgt gttccatccg ctagaattaa ctctttcgat  1560
aacttctaa                                                          1569
```

```
SEQ ID NO: 35          moltype = AA  length = 520
FEATURE                Location/Qualifiers
source                 1..520
                       mol_type = protein
                       organism = Lonicera macranthoides
SEQUENCE: 35
MSLIFDLTIS FTTLLFLIFT TALLLKVFKK NHKLQPPPSP FTLPIIGHLH LLGPLIHQSF  60
HRLSTLYGPL IQLKIGYIPC VVASTPELAK EFLKTHELAF SSRKHSAAIK LLTYDVSFAF  120
APYGPYWKFI KKTCTFELLG TRNMNHFLPI RTNEIRRFLQ VMLEKAKASE GVNVTEELIK  180
LTNNVISQMM FSTRSSGTEG EAEEVRTLVR EVTQIFGEFN VSDFIKLCKN IDIGGFKKRS  240
EDIQKRYDAL LEKIISERES ERARRGKNRE TLGEEGGKDF LDMMLDTMED GKCEVEITRD  300
HIKALVLDFL TAATDTTAIA VEWTLAELIS NPEVFDKARE EIDKVVGKHR LVTELDTPNL  360
PYIHAIIKES FRLHPPIPLV IRKSVQDCTV GGYHISANTI LFINIWAIGR NPKYWESPMK  420
FWPERFLESN EPGSVGSTDI KGHHYELLPF GSGRRGCPGM ALAMQELPVV LAAMIQCFNW  480
KPVTLDGEEL DMSERPGLTA PRAHDLVCVP SARINSFDNF                        520

SEQ ID NO: 36          moltype = DNA  length = 1563
FEATURE                Location/Qualifiers
misc_feature           1..1563
                       note = coding sequence for SEQ ID NO: 35
source                 1..1563
                       mol_type = other DNA
                       organism = synthetic construct
SEQUENCE: 36
atgtccttga tcttcgactt gactatctct ttcaccactt tgttgttctt gatcttcacc  60
accgccttgt tgttgaaggt tttcaagaag aaccacaagt tgcaaccacc accatctcca  120
ttcaccttgc caatcatcgg tcacttgcac ttgttgggtc cattgatcca ccaatccttc  180
cacagattgt ccaccttgta cggtccattg atccaattga agatcggtta catcccatgt  240
gttgttgctt ctactccaga attggctaag gaattcttaa agactcacga attggctttc  300
tcctctagaa agcactccgc tgccattaag ttgttgacct acgatgtttc tttcgctttc  360
gctccatacg gtccatactg gaagttcatc aaaaagactt gtaccttcga attgttgggt  420
actagaaaca tgaaccactt cttgccaatt agaaccaacg aaattagaag attcttgcaa  480
gttatgttgg aaaaggccaa ggcttctgaa ggtgttaacg ttactgaaga attgatcaag  540
ttgactaaca acgttatctc tcaaatgatg ttctctacta gatcttctgg taccgaaggt  600
gaagctgaag aagttagaac tttggttaga gaagttactc aaatcttcgg tgaattcaac  660
gtttctgatt tcatcaagtt gtgtaagaac attgatattg gtggtttcaa gaagagatct  720
gaagatatcc aaaagagata cgatgctttg ttggaaaaga tcatctctga aagagaatct  780
gaaagagcta gaagaggtaa gaacagagaa actttgggtg aagaaggtgg taaggatttc  840
ttggacatga tgttggatac tatggaagat ggtaagtgtg aagttgaaat cactagagat  900
cacattaagg ccttggtttt ggatttcttg actgctgcca ctgatactac tgctattgct  960
gttgaatgga ctttggctga attgatctct aacccagaag ttttcgataa ggctagagaa  1020
gaaatcgata aggtcgttgg taagcacaga ttggtcactg aattggacac tccaaacttg  1080
ccatacatcc acgctatcat caaggaatct ttcagattgc acccaccaat tccattggtc  1140
atcagaaagt ctgtccaaga ttgtactgtt ggtggttacc acatctctgc taacactatc  1200
ttgttcatca acatttgggc catcggtaga aacccaaagt actgggaatc tccaatgaag  1260
ttctggccag aaagattctt ggaatccaac gaaccaggtt ctgttggttc tactgatatt  1320
aagggtcacc actacgaatt gttgccattc ggttctggta gaagaggttg tccaggtatg  1380
gctttggcca tgcaagaatt gccagttgtt ttggccgcca tgatccaatg tttcaactgg  1440
aagccagtta ctttggacgg tgaagaattg gatatgtctg aaagaccagg tttgactgct  1500
ccaagagccc acgatttggt ttgtgttcca tccgctagaa ttaactcttt cgataacttc  1560
taa                                                                1563

SEQ ID NO: 37          moltype = AA  length = 366
FEATURE                Location/Qualifiers
source                 1..366
                       mol_type = protein
                       organism = Petroselinum crispum
SEQUENCE: 37
MSAPTTITAL AKEKTLNLDF VRDEDERPKV AYNQFSNEIP IISLAGLDDD SDGRRPEICR  60
KIVKACEDWG IFQVVDHGID SGLISEMTRL SREFFALPAE EKLEYDTTGG KRGGFTISTV  120
LQGDDAMDWR EFVTYFSYPI NARDYSRWPK KPEGWRSTTE VYSEKLMVLG AKLLEVLSEA  180
MGLEKGDLTK ACVDMEQKVL INYYPTCPQP DLTLGVRRHT DPGTITILLQ DMVGGLQATR  240
DGGKTWITVQ PVEGAFVVNL GDHGHYLSNG RFRNADHQAV VNSTSSRLSI ATFQNPAQNA  300
IVYPLKIREG EKAILDEAIT YAEMYKKCMT KHIEVATRKK LAKEKRLQDE KAKLEMKSKS  360
ADENLA                                                             366

SEQ ID NO: 38          moltype = DNA  length = 1101
FEATURE                Location/Qualifiers
misc_feature           1..1101
                       note = coding sequence for SEQ ID NO: 37
source                 1..1101
                       mol_type = other DNA
                       organism = synthetic construct
SEQUENCE: 38
atgtccgctc caactactat caccgctttg gccaaggaaa agactttgaa cttggacttc  60
gttagagatg aagatgaaag accaaaggtt gcttacaacc aattctctaa cgaaattcca  120
attatttctt tggccggttt ggatgacgat tctgatggta gaaggccaga aatctgtaga  180
aagatcgtta aggcttgtga agattggggt attttccaag ttgttgatca cggtattgac  240
tctggtttga tttccgaaat gactagattg tctagagaat tcttcgcttt gccagctgaa  300
```

```
gaaaagttgg aatacgatac tactggtggt aagagaggtg gtttcactat ctccactgtt  360
ttgcaaggtg acgacgctat ggattggaga gaattcgtta cttacttctc ttacccaatc  420
aacgctagag actactctag atggccaaag aagccagaag gttggagatc taccactgaa  480
gtttactctg aaaagttgat ggttttgggt gccaagttgt tggaagtttt gtctgaagcc  540
atgggtttgg aaaagggtga tttgactaag gcttgtgttg atatggaaca aaaggttttg  600
attaactact acccaacttg tccacaacca gacttgactt tgggtgtcag gagacacact  660
gatccaggta ctattaccat tttgttgcaa gacatggttg gtggtttgca agccaccaga  720
gatggtggta agacttggat tactgttcaa ccagttgaag gtgctttcgt tgtcaacttg  780
ggtgatcacg gtcactactt gtctaacggt agattcagaa acgctgacca ccaagctgtt  840
gttaactcta cctcttctag attgtctatt gctactttcc aaaacccagc tcaaaacgct  900
atcgtttacc cattgaagat cagagaaggt gaaaaggcta ttttggatga agccatcacc  960
tacgctgaaa tgtacaagaa gtgtatgact aagcacattg aagttgctac tagaaagaag  1020
ttggccaagg aaaagagatt gcaagacgaa aaggccaagt tggaaatgaa gtccaagtct  1080
gctgatgaaa acttggctta a                                           1101
```

```
SEQ ID NO: 39          moltype = AA  length = 507
FEATURE                Location/Qualifiers
source                 1..507
                       mol_type = protein
                       organism = Flavobacterium johnsoniae
SEQUENCE: 39
MSNTINEYLS LEEFEAIIFG NQKVTISDVV VNRVNESFNF LKEFSGNKVI YGVNTGFGPM  60
AQYRIKESDQ IQLQYNLIRS HSSGTGKPLS PVCAKAAILA RLNTLSLGNS GVHPSVINLM  120
SELINKDITP LIFEHGGVGA SGDLVQLSHL ALVLIGEGEV FYKGERRPTP EVFEIEGLKP  180
IQVEIREGLA LINGTSVMTG IGVVNVYHAK KLLDWSLKSS CAINELVQAY DDHFSAELNQ  240
TKRHKGQQEI ALKMRQNLSD STLIRKREDH LYSGENTEEI FKEKVQEYYS LRCVPQILGP  300
VLETINNVAS ILEDEFNSAN DNPIIDVKNQ HVYHGGNFHG DYISLEMDKL KIVITKLTML  360
AERQLNYLLN SKINELLPPF VNLGTLGFNF GMQGVQFTAT STTAESQMLS NPMYVHSIPN  420
NNDNQDIVSM GTNSAVITSK VIENAFEVLA IEMITIVQAI DYLGQKDKIS SVSKKWYDEI  480
RNIIPTFKED QVMYPFVQKV KDHLINN                                     507
```

```
SEQ ID NO: 40          moltype = DNA  length = 1524
FEATURE                Location/Qualifiers
misc_feature           1..1524
                       note = coding sequence for SEQ ID NO: 39
source                 1..1524
                       mol_type = other DNA
                       organism = synthetic construct
SEQUENCE: 40
atgtccaaca ctattaacga atacttgtct ttggaagaat tcgaagccat catcttcggt  60
aaccaaaagg ttactatttc tgacgttgtc gttaacagag ttaacgaatc tttcaacttc  120
ttgaaggaat tctctggtaa caaggttatt tacggtgtta acactggttt cggtccaatg  180
gctcaataca gaattaagga atctgatcaa attcaattgc aatacaactt gattagatct  240
cactcttctg gtaccggtaa gccattgtct ccagtttgtg ctaaggctgc tattttggct  300
agattgaaca ctttgtcttt gggtaactct ggtgttcacc catctgttat caacttgatg  360
tctgaattga tcaacaagga tattacccca ttgatcttcg aacacggtgg tgttggtgcc  420
tctggtgact tggttcaatt gtctcacttg gctttggttt tgattggtga aggtgaagtt  480
ttctacaagg gtgaaagaag gccaactcca gaagttttcg aaattgaagg tttgaagcca  540
attcaagttg aaattagaga aggtttggct ttgattaacg gtacttctgt tatgactggt  600
attggtgttg ttaacgttta ccacgctaag aagttgttgg actggtcttt gaaatcttct  660
tgtgctatta acgaattggt tcaagcttac gacgatcact tctctgctga attgaaccaa  720
actaagagac acaagggtca acaagaaatt gctttgaaga tgagacaaaa cttgtctgac  780
tctactttga tcagaaagag agaagatcac ttgtactctg gtgaaaacac cgaagaaatc  840
ttcaaggaaa aggttcaaga atactactct ttgagatgtg ttccacaaat tttgggtcca  900
gttttggaaa ctattaacaa cgttgcttct attttggaag atgaattcaa ctctgctaac  960
gataacccaa ttatcgatgt taagaaccaa cacgtttacc acggtggtaa cttccacggt  1020
gattacattt ctttggaaat ggataagttg aagattgtta ttaccaagtt gactatgttg  1080
gctgaaagac aattgaacta cttgttgaac tctaagatca acgaattgtt gccaccattc  1140
gttaacttgg gtactttggg tttcaacttc ggtatgcaag gtgttcaatt cactgctact  1200
tctactactg ctgaatctca aatgttgtct aacccaatgt acgttcactc tattccaaac  1260
aacaacgaca accaagatat cgtttctatg ggtactaact ctgctgttat tacctctaag  1320
gttatcgaaa acgctttcga agttttggct atcgaaatga ttactatcgt tcaagctatt  1380
gattacttgg gtcaaaagga caagatttct tctgtttcta agaagtggta cgatgaaatt  1440
agaaacatca ttccaacttt caaggaagat caagttatgt acccattcgt tcaaaaggtt  1500
aaggatcact tgatcaacaa ctaa                                        1524
```

```
SEQ ID NO: 41          moltype = AA  length = 694
FEATURE                Location/Qualifiers
source                 1..694
                       mol_type = protein
                       organism = Rhodotorula glutinis
SEQUENCE: 41
MSAPRPTSQS QARTCPTTQV TQVDIVEKML AAPTDSTLEL DGYSLNLGDV VSAARKGRPV  60
RVKDSDEIRS KIDKSVEFLR SQLSMSVYGV TTGFGGSADT RTEDAISLQK ALLEHQLCGV  120
LPSSFDSFRL GRGLENSLPL EVVRGAMTIR VNSLTRGHSA VRLVVLEALT NFLNHGITPI  180
VPLRGTISAS GDLSPLSYIA AAISGHPDSK VHVVHEGKEK ILYAREAMAL FNLEPVVLGP  240
KEGLGLVNGT AVSASMATLA LHDAHMLSLL SQSLTAMTVE AMVGHAGSFH PFLHDVTRPH  300
PTQIEVAGNI RKLLEGSRFA VHHEEEVKVK DDEGILRQDR YPLRTSPQWL GPLVSDLIHA  360
HAVLTIEAGQ STTDNPLIDV ENKTSHHGGN FQAAAVANTM EKTRLGLAQI GKLNFTQLTE  420
```

```
MLNAGMNRGL PSCLAAEDPS LSYHCKGLDI AAAAYTSELG HLANPVTTHV QPAEMANQAV  480
NSLALISARR TTESNDVLSL LLATHLYCVL QAIDLRAIEF EFKKQFGPAI VSLIDQHFGS  540
AMTGSNLRDE LVEKVNKTLA KRLEQTNSYD LVPRWHDAFS FAAGTVVEVL SSTSLSLAAV  600
NAWKVAAAES AISLTRQVRE TFWSAASTSS PALSYLSPRT QILYAFVREE LGVKARRGDV  660
FLGKQEVTIG SNVSKIYEAI KSGRINNVLL KMLA                             694

SEQ ID NO: 42          moltype = DNA  length = 2085
FEATURE                Location/Qualifiers
misc_feature           1..2085
                       note = coding sequence for SEQ ID NO: 41
source                 1..2085
                       mol_type = other DNA
                       organism = synthetic construct
SEQUENCE: 42
atgtccgctc caagaccaac ttctcaatct caagccagaa cttgtccaac cacccaagtt  60
acccaagttg atatcgttga aaagatgttg gctgctccaa ctgattctac cttggaattg  120
gacggttact ctttgaactt gggtgatgtt gtttctgctg ctagaaaggg tagaccagtt  180
agagttaagg attctgatga aatcagatct aagatcgaca agtctgttga attcttgaga  240
tctcaattgt ctatgtctgt ttacggtgtt accaccggtt tcggtggttc cgctgacacc  300
agaaccgaag atgctatttc tttgcaaaag gctttgttgg aacaccaatt gtgtggtgtt  360
ttgccatctt ctttcgactc tttcagattg ggtagaggtt tggaaaactc tttgccattg  420
gaagttgtta gaggtgctat gaccattaga gttaactctt tgaccagagg tcactctgct  480
gttagattgg ttgttttgga agctttgacc aacttcttga accacggtat taccccaatt  540
gttccattga gaggtaccat ctccgcttct ggtgatttgt ctccattgtc ttacattgct  600
gctgctattt ctggtcaccc agattctaag gttcacgttg ttcacgaagg taaggaaaag  660
atcttgtacg ctagagaagc tatggctttg ttcaacttgg aaccagttgt tttgggtcca  720
aaggaaggtt tgggtttggt taacggtacc gctgtttccg cttctatggc taccttggct  780
ttgcacgacg ctcacatgtt gtctttgttg tctcaatctt tgaccgctat gaccgttgaa  840
gctatggttg gtcacgctgg ttctttccac ccattcttgc acgatgttac cagaccacac  900
ccaacccaaa tcgaagttgc tggtaacatt agaaagttgt tggaaggttc tagattcgct  960
gttcaccacg aagaagaagt taaggttaag gatgatgaag gtattttgag acaagataga  1020
tacccattga gaacctctcc acaatggttg ggtccattgg tttccgactt gattcacgct  1080
cacgccgttt tgaccatcga agctggtcaa tctaccaccg ataacccatt gatcgatgtt  1140
gaaaacaaga cctctcacca cggtggtaac ttccaagctg ctgctgttgc caacactatg  1200
gaaaagacca gattgggttt ggcccaaatc ggtaagttga acttcaccca attgaccgaa  1260
atgttgaacg ctggtatgaa cagaggtttg ccatcttgtt tggctgctga agatccatcc  1320
ttgtcttacc actgtaaggg tttggacatt gctgctgctg cttacacctc tgaattgggt  1380
cacttggcta acccagttac cacccacgtt caaccagctg aaatggctaa ccaagctgtt  1440
aactctttgg ctttgatttc tgctagaaga accaccgaat ctaacgacgt tttgtccttg  1500
ttgttggcta cccacttgta ctgtgttttg caagctatcg acttgagagc tattgaattc  1560
gaattcaaga agcaattcgg tccagccatt gtttctttga tcgaccaaca cttcggttct  1620
gctatgaccg gttctaactt gagagatgaa ttggttgaaa aggttaacaa gactttggcc  1680
aagagattgg aacaaaccaa ctcttacgat ttggttccaa gatggcacga cgctttctct  1740
ttcgctgctg gtactgttgt tgaagttttg tcctctacct ctttgtcttt ggctgccgtt  1800
aacgcttgga aggttgctgc tgccgaatct gctatctcct tgaccagaca agttagagaa  1860
accttctggt ccgctgcttc tacctcctct ccagctttgt cttacttgtc tccaagaacc  1920
caaatcttgt acgctttcgt tagagaagaa ttgggtgtta aggccagaag aggtgacgtt  1980
ttcttgggta agcaagaagt taccatcggt tctaacgttt ctaagattta cgaagccatc  2040
aagtctggta gaatcaacaa cgttttgttg aagatgttgg cttaa                 2085

SEQ ID NO: 43          moltype = AA  length = 562
FEATURE                Location/Qualifiers
source                 1..562
                       mol_type = protein
                       organism = Arabidopsis thaliana
SEQUENCE: 43
MSAPQEQAVS QVMEKQSNNN NSDVIFRSKL PDIYIPNHLS LHDYIFQNIS EFATKPCLIN  60
GPTGHVYTYS DVHVISRQIA ANFHKLGVNQ NDVVMLLLPN CPEFVLSFLA ASFRGATATA  120
ANPFFTPAEI AKQAKASNTK LIITEARYVD KIKPLQNDDG VVIVCIDDNE SVPIPEGCLR  180
FTELTQSTTE ASEVIDSVEI SPDDVVALPY SSGTTGLPKG VMLTHKGLVT SVAQQVDGEN  240
PNLYFHSDDV ILCVLPMFHI YALNSIMLCG LRVGAAILIM PKFEINLLLE LIQRCKVTVA  300
PMVPPIVLAI AKSSETEKYD LSSIRVVKSG AAPLGKELED AVNAKFPNAK LGQGYGMTEA  360
GPVLAMSLGF AKEPFPVKSG ACGTVVRNAE MKIVDPDTGD SLSRNQPGEI CIRGHQIMKG  420
YLNNPAATAE TIDKDGWLHT GDIGLIDDDD ELFIVDRLKE LIKYKGFQVA PAELEALLIG  480
HPDITDVAVV AMKEEAAGEV PVAFVVKSKD SELSEDDVKQ FVSKQVVFYK RINKVFFTES  540
IPKAPSGKIL RKDLRAKLAN GL                                          562

SEQ ID NO: 44          moltype = DNA  length = 1689
FEATURE                Location/Qualifiers
misc_feature           1..1689
                       note = coding sequence for SEQ ID NO: 43
source                 1..1689
                       mol_type = other DNA
                       organism = synthetic construct
SEQUENCE: 44
atgtccgctc cacaagaaca agctgtttct caagttatgg aaaagcaatc taacaacaac  60
aactctgacg tcattttcag atctaagttg ccagatattt acatcccaaa ccacttgtct  120
ttgcacgact acatcttcca aaacatctcc gaattcgcca ctaagccatg tttgatcaac  180
ggtccaaccg gtcacgttta cacttactcc gacgtccacg tcatctccag acaaatcgcc  240
```

```
gccaacttcc acaagttggg tgttaaccaa aacgacgtcg tcatgttgtt gttgccaaac  300
tgtccagaat tcgtcttgtc tttcttggcc gcctccttca gaggtgctac cgccaccgcc  360
gctaacccat tcttcactcc agctgaaatc gctaagcaag ccaaggcctc caacaccaag  420
ttgatcatca ccgaagctag atacgtcgac aagatcaagc cattgcaaaa cgacgacggt  480
gttgtcatcg tctgtatcga cgacaacgaa tccgttccaa tcccagaagg ttgtttgaga  540
ttcaccgaat tgactcaatc tactaccgaa gcttctgaag tcatcgactc tgttgaaatt  600
tctccagacg acgttgttgc tttgccatac tcctctggta ctactggttt gccaaagggt  660
gttatgttga ctcacaaggg tttggtcact tctgttgctc aacaagtcga cggtgaaaac  720
ccaaacttgt acttccactc tgatgacgtc atcttgtgtg ttttgccaat gttccacatc  780
tacgctttga actctatcat gttgtgtggt ttgagagttg gtgctgctat tttgatcatg  840
ccaaagttcg aaatcaactt gttgttggaa ttgatccaaa gatgtaaggt tactgttgct  900
ccaatggttc caccaattgt tttggccatt gctaaatctt ctgaaactga aaagtacgat  960
ttatcttcta tcagagttgt taagtctggt gctgctccat tgggtaagga attggaagat  1020
gccgttaacg ccaagttccc aaacgccaag ttgggtcaag gttacggtat gactgaagct  1080
ggtccagttt tggctatgtc tttgggtttc gctaaggaac cattcccagt taagtctggt  1140
gcttgtggta ctgttgttag aaacgctgaa atgaagatcg ttgatccaga caccggtgat  1200
tctttgtcta gaaaccaacc aggtgaaatt tgtattagag gtcaccaaat catgaagggt  1260
tacttgaaca acccagctgc tactgctgaa accattgata aggacggttg gttgcacact  1320
ggtgatattg gtttgatcga tgacgatgac gaattgttca tcgttgatag attgaaggaa  1380
ttgatcaagt acaagggttt ccaagttgct ccagctgaat tggaagcttt gttgatcggt  1440
cacccagaca ttactgatgt tgctgttgtc gctatgaagg aagaagctgc tggtgaagtt  1500
ccagttgctt tcgttgttaa gtctaaggat tctgaattgt ctgaagatga tgttaagcaa  1560
ttcgtttcta agcaagttgt ttctacaaag agaatcaaca aggttttctt cactgaatcc  1620
attccaaagg ctccatctgg taagatcttg agaaaggatt tgagagctaa gttggctaac  1680
ggtttgtaa                                                         1689

SEQ ID NO: 45           moltype = AA  length = 545
FEATURE                 Location/Qualifiers
source                  1..545
                        mol_type = protein
                        organism = Petroselinum crispum
SEQUENCE: 45
MSGDCVAPKE DLIFRSKLPD IYIPKHLPLH TYCFENISKV GDKSCLINGA TGETFTYSQV  60
ELLSRKVASG LNKLGIQQGD TIMLLLPNSP EYFFAFLGAS YRGAISTMAN PFFTSAEVIK  120
QLKASQAKLI ITQACYVDKV KDYAAEKNIQ IICIDDAPQD CLHFSKLMEA DESEMPEVVI  180
NSDDVVALPY SSGTTGLPKG VMLTHKGLVT SVAQQVDGDN PNLYMHSEDV MICILPLFHI  240
YSLNAVLCCG LRAGVTILIM QKFDIVPFLE LIQKYKVTIG PFVPPIVLAI AKSPVVDKYD  300
LSSVRTVMSG AAPLGKELED AVRAKFPNAK LGQGYGMTEA GPVLAMCLAF AKEPYEIKSG  360
ACGTVVRNAE MKIVDPETNA SLPRNQRGEI CIRGDQIMKG YLNDPESTRT TIDEEGWLHT  420
GDIGFIDDDD ELFIVDRLKE IIKYKGFQVA PAELEALLLT HPTISDAAVV PMIDEKAGEV  480
PVAFVVRTNG FTTTEEEIKQ FVSKQVVFYK RIFRVFFVDA IPKSPSGKIL RKDLRARIAS  540
GDLPK                                                             545

SEQ ID NO: 46           moltype = DNA  length = 1638
FEATURE                 Location/Qualifiers
misc_feature            1..1638
                        note = coding sequence for SEQ ID NO: 45
source                  1..1638
                        mol_type = other DNA
                        organism = synthetic construct
SEQUENCE: 46
atgtccggtg attgtgttgc tccaaaggaa gatttgattt tcagatctaa gttgccagat  60
atttacatcc caaagcactt gccattgcac acttactgtt tcgaaaacat ctctaaggtt  120
ggtgacaagt cctgtttgat caacggtgct actggtgaaa ctttcactta ctctcaagtt  180
gaattgttgt ccagaaaggt tgcttctggt ttgaacaagt tgggtattca acaaggtgat  240
accatcatgt tgttgttgcc aaactcccca gaatacttct tcgctttctt gggtgcttct  300
tacagaggtg ctatttctac tatggccaac ccattcttca cttctgctga agttatcaag  360
caattgaagg cttcccaagc taagttgatc attactcaag cttgttacgt tgacaaggtt  420
aaggactacg ctgctgaaaa gaacatccaa atcatttgta tcgatgatgc tccacaagat  480
tgtttgcact tctccaagtt gatggaagct gatgaatctg aaatgccaga agttgttatc  540
aactctgacg atgtcgtcgc tttgccatac tcttctggta ctactggttt gccaaagggt  600
gttatgttga ctcacaaggg tttggttact tctgttgctc aacaagttga tggtgacaac  660
ccaaacttgt acatgcactc tgaagatgtt atgatctgta tcttgccatt gttccacatt  720
tactctttga acgctgtttt gtgttgtggt ttgagagctg gtgttactat cttgattatg  780
caaaagttcg atattgttcc attcttggaa ttgatccaaa agtacaaggt tactattggt  840
ccattcgttc caccaattgt tttggctatt gctaagtctc cagttgttga taagtacgac  900
ttatcttctg ttagaactgt tatgtctggt gctgctccat tgggtaagga attggaagat  960
gctgttagag ctaagttccc aaacgccaag ttgggtcaag gttacggtat gactgaagct  1020
ggtccagttt tggctatgtg tttggctttc gctaaggaac catacgaaat caagtctggt  1080
gcctgtggta ctgttgttag aaacgctgaa atgaagattg ttgatccaga aaccaacgcc  1140
tctttgccaa gaaaccaaag aggtgaaatt tgtattagag gtgaccaaat tatgaagggt  1200
tacttgaacg atccagaatc tactagaact actatcgacg aagaaggttg gttgcacact  1260
ggtgatatcg gtttcattga cgacgatgat gaattgttca ttgttgatag attgaaggaa  1320
atcatcaagt acaagggttt ccaagttgcc ccagctgaat tggaagcttt gttgttgact  1380
cacccaacca tttccgatgc tgctgttgtt ccaatgatcg atgaaaaggc tggtgaagtt  1440
ccagttgctt tcgttgttag aactaacggt ttcaccacca ctgaagaaga aatcaagcaa  1500
ttcgtttcta agcaagttgt ttctacaaag agaatcttca gagttttctt cgttgatgct  1560
attccaaagt ctccatctgg taagattttg agaaaggact tgagagctag aatcgcttcc  1620
ggtgatttgc caaagtaa                                               1638
```

```
SEQ ID NO: 47          moltype = AA  length = 545
FEATURE                Location/Qualifiers
source                 1..545
                       mol_type = protein
                       organism = Petroselinum crispum
SEQUENCE: 47
MSGDCVAPKE DLIFRSKLPD IYIPKHLPLH TYCFENISKV GDKSCLINGA TGETFTYSQV  60
ELLSRKVASG LNKLGIQQGD TIMLLLPNSP EYFFAFLGAS YRGAISTMAN PFFTSAEVIK  120
QLKASLAKLI ITQACYVDKV KDYAAEKNIQ IICIDDAPQD CLHFSKLMEA DESEMPEVVI  180
DSDDVVALPY SSGTTGLPKG VMLTHKGLVT SVAQQVDGDN PNLYMHSEDV MICILPLFHI  240
YSLNAVLCCG LRAGVTILIM QKFDIVPFLE LIQKYKVTIG PFVPPIVLAI AKSPVVDKYD  300
LSSVRTVMSG AAPLGKELED AVRAKFPNAK LGQGYGMTEA GPVLAMCLAF AKEPYEIKSG  360
ACGTVVRNAE MKIVDPETNA SLPRNQRGEI CIRGDQIMKG YLNDPESTRT TIDEEGWLHT  420
GDIGFIDDDD ELFIVDRLKE IIKYKGFQVA PAELEALLLT HPTISDAAVV PMIDEKAGEV  480
PVAFVVRTNG FTTTEEEIKQ FVSKQVVFYK RIFRVFFVDA IPKSPSGKIL RKDLRAKIAS  540
GDLPK                                                             545

SEQ ID NO: 48          moltype = DNA  length = 1638
FEATURE                Location/Qualifiers
misc_feature           1..1638
                       note = coding sequence for SEQ ID NO: 47
source                 1..1638
                       mol_type = other DNA
                       organism = synthetic construct
SEQUENCE: 48
atgtccggtg actgtgttgc tccaaaggaa gatttgattt tcagatctaa gttgccagat  60
atttacatcc caaagcactt gccattgcac acttactgtt tcgaaaacat ctctaaggtt  120
ggtgacaagt cctgtttgat caacggtgct actggtgaaa ctttcactta ctctcaagtt  180
gaattgttgt ccagaaaggt tgcttctggt ttgaacaagt tgggtattca acaaggtgat  240
accatcatgt tgttgttgcc aaactcccca gaatacttct tcgctttctt gggtgcttct  300
tacagaggtg ctatttctac tatggccaac ccattcttca cttctgctga agttatcaag  360
caattgaagg cttccttggc taagttgatc attactcaag cttgttacgt tgacaaggtt  420
aaggactacg ctgctgaaaa gaacatccaa atcatttgta tcgatgatgc tccacaagat  480
tgtttgcact tctccaagtt gatggaagct gatgaatctg aaatgccaga agttgttatc  540
gattctgacg atgtcgtcgc tttgccatac tcttctggta ctactggttt gccaaagggt  600
gttatgttga cccacaaggg tttggttact tctgttgctc aacaagttga tggtgacaac  660
ccaaacttgt acatgcactc tgaagatgtt atgatctgta tcttgccatt gttccacatt  720
tactctttga acgctgtttt gtgttgtggt ttgagagctg gtgttactat cttgattatg  780
caaaagttcg atattgttcc attcttggaa ttgatccaaa agtacaaggt tactattggt  840
ccattcgttc caccaattgt tttggctatt gctaagtctc cagttgttga taagtacgac  900
ttatcttctg ttagaactgt tatgtctggt gctgctccat tgggtaagga attggaagat  960
gctgttagag ctaagttccc aaacgccaag ttgggtcaag gttacggtat gactgaagct  1020
ggtccagttt tggctatgtg tttggctttc gctaaggaac catacgaaat caagtctggt  1080
gcctgtggta ctgttgttag aaacgctgaa atgaagattg ttgatccaga aaccaacgcc  1140
tctttgccaa gaaaccaaag aggtgaaatt tgtattagag gtgaccaaat tatgaagggt  1200
tacttgaacg atccagaatc tactagaact actatcgacg aagaaggttg gttgcacact  1260
ggtgatatcg gtttcattga cgacgatgat gaattgttca ttgttgatag attgaaggaa  1320
atcatcaagt acaagggttt ccaagttgcc ccagctgaat tggaagcttt gttgttgact  1380
cacccaacca tttccgatgc tgctgttgtt ccaatgatcg atgaaaaggc tggtgaagtt  1440
ccagttgctt tcgttgttag aactaacggt ttcaccacca ctgaagaaga aatcaagcaa  1500
ttcgtttcta agcaagttgt tttctacaag agaatcttca gagttttctt cgttgatgct  1560
attccaaagt ctccatctgg taagattttg agaaaggact tgagagctaa gatcgcttcc  1620
ggtgatttgc caaagtaa                                                1638

SEQ ID NO: 49          moltype = AA  length = 579
FEATURE                Location/Qualifiers
source                 1..579
                       mol_type = protein
                       organism = Streptomyces clavuligerus
SEQUENCE: 49
MSASTPSPGP SGTPSGTPPS GPSGTPSPGP AGAGTAPVFR SRYPDIEPVS EPLHEAVLGR  60
AAGYGSEPAL VDGLTGAVVS YARLDRDHRR IAAALAAAGV RKGDVVALHS PNSTGYPAVL  120
YGALRAGATV TTAHPLATAE ELARQLRDSA ARWIVTAAPC LETARRAAEL TPGIGEIFVF  180
DRAEGHTGVA AMLDSTAPEP AVPVDPDQDV ALLPYSSGTT GTPKGVMLTH RSLVTNLVQA  240
HRLIPLRPGD RVLAVLPFFH IYGLVGLMSA PLRNGATVVV LPRFDLEGFL AAVEKHRVTT  300
LYVAPPIVLA LAKHPAVARY DLSSVRHVFS AAAPLDAEIA AACAARVGVP LVRQAYGMTE  360
LSPGCYAVPL DEPAPPPGTV GLLFPSTEMR LLRLDDPGRC VGPGEDGEIA IRGPQVMKGY  420
LGRPEATAEM IDADGWLRTG DVGRVDADGW LHVVDRVKEL IKYKGFQVAP AELEALLLTH  480
GGIADAAVIG VYDEDEGTEI PHAFVVRRPG GAGDSLTAAD VAAHVAARVS PYKKVRRVSF  540
VSGVPRAASG KILRRELRAA RRSPRGTDPG DEDREGATP                        579

SEQ ID NO: 50          moltype = DNA  length = 1740
FEATURE                Location/Qualifiers
misc_feature           1..1740
                       note = coding sequence for SEQ ID NO: 49
source                 1..1740
                       mol_type = other DNA
                       organism = synthetic construct
```

SEQUENCE: 50
atgtccgctt ctactccatc tccaggtcca tctggtaccc catccggtac tccaccatcc 60
ggtccatctg gtactccatc cccaggtcca gctggtgccg gtaccgctcc agtattcaga 120
tctagatacc cagacatcga accagtttct gaaccattgc acgaagctgt tttgggtaga 180
gccgccggtt acggttccga accagccttg gtcgacggtt tgaccggtgc cgtcgtatct 240
tacgctagat tggacagaga tcacagaaga atcgccgccg ccttggccgc cgctggtgtc 300
agaaagggtg acgtcgtcgc cttgcactct ccaaactcta ccggttaccc agccgtcttg 360
tacggtgcct tgagagccgg tgccaccgtt accactgctc acccattggc tactgctgaa 420
gaattggcca gacaattgag agactctgcc gccagatgga tcgttaccgc cgccccatgt 480
ttggaaaccg ccagaagagc cgccgaattg accccaggta tcggtgaaat cttcgtattc 540
gacagagccg aaggtcacac cggtgttgcc gctatgttgg actccaccgc tccagaacca 600
gccgtcccag tcgacccaga ccaagacgtc gctttgttgc catactcctc tggtaccacc 660
ggtaccccaa agggtgttat gttgactcac agatccttgg tcaccaactt ggtccaagcc 720
cacagattga tcccattgag gccaggtgac agagtcttgg ccgttttgcc attcttccac 780
atctacggtt tggtcggttt gatgtctgcc ccattgagaa acggtgctac cgtcgtcgtc 840
ttgccaagat tcgacttgga aggtttcttg gctgccgtcg aaaagcacag agtcaccact 900
ttgtacgttg ccccaccaat cgttttggct ttggccaagc acccagctgt tgccagatac 960
gacttgtcct ctgtcagaca cgtattctct gccgccgccc cattggacgc tgaaatcgct 1020
gctgcctgtg ccgccagagt cggtgttcca ttggtcagac aagcttacgg tatgaccgaa 1080
ttgtctccag gttgttacgc cgtcccattg gacgaaccag ccccaccacc aggtactgtc 1140
ggtttgttgt tcccatccac cgaaatgaga ttgttgagat tggacgaccc aggtagatgt 1200
gtcggtccag gtgaggacgg tgaaatcgcc atcagaggtc cacaagtcat gaagggttac 1260
ttgggtagac cagaagccac cgccgaaatg atcgacgctg atggttggtt gagaaccggt 1320
gacgtcggta gagtcgacgc tgacggttgg ttgcacgtcg ttgacagagt taaggaattg 1380
atcaagtaca agggtttcca agtcgctcca gccgaattgg aagctttgtt gttgacccac 1440
ggtggtatcg ctgacgccgc cgttatcggt gtttacgacg aggacgaagg tactgaaatc 1500
ccacacgctt tcgttgtcag aaggccaggt ggtgctggtg actccttgac cgccgccgac 1560
gtcgccgccc acgtcgccgc tagagtctcc ccatacaaga aggtcagaag agtctctttc 1620
gtatccggtg ttccaagagc cgcttctggt aagatcttga gaagagaatt gagagccgct 1680
agaagatccc caagaggtac tgacccaggt gacgaggaca gagaaggtgc cactccataa 1740

SEQ ID NO: 51 moltype = AA length = 400
FEATURE Location/Qualifiers
source 1..400
mol_type = protein
organism = Hordeum vulgare
SEQUENCE: 51
MSAAVRLKEV RMAQRAEGLA TVLAIGTAVP ANCVYQATYP DYYFRVTKSE HLADLKEKFQ 60
RMCDKSMIRK RHMHLTEEIL IKNPKICAHM ETSLDARHAI ALVEVPKLGQ GAAEKAIKEW 120
GQPLSKITHL VFCTTSGVDM PGADYQLTKL LGLSPTVKRL MMYQQGCFGG ATVLRLAKDI 180
AENNRGARVL VVCSEITAMA FRGPCKSHLD SLVGHALFGD GAAAAIIGAD PDQLDEQPVF 240
QLVSASQTIL PESEGAIDGH LTEAGLTIHL LKDVPGLISE NIEQALEDAF EPLGIHNWNS 300
IFWIAHPGGP AILDRVEDRV GLDKKRMRAS REVLSEYGNM SSASVLFVLD VMRKSSAKDG 360
LATTGEGKDW GVLFGFGPGL TVETLVLHSV PVPVPTAASA 400

SEQ ID NO: 52 moltype = DNA length = 1203
FEATURE Location/Qualifiers
misc_feature 1..1203
note = coding sequence for SEQ ID NO: 51
source 1..1203
mol_type = other DNA
organism = synthetic construct
SEQUENCE: 52
atgtccgctg ctgttagatt gaaggaagtt agaatggctc aaagagctga aggtttggct 60
actgttttgg ccattggtac cgccgttcca gccaactgtg tttaccaagc tacctaccca 120
gactactact tcagagtcac taagtctgaa cacttggctg acttgaagga aaagttccaa 180
agaatgtgtg acaagtccat gatcagaaag agacacatgc acttgaccga agaaatcttg 240
attaagaacc caaagatctg tgctcacatg gaaacctctt tggacgctag acacgccatt 300
gctttggtcg aagtcccaaa gttgggtcaa ggtgctgctg aaaaggctat caaggaatgg 360
ggtcaaccat tgtccaagat cacccacttg gttttctgta ctacctctgg tgtcgacatg 420
ccaggtgccg actaccaatt gaccaagttg ttgggtttgt ccccaactgt taagagattg 480
atgatgtacc aacaaggttg tttcggtggt gccactgttt tgagattggc caaggacatc 540
gctgaaaaca acagaggtgc tagagttttg gttgtctgtt ctgaaatcac cgccatggcc 600
ttcagaggtc catgtaagtc ccacttggac tctttggtcg gtcacgcttt gttcggtgat 660
ggtgctgctg ctgccatcat cggtgctgac ccagaccaat tggacgaaca accagttttc 720
caattggttt ctgcttctca aaccatcttg ccagaatctg aaggtgccat cgacggtcac 780
ttgactgaag ctggtttgac catccacttg ttgaaggacg ttccaggttt gatctctgaa 840
aacatcgaac aagctttgga agatgctttc gaaccattgg gtatccacaa ctggaactcc 900
atcttctgga ttgctcaccc aggtggtcca gccatcttgg acagagtcga agatagagtt 960
ggtttggaca agaagagaat gagagcttct agagaagttt tgtctgaata cggtaacatg 1020
tcctctgctt ctgttttgtt cgtcttggac gttatgagaa agtcatccgc caaggatggt 1080
ttggccacta ctggtgaagg taaggactgg ggtgtcttgt tcggtttcgg tccaggtttg 1140
accgtcgaaa ctttggtctt gcactctgtc ccagtcccag tcccaaccgc cgcttctgct 1200
taa 1203

SEQ ID NO: 53 moltype = AA length = 392
FEATURE Location/Qualifiers
source 1..392
mol_type = protein

```
                        organism = Citrus sinensis
SEQUENCE: 53
MSATVQEIRN AQRADGPATV LAIGTATPAH SVNQADYPDY YFRITKSEHM TELKEKFKRM  60
CDKSMIKKRY MYLTEEILKE NPNMCAYMAP SLDARQDIVV VEVPKLGKEA ATKAIKEWGQ  120
PKSKITHLIF CTTSGVDMPG ADYQLTKLIG LRPSVKRFMM YQQGCFAGGT VLRLAKDLAE  180
NNKGARVLVV CSEITAVTFR GPADTHLDSL VGQALFGDGA AAVIVGADPD TSVERPLYQL  240
VSTSQTILPD SDGAIDGHLR EVGLTFHLLK DVPGLISKNI EKSLSEAFAP LGISDWNSIF  300
WIAHPGGPAI LDQVESKLGL KGEKLKATRQ VLSEYGNMSS ACVLFILDEM RKKSVEEAKA  360
TTGEGLDWGV LFGFGPGLTV ETVVLHSVPI KA                               392

SEQ ID NO: 54           moltype = DNA  length = 1179
FEATURE                 Location/Qualifiers
misc_feature            1..1179
                        note = coding sequence for SEQ ID NO: 53
source                  1..1179
                        mol_type = other DNA
                        organism = synthetic construct
SEQUENCE: 54
atgtccgcta ccgttcaaga aatcagaaac gctcaaagag ccgacggtcc agccaccgtc  60
ttggccatcg gtactgccac tccagcccac tctgtcaacc aagctgatta cccagactac  120
tacttcagaa tcactaagtc tgaacacatg actgaattga aggaaaagtt caagagaatg  180
tgtgacaagt ctatgattaa gaagagatac atgtacttga ctgaagaaat tttgaaggaa  240
aacccaaaca tgtgtgctta catggctcca tctttggacg ctagacaaga cattgttgtt  300
gtcgaagttc caaagttggg taaggaagct gctactaagg ccatcaagga atggggtcaa  360
ccaaagtcta agatcaccca cttgatcttc tgtaccacct ccggtgtcga catgccaggt  420
gccgactacc aattgaccaa gttgatcggt ttaagaccat ccgtcaagag attcatgatg  480
taccaacaag gttgtttcgc cggtggtact gttttgagat tggctaagga cttggctgaa  540
aacaacaagg gtgctagagt tttggttgtc tgttctgaaa tcactgctgt cactttcaga  600
ggtccagccg atactcactt ggattctttg gttggtcaag ctttgttcgg tgatggtgct  660
gctgctgtta tcgttggtgc cgatccagac acttctgtcg aaagaccatt gtaccaattg  720
gtttctactt ctcaaactat cttgccagac tctgacggtg ctattgacgg tcacttgaga  780
gaagtcggtt tgactttcca cttgttgaag gacgtcccag gtttgatctc taagaacatc  840
gaaaagtctt tgtctgaagc tttcgcccca ttgggtatct ctgactggaa ctctatcttc  900
tggatcgctc acccaggtgg tccagctatt ttggaccaag ttgaatctaa gttgggtttg  960
aagggtgaaa agttgaaggc cactagacaa gttttgtctg aatacggtaa catgtcatct  1020
gcttgtgtct tgttcatctt ggacgaaatg agaaagaagt ctgttgaaga agctaaggcc  1080
accaccggtg aaggtttgga ttggggtgtt ttgttcggtt tcggtccagg tttgaccgtc  1140
gaaaccgttg ttttgcactc tgtcccaatc aaggcttaa                        1179

SEQ ID NO: 55           moltype = AA  length = 391
FEATURE                 Location/Qualifiers
source                  1..391
                        mol_type = protein
                        organism = Citrus sinensis
SEQUENCE: 55
MSLTVDEVRK AQRAEGPATI MAIGTATPPN CVDQSTYPDY YFRITNSEHM TDLKEKFKRM  60
CDKSMIKKRY MYLTEEILKE NPNVCAYMAP SLDTRQDMVV VEVPRLGKEA ATKAIKEWGQ  120
PKSKITHLVF CTTSGVDMPG ADYRLTKLLG LRPSVKRLMM YQQGCFAGGT VLRLAKDLAE  180
NNKGARVLVV CSEITAVTFR GPSDTHLDSL VGQALFGDGA AAIIIGADPI PEIEKPMFEL  240
VSTAQTILPD SDGSIDGHLR EVGLTFHLLK DVPGLISKNI QKSLTEAFKP LGISDWNSIF  300
WIAHPGGPTI LDQVEEKLGL KPEKLRATRH VLSEYGNMSS ACVLFILDEM RKKSAEDGLE  360
TAGEGLEWGV LFGFGPGLTV ETVVLHSVAA A                                391

SEQ ID NO: 56           moltype = DNA  length = 1176
FEATURE                 Location/Qualifiers
misc_feature            1..1176
                        note = coding sequence for SEQ ID NO: 55
source                  1..1176
                        mol_type = other DNA
                        organism = synthetic construct
SEQUENCE: 56
atgtccttga ccgtcgatga agttagaaag gctcaaagag ccgaaggtcc agccactatc  60
atggccattg gtactgctac cccaccaaac tgtgttgatc aatctactta cccagattac  120
tacttcagaa tcactaactc tgaacacatg actgatttga aggaaaagtt caagagaatg  180
tgtgacaagt ccatgatcaa gaagagatac atgtacttga ctgaagaaat cttgaaggaa  240
aacccaaacg tttgtgctta catggctcca tctttggata ctagacaaga tatggttgtt  300
gttgaagttc caagattggg taaggaagct gccaccaagg ccattaagga atggggtcaa  360
ccaaagtcca agatcaccca cttggtattc tgtaccactt ctggtgttga catgccaggt  420
gccgattaca gattgactaa gttgttgggt ttaagaccat ccgtcaagag attgatgatg  480
taccaacaag gttgtttcgc cggtggtact gttttgagat tggccaagga cttggccgaa  540
aacaacaagg gtgctagagt cttggttgtt tgttccgaaa tcaccgctgt tactttcaga  600
ggtccatctg acacccactt ggattctttg gttggtcaag ccttgttcgg tgatggtgct  660
gctgctatta tcattggtgc cgacccaatc ccagaaatcg aaaagccaat gttcgaattg  720
gtatctactg cccaaactat cttgccagat tctgatggtt ctatcgacgg tcacttgaga  780
gaagttggtt tgaccttcca cttgttgaag gatgttccag gtttgatttc taagaacatc  840
caaaagtctt tgaccgaagc tttcaagcca ttgggtatct ctgactggaa ctctattttc  900
tggatcgctc acccaggtgg tccaactatt ttggaccaag tcgaagaaaa gttgggtttg  960
aagccagaaa agttgagagc cactagacac gttttgtctg aatacggtaa catgtcatct  1020
gcttgtgttt tgttcatttt ggacgaaatg agaaagaagt ctgctgaaga tggtttggaa  1080
```

```
accgctggtg aaggtttgga atggggtgtc ttgttcggtt tcggtccagg tttgactgtt  1140
gaaaccgttg tcttgcactc tgttgccgct gcttaa                            1176

SEQ ID NO: 57          moltype = AA  length = 352
FEATURE                Location/Qualifiers
source                 1..352
                       mol_type = protein
                       organism = Streptomyces clavuligerus
SEQUENCE: 57
MSAVLCKPAI AVPDHIITNE ETLELARRLH SDHPQLALAC RLIEHTGVRK RHLIQPIDEV  60
LKHPGLDARS ATYETESKAR VPSVVRRALD QAELEPDQID LIIYVSCTGF MMPSLASWLV  120
NTMGFRADTR QLPIAQLGCA AGGAAVNRAH DFCTAYPGTN VLIVACEFCS LCYQPTDLGI  180
GSLLSNGLFG DGIAAAVVRG EEGTGMRLER NGTYLIPHTE EWISYAVRST GFHFQLDKRV  240
PGTMEPLSPA LRALAEQHQW NAGKLDFYII HAGGPRILDD LSRFLDVPPG AFRHSRATLT  300
EYGNIASAVV LDALGRLFDE QSALDGHHGM LAGFGPGIIA EMSLGTWVSP ES          352

SEQ ID NO: 58          moltype = DNA  length = 1059
FEATURE                Location/Qualifiers
misc_feature           1..1059
                       note = coding sequence for SEQ ID NO: 57
source                 1..1059
                       mol_type = other DNA
                       organism = synthetic construct
SEQUENCE: 58
atgtccgctg ttttgtgtaa gccagccatc gccgttccag accacatcat caccaacgaa  60
gaaaccttgg aattggctag aagattgcac tctgaccacc cacaattggc tttggcttgt  120
agattgatcg aacacactgg tgttagaaag agacacttga tccaaccaat cgacgaagtt  180
ttgaagcacc caggtttgga cgctagatct gccacctacg aaaccgaatc caaggctaga  240
gttccatctg ttgttagaag agctttggac caagctgaat tggaaccaga tcaaatcgac  300
ttgatcatct acgtatcctg taccggtttc atgatgccat ccttggcctc ctggttggtc  360
aacaccatgg gtttcagagc tgacaccaga caattgccaa tcgcccaatt gggttgtgct  420
gctggtggtg ctgccgtcaa cagagcccac gacttctgta ccgcctaccc aggtaccaac  480
gtcttgatcg ttgcctgtga attctgttct ttgtgttacc aaccaaccga tttgggtatc  540
ggttctttgt tgtccaacgg tttgttcggt gacggtatcg ccgccgctgt tgtcagaggt  600
gaagaaggta ccggtatgag attggaaaga aacggtacct acttgatccc acacaccgaa  660
gaatggatct cctacgctgt tagatccacc ggtttccact tccaattgga caagagagtc  720
ccaggtacca tggaaccatt gtctccagct ttgagagcct tggccgaaca acaccaatgg  780
aacgccggta agttggactt ctacatcatc cacgctggtg gtccaagaat cttggacgat  840
ttgtctagat tcttggacgt tccaccaggt gccttcagac actctagagc cactttgacc  900
gaatacggta acatcgcctc tgccgtcgtt ttggacgcct tgggtagatt gttcgacgaa  960
caatccgcct tggacggtca ccacggtatg ttggctggtt tcggtccagg tatcatcgcc  1020
gaaatgtcct tgggtacctg ggtttctcca gaatcctaa                         1059

SEQ ID NO: 59          moltype = AA  length = 401
FEATURE                Location/Qualifiers
source                 1..401
                       mol_type = protein
                       organism = Streptomyces clavuligerus
SEQUENCE: 59
MSSTGSSAHY CPFDYAEALE FDPTLRRFMR EEPVARIRLP HGAGEAWLVT GYDDVRTVTT  60
DRRFSRHAVV GRDFPRMTPE PIVQDEAINV MDPPASSRLR SLVSKGFAPE QIERMRPYIQ  120
RAVDDLLDRM AEDSSADLMR HLAGPLPLIT ICEVLEIPPA DQETLRGHAR TMMNISVDNK  180
AAAVRAKADL RAYFADLTAR RRADPGEDLI SVLATARDGD ELLDDQELTV MAMVLLITGQ  240
DTTTYELGNL SYTLLTRPDV RDLLRDRPER LAQTINELLR FIPFRKGVGI PRVATEDVEL  300
SGVTIPAGDI VHVSYLTANR DGRKFDRPDE LDFDRTAPSH MTFGWGAHHC LGAPLAQAEM  360
ETAFRTLLER FPGIALAKPA EDVEWNTTSI WRYPLALPVT W                      401

SEQ ID NO: 60          moltype = DNA  length = 1206
FEATURE                Location/Qualifiers
misc_feature           1..1206
                       note = coding sequence for SEQ ID NO: 59
source                 1..1206
                       mol_type = other DNA
                       organism = synthetic construct
SEQUENCE: 60
atgtcctcca ccggttcctc tgctcactac tgtccattcg actacgccga agccttggaa  60
ttcgacccaa ctttgagaag attcatgaga gaagaaccag tcgctagaat cagattgcca  120
cacggtgctg gtgaagcttg gttggtcacc ggttacgacg atgttagaac cgttaccacc  180
gacagaagat tctctagaca cgccgttgtc ggtagagact tcccaagaat gactccagaa  240
ccaatcgtcc aagacgaagc catcaacgtc atggacccac cagcttcttc tagattgaga  300
tctttggttt ccaagggttt cgccccagaa caaatcgaaa gaatgaggcc atacatccaa  360
agagccgttg acgacttgtt ggacagaatg gctgaggact cctccgccga cttgatgaga  420
cacttggctg gtccattgcc attgatcacc atctgtgaag tcttggaaat cccaccagcc  480
gaccaagaaa ccttgagagg tcacgccaga actatgatga acatctctgt tgacaacaag  540
gccgccgccg ttagagccaa ggccgatttg agagcctact tcgctgactt gactgccaga  600
agaagagctg acccaggtga ggacttgatc tctgttttgg ccactgccag ggacggtgac  660
gaattgttgg acgaccaaga attgaccgtc atggctatgg tcttgttgat caccggtcaa  720
gacaccacca cctacgaatt gggtaacttg tcctacacct tgttgaccag accagacgtc  780
agagatttgt tgagagacag accagaaaga ttggctcaaa ctatcaacga attgttgaga  840
```

```
ttcatcccat tcagaaaggg tgtcggtatc ccaagagttg ccaccgagga cgttgaattg  900
tctggtgtta ctatcccagc cggtgacatc gtccacgtat cctacttgac cgccaacaga  960
gatggtagaa agttcgacag accagacgaa ttggacttcg acagaaccgc cccatcccac  1020
atgaccttcg gttggggtgc tcaccactgt ttgggtgccc cattggctca agccgaaatg  1080
gaaaccgcct tcagaacttt gttggaaaga ttcccaggta tcgctttggc taagccagcc  1140
gaggacgttg aatggaacac cacctctatc tggagatacc cattggcttt gccagtcacc  1200
tggtaa                                                             1206

SEQ ID NO: 61          moltype = AA  length = 246
FEATURE                Location/Qualifiers
source                 1..246
                       mol_type = protein
                       organism = Arabidopsis thaliana
SEQUENCE: 61
MSSSNACASP SPFPAVTKLH VDSVTFVPSV KSPASSNPLF LGGAGVRGLD IQGKFVIFTV  60
IGVYLEGNAV PSLSVKWKGK TTEELTESIP FFREIVTGAF EKFIKVTMKL PLTGQQYSEK  120
VTENCVAIWK QLGLYTDCEA KAVEKFLEIF KEETFPPGSS ILFALSPTGS LTVAFSKDDS  180
IPETGIAVIE NKLLAEAVLE SIIGKNGVSP GTRLSVAERL SQLMMKNKDE KEVSDHSVEE  240
KLAKEN                                                             246

SEQ ID NO: 62          moltype = DNA  length = 741
FEATURE                Location/Qualifiers
misc_feature           1..741
                       note = coding sequence for SEQ ID NO: 61
source                 1..741
                       mol_type = other DNA
                       organism = synthetic construct
SEQUENCE: 62
atgtcctcta gcaatgcgtg tgcctccccg tccccgttcc cggctgttac gaagctgcat  60
gtcgattcag ttacctttgt cccgtccgtg aagtccccgg cgagcagcaa cccgctgttt  120
ctgggcggtg caggtgtccg tggtctggat attcagggca aatttgtgat tttcaccgtg  180
atcggcgttt atctggaagg caatgcggtc ccgtcactgt cggtgaaatg gaagggtaaa  240
accacggaag aactgaccga atctattccg tttttccgcg aaatcgttac gggcgcgttc  300
gaaaagttca tcaaggtcac catgaaactg ccgctgacgg gtcagcaata ttcagaaaag  360
gttaccgaaa actgcgtcgc catctggaaa caactgggcc tgtacacgga ctgtgaagcg  420
aaggccgtcg aaaagtttct ggaaattttc aaagaagaaa cctttccgcc gggcagttcc  480
atcctgttcg cactgagccc gaccggttct ctgacggttg ctttcagtaa agatgactcc  540
atcccggaaa ccggcattgc agtgatcgaa aacaagctgc tggcagaagc tgttctggaa  600
agcattatcg gcaaaaatgg tgtgtcaccg ggtacgcgtc tgtcggttgc ggaacgcctg  660
agccagctga tgatgaaaaa taaagatgaa aaggaagtgt cggaccacag cgttgaagaa  720
aaactggcaa aggaaaacta a                                            741

SEQ ID NO: 63          moltype = AA  length = 719
FEATURE                Location/Qualifiers
source                 1..719
                       mol_type = protein
                       organism = Citrus sinensis
SEQUENCE: 63
MSEIGATTEN GHQNGGLEGL CKNNNYNYSS GDALNWGVMA ETLKGSHLEE VKRMVAEYRK  60
PVVNLGGETL TVAQVAAIAT SSTNVELSES AREGVKASSD WVMESMNKGT DSYGVTTGFG  120
ATSHRRTKNG GALQKELIRF LNAGIFGNGT ESSHTLPHSA TRAAMLVRVN TLLQGYSGIR  180
FEILEAITKL LNHNITPCLP LRGTITASGD LVPLSYIAGL LTGRPNSKAT GPNGEIIDAQ  240
EASKQAGFGF FELQPKEGLA LVNGTAVGSG LASMVLFEAN NLALLSEILS AIFAEVMQGK  300
PEFTDHLTHK LKHHPGQIEA AAIMEHILDG SSYVNVAKKL HEIDPLQKPK QDRYALRTSP  360
QWLGPQIEVI RFATKSIERE INSVNDNPLI DVSRNKALHG GNFQGTPIGV SMDNTRLAIA  420
AIGKLMFAQF SELVNDFYNN GLPSNLSGGR NPSLDYGFKG AEIAMASYCS ELQFLANPVT  480
NHVQSAEQHN QDVNSLGLIS SRKTAEAVDI LKLMSSTFLV ALCQAIDLRH LEENLKHTVK  540
NTVSQVAKKV LTVGASGELH PSRFCEKDLL KAADREHVFA YIDDPCSATY PLMQKLRQVL  600
VEHALNNGEN EKTANSSIFQ KIAAFEEELK TVLPKEVENA RQTVENGSPT IPNRIKECRS  660
YPLYRFVREG LGSNFLTGEK VTSPGEEFDK VFTAMCQGKI IDPMLECLRE WNGAPLPIC   719

SEQ ID NO: 64          moltype = DNA  length = 2160
FEATURE                Location/Qualifiers
misc_feature           1..2160
                       note = coding sequence for SEQ ID NO: 63
source                 1..2160
                       mol_type = other DNA
                       organism = synthetic construct
SEQUENCE: 64
atgtccgaaa tcggtgccac tactgaaaac ggtcaccaaa acggtggcct cgaaggcttg  60
tgtaagaaca ataactacaa ctactcttct ggtgatgctt tgaactgggg tgttatggct  120
gaaactttga agggttctca cttggaagaa gttaagagaa tggttgctga atacagaaag  180
ccagttgtca acttgggtgg tgaaactttg accgttgctc aagttgctgc cattgccact  240
tcctctacta acgttgaatt gtctgaatct gccagagaag gtgtcaaggc ctcttctgat  300
tgggttatgg aatctatgaa caagggtacc gactcttacg gtgttactac tggcttcggt  360
gccacttcgc acagaagaac caagaacggt ggtgctttgc aaaaggaatt gattagattc  420
ttgaacgctg gtatcttcgg taacggtact gaatcttctc acactttgcc acactctgct  480
actagagctg ccatgttggt tcgtgttaac acattgttgc aaggttactc cggtatcaga  540
ttcgaaatct tggaagctat cactaagttg ttgaaccaca acatcactcc atgtttgcca  600
```

```
ttgagaggta ctatcactgc ttctggtgat ttggttccat tgtcctacat agccggcttg  660
ttgaccggtc gtccaaactc taaggccacc ggtccaaacg gtgaaatcat tgatgcccaa  720
gaagcctcta agcaagctgg tttcggtttc ttcgaattgc aaccaaagga gggcttggct  780
ctcgtcaacg gtactgctgt tggttctggt ttggcttcta tggttttgtt cgaagctaac  840
aatctcgcgt tgttgtcgga aattttgtct gctattttcg ctgaagtcat gcaaggtaag  900
ccagaattca ccgatcactt gactcacaag ttgaagcacc acccaggtca aattgaagct  960
gctgctatca tggaacacat cttggatggt tcttcttacg ttaacgttgc taagaagttg  1020
cacgaaattg atccattgca aaagccaaag caagatagat acgccttgag aacttctcca  1080
caatggttgg gtccacaaat cgaagttatt agattcgcta ccaagtctat tgaaagagaa  1140
atcaactctg ttaacgacaa cccattgatc gacgtttcta gaaacaaggc cttgcacggt  1200
ggtaacttcc aaggtacccc aattggtgtc tctatggaca acaccagatt ggctattgct  1260
gctatcggta agttgatgtt cgcccaattc tctgaattgg tcaacgattt ctacaacaac  1320
ggtttgccat ctaacttgtc tggtggtaga aacccatctt tggattacgg tttcaagggt  1380
gctgaaattg ctatggcttc ctactgttct gaattgcaat tcttggccaa cccagttact  1440
aaccacgtcc aatctgctga acaacacaac caagatgtta actccttggg tttgatctct  1500
tccagaaaga ctgctgaagc tgtcgacatc ttgaagttga tgtcatccac tttcttggtt  1560
gctttgtgtc aagctattga tttgagacac ttggaagaaa acttgaagca cactgtcaag  1620
aacactgtct ctcaagttgc taagaaggtc ttgaccgtcg gtgcttctgg tgaattgcac  1680
ccatctagat tctgtgaaaa ggatttgttg aaggctgctg atagagaaca cgttttcgct  1740
tacattgatg acccatgttc tgctacctac ccattgatgc aaaagttgag acaagttttg  1800
gttgaacacg ctttgaacaa cggtgaaaac gaaaagactg ccaactcttc tatcttccaa  1860
aagattgctg ccttcgaaga agaattaaag accgtttttgc caaaggaagt tgaaaacgcc  1920
agacaaactg ttgaaaacgg ttctccaact attccaaaca gaatcaagga atgtagatct  1980
tacccattgt acagattcgt tagagaaggt ttgggttcta acttcttgac tggtgaaaag  2040
gttacttctc caggtgaaga attcgacaag gttttcactg ctatgtgtca aggtaagatc  2100
attgatccaa tgttggaatg tttgagagaa tggaacggtg ccccattgcc aatttgttaa  2160
```

```
SEQ ID NO: 65          moltype = AA  length = 715
FEATURE                Location/Qualifiers
source                 1..715
                       mol_type = protein
                       organism = Citrus sinensis
SEQUENCE: 65
MSEASHENQS GGNIPSGKLC TNIDPLNWVS ASESLKGSHL DEVKRMVSEY RKQVVRLGGE  60
TLTIAQVAAV ASRDGGVTVE LNEEARAGVK ASSDWVMESM NKGTDSYGIT TGFGATSHRR  120
TKQGAALQKE LIRFLNAGIF GKGTESCQML PHTATRAAML VRINTLLQGY SGIRFEILEA  180
ITKFLNRNIT PCLPLRASIT ASGDLIPFSY IAGLLTGRLN SVAVGPNGES LNAAEAFSQA  240
GIDGGFFELQ PKEGLALVNG TGVGAGLASI VLFEANILTV LSEVLSAIFA EAMLGKPEFT  300
DHLTHKLKHH PGQIEAAAIM EHILDGSSYV KAAQKLHEID PLQKPKQDRY ALRTSPQWLG  360
PQAEVIRAST KSIEREINSV NDNPLIDVSR NKALHGGNFQ GTPIGVSMDN SRLAIASIGK  420
LMFAQFSELV NDFYSNGLPS NLSGGRNPSL DYGFKGAEIA MAAYCSELQF LANPVTNHVQ  480
SAEQHNQDVN SLGLISARKT AEAVDILKLM SSTYLIALCQ AIDLRHLEEN LKSTVKNTIS  540
QVVKKVLTMG VNGELHPSRF CEKDLLKVVD REYVFSYADD PCSATYPLMQ KLRQVLVDHA  600
LTNNEDLKNA NASIFLKIGA FEEELKTLLP KEVESARSAF ESGNLEIPNR IKECRSYPLY  660
RFVREELGAR YLTGEKAISP GEECDKVFTA ICQGKIIDPL LECLKEWDGS PLPIC       715
```

```
SEQ ID NO: 66          moltype = DNA  length = 2148
FEATURE                Location/Qualifiers
misc_feature           1..2148
                       note = coding sequence for SEQ ID NO: 65
source                 1..2148
                       mol_type = other DNA
                       organism = synthetic construct
SEQUENCE: 66
atgtccgaag cttctcacga aaaccaatct ggtggtaaca ttccatctgg taagttgtgt  60
actaacattg atccattgaa ctgggtttct gcttctgaat ctttgaaggg ttctcacttg  120
gatgaagtta agagaatggt ttctgaatac agaaagcaag ttgttagatt gggtggtgaa  180
accttgacta tcgctcaagt tgctgctgtt gcttctagag atggtggtgt cactgttgaa  240
ttgaacgaag aagccagagc tggtgtcaag gcttcttctg attgggttat ggaatctatg  300
aacaagggta ctgattctta cggcatcact actggcttcg gtgctacttc gcacagaaga  360
accaagcaag gtgctgcctt gcaaaaggaa ttgattagat tcttgaacgc tggtatcttc  420
ggtaagggta ctgaatcctg tcaaatgttg ccacacactg ctactagagc tgctatgctc  480
gttcgtatca acacattgtt gcaaggttac tctggtatta gattcgaaat tttggaagct  540
atcactaagt tcttgaacag aaacattact ccatgtttgc cattgagagc ctccatcact  600
gcgtcgggtg atctcatccc attctcgtac atcgccggtt tgttgaccgg tagattgaac  660
tctgttgctg ttggtccaaa cggtgaatct ttgaacgctg ctgaagcttt ctctcaagct  720
ggtattgatg gtggtttctt cgaattgcaa ccaaaggagg gcttggcgtt ggttaacggt  780
actggtgttg gtgctggttt ggcttctatt gttttgttcg aagctaacat tttgactgtt  840
ttgtccgaag ttttgtctgc tattttcgct gaagctatgt tgggtaagcc agaattcact  900
gatcacttga ctcacaagtt gaagcaccac ccaggtcaaa ttgaagctgc tgctatcatg  960
gaacacatct tggatggttc ttcttacgtt aaggctgctc aaaagttgca cgaaattgac  1020
ccattgcaaa agccaaagca agatagatac gctttgagaa cttctccaca atggttgggt  1080
ccacaagctg aagttattag agcttctact aagtctattg aaagagaaat taactctgtt  1140
aacgataacc cattgattga tgtttctaga aacaaggctt tgcacggtgg taacttccaa  1200
ggtaccccaa ttggtgtctc tatggataac tctagattgg ctattgcttc tattggtaag  1260
ttgatgttcg ctcaattctc tgaattggtt aacgatttct actctaacgg tttgccatct  1320
aacttgtctg gtggtagaaa cccatctttg gattacggtt tcaagggtgc cgaaatcgct  1380
atggctgctt actgttccga attgcaattc ttggccaacc cagttactaa ccacgtccaa  1440
tctgctgaac aacacaacca agatgttaac tctttgggtt tgatctctgc cagaaagact  1500
```

```
gctgaagctg ttgatatctt gaagttgatg tcctctactt acttgattgc tttgtgtcaa  1560
gctatcgact tgagacactt ggaagaaaac ttgaagtcta ctgttaagaa cactatctct  1620
caagttgtta agaaggtctt gactatgggt gtcaacggtg aattgcaccc atctagattc  1680
tgtgaaaagg atttgttgaa ggttgttgat agagaatacg ttttctctta cgctgatgat  1740
ccatgttctg ctacttaccc attgatgcaa aagttgagac aagtcttggt tgatcacgct  1800
ttgactaaca acgaagattt gaagaacgct aacgcttcta tcttcttgaa aataggtgcg  1860
ttcgaagaag aactcaagac cttgttgcca aaggaagttg aatctgctag atctgctttc  1920
gaatctggta acttggaaat cccaaacaga attaaggaat gtagatccta cccattgtac  1980
agattcgtta gagaagaatt gggtgctaga tacttgactg gtgaaaaggc tatctctcca  2040
ggtgaagaat gtgataaggt tttcactgct atttgtcaag gtaagatcat tgatccattg  2100
ttggaatgtt tgaaggaatg ggatggttct ccattgccaa tttgttaa              2148
```

```
SEQ ID NO: 67          moltype = AA  length = 537
FEATURE                Location/Qualifiers
source                 1..537
                       mol_type = protein
                       organism = Citrus sinensis
SEQUENCE: 67
MSANLVTISF FSILLTISLL SFNKSLNLIS ITLPLVPLIA YVLKSFLKSS KAFYPPTPIS  60
IPIFGNWLQV GNDLNHRLLA SMAQIYGPVF RLKLGSKNLI VVSEPDLATQ VLHTQGVEFG  120
SRPRNVVFDI FTGNGQDMVF TVYGEHWRKM RRIMTLPFFT NKVVHNYSDM WEQEMDLVVH  180
DLKNDYESVS TKGIVIRKRL QLMLYNIMYR MMFDAKFESQ EDPLFIEATR FNSERSRLAQ  240
SFEYNYGDFI PLLRPFLRGY LNKCRDLQCR RLAFFNNNFV EKRRKIMAAN GEKHKISCAI  300
DHIIDAQMKG EITEENVIYI VENINVAAIE TTLWSMEWAI AELVNHPEVQ QKIRREISTV  360
LKGNPVTESN LHELPYLQAA VKEVLRLHTP IPLLVPHMNL EEAKLGGFTI PKESKIVVNA  420
WWLANNPKWW EKPEEFRPER FLEEECNIDA VAGGGKVDFR YLPFGVGRRS CPGIILALPI  480
LGLVIAKLVT SFEMKAPQGI DKIDVSEKGG QFSLHIANHS TVVFDPIMES LSQPMPQ     537
```

```
SEQ ID NO: 68          moltype = DNA  length = 1614
FEATURE                Location/Qualifiers
misc_feature           1..1614
                       note = coding sequence for SEQ ID NO: 67
source                 1..1614
                       mol_type = other DNA
                       organism = synthetic construct
SEQUENCE: 68
atgtccgcta acttggttac tatttctttc ttctctatct tgttgactat ctctttgttg  60
tctttcaaca agtctttgaa cttgatctct atcactttgc cattggttcc attgattgct  120
tacgttttga agtccttctt gaagtcatct aaggccttct acccaccaac tccaatctct  180
atcccaatct tcggtaactg gttgcaagtt ggtaacgact tgaaccacag attgttggct  240
tctatggctc aaatttacgg tccagttttc agattgaagt tgggttctaa gaacttgatc  300
gttgtttctg aaccagacct cgctactcaa gtgctacaca ctcaaggtgt tgaattcggt  360
tccagaccaa gaaacgttgt tttcgatatt ttcactggta acggtcaaga catggtattt  420
actgtctacg gcgaacactg gagaaagatg agaagaatta tgactttgcc attcttcacc  480
aacaaggttg ttcacaacta ctctgacatg tgggaacaag aaatggactt ggttgttcac  540
gacttgaaga acgattacga gtctgtaagc actaagggta ttgttattag aaagagattg  600
caattgatgt tgtacaacat tatgtacaga atgatgttcg atgctaagtt cgaatctcaa  660
gaagatccat tgttcattga agctactaga ttcaactctg aaagatctag attggcgcag  720
agcttcgaat acaactacgg tgatttcatt ccattgttaa gaccattctt gagaggttac  780
ttgaacaagt gtagagactt gcaatgtaga agattggctt tcttcaacaa caacttcgtt  840
gaaaagagaa gaaagatcat ggctgccaac ggtgaaaagc acaagatctc ttgtgccatt  900
gatcacatca ttgatgctca aatgaagggt gaaatcactg aagaaaacgt tatttacatt  960
gttgaaaaca tcaacgttgc tgctatcgaa actactttgt ggtccatgga atgggctatc  1020
gctgaattgg tcaaccaccc agaagttcaa caaaagatca gaagagaaat ctctactgtc  1080
ttgaagggta acccagtcac tgaatctaac ttgcacgaat tgccatactt gcaagccgct  1140
gttaaggaag ttttgagatt gcacactcca attccattgt tggttccaca catgaacttg  1200
gaagaagcta agttgggtgg tttcactatt ccaaaggaat ccaagattgt tgttaacgct  1260
tggtggttgg ctaacaaccc aaagtggtgg gaaaagccag aagaattcag accagaaaga  1320
ttcttggaag aagaatgtaa cattgatgct gttgctggtg gtggtaaggt tgacttcaga  1380
tacttgccat tcggtgttgg tagaagatct tgtccaggta taatattggc tctcccaatc  1440
ttgggcttgg ttattgctaa gttggttact tctttcgaaa tgaaggctcc acaaggtatc  1500
gataagattg acgtttctga aaagggtggt caattctctt tgcacattgc taaccactct  1560
actgttgtct ttgatccaat catggaatct ttgtcccaac caatgccaca ataa        1614
```

```
SEQ ID NO: 69          moltype = AA  length = 520
FEATURE                Location/Qualifiers
source                 1..520
                       mol_type = protein
                       organism = Citrus sinensis
SEQUENCE: 69
MSDLNGWCNS GNQNMCCCQS YVKRGYDRVL SFNGLITVSK LRGKRFKLPP GPLPVPVFGN  60
WLQVGDDLNH RNLSDLAKKY GDVLLLRMGQ RNLVVVSSPD HAKEVLHTQG VEFGSRTRNV  120
VFDIFTGKGQ DMVFTVYGEH WRKMRRIMTV PFFTNKVVQQ QRFNWEDEAA RVVEDVKKDP  180
EAATNGIVLR RRLQLMMYNN MYRIMFDRRF ESQDDPLFNR LKALNGERSR LAQSFEYNYG  240
DFIPILRPFL RGYLKICKEV KERRLQLFKD YFVEERKKLA STKSMSNESL KCAIDHILDA  300
QTKGEINEDN VLYIVENINV AAIETTLWSI EWGIAELVNH PEIQKKLRNE LDTVLGPGHQ  360
ITEPDTHKLP YLQAVIKETL RLRMAIPLLV PHMNLHDAKL GGYDVPAESK ILVNAWWLAN  420
NPAQWKKPEE FRPERFLEEE SKVEANGNDF RYLPFGVGRR SCPGIILALP ILGITIGRLV  480
QNFELLPPPG QSKIDTAEKG GQFSLHILKH STIVAKPRSF                       520
```

```
SEQ ID NO: 70          moltype = DNA  length = 1563
FEATURE                Location/Qualifiers
misc_feature           1..1563
                       note = coding sequence for SEQ ID NO: 69
source                 1..1563
                       mol_type = other DNA
                       organism = synthetic construct
SEQUENCE: 70
atgtccgact tgaacggttg gtgtaactct ggtaaccaaa acatgtgttg ttgtcaatct  60
tacgttaaga gaggttacga tagagttttg tctttcaacg gtttgattac cgtttctaag  120
ttgagaggta agagattcaa gttgccacca ggtccattgc cagtcccagt tttcggtaac  180
tggttgcaag tcggtgatga cttgaaccac agaaacttgt ccgacttggc caagaagtac  240
ggtgatgtct tgttgttgag aatgggtcaa agaaacttgg tcgtcgtttc ttctccagac  300
cacgccaagg aagtcttgca cactcaaggt gttgaattcg gttctagaac tcgtaatgtc  360
gtgttcgaca tcttcactgg taagggtcaa gatatggttt tcactgtcta cggcgaacac  420
tggagaaaga tgagaagaat catgaccgtc ccattcttca ctaacaaggt tgttcaacaa  480
caaagattca actgggaaga tgaagccgct agagtcgttg aagatgttaa gaaggaccca  540
gaagctgcta ccaacggtat cgtcttgaga agaagattgc aattgatgat gtacaacaac  600
atgtacagaa ttatgttcga tagaagattc gaatctcaag atgatccatt gttcaacaga  660
ttgaaggctt tgaacggtga aagatctaga ttggcgcaga gcttcgaata caactacggt  720
gatttcattc caattttaag accattcttg agaggttact tgaagatttg taaggaagtt  780
aaggaaagaa gattgcaatt gttcaaggac tacttcgttg aagaaagaaa gaagttggct  840
tctactaagt ctatgtctaa cgaatctttg aagtgtgcta tcgatcacat tttggacgct  900
caaactaagg gtgaaatcaa cgaagataac gttttgtaca tcgttgaaaa catcaacgtt  960
gccgctatcg aaactacttt gtggtctatc gaatggggta ttgctgaatt ggttaaccac  1020
ccagaaatcc aaaagaagtt gagaaacgaa ttggacaccg ttttgggtcc aggtcaccaa  1080
atcactgaac cagacaccca caagttgcca tacttgcaag ccgttatcaa ggaaactttg  1140
agattgagaa tggctattcc attgttggtt ccacacatga acttgcacga cgccaagttg  1200
ggtggttacg acgtcccagc tgaatctaag atcttggtta acgcttggtg gttggccaac  1260
aacccagccc aatggaagaa gccagaagaa ttcagaccag aaagattctt ggaagaagaa  1320
tccaaggttg aagctaacgg taacgacttc agatacttgc cattcggtgt tggtagaaga  1380
tcttgtccag gtataatatt ggctctccca attttgggca tcactattgg tagattggtt  1440
caaaacttcg aattgttgcc accaccaggt caatctaaga ttgacactgc tgaaaagggt  1500
ggtcaattct ctttgcacat tttgaagcac tctaccattg ttgccaagcc aagatctttc  1560
taa                                                                1563

SEQ ID NO: 71          moltype = AA  length = 513
FEATURE                Location/Qualifiers
source                 1..513
                       mol_type = protein
                       organism = Saccharothrix espanaensis
SEQUENCE: 71
MSTITSPAPA GRLNNVRPMT GEEYLESLRD GREVYIYGER VDDVTTHLAF RNSVRSIARL  60
YDVLHDPASE GVLRVPTDTG NGGFTHPFFK TARSSEDLVA AREAIVGWQR LVYGWMGRTP  120
DYKAAFFGTL DANAEFYGPF EANARRWYRD AQERVLYFNH AIVHPPVDRD RPADRTADIC  180
VHVEEETDSG LIVSGAKVVA TGSAMTNANL IAHYGLPVRD KKFGLVFTVP MNSPGLKLIC  240
RTSYELMVAT QGSPFDYPLS SRLDENDSIM IFDRVLVPWE NVFMYDAGAA NSFATGSGFL  300
ERFTFHGCTR LAVKLDFIAG CVMKAVEVTG TTHFRGVQAQ VGEVLNWRDV FWGLSDAMAK  360
SPNSWVGGSV QPNLNYGLAY RTFMGVGYPR IKEIIQQTLG SGLIYLNSSA ADWKNPDVRP  420
YLDRYLRGSR GIQAIDRVKL LKLLWDAVGT EFAGRHELYE RNYGGDHEGI RVQTLQAYQA  480
NGQAAALKGF AEQCMSEYDL DGWTRPDLIN PGT                               513

SEQ ID NO: 72          moltype = DNA  length = 1542
FEATURE                Location/Qualifiers
misc_feature           1..1542
                       note = coding sequence for SEQ ID NO: 71
source                 1..1542
                       mol_type = other DNA
                       organism = synthetic construct
SEQUENCE: 72
atgtccacca tcacttctcc agctccagct ggtagattga acaacgtcag accaatgact  60
ggtgaagaat acttggaatc tttgagagat ggtagagaag tctacatcta cggtgaaaga  120
gtcgacgacg tcaccactca cttggcctta agaaactctg ttagatccat cgctagattg  180
tacgacgttt tgcacgaccc agcttcggag ggtgtactaa gagttccaac cgacactggt  240
aatggtggct tcactcatcc attcttcaag accgcccgtt cttctgaaga tttggtcgcc  300
gctagagaag ccatcgtcgg ttggcaaaga ttggtttacg gttggatggg tagaacccca  360
gattacaagg ctgcgttctt cggtactctc gacgccaacg ccgaattcta cggtccattc  420
gaagccaacg ccagaagatg gtacagagat gcccaagaaa gagttttgta cttcaaccac  480
gctatcgttc acccaccagt cgacagagac agaccagccg acagaaccgc cgacatctgt  540
gttcacgttg aagaagaaac cgactctggt ttgatcgttt ccggtgccaa ggttgtcgct  600
accggttccg ctatgaccaa cgctaacttg atcgctcact acggtttgcc agttagagac  660
aagaagttcg gtttggtttt cactgtccca atgaactctc caggtttgaa gttgatctgt  720
agaacctcct acgaattgat ggtcgctact caaggttctc cattcgacta cccattatct  780
tctagattgg acgaaaacga ctctatcatg atcttcgaca gagttttggt tccatgggaa  840
aacgttttca tgtacgacgc tggtgctgcc aactccttcg ccaccggttc tggtttcttg  900
gaaagattca ccttccacgg ttgtaccaga ttggctgtca agttggactt catcgccggt  960
tgtgtcatga aggctgttga agtcaccggt accactcact tcagaggtgt tcaagctcaa  1020
gtcggtgaag ttttgaactg gagagatgtt ttctggggtt tgtccgacgc tatggccaag  1080
```

```
tctccaaact cttgggtcgg tggttctgtt caaccaaact tgaactacgg tttggcttac  1140
agaaccttca tgggtgttgg ttacccaaga atcaaggaaa tcatccaaca aaccttgggt  1200
tctggtttga tctacttgaa ctcctctgcc gccgactgga agaacccaga cgtcagacca  1260
tacttggaca gatacttgag aggttctaga ggtatccaag ctatcgacag agtcaagttg  1320
ttgaagttgt tgtgggacgc tgtcggtacc gaattcgccg gtagacacga attgtacgaa  1380
agaaactacg gtggtgacca cgaaggtatc agagttcaaa ccttgcaagc ttaccaagct  1440
aacggtcagg cggccgctct caagggtttc gcggaacaat gtatgtccga atacgacttg  1500
gacggttgga ctagaccaga cttgatcaac ccaggtacct aa                     1542

SEQ ID NO: 73           moltype = AA  length = 498
FEATURE                 Location/Qualifiers
source                  1..498
                        mol_type = protein
                        organism = Beta vulgaris
SEQUENCE: 73
MSDHATLAMI LAILFISFHF IKLLFSQQTT KLLPPGPKPL PIIGNILEVG KKPHRSFANL  60
AKIHGPLISL RLGSVTTIVV SSADVAKEMF LKKDHPLSNR TIPNSVTAGD HHKLTMSWLP  120
VSPKWRNFRK ITAVHLLSPQ RLDACQTFRH AKVQQLYEYV QECAQKGQAV DIGKAAFTTS  180
LNLLSKLFFS VELAHHKSHT SQEFKELIWN IMEDIGKPNY ADYFPILGCV DPSGIRRRLA  240
CSFDKLIAVF QGIICERLAP DSSTTTTTTT DDVLDVLLQL FKQNELTMGE INHLLVDIFD  300
AGTDTTSSTL EWVMTELIRN PEMMEKAQEE IKQVLGKDKQ IQESDIINLP YLQAIIKETL  360
RLHPPTVFLL PRKADTDVEL YGYIVPKDAQ ILVNLWAIGR DPNAWQNADI FSPERFIGCE  420
IDVKGRDFGL LPFGAGRRIC PGMNLAIRML TLMLATLLQF FNWKLEGDIS PKDLDMDEKF  480
GIALQKTKPL KLIPIPRY                                               498

SEQ ID NO: 74           moltype = DNA  length = 1497
FEATURE                 Location/Qualifiers
misc_feature            1..1497
                        note = coding sequence for SEQ ID NO: 73
source                  1..1497
                        mol_type = other DNA
                        organism = synthetic construct
SEQUENCE: 74
atgtccgatc acgctacttt ggcgatgata ttggccatcc tattcatttc tttccacttc  60
atcaagttgt tgttctctca acaaactacc aagttgttgc caccaggtcc aaagccattg  120
ccaatcattg gtaacatctt ggaagttggt aagaagccac acagatcttt cgctaacttg  180
gctaagattc acggtccatt gatctctttg agattgggtt ctgttactac tattgttgtt  240
tcttctgctg atgttgctaa ggaaatgttc ttgaagaagg accacccatt gtctaacaga  300
actattccaa actctgtcac tgccggtgac caccacaagt tgaccatgtc ttggttgcca  360
gtttctccaa agtggagaaa cttcagaaag attactgccg tccacttgtt gtctccacaa  420
agattggatg cttgtcaaac cttcagacac gccaaggttc aacaattgta cgaatacgtt  480
caagaatgtg ctcaaaaggg tcaagctgtt gatattggta aggctgcttt cactacctcc  540
ttgaacttgt tgtctaagtt gttcttctct gttgaattgg cccaccacaa gtctcacact  600
tctcaagaat tcaaggaatt gatctggaac attatggaag atattggtaa gccaaactac  660
gctgattact tcccaatttt gggttgtgtt gatccatctg gtattagaag aagattggct  720
tgttctttcg acaagttgat tgctgttttc caaggtatca tctgtgaaag attggctcca  780
gattcttcta ctacaaccac tactaccact gatgatgttt tggacgtttt gttgcaattg  840
ttcaagcaaa acgaattgac tatgggtgaa attaaccact tgttggtcga cattttcgat  900
gctggtactg acactacttc ttctactttg gaatgggtca tgactgaatt gattagaaac  960
ccagaaatga tggaaaaggc tcaagaagaa attaagcaag ttttgggtaa ggataagcaa  1020
attcaagaat ctgacattat taacttgcca tacttgcaag ccattatcaa ggaaactttg  1080
agattgcacc caccaactgt tttcttgttg ccaagaaagg ccgacactga tgttgaattg  1140
tacggttaca ttgttccaaa ggatgctcaa atcttggtta acttgtgggc tattggtaga  1200
gatccaaacg cttggcaaaa cgctgatatt ttctctccag aaagattcat cggttgtgaa  1260
attgatgtca agggtagaga tttcggtttg ttgccattcg gtgccggtag aagaatctgt  1320
ccaggtatga acttggccat tagaatgttg actttgatgt tggctacttt gttgcaattc  1380
ttcaactgga agttggaagg tgacatctct ccaaaggact tggacatgga tgaaaagttc  1440
ggtattgctt tgcaaaagac taagccattg aagttgattc caatcccaag atactaa     1497

SEQ ID NO: 75           moltype = AA  length = 413
FEATURE                 Location/Qualifiers
source                  1..413
                        mol_type = protein
                        organism = Rhodopseudomonas palustris
SEQUENCE: 75
MSTTAPSLVP VTTPSQHGAG VPHLGIDPFA LDYFADPYPE QETLREAGPV VYLDKWNVYG  60
VARYAEVYAV LNDPLTFCSS RGVGLSDFKK EKPWRPPSLI LEADPPAHTR TRAVLSKVLS  120
PATMKRLRDG FAAAADAKID ELLARGGNID AIADLAEAYP LSVFPDAMGL KQEGRENLLP  180
YAGLVLNAFG PPNELRQSAI ERSAPHQAYV AEQCQRPNLA PGGFGACIHA FSDTGEITPE  240
EAPLLVRSLL SAGLDTTVNG IAAAVYCLAR FPDEFARLRA DPSLARNAFE EAVRFESPVQ  300
TFFRTTTRDV ELAGATIGEG EKVLMFLGSA NRDPRRWDDP DRYDITRKTS GHVGFGSGVH  360
MCVGQLVARL EGEVVLAALA RKVAAIEIAG PLKRRFNNTL RGLESLPIQL TPA        413

SEQ ID NO: 76           moltype = DNA  length = 1242
FEATURE                 Location/Qualifiers
misc_feature            1..1242
                        note = coding sequence for SEQ ID NO: 75
source                  1..1242
                        mol_type = other DNA
```

```
                         organism = synthetic construct
SEQUENCE: 76
atgtccacca ctgctccatc tttggttcca gttaccactc catcccaaca cggtgctggt  60
gttccacact tgggtatcga tccattcgct ttggactact tcgccgatcc atacccagaa  120
caagaaactt tgagagaagc tggtccagtt gtctacttgg acaagtggaa cgtctacggt  180
gtcgccagat acgctgaagt atacgccgta ctcaacgatc cattgacctt ctgttcctct  240
agaggtgttg gtttgtctga tttcaagaag gaaaagccat ggaggccacc atctttgatc  300
ttggaagccg acccaccagc tcacaccaga accagagctg ttttgtctaa ggttttgtct  360
ccagctacta tgaagagatt gagagatggt ttcgctgctg ctgctgacgc caagatcgat  420
gaattgttgg ccagaggtgg taacatcgat gctatcgccg acttggccga agcctaccca  480
ttgtctgttt tcccagatgc gatgggtttg aagcaagaag gcagagaaaa cttgttgcca  540
tacgcgggct tggttttgaa cgcattcggt ccaccaaacg aattgagaca atctgctatc  600
gaaagatctg ctccacacca agcctacgtt gccgaacaat gtcaaagacc aaacttggct  660
ccaggtggtt tcggtgcctg tatccacgcc ttctctgaca ccggtgaaat cactccagaa  720
gaagccccat tgttggttag atctttgttg tctgctggtt tggacactac cgtcaacggt  780
attgctgctg ctgtttactg tttggctaga ttcccagacg aattcgctag attgagagcc  840
gatccatctt tggccagaaa cgccttcgaa gaagctgtta gattcgaatc tccagttcaa  900
accttcttca gaaccaccac tagagatgtc gaattggctg gtgccactat cggtgaaggt  960
gaaaaggttt tgatgttctt gggttccgcc aacagagatc caagaagatg ggacgatcca  1020
gacagatacg acatcaccag aaagacctct gggcatgtcg gcttcggttc tggtgttcac  1080
atgtgtgtcg gtcaattggt cgccagattg gaaggtgaag ttgttttggc cgctttggct  1140
agaaaggttg ctgctatcga aatcgccggt ccattgaaga gaagattcaa caacactttg  1200
agaggtttgg aatctttgcc aatccaattg actccagctt aa                     1242

SEQ ID NO: 77            moltype = AA  length = 718
FEATURE                  Location/Qualifiers
source                   1..718
                         mol_type = protein
                         organism = Arabidopsis thaliana
SEQUENCE: 77
MSDQIEAMLC GGGEKTKVAV TTKTLADPLN WGLAADQMKG SHLDEVKKMV EEYRRPVVNL  60
GGETLTIGQV AAISTVGGSV KVELAETSRA GVKASSDWVM ESMNKGTDSY GVTTGFGATS  120
HRRTKNGTAL QTELIRFLNA GIFGNTKETC HTLPQSATRA AMLVRVNTLL QGYSGIRFEI  180
LEAITSLLNH NISPSLPLRG TITASGDLVP LSYIAGLLTG RPNSKATGPD GESLTAKEAF  240
EKAGISTGFF DLQPKEGLAL VNGTAVGSGM ASMVLFEANV QAVLAEVLSA IFAEVMSGKP  300
EFTDHLTHRL KHHPGQIEAA AIMEHILDGS SYMKLAQKVH EMDPLQKPKQ DRYALRTSPQ  360
WLGPQIEVIR QATKSIEREI NSVNDNPLID VSRNKAIHGG NFQGTPIGVS MDNTRLAIAA  420
IGKLMFAQFS ELVNDFYNNG LPSNLTASSN PSLDYGFKGA EIAMASYCSE LQYLANPVTS  480
HVQSAEQHNQ DVNSLGLISS RKTSEAVDIL KLMSTTFLVG ICQAVDLRHL EENLRQTVKN  540
TVSQVAKKVL TTGINGELHP SRFCEKDLLK VVDREQVFTY VDDPCSATYP LMQRLRQVIV  600
DHALSNGETE KNAVTSIFQK IGAFEEELKA VLPKEVEAAR AAYGNGTAPI PNRIKECRSY  660
PLYRFVREEL GTKLLTGEKV VSPGEEFDKV FTAMCEGKLI DPLMDCLKEW NGAPIPIC    718

SEQ ID NO: 78            moltype = DNA  length = 2157
FEATURE                  Location/Qualifiers
misc_feature             1..2157
                         note = coding sequence for SEQ ID NO: 77
source                   1..2157
                         mol_type = other DNA
                         organism = synthetic construct
SEQUENCE: 78
atgtccgatc aaatcgaagc tatgttgtgt ggtggtggtg aaaaaacaaa agttgctgtt  60
actactaaga ccttggccga tccattgaat tggggtttgg ctgctgatca aatgaagggt  120
tctcatttgg atgaagtcaa gaagatggtc gaagaataca gaaggccagt tgttaatttg  180
ggtggtgaaa ctttgactat tggtcaagtt gctgctattt ctactgttgg tggttctgtt  240
aaggttgaat tggctgaaac ttctagagct ggtgttaagg cttcttctga ttgggttatg  300
gaatctatga acaagggtac tgattcttac ggtgttacta caggttttgg tgctacttct  360
catagaagaa ctaagaatgg tactgccttg caaaccgaat tgatcagatt tttgaacgcc  420
ggtattttcg gtaacaccaa agaaacttgt catacccttgc cacaatctgc tactagagct  480
gctatgttgg ttagagttaa cactttgttg caaggttact ccggtatcag attcgaaatt  540
ttggaagcta tcacctcctt gttgaaccat aacatttctc catctttgcc attgagaggt  600
actattactg cttctggtga tttggttcca ttgtcttata ttgctggttt gttgactggt  660
agaccaaact ctaaagctac tggtccagat ggtgaatcat tgactgctaa agaagctttt  720
gaaaaggctg gtatctctac tggttttttc gacttgcaac ctaaagaagg tttggctttg  780
gttaatggta cagctgttgg ttctggtatg gcttctatgg ttttgtttga agctaacgtt  840
caagctgttt tggccgaagt tttgtctgct atttttgctg aagttatgtc cggtaagcca  900
gaattcactg atcatttgac ccatagattg aaacatcacc caggtcaaat tgaagctgct  960
gcaattatgg aacatatctt ggatggttcc tcttacatga agttggctca aaaagttcac  1020
gaaatggacc cattgcaaaa gccaaaacaa gatagatacg ctttgagaac ttctccacaa  1080
tggttgggtc cacaaataga agttattaga caagccacca agtccatcga aagagaaatc  1140
aattctgtta acgacaaccc attgatcgac gtcagtagaa acaaagctat tcatggtggt  1200
aacttccaag gtactccaat tggtgtttct atggacaaca ctagattggc tattgctgcc  1260
attggtaaat tgatgttcgc tcaattctcc gaattggtca acgattttta caacaacggt  1320
ttgccttcta acttgaccgc ttcttctaat ccatcattgg attacggttt taagggtgct  1380
gaaattgcta tggcttcata ctgttctgaa ttgcaatact tggctaaccc agttacctct  1440
catgttcaat ctgctgaaca acacaatcaa gacgttaact ccttgggttt gatctcttct  1500
agaaagactt ctgaagccgt tgacatcttg aagttgatgt ctactacatt cttggtcggt  1560
atttgccaag ctgttgattt gagacatttg gaagaaaact tgagacaaac cgtcaagaac  1620
accgtttcac aagttgctaa gaaagttttg accaccggta ttaacggtga attgcatcca  1680
```

```
tctagattct gcgaaaagga tttgttgaag gtcgttgata gagaacaagt tttcacctac  1740
gttgatgatc catgttctgc tacttatcca ttgatgcaaa gattgagaca agtcatcgtt  1800
gatcatgctt tgtctaatgg tgaaaccgaa aagaacgctg ttacctccat tttccaaaag  1860
attggtgctt tcgaagaaga attgaaggcc gttttgccaa aagaagttga agcagctaga  1920
gcagcttacg gtaacggtac tgctccaatt ccaaatagaa tcaaagaatg cagatcctac  1980
ccattataca gattcgttag agaagaatta ggtactaagt tgttgaccgg tgaaaaggtt  2040
gtttctccag gtgaagaatt cgataaggtt ttcactgcta tgtgcgaagg taaattgatc  2100
gatccattga tggactgctt gaaagaatgg aatggtgctc ctattcctat ctgctaa     2157

SEQ ID NO: 79          moltype = AA  length = 506
FEATURE                Location/Qualifiers
source                 1..506
                       mol_type = protein
                       organism = Arabidopsis thaliana
SEQUENCE: 79
MSDLLLLEKS LIAVFVAVIL ATVISKLRGK KLKLPPGPIP IPIFGNWLQV GDDLNHRNLV  60
DYAKKFGDLF LLRMGQRNLV VVSSPDLTKE VLLTQGVEFG SRTRNVVFDI FTGKGQDMVF  120
TVYGEHWRKM RRIMTVPFFT NKVVQQNREG WEFEAASVVE DVKKNPDSAT KGIVLRKRLQ  180
LMMYNNMFRI MFDRRFESED DPLFLRLKAL NGERSRLAQS FEYNYGDFIP ILRPFLRGYL  240
KICQDVKDRR IALFKKYFVD ERKQIASSKP TGSEGLKCAI DHILEAEQKG EINEDNVLYI  300
VENINVAAIE TTLWSIEWGI AELVNHPEIQ SKLRNELDTV LGPGVQVTEP DLHKLPYLQA  360
VVKETLRLRM AIPLLVPHMN LHDAKLAGYD IPAESKILVN AWWLANNPNS WKKPEEFRPE  420
RFFEEESHVE ANGNDFRYVP FGVGRRSCPG IILALPILGI TIGRMVQNFE LLPPPGQSKV  480
DTSEKGGQFS LHILNHSIIV MKPRNC                                     506

SEQ ID NO: 80          moltype = DNA  length = 1521
FEATURE                Location/Qualifiers
misc_feature           1..1521
                       note = coding sequence for SEQ ID NO: 79
source                 1..1521
                       mol_type = other DNA
                       organism = synthetic construct
SEQUENCE: 80
atgtccgact tgttgttgtt ggaaaagtcc ttgattgctg ttttcgttgc tgttattttg  60
gccaccgtta tctctaaatt gagaggtaag aaattgaagt tgccaccagg tccaattcca  120
atcccaattt ttggtaattg gttgcaagtt ggtgatgact tgaaccacag aaacttggtt  180
gattacgcta aaaagttcgg tgatttgttc ttgttgagaa tgggtcaaag aaatttggtc  240
gttgtttcct caccagactt gaccaaagaa gttttgttga ctcaaggtgt cgaattcggt  300
tccagaacta gaaatgttgt tttcgatatc ttcaccggta agggtcaaga tatggttttt  360
actgtttacg gtgaacattg gagaaagatg agaagaatta tgaccgttcc attcttcacc  420
aacaaggttg tccaacaaaa cagagaaggt tgggaatttg aagctgcttc tgttgttgaa  480
gatgtcaaga agaatccaga ttctgctact aagggtatcg ttttgagaaa aagattgcaa  540
ttgatgatgt acaacaacat gttcagaatc atgttcgaca gaagatttga atccgaagat  600
gacccctttgt ttttgagatt gaaggctttg aacggtgaaa gatctagatt ggctcaatcc  660
ttcgaataca actacggtga tttcatccca atcttaagac cattcttgag aggttacttg  720
aagatctgcc aagatgttaa ggatagaaga atcgccttgt tcaaaaagta cttcgttgac  780
gaaagaaagc aaatcgcttc ttctaaacct actggttctg aaggtttgaa gtgcgccatt  840
gatcatattt tggaagctga acaaaagggt gaaatcaacg aagataacgt cttgtacatc  900
gtcgaaaaca ttaacgttgc tgctattgaa actaccttgt ggtctattga atggggtatt  960
gctgaattgg ttaatcaccc agaaatccaa tccaagttga gaaacgaatt ggatactgtt  1020
ttgggtccag gtgttcaagt tactgaacct gacttgcata agttgccata cttgcaagct  1080
gttgtaaaag aaaccttgag attaagaatg gccatccctt tgttggttcc acatatgaac  1140
ttgcatgatg ctaaattggc cggttatgat attccagccg aatccaagat tttggttaat  1200
gcttggtggt tggctaacaa tccaaattct tggaaaaagc cagaagaatt cagaccagaa  1260
agatttttcg aagaagaaag tcacgttgaa gccaacggta atgattttag atacgttcca  1320
tttggtgttg gtagaagatc ttgtccaggt attatcttgg ctttgccaat tttgggtatt  1380
accatcggta gaatggtcca aaacttcgaa ttattgccac cacctggtca atctaaggtt  1440
gatacttctg aaaagggtgg tcaattctcc ttgcatattt tgaaccactc catcatcgtt  1500
atgaagccaa gaaactgtta a                                          1521

SEQ ID NO: 81          moltype = AA  length = 384
FEATURE                Location/Qualifiers
source                 1..384
                       mol_type = protein
                       organism = Saccharomyces cerevisiae
SEQUENCE: 81
MSKSKTFLFT SESVGEGHPD KICDQVSDAI LDACLEQDPF SKVACETAAK TGMIMVFGEI  60
TTKARLDYQQ IVRDTIKKIG YDDSAKGFDY KTCNVLVAIE QQSPDIAQGL HYEKSLEDLG  120
AGDQGIMFGY ATDETPEGLP LTILLAHKLN MAMADARRDG SLPWLRPDTK TQVTVEYEDD  180
NGRWVPKRID TVVISAQHAD EISTADLRTQ LQKDIVEKVI PKDMLDENTK YFIQPSGRFV  240
IGGPQGDAGL TGRKIIVDAY GGASSVGGGA FSGKDYSKVD RSAAYAARWV AKSLVAAGLC  300
KRVQVQFSYA IGIAEPLSLH VDTYGTATKS DDEIIEIIKK NFDLRPGVLV KELDLARPIY  360
LPTASYGHFT NQEYSWEKPK KLEF                                       384

SEQ ID NO: 82          moltype = DNA  length = 1155
FEATURE                Location/Qualifiers
misc_feature           1..1155
                       note = coding sequence for SEQ ID NO: 81
source                 1..1155
```

```
                        mol_type = other DNA
                        organism = synthetic construct
SEQUENCE: 82
atgtccaaga gcaaaacttt cttatttacc tctgaatccg tcggtgaagg tcacccagac  60
aagatttgtg accaagtttc tgatgctatt ttggacgctt gtttagaaca agatccattc  120
tccaaggttg cctgtgaaac agctgccaaa actggtatga ttatggtttt cggtgaaatt  180
accaccaaag ctagacttga ctaccaacaa atagtaagag ataccatcaa gaagattggt  240
tatgacgatt ctgccaaggg tttcgactac aagacatgta atgttttagt agctatcgaa  300
caacaatctc cagatatcgc tcaaggtctg cactatgaaa agagcttaga agatttaggt  360
gctggtgacc aaggtataat gtttggttac gctacagacg aaactccaga agggttacca  420
ttgaccattc ttttggctca caaattgaac atggctatgg cagatgctag aagagatggt  480
tctctcccat ggttgaggcc agacacaaag actcaagtca ctgtcgaata cgaggacgac  540
aatggtagat gggttccaaa gaggatagat accgttgtta tttctgctca acatgctgat  600
gaaatttcca ccgctgactt gagaactcaa cttcaaaaag atattgttga aaaggtcata  660
ccaaaggata tgttagacga aaataccaaa tatttcatcc aaccatccgg tagattcgtc  720
atcggtggtc ctcaaggtga cgctggtttg accggtagaa agattattgt cgacgcttac  780
ggtggtgcct catccgtcgg tggtggtgcc ttctccggta aggactattc caaggtcgat  840
cgttccgctg cttacgctgc tagatgggtt gccaagtctc tagttgccgc tggtttgtgt  900
aagagagtcc aagtccaatt ttcatatgct attggtattg ctgaaccatt gtctttacat  960
gtggacacct atggtacagc tacaaaatca gatgacgaaa tcattgaaat tattaagaag  1020
aacttcgact tgaggccagg tgtgttagta aaggaattag atttggctag accaatttac  1080
ttaccaaccg cttcttatgg tcacttcact aatcaagagt actcatggga aaaaccaaag  1140
aaattggaat tttaa                                                   1155

SEQ ID NO: 83           moltype = AA  length = 521
FEATURE                 Location/Qualifiers
source                  1..521
                        mol_type = protein
                        organism = Escherichia coli
SEQUENCE: 83
MSKPEDFRAS TQRPFTGEEY LKSLQDGREI YIYGERVKDV TTHPAFRNAA ASVAQLYDAL  60
HKPEMQDSLC WNTDTGSGGY THKFFRVAKS ADDLRQQRDA IAEWSRLSYG WMGRTPDYKA  120
AFGCALGANP GFYGQFEQNA RNWYTRIQET GLYFNHAIVN PPIDRHLPTD KVKDVYIKLE  180
KETDAGIIVS GAKVVATNSA LTHYNMIGFG SAQVMGENPD FALMFVAPMD ADGVKLISRA  240
SYEMVAGATG SPYDYPLSSR FDENDAILVM DNVLIPWENV LIYRDFDRCR RWTMEGGFAR  300
MYPLQACVRL AVKLDFITAL LKKSLECTGT LEFRGVQADL GEVVAWRNTF WALSDSMCSE  360
ATPWVNGAYL PDHAALQTYR VLAPMAYAKI KNIIERNVTS GLIYLPSSAR DLNNPQIDQY  420
LAKYVRGSNG MDHVQRIKIL KLMWDAIGSE FGGRHELYEI NYSGSQDEIR LQCLRQAQNS  480
GNMDKMMAMV DRCLSEYDQD GWTVPHLHNN DDINMLDKLL K                      521

SEQ ID NO: 84           moltype = DNA  length = 1566
FEATURE                 Location/Qualifiers
misc_feature            1..1566
                        note = coding sequence for SEQ ID NO: 83
source                  1..1566
                        mol_type = other DNA
                        organism = synthetic construct
SEQUENCE: 84
atgtccaaac cagaagattt ccgcgccagt acccaacgtc ctttcaccgg ggaagagtat  60
ctgaaaagcc tgcaggatgg tcgcgagatc tatatctatg gcgagcgagt gaaagacgtc  120
accactcatc cggcatttcg taatgcggca gcgtctgttg cccagctgta cgacgcactg  180
cacaaaccgg agatgcagga ctctctgtgt tggaacaccg acaccggcag cggcggctat  240
acccataaat tcttccgcgt ggcgaaaagt gccgacgacc tgcgccagca acgcgacgcc  300
atcgctgagt ggtcacgcct gagctatggc tggatgggcc gtaccccaga ctacaaagcc  360
gctttcggtt gcgcactggg cgcgaatccg ggcttttacg gtcagttcga gcagaacgcc  420
cgtaactggt acacccgtat tcaggaaact ggcctctact ttaaccacgc gattgttaac  480
ccaccgatcg atcgtcattt gccgaccgat aaagtgaaag acgtttacat caagctggaa  540
aaagagactg acgccgggat tatcgtcagc ggtgcgaaag tggttgccac caactcggcg  600
ctgactcact acaacatgat tggcttcggc tcggcacaag tgatgggcga aaacccggac  660
ttcgcactga tgttcgttgc gccaatggat gccgatggcg tgaaattaat ctcccgcgcc  720
tcttatgaga tggtcgcggg tgctaccggc tcgccatacg actacccgct ctccagccgc  780
ttcgatgaga acgatgcgat tctggtgatg gataacgtgc tgattccatg ggaaaacgtg  840
ctgatctacc gcgattttga tcgctgccgt cgctggacga tggaaggcgg ttttgcccgt  900
atgtatccgc tgcaagcctg tgtgcgcctg gcagtgaaat tagacttcat tacggcactg  960
ctgaaaaaat cactcgaatg taccggcacc ctggagttcc gtggtgtgca ggccgatctc  1020
ggtgaagtgg tagcgtggcg caacaccttc tgggcattga gtgactcgat gtgttcagaa  1080
gcaacgccgt gggtcaacgg ggcttattta ccggatcatg ccgcactgca aacctatcgc  1140
gtactggcac caatggccta cgcgaagatc aaaaacatta tcgaacgcaa cgttaccagt  1200
ggcctgatct atctcccttc cagtgcccgt gacctgaata atccgcagat cgaccagtat  1260
ctggcgaagt atgtgcgcgg ttcgaacggt atggatcacg tccagcgcat caagatcctc  1320
aaactgatgt gggatgctat tggcagcgaa tttggtggtc gtcacgaact gtatgaaatc  1380
aactactccg gtagccagga tgagattcgc ctgcagtgtc tgcgccaggc acaaaactcc  1440
ggcaatatgg acaagatgat ggcgatggtt gatcgctgcc tgtcggaata cgaccaggac  1500
ggctggactg tgccgcacct gcacaacaac gacgatatca acatgctgga taagctgctg  1560
aaataa                                                             1566

SEQ ID NO: 85           moltype = AA  length = 171
FEATURE                 Location/Qualifiers
source                  1..171
```

```
                        mol_type = protein
                        organism = Escherichia coli
SEQUENCE: 85
MSQLDEQRLR FRDAMASLSA AVNIITTEGD AGQCGITATA VCSVTDTPPS LMVCINANSA  60
MNPVFQGNGK LCVNVLNHEQ ELMARHFAGM TGMAMEERFS LSCWQKGPLA QPVLKGSLAS  120
LEGEIRDVQA IGTHLVYLVE IKNIILSAEG HGLIYFKRRF HPVMLEMEAA I           171

SEQ ID NO: 86           moltype = DNA  length = 516
FEATURE                 Location/Qualifiers
misc_feature            1..516
                        note = coding sequence for SEQ ID NO: 85
source                  1..516
                        mol_type = other DNA
                        organism = synthetic construct
SEQUENCE: 86
atgtcccaat tagatgaaca acgcctgcgc tttcgtgacg cgatggccag cctgtcggca  60
gcggtaaata ttatcaccac cgagggcgac gccggacaat gcgggattac ggcaacggcc  120
gtctgctcgg tcacggatac accaccgtcg ctgatggtgt gcattaacgc caacagtgcg  180
atgaacccgg tttttcaggg caacggcaag ttgtgcgtca acgtcctcaa ccatgagcag  240
gaactgatgg cacgccactt cgcgggcatg acaggcatgg cgatggaaga gcgttttagc  300
ctctcatgct ggcaaaaagg tccgctggcg cagccggtgc taaaaggttc gctggccagt  360
cttgaaggtg agatccgcga tgtgcaggca attggcacac atctggtgta tctggtggag  420
attaaaaaca tcatcctcag tgcagaaggt catggactta tctactttaa acgccgtttc  480
catccggtga tgctggaaat ggaagctgcg atttaa                            516

SEQ ID NO: 87           moltype = AA  length = 233
FEATURE                 Location/Qualifiers
source                  1..233
                        mol_type = protein
                        organism = Arabidopsis thaliana
SEQUENCE: 87
MSAKDEAKGL LKSEELYKYI LETSVYPREP EVLRELRNIT HNHPQAGMAT APDAGQLMGM  60
LLNLVNARKT IEVGVFTGYS LLLTALTLPE DGKVIAIDMN RDSYEIGLPV IKKAGVEHKI  120
DFKESEALPA LDELLNNKVN EGGFDFAFVD ADKLNYWNYH ERLIRLIKVG GIIVYDNTLW  180
GGSVAEPDSS TPEWRIEVKK ATLELNKKLS ADQRVQISQA ALGDGITICR RLY         233

SEQ ID NO: 88           moltype = DNA  length = 702
FEATURE                 Location/Qualifiers
misc_feature            1..702
                        note = coding sequence for SEQ ID NO: 87
source                  1..702
                        mol_type = other DNA
                        organism = synthetic construct
SEQUENCE: 88
atgtccgcta aggatgaagc caagggtttg ttgaagtctg aagaattgta caagtacatc  60
ttggaaactt ctgtttaccc aagagaacca gaagttttga gagaattgag aaacattact  120
cacaaccacc cacaagctgg tatggctact gctccagacg ctggtcaatt gatgggtatg  180
ttgttgaact tggttaacgc tagaaagact atcgaagttg gtgttttcac tggttactct  240
ttgttgttga ctgctttgac tttgccagaa gatggtaagg ttatcgccat tgacatgaac  300
agagactctt acgaaatcgg tttgccagtt atcaagaagg ctggtgttga acacaagatt  360
gatttcaagg aatctgaagc tttgccagcc ttggacgaat tgttgaacaa caaggttaac  420
gaaggtggtt tcgacttcgc tttcgttgat gctgacaagt tgaactactg gaactaccac  480
gaaagattga ttagattgat caaggttggt ggtatcatcg tttacgataa cactttgtgg  540
ggtggttctg ttgctgaacc agactcttcc actccagaat ggagaatcga agtcaagaag  600
gctaccttgg aattgaacaa gaagttgtct gctgatcaaa gagttcaaat ctctcaagct  660
gctttgggtg atggtatcac tatttgtaga agattgtact aa                     702

SEQ ID NO: 89           moltype = AA  length = 222
FEATURE                 Location/Qualifiers
source                  1..222
                        mol_type = protein
                        organism = Homo sapiens
SEQUENCE: 89
MSGDTKEQRI LNHVLQHAEP GNAQSVLEAI DTYCEQKEWA MNVGDKKGKI VDAVIQEHQP  60
SVLLELGAYC GYSAVRMARL LSPGARLITI EINPDCAAIT QRMVDFAGVK DKVTLVVGAS  120
QDIIPQLKKK YDVDTLDMVF LDHWKDRYLP DTLLLEECGL LRKGTVLLAD NVICPGAPDF  180
LAHVRGSSCF ECTHYQSFLE YREVVDGLEK AIYKGPGSEA GP                     222

SEQ ID NO: 90           moltype = DNA  length = 669
FEATURE                 Location/Qualifiers
misc_feature            1..669
                        note = coding sequence for SEQ ID NO: 89
source                  1..669
                        mol_type = other DNA
                        organism = synthetic construct
SEQUENCE: 90
atgtccggtg acaccaagga acaaagaatc ttgaaccacg ttttgcaaca cgctgaacca  60
ggtaacgctc aatctgtttt ggaagccatt gacacctact gtgaacaaaa ggaatgggcc  120
atgaacgttg gtgacaagaa gggtaagatc gttgacgccg ttattcaaga acaccaacca  180
```

```
tccgttttgt tggaattggg tgcctactgt ggttactctg ctgttagaat ggccagattg  240
ttgtctccag gtgctagatt gatcaccatc gaaatcaacc cagactgtgc cgccatcacc  300
caaagaatgg ttgatttcgc tggtgttaag gacaaggtca ccttggttgt tggtgcttcc  360
caagacatca tcccacaatt gaagaagaag tacgatgttg acactttgga catggttttc  420
ttggaccact ggaaggacag atacttgcca gacactttgt tgttggaaga atgtggtttg  480
ttgagaaagg gtactgtttt gttggctgac aacgttatct gtccaggtgc tccagacttc  540
ttggctcacg ttagaggttc ttcttgtttc gaatgtactc actaccaatc tttcttggaa  600
tacagagaag ttgttgacgg tttggaaaag gccatctaca agggtccagg ttctgaagct  660
ggtccataa                                                          669

SEQ ID NO: 91          moltype = AA  length = 489
FEATURE                Location/Qualifiers
source                 1..489
                       mol_type = protein
                       organism = Arabidopsis thaliana
SEQUENCE: 91
MSGTPVEVSK LHFLLFPFMA HGHMIPTLDM AKLFATKGAK STILTTPLNA KLFFEKPIKS  60
FNQDNPGLED ITIQILNFPC TELGLPDGCE NTDFIFSTPD LNVGDLSQKF LLAMKYFEEP  120
LEELLVTMRP DCLVGNMFFP WSTKVAEKFG VPRLVFHGTG YFSLCASHCI RLPKNVATSS  180
EPFVIPDLPG DILITEEQVM ETEEESVMGR FMKAIRDSER DSFGVLVNSF YELEQAYSDY  240
FKSFVAKRAW HIGPLSLGNR KFEEKAERGK KASIDEHECL KWLDSKKCDS VIYMAFGTMS  300
SFKNEQLIEI AAGLDMSGHD FVWVVNRKGS QVEKEDWLPE GFEEKTKGKG LIIRGWAPQV  360
LILEHKAIGG FLTHCGWNSL LEGVAAGLPM VTWPVGAEQF YNEKLVTQVL KTGVSVGVKK  420
MMQVVGDFIS REKVEGAVRE VMVGEERRKR AKELAEMAKN AVKEGGSSDL EVDRLMEELT  480
LVKLQKEKV                                                          489

SEQ ID NO: 92          moltype = DNA  length = 1470
FEATURE                Location/Qualifiers
misc_feature           1..1470
                       note = coding sequence for SEQ ID NO: 91
source                 1..1470
                       mol_type = other DNA
                       organism = synthetic construct
SEQUENCE: 92
atgtccggta ctccagtcga agtctctaag ttgcacttct tgttgttccc attcatggct  60
cacggtcaca tgatcccaac tttggacatg gctaagttgt tcgccaccaa gggtgctaag  120
tccactatct tgactactcc attgaacgcc aagttgttct tcgaaaagcc aatcaagtct  180
ttcaaccaag acaacccagg tttggaagat atcaccatcc aaatcttgaa cttcccatgt  240
actgaattgg gtttgccaga tggttgtgaa aacactgatt tcatcttctc cactccagac  300
ttgaacgttg gtgacttgtc tcaaaagttc ttgttggcta tgaagtactt cgaagaacca  360
ttggaagaat tgttggttac tatgaggcca gactgtttgg tcggtaacat gttcttccca  420
tggtccacta aggttgctga aaagttcggt gttccaagat tggttttcca cggtactggt  480
tacttctctt tgtgtgcttc tcactgtatc agattgccaa agaacgttgc tacttcttct  540
gaaccattcg ttattccaga tttgccaggt gacattttga ttactgaaga acaagtcatg  600
gaaactgaag aagaatctgt tatgggtaga ttcatgaagg ctatcagaga ctctgaaaga  660
gattctttcg gtgttttggt taactctttc tacgaattgg aacaagctta ctctgattac  720
ttcaagtctt tcgttgctaa gagagcttgg cacatcggtc cattgtcctt gggtaacaga  780
aagttcgaag aaaaggctga aagaggtaag aaggcttcta ttgatgaaca cgaatgtttg  840
aagtggttgg actccaagaa gtgtgattct gttatttaca tggccttcgg taccatgtcc  900
tctttcaaga acgaacaatt gatcgaaatt gctgctggtt tggatatgtc tggtcacgat  960
ttcgtctggg ttgttaacag aaagggttct caagttgaaa aggaagattg gttgccagaa  1020
ggtttcgaag aaaagaccaa gggtaagggt ttgatcatca gaggttgggc tccacaagtt  1080
ttgatcttgg aacacaaggc tattggtggt ttcttgactc actgtggttg gaactctttg  1140
ttggaaggtg ttgctgctgg tttgccaatg gttacttggc cagttggtgc cgaacaattc  1200
tacaacgaaa agttggttac tcaagtttta aagactggtg tttctgttgg tgttaagaag  1260
atgatgcaag ttgttggtga cttcatttct agagaaaagg ttgaaggtgc tgttagagaa  1320
gttatggttg gtgaagaaag aagaaagaga gccaaggaat tggctgaaat ggctaagaac  1380
gctgttaagg aaggtggttc ttctgatttg gaagttgata gattgatgga agaattgact  1440
ttggttaagt tgcaaaagga aaaggtttaa                                   1470

SEQ ID NO: 93          moltype = AA  length = 470
FEATURE                Location/Qualifiers
source                 1..470
                       mol_type = protein
                       organism = Scutellaria baicalensis
SEQUENCE: 93
MSGQLHIVLV PMIAHGHMIP MLDMAKLFSS RGVRTTIIAT PAFAEPIRKA RESGHDIGLT  60
TTKFPPKGSS LPDNILSLDQ VTHDLLPHFF RALELLQEPV EEIMEDLKPN CLVSDMFLPW  120
TTDSAAKFGI PRLLFHGTSL FARCFAEQMS LQKPYKNVSS DSEPFVLRGL PHEVSFVRTQ  180
IPGYELQEGG DDAFSKMAKQ MRDADKKSYG DVINSFEELE SEYVDHYKNV FGKKAWHIGP  240
LSLCNNRAEQ KSPIDDHECL AWLNSKKPNS VVYMCFGSMA TFSPAQLHET AVGLESSGQD  300
FIWVVRNGGE NEDWLPQGFE ERIKGKGLMI RGWAPQVVIL DHPSTGAFVT HCGWNSTLEG  360
ICAGLPMVTW PVFAEQFYNE KLVTEVLKTG VSVGNKKWQR VGEWVGSEAV KEAVEWVMVG  420
DGAAEMRSRA NYYKEMARKA VEDGGSSYNN LNALIQELSA YVPPMKQGLN              470

SEQ ID NO: 94          moltype = DNA  length = 1413
FEATURE                Location/Qualifiers
misc_feature           1..1413
                       note = coding sequence for SEQ ID NO: 93
```

source 1..1413
mol_type = other DNA
organism = synthetic construct
SEQUENCE: 94
atgtccggtc aattgcacat cgtcttggtt ccaatgatcg ctcacggtca catgatccca 60
atgttggaca tggccaagtt gttctcttcc agaggtgtca gaaccaccat catcgccact 120
ccagccttcg ctgaaccaat cagaaaggcc agagaatctg gtcacgacat cggtttgacc 180
accaccaagt tcccaccaaa gggttcctct ttgccagaca acatcttgtc tttggatcaa 240
gttactcacg atttgttgcc acacttcttc agagccttgg aattgttgca agaaccagtt 300
gaagaaatca tggaagattt gaagccaaac tgtttggttt ctgacatgtt cttgccatgg 360
actaccgact ctgctgccaa gttcggtatt ccaagattgt tgttccacgg tacctctttg 420
ttcgctagat gtttcgctga acaaatgtct ttgcaaaagc catacaagaa cgtttcttct 480
gattccgaac cattcgtttt gagaggtttg ccacacgaag tttctttcgt tagaactcaa 540
atcccaggtt acgaattgca agaaggtggt gatgatgcct tctctaagat ggctaagcaa 600
atgagagatg ctgataagaa gtcttacggt gacgttatca actctttcga agaattggaa 660
tctgaatacg ttgatcacta caagaacgtt ttcggtaaga aggcttggca catcggtcca 720
ttgtctttgt gtaacaacag agctgaacaa aagtctccaa tcgacgatca cgaatgtttg 780
gcttggttga actctaagaa gccaaactct gttgtttaca tgtgtttcgg ttctatggcc 840
actttctctc cagcccaatt gcacgaaact gctgtcggtt tggaatcctc tggtcaagat 900
ttcatctggg ttgttagaaa cggtggtgaa aacgaagatt ggttgccaca aggtttcgaa 960
gaaagaatca agggtaaggg tttgatgatc agaggttggg ccccacaagt tgttattttg 1020
gatcacccat ctactggtgc tttcgttact cactgtggtt ggaactctac tttggaaggt 1080
atctgtgctg gtttgccaat ggttacttgg ccagttttcg ctgaacaatt ctacaacgaa 1140
aagttggtta ctgaagtttt aaagactggt gtttctgttg gtaacaagaa gtggcaaaga 1200
gttggtgaat gggttggttc tgaagccgtt aaggaagctg ttgaatgggt catggtcggt 1260
gacggtgctg ctgaaatgag atctagagct aactactaca aggaaatggc tagaaaggct 1320
gttgaagatg gtggttcttc ttacaacaac ttgaacgctt tgatccaaga attgtctgcc 1380
tacgtcccac caatgaagca aggtttgaac taa 1413

SEQ ID NO: 95 moltype = AA length = 470
FEATURE Location/Qualifiers
source 1..470
mol_type = protein
organism = Scutellaria baicalensis
SEQUENCE: 95
MSGQLHIVLV PMIAHGHMIP MLDMAKLFSS RGVKTTIIAT PAFAEPIRKA RESGHDIGLT 60
TTKFPPKGSS LPDNIWSLDQ VTDDLLPHFF RALELLQEPV EEIMEDLKPN CLVSDMFLPW 120
TTDSAAKFGI PRLLFHGTSL FARCFAEQMS LQKPYKNVSS DSEPFVLRGL PHEVSFVRTQ 180
IPGYELQEGG DDAFSKMAKQ MRDADKKSYG DVINNFEELE SEYVDHYKNV FGKKAWHIGP 240
LSLCNNRAEQ KSPIDDHECL AWLNSKKPNS VVYMCFGSMA TFTPAQLHET AVGLESSGQD 300
FIWVVRNGGE NEDWLPQGFE ERIKGKGLMI RGWAPQVMIL DHPSTGAFVT HCGWNSTLEG 360
ICAGLPMVTW PVFAEQFYNE KLVTEVLKTG VSVGNKKWQR VGEGVGSEAV KEAVERVMVG 420
DGAAEMRSRA IYYKEMARKA VEEGGSSYNN LNALIEELSA YVPPMKQGLN 470

SEQ ID NO: 96 moltype = DNA length = 1413
FEATURE Location/Qualifiers
misc_feature 1..1413
note = coding sequence for SEQ ID NO: 95
source 1..1413
mol_type = other DNA
organism = synthetic construct
SEQUENCE: 96
atgtccggtc aattgcacat cgtcttggtt ccaatgatcg ctcacggtca catgatccca 60
atgttggaca tggccaagtt gttctcttcc agaggtgtca agaccaccat catcgccact 120
ccagccttcg ctgaaccaat cagaaaggcc agagaatctg gtcacgacat cggtttgacc 180
accaccaagt tcccaccaaa gggttcctct ttgccagaca acatctggtc tttggatcaa 240
gttactgatg atttgttgcc acacttcttc agagccttgg aattgttgca agaaccagtt 300
gaagaaatca tggaagattt gaagccaaac tgtttggttt ctgacatgtt cttgccatgg 360
actaccgact ctgctgccaa gttcggtatt ccaagattgt tgttccacgg tacctctttg 420
ttcgctagat gtttcgctga acaaatgtct ttgcaaaagc catacaagaa cgtttcttct 480
gattccgaac cattcgtttt gagaggtttg ccacacgaag tttctttcgt tagaactcaa 540
atcccaggtt acgaattgca agaaggtggt gatgatgcct tctctaagat ggctaagcaa 600
atgagagatg ctgataagaa gtcttacggt gacgttatca acaacttcga agaattggaa 660
tctgaatacg ttgatcacta caagaacgtt ttcggtaaga aggcttggca catcggtcca 720
ttgtctttgt gtaacaacag agctgaacaa aagtctccaa tcgacgatca cgaatgtttg 780
gcttggttga actctaagaa gccaaactct gttgtttaca tgtgtttcgg ttctatggcc 840
actttcactc cagcccaatt gcacgaaact gctgtcggtt tggaatcctc tggtcaagat 900
ttcatctggg ttgttagaaa cggtggtgaa aacgaagatt ggttgccaca aggtttcgaa 960
gaaagaatca agggtaaggg tttgatgatc agaggttggg ccccacaagt tatgattttg 1020
gatcacccat ctactggtgc tttcgttact cactgtggtt ggaactctac tttggaaggt 1080
atctgtgctg gtttgccaat ggttacttgg ccagttttcg ctgaacaatt ctacaacgaa 1140
aagttggtta ctgaagtttt aaagactggt gtttctgttg gtaacaagaa gtggcaaaga 1200
gttggtgaag gtgttggttc tgaagctgtt aaggaagctg ttgaaagagt catggtcggt 1260
gacggtgctg ctgaaatgag atctagagct atctactaca aggaaatggc tagaaaggct 1320
gttgaagaag gtggttcttc ttacaacaac ttgaacgctt tgatcgaaga attgtctgcc 1380
tacgtcccac caatgaagca aggtttgaac taa 1413

SEQ ID NO: 97 moltype = AA length = 477
FEATURE Location/Qualifiers

```
source                  1..477
                        mol_type = protein
                        organism = Scutellaria baicalensis
SEQUENCE: 97
MSGQLHIVLV PMIAHGHMIP MLDMAKLFSS RGVKTTIIAT PAFAEPIRKA RESGHDIGLT  60
TTKFPPKGSS LPDNIRSLDQ VTGDLLPHFF RALELLQEPV EEIMEDLKPN CLVSDMFLPW  120
TTDSAAKFGI PRLVFHGTSL FARCFSEQMS IQKPYKNVSS DSEPFVLRGL PHEVSFVRTQ  180
IPDYELQEGG DDAFSKMAKQ MRDADKKSYG DVINSFEELE SEYADYNKNV FGKKAWHIGP  240
LKLFNNRAEQ KSSQRGKESA IDDHECLAWL NSKKPNSVVY MCFGSMATFT PAQLHETAVG  300
LESSGQDFIW VVRNGGKNED WLPQGFEERI KGKGLMIRGW APQVMILDHP STGAFVTHCG  360
WNSTLEGICA GLPMVTWPVF AEQFYNEKLV TEVLKTGVSV GNKKWQRVGE GVGSEAVKEA  420
VERVMVGDGA AEMRSRAVYY KEMARKAVEE GGSSYNNLNA LIQELSAYVP PMKQGLN     477

SEQ ID NO: 98           moltype = DNA  length = 1434
FEATURE                 Location/Qualifiers
misc_feature            1..1434
                        note = coding sequence for SEQ ID NO:97
source                  1..1434
                        mol_type = other DNA
                        organism = synthetic construct
SEQUENCE: 98
atgtccggtc aattgcacat cgtcttggtt ccaatgatcg ctcacggtca catgatccca  60
atgttggaca tggccaagtt gttctcttcc agaggtgtca agaccaccat catcgccact  120
ccagccttcg ctgaaccaat cagaaaggcc agagaatctg gtcacgacat cggtttgacc  180
accaccaagt tcccaccaaa gggttcctct ttgccagaca acatcagatc tttggatcaa  240
gttactggtg atttgttgcc acacttcttc agagccttgg aattgttgca agaaccagtt  300
gaagaaatca tggaagattt gaagccaaac tgtttggttt ctgacatgtt cttgccatgg  360
actaccgact ctgctgccaa gttcggtatt ccaagattgg ttttccacgg tacctctttg  420
ttcgctagat gtttctctga acaaatgtct atccaaaagc catacaagaa cgtttcttct  480
gattccgaac cattcgtttt gagaggtttg ccacacgaag tttctttcgt tagaactcaa  540
atcccagatt acgaattgca agaaggtggt gatgatgcct tctctaagat ggctaagcaa  600
atgagagatg ctgataagaa gtcttacggt gacgttatca actctttcga agaattggaa  660
tctgaatacg ctgattacaa caagaacgtt ttcggtaaga aggcttggca catcggtcca  720
ttgaagttgt tcaacaacag agctgaacaa aagtcatctc aaagaggtaa ggaatctgcc  780
atcgacgatc acgaatgttt ggcttggttg aactctaaga agccaaactc tgttgtttac  840
atgtgtttcg gttctatggc cactttcact ccagcccaat tgcacgaaac tgctgtcggt  900
ttggaatcct ctggtcaaga tttcatctgg gttgttagaa acggtggtaa gaacgaagat  960
tggttgccac aaggtttcga agaaagaatc aagggtaagg gtttgatgat cagaggttgg  1020
gccccacaag ttatgatttt ggatcaccca tctactggtg ctttcgttac tcactgtggt  1080
tggaactcta ctttggaagg tatctgtgcc ggtttgccaa tggttacttg gccagttttc  1140
gctgaacaat tctacaacga aaagttggtt actgaagttt taaagactgg tgtttctgtt  1200
ggtaacaaga agtggcaaag agttggtgaa ggtgttggtt ctgaagctgt taaggaagct  1260
gttgaaagag tcatggtcgg tgacggtgct gctgaaatga gatctagagc tgtctactac  1320
aaggaaatgg ctagaaaggc tgttgaagaa ggtggttctt cttacaacaa cttgaacgct  1380
ttgatccaag aattgtctgc ctacgttcca ccaatgaagc aaggtttgaa ctaa        1434

SEQ ID NO: 99           moltype = AA  length = 533
FEATURE                 Location/Qualifiers
source                  1..533
                        mol_type = protein
                        organism = Homo sapiens
SEQUENCE: 99
MSACLLRSFQ RISAGVFFLA LWGMVVGDKL LVVPQDGSHW LSMKDIVEVL SDRGHEIVVV  60
VPEVNLLLKE SKYYTRKIYP VPYDQEELKN RYQSFGNNHF AERSFLTAPQ TEYRNNMIVI  120
GLYFINCQSL LQDRDTLNFF KESKFDALFT DPALPCGVIL AEYLGLPSVY LFRGFPCSLE  180
HTFSRSPDPV SYIPRCYTKF SDHMTFSQRV ANFLVNLLEP YLFYCLFSKY EELASAVLKR  240
DVDIITLYQK VSVWLLRYDF VLEYPRPVMP NMVFIGGINC KKRKDLSQEF EAYINASGEH  300
GIVVFSLGSM VSEIPEKKAM AIADALGKIP QTVLWRYTGT RPSNLANNTI LVKWLPQNDL  360
LGHPMTRAFI THAGSHGVYE SICNGVPMVM MPLFGDQMDN AKRMETKGAG VTLNVLEMTS  420
EDLENALKAV INDKSYKENI MRLSSLHKDR PVEPLDLAVF WVEFVMRHKG APHLRPAAHD  480
LTWYQYHSLD VIGFLLAVVL TVAFITFKCC AYGYRKCLGK KGRVKKAHKS KTH         533

SEQ ID NO: 100          moltype = DNA  length = 1602
FEATURE                 Location/Qualifiers
misc_feature            1..1602
                        note = coding sequence for SEQ ID NO: 99
source                  1..1602
                        mol_type = other DNA
                        organism = synthetic construct
SEQUENCE: 100
atgtccgcct gtttgttgag atctttccaa agaatttctg ctggtgtttt cttcttggct  60
ttgtggggta tggttgttgg tgacaagttg ttggttgtcc cacaagacgg ttctcactgg  120
ttgtctatga aggatatcgt tgaagttttg tctgacagag gtcacgaaat tgttgttgtt  180
gttccagaag ttaacttgtt gttgaaggaa tccaagtact acactagaaa gatctaccca  240
gttccatacg accaagaaga attgaagaac agataccaat ctttcggtaa caaccacttc  300
gctgaaagat ctttcttgac tgctccacaa actgaataca gaaacaacat gattgttatt  360
ggtttgtact tcatcaactg tcaatctttg ttgcaagaca gagacacctt gaacttcttc  420
aaggaatcta agttcgatgc tttgttcact gacccagcct tgccatgtgg tgttatcttg  480
gctgaatact tgggtttgcc atctgtttac ttgttcagag gtttcccatg ttccttggaa  540
```

```
cacactttct ctagatctcc agacccagtt tcctacattc caagatgtta cactaagttc  600
tctgaccaca tgactttctc ccaaagagtt gccaacttct tggttaactt gttggaacca  660
tacttgttct actgtttgtt ctctaagtac gaagaattgg cttctgctgt cttgaagaga  720
gatgttgata tcatcacctt gtaccaaaag gtatctgttt ggttgttgag atacgacttc  780
gttttggaat acccaagacc agtcatgcca aacatggtat tcattggtgg tatcaactgt  840
aagaagagaa aggacttgtc tcaagaattc gaagcctaca ttaacgcttc tggtgaacac  900
ggtattgttg ttttctcttt gggttctatg gtatctgaaa ttccagaaaa gaaggctatg  960
gctattgctg atgctttggg taagatccca caaactgtct tgtggagata cactggtacc  1020
agaccatcta acttggctaa caacactatc ttggttaagt ggttgccaca aaacgatttg  1080
ttgggtcacc caatgaccag agccttcatc acccacgctg gttcccacgg tgtttacgaa  1140
tctatctgta acggtgttcc aatggttatg atgccattgt tcggtgatca aatggacaac  1200
gctaagagaa tggaaactaa gggtgctggt gttaccttga acgttttgga aatgacttct  1260
gaagatttgg aaaacgcttt gaaggctgtc atcaacgaca agtcttacaa ggaaaacatc  1320
atgagattgt cctctttgca caaggacaga ccagttgaac cattggactt ggccgttttc  1380
tgggttgaat tcgttatgag acacaagggt gctccacact taagaccagc tgcccacgac  1440
ttgacctggt accaatacca ctccttggac gttattggtt tcttgttggc cgtcgttttg  1500
actgttgcct tcatcacctt caagtgttgt gcttacggtt acagaaagtg tttgggtaag  1560
aagggtagag ttaagaaggc ccacaagtcc aagacccact aa                     1602

SEQ ID NO: 101         moltype = AA  length = 531
FEATURE                Location/Qualifiers
source                 1..531
                       mol_type = protein
                       organism = Homo sapiens
SEQUENCE: 101
MVARAGWTGL LPLYVCLLLT CGFAKAGKLL VVPMDGSHWF TMQSVVEKLI LRGHEVVVVM  60
PEVSWQLGRS LNCTVKTYST SYTLEDQDRE FMVFADARWT APLRSAFSLL TSSSNGIFDL  120
FFSNCRSLFN DRKLVEYLKE SCFDAVFLDP FDACGLIVAK YFSLPSVVFA RGIFCHYLEE  180
GAQCPAPLSY VPRLLLGFSD AMTFKERVWN HIMHLEEHLF CPYFFKNVLE IASEILQTPV  240
TAYDLYSHTS IWLLRTDFVL EYPKPVMPNM IFIGGINCHQ GKPVPMEFEA YINASGEHGI  300
VVFSLGSMVS EIPEKKAMAI ADALGKIPQT VLWRYTGTRP SNLANNTILV KWLPQNDLLG  360
HPMTRAFITH AGSHGVYESI CNGVPMVMMP LFGDQMDNAK RMETKGAGVT LNVLEMTSED  420
LENALKAVIN DKSYKENIMR LSSLHKDRPV EPLDLAVFWV EFVMRHKGAP HLRPAAHDLT  480
WYQYHSLDVI GFLLAVVLTV AFITFKCCAY GYRKCLGKKG RVKKAHKSKT H           531

SEQ ID NO: 102         moltype = DNA  length = 1596
FEATURE                Location/Qualifiers
misc_feature           1..1596
                       note = coding sequence for SEQ ID NO: 101
source                 1..1596
                       mol_type = other DNA
                       organism = synthetic construct
SEQUENCE: 102
atgtccgcta gagctggttg gactggtttg ttgccattgt acgtttgttt gttgttgacc  60
tgtggtttcg ccaaggctgg taagttgttg gttgttccaa tggatggttc tcactggttc  120
accatgcaat ctgttgttga aaagttgatc ttgagaggtc acgaagttgt cgttgtcatg  180
ccagaagttt cttggcaatt gggtagatct ttgaactgta ctgttaagac ttactctacc  240
tcttacactt tggaagatca agacagagaa ttcatggttt tcgccgatgc tagatggact  300
gctccattga gatctgcttt ctctttgttg acttcttctt ccaacggtat tttcgacttg  360
ttcttctcta actgtagatc tttgttcaac gacagaaagt tggttgaata cttgaaggaa  420
tcttgtttcg atgctgtttt cttggatcca ttcgatgcct gtggtttgat tgttgccaag  480
tacttctcct tgccatctgt tgtattcgcc agaggtatct tctgtcacta cttggaagaa  540
ggtgctcaat gtccagctcc attgtcctac gtcccaagat tgttgttggg tttctctgac  600
gccatgactt tcaaggaaag agtttggaac cacatcatgc acttggaaga acacttgttc  660
tgtccatact tcttcaagaa cgtcttggaa atcgcctctg aaattttgca aaccccagtc  720
actgcttacg atttgtactc tcacacttct atttggttgt tgagaactga cttcgttttg  780
gaatacccaa agccagttat gccaaacatg atcttcattg gtggtatcaa ctgtcaccaa  840
ggtaagccag ttccaatgga attcgaagcc tacattaacg cttctggtga acacggtatt  900
gttgtttttct ctttgggttc tatggtatct gaaattccag aaaagaaggc tatggctatt  960
gctgatgctt tgggtaagat cccacaaact gtcttgtgga gatacactgg taccagacca  1020
tctaacttgg ctaacaacac tatcttggtt aagtggttgc cacaaaacga tttgttgggt  1080
cacccaatga ccagagcctt catcacccac gctggttccc acggtgttta cgaatctatc  1140
tgtaacggtg ttccaatggt tatgatgcca ttgttcggtg atcaaatgga caacgctaag  1200
agaatggaaa ctaagggtgc tggtgttacc ttgaacgttt tggaaatgac ttctgaagat  1260
ttggaaaacg ctttgaaggc tgtcatcaac gacaagtctt acaaggaaaa catcatgaga  1320
ttgtcctctt tgcacaagga cagaccagtt gaaccattgg acttggccgt tttctgggtt  1380
gaattcgtta tgagacacaa gggtgctcca cacttaagac cagctgccca cgacttgacc  1440
tggtaccaat accactcctt ggacgttatt ggtttcttgt tggccgtcgt tttgactgtt  1500
gccttcatca ccttcaagtg ttgtgcttac ggttacagaa agtgtttggg taagaagggt  1560
agagttaaga aggcccacaa gtccaagacc cactaa                            1596

SEQ ID NO: 103         moltype = AA  length = 482
FEATURE                Location/Qualifiers
source                 1..482
                       mol_type = protein
                       organism = Citrus clementina
SEQUENCE: 103
MSHASSNMHA PSNQHHKMGT ESAEADQLHV VMFPWFAFGH ISPFVQLSNK LSLHGVKVSF  60
FSAPGNIPRI KSSLNLTPMA DIIPLQIPHV DGLPPGLDST SEMTPHMAEL LKQALDLMQP  120
```

```
QIKTLLSQLK PHFVFFDFTH YWLPGLVGSQ LGIKTVNFSV FSAISQAYLV VPARKLNNSL  180
ADLMKSPDGF PATSITSLDE FVARDYLYVY TKFNGGPSVY ERGIQGVDGC DVLAIKTCNE  240
MEGPYLDFVR TQFKKPVLLT GPLVNPEPPS GELEERWAKW LCKYPPKSVI YCSFGSETFL  300
TVDQIKELAI GLEITGLPFF LVLNFPPNVD AQSELVRTLP PGFMDRVKDR GVVHTGWVQQ  360
QLILRHESVG CYVCHSGFSS VTEAVISDCQ LVLLPLKGDQ FLNSKLVAGD LKAGVEVNRR  420
DHDGHFGKED IFKAVKTVMV DVNKEPGASI RANQKWWREF LLNGQIQDKF IADFVKDLKT  480
LA                                                                482

SEQ ID NO: 104          moltype = DNA  length = 1449
FEATURE                 Location/Qualifiers
misc_feature            1..1449
                        note = coding sequence for SEQ ID NO: 103
source                  1..1449
                        mol_type = other DNA
                        organism = synthetic construct
SEQUENCE: 104
atgtcccacg cctcttctaa catgcacgcc ccatctaacc aacaccacaa gatgggtact  60
gaatctgctg aagctgatca attgcacgtt gttatgttcc catggttcgc tttcggtcac  120
atctctccat tcgttcaatt gtccaacaag ttgtctttgc acggtgtcaa ggtatctttc  180
ttctctgctc caggtaacat tccaagaatc aagtcatctt tgaacttgac tccaatggcc  240
gacattatcc cattgcaaat cccacacgtc gatggtttgc caccaggttt ggattctacc  300
tctgaaatga ctccacacat ggctgaattg ttgaagcaag ccttggactt gatgcaacca  360
caaatcaaga ctttgttgtc tcaattgaag ccacacttcg ttttcttcga tttcacccac  420
tactggttgc caggtttggt tggttctcaa ttgggtatca agactgttaa cttctctgtt  480
ttctctgcca tttctcaagc ctacttggtt gttccagcca gaaagttgaa caactctttg  540
gctgatttga tgaagtctcc agatggtttc ccagctactt ccattacctc tttggatgaa  600
ttcgttgcta gagattactt gtacgtttac actaagttca acggtggtcc atctgtttac  660
gaaagaggta ttcaaggtgt tgatggttgt gatgttttgg ccatcaagac ttgtaacgaa  720
atggaaggtc catacttgga tttcgttaga acccaattca agaagccagt tttgttgacc  780
ggtccattgg ttaacccaga accaccatcc ggtgaattgg aagaaagatg ggctaagtgg  840
ttgtgtaagt acccaccaaa gtctgttatt tactgttcct tcggttctga aactttcttg  900
accgttgatc aaatcaagga attggccatt ggtttggaaa ttactggttt gccattcttc  960
ttggtcttga acttcccacc aaacgtcgat gctcaatctg aattggtcag aactttgcca  1020
ccaggtttca tggacagagt taaggacaga ggtgttgttc acactggttg ggttcaacaa  1080
caattgattt tgagacacga atctgttggt tgttacgttt gtcactctgg tttctcttct  1140
gttactgaag ctgttatttc tgattgtcaa ttggttttgt tgccattgaa gggtgaccaa  1200
ttcttgaact ccaagttggt tgctggtgac ttgaaggctg gtgttgaagt taacagaaga  1260
gatcacgatg gtcacttcgg taaggaagat attttcaagg ctgttaagac tgttatggtt  1320
gatgttaaca aggaaccagg tgcttctatc agagctaacc aaaagtggtg gagagaattc  1380
ttgttgaacg gtcaaattca agataagttc attgctgatt tcgtcaagga tttaaagacc  1440
ttggcttaa                                                         1449

SEQ ID NO: 105          moltype = AA  length = 476
FEATURE                 Location/Qualifiers
source                  1..476
                        mol_type = protein
                        organism = Citrus sinensis
SEQUENCE: 105
MSHAPSNQHH KMGTESAEAD QLHVVMFPWF ASGHISPFVQ LSNKLSLHGV KVSFFSAPGN  60
IPRIKSSLNL TPMADIIPLQ IPHVDGLPPG LDSTSEMTPH MAELLKQALD LMQPQIKTLL  120
SQLKPHFVFF DFTHYWLPGL VGSQLGIKTV NFSVFSAISQ AYLVVPARKL NNSLADLMKS  180
PDGFPATSIT SLDEFVARDY LYVYTKFNGG PSVYERGIQG VDGCDVLAIK TCNEMEGPYL  240
DFVRTQFKKP VLLTGPLVNP EPPSGELEER WANWLGKFPP KSVIYCSFGS ETFLTVDQIK  300
ELAIGLEITG LPFFLVLNFP PNVDGQSELV RTLPPGFMDR VKDRGVVHTG WVQQQLILRH  360
ESVGCYVCHS GFSSVTEAVI SDCQLVLLPL KGDQFLNSKL VAGDLKAGVE VNRRDHDGHF  420
GKEDIFKAVK TVMVDVNKEP GASIRANQKW WREFLLNGQI QDKFIADFVK DLKALA      476

SEQ ID NO: 106          moltype = DNA  length = 1431
FEATURE                 Location/Qualifiers
misc_feature            1..1431
                        note = coding sequence for SEQ ID NO: 105
source                  1..1431
                        mol_type = other DNA
                        organism = synthetic construct
SEQUENCE: 106
atgtcccacg ccccatctaa ccaacaccac aagatgggta ctgaatctgc tgaagctgat  60
caattgcacg ttgttatgtt cccatggttc gcttctggtc acatctctcc attcgttcaa  120
ttgtccaaca agttgtcttt gcacggtgtc aaggtatctt tcttctctgc tccaggtaac  180
attccaagaa tcaagtcatc tttgaacttg actccaatgg ccgacattat cccattgcaa  240
atcccacacg tcgatggttt gccaccaggt ttggattcta cctctgaaat gactccacac  300
atggctgaat tgttgaagca agccttggac ttgatgcaac cacaaatcaa gactttgttg  360
tctcaattga agccacactt cgttttcttc gatttcaccc actactggtt gccaggtttg  420
gttggttctc aattgggtat caagaccgtt aacttctctg ttttctctgc catttctcaa  480
gcctacttgg ttgtcccagc cagaaagttg aacaactctt tggctgattt gatgaagtct  540
ccagatggtt tcccagctac ttccattacc tctttggatg aattcgttgc tagagattac  600
ttgtacgttt acactaagtt caacggtggt ccatctgttt acgaaagagg tattcaaggt  660
gttgatggtt gtgatgtttt ggccatcaag acttgtaacg aaatggaagg tccatacttg  720
gatttcgtta gaacccaatt caagaagcca gttttgttga ccggtccatt ggttaaccca  780
gaaccaccat ccggtgaatt ggaagaaaga tgggctaact ggttgggtaa gttcccacca  840
```

```
aagtctgtca tttactgttc tttcggttct gaaactttct tgaccgttga tcaaatcaag  900
gaattggcca ttggtttgga aattactggt ttgccattct tcttggtctt gaacttccca  960
ccaaacgttg atggtcaatc tgaattggtc agaactttgc caccaggttt catggacaga  1020
gttaaggaca gaggtgttgt tcacactggt tgggttcaac aacaattgat tttgagacac  1080
gaatctgttg gttgttacgt ttgtcactct ggtttctctt ctgttactga agctgttatt  1140
tctgattgtc aattggtttt gttgccattg aagggtgacc aattcttgaa ctccaagttg  1200
gttgctggtg acttgaaggc tggtgttgaa gttaacagaa gagatcacga tggtcacttc  1260
ggtaaggaag atattttcaa ggctgttaag actgttatgg ttgatgttaa caaggaacca  1320
ggtgcttcta tcagagctaa ccaaaagtgg tggagagaat tcttgttgaa cggtcaaatt  1380
caagataagt tcattgctga tttcgtcaag gatttgaagg ccttggctta a           1431

SEQ ID NO: 107         moltype = AA  length = 669
FEATURE                Location/Qualifiers
source                 1..669
                       mol_type = protein
                       organism = Citrus sinensis
SEQUENCE: 107
MSATYTPKNI LITGAAGFIA SHVCNRLIRN YPEYKIVVLD KLDYCSNLKN LIPSKASSNF  60
KFVKGDIASA DLVNFLLITE SIDTIMHFAA QTHVDNSFGN SFEFTKNNIY GTHVLLEACK  120
VTGQIRRFIH VSTDEVYGET DEDAVVGNHE ASQLLPTNPY SATKAGAEML VMAYGRSYGL  180
PVITTRGNNV YGPNQFPEKL IPKFILLAMR GLPLPIHGDG SNVRSYLYCE DVAEAFECIL  240
HKGEVGHVYN VGTKKERRVI DVAKDICKLF SMDPETSIKF VENRPFNDQR YFLDDQKLTS  300
LGWSERTIWE EGLRKTIEWY TQNPDWWGDV SGALLPHPRM LMMPGGRHFD GSEENKAVSS  360
VSTNNIQSRM VVPVSKCSSP RKPSMKFLIY GRTGWIGGLL GKLCEKEGIP FEYGKGRLED  420
RSSLIADVQS VKPTHVFNAA GVTGRPNVDW CESHKTDTIR TNVAGTLTLA DVCRDHGILM  480
MNYATGCIFE YDAAHPEGSG IGYKEEDTPN FTGSFYSKTK AMVEELLKEY DNVCTLRVRM  540
PISSDLNNPR NFITKISRYN KVVNIPNSMT VLDELLPISI EMAKRNLRGI WNFTNPGVVS  600
HNEILEMYKK YINPEFKWVN FTLDEQAKVI VAPRSNNEMD ASKLKKEFPE LLSIKDSLIK  660
YVFEPNKKT                                                          669

SEQ ID NO: 108         moltype = DNA  length = 2010
FEATURE                Location/Qualifiers
misc_feature           1..2010
                       note = coding sequence for SEQ ID NO: 107
source                 1..2010
                       mol_type = other DNA
                       organism = synthetic construct
SEQUENCE: 108
atgtccgcta cttacacccc aaagaacatc ttgatcactg gtgctgctgg tttcattgct  60
tcccacgttt gtaacagatt gattagaaac tacccagaat acaagattgt tgttttggac  120
aagttggatt actgttctaa cttgaagaac ttgatcccat ccaaggcttc ctccaacttc  180
aagttcgtta agggtgacat tgcctctgct gacttggtca acttcttgtt gatcaccgaa  240
tccattgaca ctattatgca cttcgctgct caaactcacg ttgacaactc tttcggtaac  300
tctttcgaat tcaccaagaa caacatctac ggtactcacg tcttgttgga agcctgtaag  360
gttactggtc aaatcagaag attcatccac gtatctactg atgaagtcta cggtgaaact  420
gatgaagatg ctgttgttgg taaccacgaa gcttcccaat tgttgccaac taacccatac  480
tctgctacta aggctggtgc tgaaatgttg gttatggctt acggtagatc ttacggtttg  540
ccagttatta ctaccagagg taacaacgtt tacggtccaa accaattccc agaaaagttg  600
attccaaagt tcatcttgtt ggccatgaga ggtttgccat tgccaattca cggtgatggt  660
tctaacgtta gatcttactt gtactgtgaa gatgttgctg aagctttcga atgtattttg  720
cacaagggtg aagttggtca cgtttacaac gttggtacta agaaggaaag aagagttatt  780
gatgttgcta aggatatttg taagttgttc tctatggacc cagaaacttc tatcaagttc  840
gttgaaaaca gaccattcaa cgatcaaaga tacttcttgg atgatcaaaa gttgacttct  900
ttgggttggt ctgaaagaac catctgggaa gaaggtttga gaaagactat tgaatggtac  960
actcaaaacc cagattggtg gggtgatgtc tctggtgctt tgttgccaca cccaagaatg  1020
ttgatgatgc caggtggtag acacttcgat ggttctgaag aaaacaaggc tgtttcctct  1080
gtctctacta acaacattca atccagaatg gttgttccag tttccaagtg ttcttctcca  1140
agaaagccat ccatgaagtt cttgatctac ggtagaactg gttggattgg tggtttgttg  1200
ggtaagttgt gtgaaaagga aggtattcca ttcgaatacg gtaagggtag attggaagat  1260
agatcttctt tgattgctga tgttcaatct gttaagccaa ctcacgtttt caacgctgct  1320
ggtgttactg gtagaccaaa cgttgattgg tgtgaatctc acaagactga caccattaga  1380
accaacgttg ctggtacctt gaccttggct gatgtttgta gagatcacgg tatcttgatg  1440
atgaactacg ctaccggttg tatcttcgaa tacgatgctg ctcacccaga aggttctggt  1500
attggttaca aggaagaaga tactccaaac ttcactggtt ctttctactc taagaccaag  1560
gccatggttg aagaattgtt gaaggaatac gacaacgttt gtactttgag agtcagaatg  1620
ccaatctctt ctgacttgaa caacccaaga aacttcatta ccaagatttc tagatacaac  1680
aaggttgtca acattccaaa ctctatgact gttttggatg aattgttgcc aatttctatt  1740
gaaatggcta agagaaactt gagaggtatt tggaacttca ctaacccagg tgttgtttct  1800
cacaacgaaa ttttggaaat gtacaagaag tacattaacc cagaattcaa gtgggttaac  1860
ttcactttgg atgaacaagc taaggttatc gtcgccccaa gatctaacaa cgaaatggat  1920
gcttctaagt tgaagaagga attcccagaa ttgttgtcca tcaaggattc tttgatcaag  1980
tacgtattcg aaccaaacaa gaaaacctaa                                   2010

SEQ ID NO: 109         moltype = AA  length = 670
FEATURE                Location/Qualifiers
source                 1..670
                       mol_type = protein
                       organism = Arabidopsis thaliana
SEQUENCE: 109
```

```
MSASYTPKNI LITGAAGFIA SHVANRLIRS YPDYKIVVLD KLDYCSNLKN LNPSKHSPNF  60
KFVKGDIASA DLVNHLLITE GIDTIMHFAA QTHVDNSFGN SFEFTKNNIY GTHVLLEACK  120
VTGQIRRFIH VSTDEVYGET DEDALVGNHE ASQLLPTNPY SATKAGAEML VMAYGRSYGL  180
PVITTRGNNV YGPNQFPEKL IPKFILLAMR GQVLPIHGDG SNVRSYLYCE DVAEAFEVVL  240
HKGEVGHVYN IGTKKERRVN DVAKDICKLF NMDPEANIKF VDNRPFNDQR YFLDDQKLKK  300
LGWSERTTWE EGLKKTMDWY TQNPEWWGDV SGALLPHPRM LMMPGGRHFD GSEDNSLAAT  360
LSEKPSQTHM VVPSQRSNGT PQKPSLKFLI YGKTGWIGGL LGKICDKQGI AYEYGKGRLE  420
DRSSLLQDIQ SVKPTHVFNS AGVTGRPNVD WCESHKTETI RANVAGTLTL ADVCREHGLL  480
MMNFATGCIF EYDDKHPEGS GIGFKEEDTP NFTGSFYSKT KAMVEELLKE YDNVCTLRVR  540
MPISSDLNNP RNFITKISRY NKVVNIPNSM TVLDELLPIS IEMAKRNLKG IWNFTNPGVV  600
SHNEILEMYR DYINPEFKWA NFTLEEQAKV IVAPRSNNEM DASKLKKEFP ELLSIKESLI  660
KYAYGPNKKT                                                        670

SEQ ID NO: 110         moltype = DNA  length = 2013
FEATURE                Location/Qualifiers
misc_feature           1..2013
                       note = coding sequence for SEQ ID NO: 109
source                 1..2013
                       mol_type = other DNA
                       organism = synthetic construct
SEQUENCE: 110
atgtccgctt cttacactcc aaagaacatt ttgatcaccg gtgctgctgg tttcattgct  60
tctcacgtcg ccaacagatt gatcagatct tacccagatt acaagatcgt tgttttggac  120
aagttggatt actgttctaa cttgaagaac ttgaacccat ctaagcactc tccaaacttc  180
aagttcgtca agggtgatat cgcttctgct gacttggtta accacttgtt gatcactgaa  240
ggtattgaca ccatcatgca cttcgctgct caaactcacg tcgacaactc cttcggtaac  300
tctttcgaat tcactaagaa caacatctac ggtactcacg tcttgttgga agcttgtaag  360
gttactggtc aaattagaag attcattcac gtttctactg atgaagttta cggtgaaact  420
gatgaagatg ctttggttgg taaccacgaa gcttctcaat tgttgccaac taacccatac  480
tctgccacta aggctggtgc tgaaatgttg gttatggctt acggtagatc ttacggtttg  540
ccagttatta ccactagagg taacaacgtc tacggtccaa accaattccc agaaaagttg  600
attccaaagt tcattttgtt ggctatgaga ggtcaagttt tgccaattca cggtgatggt  660
tctaacgtca gatcttactt gtactgtgag gacgttgctg aagctttcga agttgttttg  720
cacaagggtg aagttggtca cgtttacaac attggtacta agaaggaaag aagagttaac  780
gatgttgcca aggacatctg taagttgttc aacatggacc cagaagctaa catcaagttc  840
gtcgacaaca gaccattcaa cgatcaaaga tacttcttgg acgatcaaaa gttgaagaag  900
ttgggttggt ctgaaagaac cacttgggaa gaaggtttga agaaaactat ggattggtac  960
actcaaaacc cagaatggtg gggtgatgtt tctggtgctt tgttgccaca cccaagaatg  1020
ttgatgatgc caggtggtag acacttcgat ggttccgaag ataactcttt ggctgctact  1080
ttgtctgaaa agccatctca aacccacatg gttgttccat ctcaaagatc taacggtact  1140
ccacaaaagc catctttgaa gttcttgatc tacggtaaga ccggttggat cggtggtttg  1200
ttgggtaaga tctgtgataa gcaaggtatt gcttacgaat acggtaaggg tagattggaa  1260
gatagatctt ctttgttgca agatattcaa tctgttaagc caacccacgt tttcaactcc  1320
gctggtgtta ctggtagacc aaacgttgac tggtgtgaat ctcacaagac cgaaactatc  1380
agagccaacg ttgctggtac tttgactttg gctgatgtct gtagagaaca cggtttgttg  1440
atgatgaact tcgctactgg ttgtatcttc gaatacgacg acaagcaccc agaaggttct  1500
ggtattggtt tcaaggaaga agatactcca aacttcactg gttctttcta ctctaagacc  1560
aaggccatgg tcgaagaatt gttgaaggaa tacgacaacg tttgtacttt gagagttaga  1620
atgccaatct cctctgattt gaacaaccca agaaacttca tcaccaagat ctccagatac  1680
aacaaggttg ttaacatccc aaactctatg actgttttgg acgaattgtt gccaatctcc  1740
atcgaaatgg ctaagagaaa cttgaagggt atctggaact tcactaaccc aggtgttgtt  1800
tctcacaacg aaatcttgga aatgtacaga gactacatca acccagaatt caagtgggct  1860
aacttcactt tggaagaaca agctaaggtc attgttgctc caagatctaa caacgaaatg  1920
gatgcttcca agttgaagaa ggaattccca gaattgttgt ctatcaagga atctttgatt  1980
aagtacgctt acggtccaaa caagaaaacc taa                              2013

SEQ ID NO: 111         moltype = AA  length = 668
FEATURE                Location/Qualifiers
source                 1..668
                       mol_type = protein
                       organism = Arabidopsis thaliana
SEQUENCE: 111
MSDDTTYKPK NILITGAAGF IASHVANRLI RNYPDYKIVV LDKLDYCSDL KNLDPSFSSP  60
NFKFVKGDIA SDDLVNYLLI TENIDTIMHF AAQTHVDNSF GNSFEFTKNN IYGTHVLLEA  120
CKVTGQIRRF IHVSTDEVYG ETDEDAAVGN HEASQLLPTN PYSATKAGAE MLVMAYGRSY  180
GLPVITTRGN NVYGPNQFPE KMIPKFILLA MSGKPLPIHG DGSNVRSYLY CEDVAEAFEV  240
VLHKGEIGHV YNVGTKRERR VIDVARDICK LFGKDPESSI QFVENRPFND QRYFLDDQKL  300
KKLGWQERTN WEDGLKKTMD WYTQNPEWWG DVSGALLPHP RMLMMPGGRL SDGSSEKKDV  360
SSNTVQTFTV VTPKNGDSGD KASLKFLIYG KTGWLGGLLG KLCEKQGITY EYGKGRLEDR  420
ASLVADIRSI KPTHVFNAAG LTGRPNVDWC ESHKPETIRV NVAGTLTLAD VCRENDLLMM  480
NFATGCIFEY DATHPEGSGI GFKEEDKPNF FGSFYSKTKA MVEELLREFD NVCTLRVRMP  540
ISSDLNNPRN FITKISRYNK VVDIPNSMTV LDELLPISIE MAKRNLRGIW NFTNPGVVSH  600
NEILEMYKNY IEPGFKWSNF TVEEQAKVIV AARSNNEMDG SKLSKEFPEM LSIKESLLKY  660
VFEPNKRT                                                          668

SEQ ID NO: 112         moltype = DNA  length = 2007
FEATURE                Location/Qualifiers
misc_feature           1..2007
                       note = coding sequence for SEQ ID NO: 111
```

```
source                  1..2007
                        mol_type = other DNA
                        organism = synthetic construct
SEQUENCE: 112
atgtccgatg atactactta caagccaaag aacattttga ttactggtgc tgctggtttc  60
attgcttctc acgttgccaa cagattgatc agaaactacc cagattacaa gatcgttgtt  120
ttggacaagt tggattactg ttctgatttg aagaacttgg atccatcttt ctcttctcca  180
aacttcaagt tcgtcaaggg tgatatcgct tctgatgatt tggttaacta cttgttgatc  240
actgaaaaca ttgatactat catgcacttc gctgctcaaa ctcacgttga taactctttc  300
ggtaactctt tcgaattcac caagaacaac atttacggta ctcacgtttt gttggaagcc  360
tgtaaggtta ctggtcaaat cagaagattc atccacgttt ctaccgatga agtctacggt  420
gaaaccgatg aagatgctgc tgttggtaac cacgaagctt ctcaattgtt gccaactaac  480
ccatactctg ctactaaggc tggtgctgaa atgttggtta tggcttacgg tagatcttac  540
ggtttgccag ttattactac tagaggtaac aacgtttacg gtccaaacca attcccagaa  600
aagatgattc caaagttcat cttgttggct atgtctggta agccattgcc aatccacggt  660
gatggttcta acgtcagatc ttacttgtac tgtgaggacg ttgctgaagc tttcgaagtt  720
gttttgcaca agggtgaaat cggtcacgtc tacaacgtcg gtactaagag agaaagaaga  780
gttatcgatg ttgctagaga catctgtaag ttgttcggta aggacccaga atcttctatt  840
caattcgttg aaaacagacc attcaacgat caaagatact tcttggatga tcaaaagttg  900
aagaagttgg gttggcaaga aagaactaac tgggaagatg gtttgaagaa aactatggac  960
tggtacactc aaaacccaga atggtggggt gatgtttctg gtgctttgtt gccacaccca  1020
agaatgttga tgatgccagg tggtagattg tctgatggtt cttctgaaaa gaaggacgtt  1080
tcttctaaca ctgtccaaac tttcactgtt gttactccaa agaacggtga ttctggtgac  1140
aaggcttctt tgaagttctt gatctacggt aagactggtt ggttgggtgg tttgttgggt  1200
aagttgtgtg aaaagcaagg tattacttac gaatacggta agggtagatt ggaagataga  1260
gcttctttgg ttgctgatat tagatctatc aagccaactc acgttttcaa cgctgctggt  1320
ttgactggta gaccaaacgt tgactggtgt gaatctcaca agccagaaac cattagagtt  1380
aacgtcgctg gtactttgac tttggctgat gtttgtagag aaaacgattt gttgatgatg  1440
aacttcgcca ccggttgtat cttcgaatac gacgctactc acccagaagg ttctggtatc  1500
ggtttcaagg aagaagataa gccaaacttc ttcggttctt tctactctaa gaccaaggcc  1560
atggttgaag aattgttgag agaattcgac aacgtttgta ccttgagagt cagaatgcca  1620
atctcctctg acttgaacaa cccaagaaac ttcatcacta agatctctag atacaacaag  1680
gttgttgaca tcccaaactc tatgaccgtt ttggacgaat tgttgccaat ctctatcgaa  1740
atggctaaga gaaacttgag aggtatctgg aacttcacca acccaggtgt tgtttctcac  1800
aacgaaatct tggaaatgta caagaactac atcgaaccag gtttcaagtg gtccaacttc  1860
actgttgaag aacaagctaa ggtcattgtt gctgctagat ctaacaacga aatggatggt  1920
tctaagttgt ctaaggaatt cccagaaatg ttgtccatca aggaatcttt gttgaagtac  1980
gtattcgaac caaacaagag aacctaa                                     2007

SEQ ID NO: 113          moltype = AA  length = 482
FEATURE                 Location/Qualifiers
source                  1..482
                        mol_type = protein
                        organism = Citrus sinensis
SEQUENCE: 113
MSKDTIVFYT SPGRGHLNSM VELGKLILTY HPCFSIDIII PTAPFVSSAG TDDYIASVSA  60
TAPSVTFHQL PPPVSGLPDT LRSPADFPAL VYELGELNNP NLHETLITIS KRSNLKAFVI  120
DFLCNPAFQV SSSTLSIPTY YYFTTAGSVL AANLYLPTLH KNTTKSFREL GSALLNFPGF  180
PPFPARDMAL PMHDREGKVY KGLVDTGIQM AKSAGVIVNT FELLEERAIK AMLEGQCTPG  240
DTSPPLYCIG PVVGRGNGEN RGRDRHECLS WLDSKPSRSV LFLCFGSLGS FSCKQLKEMA  300
IGLERSGVKF LWVVRAPAPD SVENRSSLES LLPEGFLDRT KDRGLVVESW APQVEVLNHE  360
SVGGFVTHCG WNSVLEGVCA GVPMLAWPLY AEQKMIRAVV VEEMKVGLAV TRSEEGDGLV  420
SSAELEQRVS ELMDSEKGRA VKERAVAMKE AAAAAMRDGG SSRVALDNLV ESFKRGCIAP  480
FG                                                                482

SEQ ID NO: 114          moltype = DNA  length = 1449
FEATURE                 Location/Qualifiers
misc_feature            1..1449
                        note = coding sequence for SEQ ID NO: 113
source                  1..1449
                        mol_type = other DNA
                        organism = synthetic construct
SEQUENCE: 114
atgtccaagg atactattgt tttctacact tctccaggta gaggtcactt gaactccatg  60
gttgaattgg gtaagttgat cttgacttac cacccatgtt tctccattga catcatcatc  120
ccaaccgccc cattcgtttc ttctgccggt accgatgatt acatcgcctc cgtttccgcc  180
actgctccat ccgttacctt ccaccaattg ccaccaccag ttagtggttt gccagacact  240
ctcagatctc cagctgactt cccagccttg gtttacgaat tgggtgaatt gaacaaccca  300
aacttgcacg aaaccttgat cactatttcc aagagatcta acttgaaggc cttcgttatc  360
gatttcttgt gtaacccagc tttccaagtt tcctcttcta ctttgtctat cccaacttac  420
tactacttca ccaccgctgg ttctgttttg gctgctaact tgtacttgcc aactttgcac  480
aagaacacca ctaagtcttt cagagaattg ggttctgctt tgttgaactt cccaggtttc  540
ccaccattcc cagctagaga catggctttg ccaatgcacg atagagaagg taaggtttac  600
aagggtttgg tcgacaccgg tatccaaatg gctaagtctg ctggtgtaat tgttaacaca  660
ttcgaattgt tggaggaaag agctatcaag gctatgttgg aaggtcaatg tactccaggt  720
gatacttctc caccattgta ctgtatcggt ccagttgttg gtagaggtaa cggtgaaaac  780
agaggtagag atagacacga atgtttgtct tggttggact ctaagccatc tagatctgtc  840
ttgttcttgt gtttcggttc tttgggttct ttctcttgta agcaattgaa ggaaatggcc  900
attggtttgg aaagatctgg tgttaagttc ttgtgggtcg ttagagctcc agctccagac  960
```

```
tctgtcgaaa acagatcttc tttggaatct ttgttgccag aaggtttctt ggatagaact  1020
aaggatagag gtttggttgt tgaatcttgg gctccacaag ttgaagtttt gaaccacgaa  1080
tctgttggcg gcttcgttac tcactgcggt tggaactctg ttttggaagg tgtttgtgcc  1140
ggtgttccaa tgttggcttg gccattgtac gccgaacaaa agatgattag agctgtcgtt  1200
gttgaagaaa tgaaggttgg tttggctgtt actagatctg aagaaggtga cggtttggtt  1260
tcttctgccg aattggaaca aagagtttct gaattgatgg actctgaaaa gggtagagct  1320
gttaaggaaa gagctgttgc tatgaaggaa gctgctgctg ctgctatgag agatggtggt  1380
tcttctagag ttgcgctcga caacttggtt gaaagcttta agagaggttg catcgctcca  1440
ttcggttaa                                                          1449

SEQ ID NO: 115         moltype = AA  length = 477
FEATURE                Location/Qualifiers
source                 1..477
                       mol_type = protein
                       organism = Citrus clementina
SEQUENCE: 115
MSEKQDHVHV AILPLPAVGH VNSMLNLAEL LGHAGIKITF LNTEHYYDRV IRHSSDAFSR  60
YMQIPGFQFK TLTDGLPRDH PRTPDKFPEL VDSLNCATPP LLKEMVSDSK SPVNCIITDG  120
YMSRAIDAAR EVGVSIIYFR TISACAFWSF HCIPDIIDAG ELPIKGTEDM DRLITTVPGM  180
EGFLRCRDLP SFCRVNDPMD PHLLLFARET RLSAHADGLI LNTFEDLEGP ILSQIRNHSC  240
PNIYSIGPLN AHLKVRIPEK TYSSSSLWKI DRSCMAWLDK QPKQSVIYVS FGSIAVMSRD  300
QLIEFYYGLV HSKKNFLWVI RPDLISGKDG ENQIPEELLE ATKERGCIAG WVPQEEVLAH  360
SAVGGFLTHC GWNSTLESIV AGMPMICWPS FADQQINSRF VGEVWKLGLD IKDLCDRNIV  420
EKTVNDLMVE RKEEFMESAD RMANLAKKSV NKGGSSYCNL DRLVNDIKMM SSQPQNC     477

SEQ ID NO: 116         moltype = DNA  length = 1434
FEATURE                Location/Qualifiers
misc_feature           1..1434
                       note = coding sequence for SEQ ID NO: 115
source                 1..1434
                       mol_type = other DNA
                       organism = synthetic construct
SEQUENCE: 116
atgtccgaaa agcaagatca cgttcacgtt gctatcttgc cattgccagc cgttggtcac  60
gtcaactcca tgttgaactt ggctgaattg ttgggtcacg ccggtatcaa gattactttc  120
ttgaacaccg aacactacta cgatagagtc atcagacact cttctgatgc cttctctaga  180
tacatgcaaa ttccaggttt ccaattcaag accttgactg atggtttgcc aagagatcac  240
ccaagaactc cagataagtt cccagaattg gttgattctt tgaactgtgc cactccacca  300
ttgttgaagg aaatggtatc tgattctaag tctccagtta actgtattat cactgatggt  360
tacatgtcta gagctattga cgctgccaga gaagttggtg tttccattat ttacttcaga  420
actatttctg cttgtgcttt ctggtctttc cactgtatcc cagatatcat tgatgctggt  480
gaattgccaa tcaagggtac tgaagatatg gatagattga tcaccactgt tccaggtatg  540
gaaggtttct tgagatgtag agatttgcca tctttctgta gagttaacga cccaatggat  600
ccacacttgt tgttgttcgc tagagaaacc agattgagtg ctcatgctga cggcttgatc  660
ttgaacactt tcgaagattt ggaaggtcca atcttgtccc aaatcagaaa ccactcttgt  720
ccaaacatct actctattgg tccattgaac gctcacttga aggttagaat cccagaaaag  780
acttactcct cttcttcttt gtggaagatt gacagatctt gtatggcttg gttggacaag  840
caaccaaagc aatctgttat ctacgtatct ttcggttcta ttgctgttat gtctagagat  900
caattgatcg aattctacta cggtttggtt cactctaaga agaacttctt gtgggtcatc  960
agaccagact tgatttctgg taaggatggt gaaaaccaaa ttccagaaga attgttggaa  1020
gctaccaagg aaagaggttg tattgctggt tgggttccac aagaagaagt tttggcccac  1080
tctgctgttg gtggtttctt gacccactgt ggttggaact ctaccttgga atctatcgtt  1140
gctggtatgc caatgatttg ctggccaagc ttcgctgatc aacagatcaa ctctagattc  1200
gttggtgaag tttggaagtt gggtttggat atcaaggatt tgtgtgatag aaacattgtt  1260
gaaaagactg ttaacgattt gatggttgaa agaaaggaag aattcatgga atctgctgat  1320
agaatggcta acttggctaa gaagtctgtt aacaagggtg gttcctctta ctgtaacttg  1380
gacagattgg ttaacgatat caagatgatg tcctctcaac cacaaaactg ttaa        1434

SEQ ID NO: 117         moltype = AA  length = 354
FEATURE                Location/Qualifiers
source                 1..354
                       mol_type = protein
                       organism = Citrus clementina
SEQUENCE: 117
MSGSIVDGER DQSFAYANQL AMGTVLPMAM QAVYELGIFQ IIDKAGPGAK LSASDIAAQL  60
PTKNKDAPTM LDRILRLLAS YSVVECSLDG SGARRRYSLN SVSKYYVPNK DGVSLGPALQ  120
MIQDKVFLES WSHLKDAILE GGIPFNRAHG MHAFEYGRVD PRFNKHFNTA MYNHTSLIMS  180
NILESYKGFA NIKQLVDVGG NLGVTLQAIT SKYPYIKGIN FDQPHVIEHA PLHPHIEHVA  240
GDMFQSVPKG DAIFLKWILH DWDDEHCLKL LKNCYKSVPE DGKVIVVELM LPEVPNTSIE  300
SKSNSHIDVL MMTQNPGGKE RTKHEFMTLA TGAGFSGIRF DLVTGNFWVM EFYK        354

SEQ ID NO: 118         moltype = DNA  length = 1065
FEATURE                Location/Qualifiers
misc_feature           1..1065
                       note = coding sequence for SEQ ID NO:117
source                 1..1065
                       mol_type = other DNA
                       organism = synthetic construct
SEQUENCE: 118
```

```
atgtccggtt ctatcgttga tggtgaaaga gatcaatctt tcgcttacgc taaccaattg  60
gctatgggta ctgttttgcc aatggccatg caagctgttt acgaattggg tattttccaa  120
atcatcgaca aggctggtcc aggtgctaag ttgtctgctt ctgatattgc tgcccaattg  180
ccaaccaaga acaaggacgc tccaactatg ctcgacagaa tactaagatt gttggcttct  240
tactctgttg ttgaatgttc tttggatggt tctggtgcca gaagaagata ctctttgaac  300
tctgtctcca agtactacgt tccaaacaag gatggtgtct ctttgggtcc agctttgcaa  360
atgattcaag acaaggtttt cttggaatct tggtcccact tgaaggatgc tattttggaa  420
ggtggtattc cattcaacag agcccacggt atgcacgctt tcgaatacgg tagagttgac  480
ccaagattca acaagcactt caacactgct atgtacaacc acacctcttt gattatgtct  540
aacattttgg aatcttacaa gggtttcgcc aacatcaagc aattggtcga tgttggtggt  600
aacttgggcg taactctcca agccatcact tccaagtacc catacattaa gggtatcaac  660
ttcgaccaac cacacgttat tgaacacgcc ccattgcacc cacacattga acacgttgct  720
ggtgatatgt tccaatctgt tccaaagggt gacgccattt tcttgaagtg gatcttgcac  780
gattgggacg atgaacactg tttgaagttg ttgaagaact gttacaagtc tgttccagaa  840
gatggtaagg ttatcgttgt tgaattgatg ttgccagaag ttccaaacac ttctattgaa  900
tctaagtcta actcccacat tgacgttttg atgatgactc aaaacccagg tggtaaggaa  960
agaactaagc acgaattcat gaccttggct actggtgctg gtttctctgg tatcagattc  1020
gatttggtta ctggtaactt ctgggttatg gaattctaca agtaa                1065

SEQ ID NO: 119          moltype = AA  length = 250
FEATURE                 Location/Qualifiers
source                  1..250
                        mol_type = protein
                        organism = Citrus sinensis
SEQUENCE: 119
MSAANREDQE ENKDRYFKAV HGNKTLLQSE KLYEYILETS VYPREPQCLK EIRELTYKHP  60
LSPMMTSPDE AQFFSMLLKL INAKNTMEIG VFTGYSLLAT ALAIPDDGKI LALDITKEHY  120
EKGLPIIQKA GVAHKIDFRE GPALPLLDQL IQHEKYHGTF DFVFVDADKD NYVNYHKRLI  180
ELVKVGGVIG YDNTLWGGSV VAPPDADLDE HILYLRDFVQ ELNKALAVDP RIEICQLSIA  240
DGVTLCRRIG                                                       250

SEQ ID NO: 120          moltype = DNA  length = 753
FEATURE                 Location/Qualifiers
misc_feature            1..753
                        note = coding sequence for SEQ ID NO:119
source                  1..753
                        mol_type = other DNA
                        organism = synthetic construct
SEQUENCE: 120
atgtccgctg ctaacagaga agatcaagaa gaaaacaagg atagatactt caaggctgtt  60
cacggtaaca agaccttgtt gcaatctgaa aagttgtacg aatacatctt ggaaacctct  120
gtttacccaa gagaaccaca atgtttgaag gaaatcagag aattgactta caagcaccca  180
ttgtctccaa tgatgacttc tccagatgaa gctcaattct tctctatgtt gttgaagttg  240
atcaacgcca agaacaccat ggagataggt gtattcaccg gttactcttt gttggccact  300
gccttggcca ttccagacga tggtaagatt ttggccttgg acatcaccaa ggaacactac  360
gaaaagggtt tgccaatcat tcaaaaggct ggtgttgctc acaagattga cttcagagaa  420
ggtccagctt tgccattatt ggatcaatta atccaacacg aaaagtacca tggcacattc  480
gacttcgtct ttgttgatgc tgacaaggat aactacgtta actaccacaa gagattgatt  540
gaattggtta aggttggtgg tgttattggt tacgacaaca ccttgtgggg tggttctgtt  600
gttgctccac cagatgccga cttggatgaa cacatcttgt acttgagaga tttcgttcaa  660
gaattgaaca aggccttggc cgttgatcca agaatagaaa tttgtcaatt gtccattgct  720
gatggtgtta ctttgtgtag aagaattggt taa                             753

SEQ ID NO: 121          moltype = AA  length = 514
FEATURE                 Location/Qualifiers
source                  1..514
                        mol_type = protein
                        organism = Arabidopsis thaliana
SEQUENCE: 121
MSATLFLTIL LATVLFLILR IFSHRRNRSH NNRLPPGPNP WPIIGNLPHM GTKPHRTLSA  60
MVTTYGPILH LRLGFVDVVV AASKSVAEQF LKIHDANFAS RPPNSGAKHM AYNYQDLVFA  120
PYGHRWRLLR KISSVHLFSA KALEDFKHVR QEEVGTLTRE LVRVGTKPVN LGQLVNMCVV  180
NALGREMIGR RLFGADADHK ADEFRSMVTE MMALAGVFNI GDFVPSLDWL DLQGVAGKMK  240
RLHKRFDAFL SSILKEHEMN GQDQKHTDML STLISLKGTD LDGDGGSLTD TEIKALLLNM  300
FTAGTDTSAS TVDWAIAELI RHPDIMVKAQ EELDIVVGRD RPVNESDIAQ LPYLQAVIKE  360
NFRLHPPTPL SLPHIASESC EINGYHIPKG STLLTNIWAI ARDPDQWSDP LAFKPERFLP  420
GGEKSGVDVK GSDFELIPFG AGRRICAGLS LGLRTIQFLT ATLVQGFDWE LAGGVTPEKL  480
NMEESYGLTL QRAVPLVVHP KPRLAPNVYG LGSG                            514

SEQ ID NO: 122          moltype = DNA  length = 1545
FEATURE                 Location/Qualifiers
misc_feature            1..1545
                        note = coding sequence for SEQ ID NO:121
source                  1..1545
                        mol_type = other DNA
                        organism = synthetic construct
SEQUENCE: 122
atgtccgcta ctttgttctt gactatcttg ttggctactg ttttgttctt gatcttgaga  60
atcttctctc acagaagaaa cagatctcac aacaacagat tgccaccagg tccaaaccca  120
```

```
tggccaatca tcggtaactt gccacacatg ggtactaagc cacacagaac tttgtctgct  180
atggttacta cttacggtcc aatcttgcac ttgagattgg gtttcgttga cgttgttgtt  240
gctgcttcta agtctgttgc tgaacaattc ttgaagatcc acgacgctaa cttcgcttct  300
agaccaccaa actctggtgc taagcacatg gcttacaact accaagactt ggttttcgct  360
ccatacggtc acagatggag attgttgaga aagatctctt ctgttcactt gttctctgct  420
aaggctttgg aagatttcaa gcacgttaga caagaagaag ttggtacttt gactagagaa  480
ttggttagag ttggtactaa gccagttaac ttgggtcaat tggttaacat gtgtgttgtt  540
aacgctttgg gtagagaaat gatcggtaga agattgttcg gtgctgacgc tgaccacaag  600
gctgacgaat tcagatctat ggttactgaa atgatggctt tggctggtgt tttcaacatc  660
ggtgacttcg ttccatcttt ggactggttg gacttgcaag gtgttgctgg taagatgaag  720
agattgcaca agagattcga cgctttcttg tcatctatct tgaaggaaca cgaaatgaac  780
ggtcaagacc aaaagcacac tgacatgttg tctactttga tctctttgaa gggtactgac  840
ttggacggtg acggtggttc tttgactgac actgaaatca aggctttgtt gttgaacatg  900
ttcactgctg gtactgacac ttctgcttct actgttgact gggctatcgc tgaattgatc  960
agacacccag acatcatggt taaggctcaa gaagaattgg acatcgttgt tggtagagac  1020
agaccagtta acgaatctga catcgctcaa ttgccatact tgcaagctgt tatcaaggaa  1080
aacttcagat tgcacccacc aactccattg tctttgccac acatcgcttc tgaatcttgt  1140
gaaatcaacg gttaccacat cccaaagggt tctactttgt tgactaacat ctgggctatc  1200
gctagggacc cagaccaatg gtctgaccca ttggctttca agccagaaag attcttgcca  1260
ggtggtgaaa agtctggtgt tgacgttaag ggttctgact tcgaattgat cccattcggt  1320
gctggtagaa gaatctgtgc tggtttgtct ttgggtttga gaactatcca attcttgact  1380
gctactttgg ttcaaggttt cgactgggaa ttggctggtg gtgttactcc agaaaagttg  1440
aacatggaag aatcttacgg tttgactttg caaagagctg ttccattggt tgttcaccca  1500
aagccaagat tggctccaaa cgtttacggt ttgggttctg gttaa                  1545

SEQ ID NO: 123          moltype = AA  length = 571
FEATURE                 Location/Qualifiers
source                  1..571
                        mol_type = protein
                        organism = Arabidopsis thaliana
SEQUENCE: 123
MSVLQQQTHF LTKKIDQEDE EEEPSHDFIF RSKLPDIFIP NHLPLTDYVF QRFSGDGDGD  60
SSTTCIIDGA TGRILTYADV QINMRRIATG IHRLGIRHGD VVMLLLPNSP EFALSFLAVA  120
YLGAVSTTAN PFYTQPEIAK QAKASAAKMI ITKKCLVDKL TNLKNDGVLI VCLDDDGDNG  180
VVSSSDDGCV SFTELTQADE TELLKPKISP EDTVAMPYSS GTTGLPKGVM ITHKGLVTSI  240
AQKVDGENPN LNFTANDVIL CFLPMFHIYA LDALMLSAMR TGAALLIVPR FELNLVMELI  300
QRYKVTVVPV APPVVLAFIK SPETERYDLS SVRIMLSGAA TLKKELEDAV RLKFPNAIFG  360
QGYGMTESGT VAKSLAFAKN PFKTKSGACG TVIRNAEMKV VDTETGISLP RNKSGEICVR  420
GHQLMKGYLN DPEATARTID KDGWLHTGDI GFVDDDDEIF IVDRLKELIK FKGYQVAPAE  480
LEALLISHPS IDDAAVVAMK DEVADEVPVA FVARSQGSQL TEDDVKSYVN KQVVHYKRIK  540
MVFFIEVIPK AVSGKILRKD LRAKLETMCS K                                 571

SEQ ID NO: 124          moltype = DNA  length = 1716
FEATURE                 Location/Qualifiers
misc_feature            1..1716
                        note = coding sequence for SEQ ID NO:123
source                  1..1716
                        mol_type = other DNA
                        organism = synthetic construct
SEQUENCE: 124
atgtccgttt tgcaacaaca aactcacttc ttgactaaga agatcgatca agaagatgaa  60
gaagaagaac catctcacga tttcattttc agatctaagt tgccagatat cttcatccca  120
aaccacttgc cattgaccga ttacgtattc caaagattct ccggtgatgg tgacggtgat  180
tcctctacta cctgtatcat cgacggtgcc actggccgta tcctcaccta cgccgatgtt  240
caaatcaaca tgagaagaat cgctaccggt atccacagat tgggtatcag acacggtgac  300
gtcgttatgt tgttgttgcc aaactctcca gaattcgctt tgtctttctt ggccgttgct  360
tacttgggtg ccgtttccac taccgctaac ccattctaca ctcaaccaga aatcgctaag  420
caagctaagg cctccgccgc taagatgatc atcactaaga aatgcctggt cgataagttg  480
actaacttga agaacgacgg tgttttgatc gtttgtttgg acgatgacgg tgacaatggc  540
gttgtgagct cttctgatga tggttgtgtt tctttcactg aattgactca agctgacgaa  600
actgaattgt tgaagccaaa gatctctcca gaagatactg ttgctatgcc atactcttcc  660
ggcactactg gtttaccaaa gggtgttatg attactcaca agggtttggt tacttctatc  720
gctcaaaagg tcgacggtga aaacccaaac ttgaacttca ctgccaacga cgtcatcttg  780
tgtttcttgc caatgttcca catttacgct ttggacgctt tgatgttgtc tgctatgaga  840
accggtgctg ctttgttgat cgttccaaga ttcgaattga acttggttat ggaattgatt  900
caaagataca aggtcactgt tgttccagtt gctccaccag ttgttttggc tttcattaag  960
tccccagaaa ctgaaagata cgacttatct tctgttagaa ttatgttgtc tggtgctgct  1020
actttgaaga aggaattgga agatgccgtt agattgaagt tcccaaacgc cattttcggt  1080
caaggttacg gtatgaccga atccggtact gttgctaagt cgctcgcgtt cgctaagaac  1140
ccattcaaga ccaagtccgg tgcttgtggt actgttatca gaaacgccga aatgaaggtt  1200
gtcgataccg aaaccggtat ctccttgcca agaaacaagt ctggtgaaat ctgtgtcaga  1260
ggtcaccaat tgatgaaggg ttacttgaac gatccagaag ctactgctag aaccatcgac  1320
aaggacggtt ggttgcacac tggtgatatt ggtttcgttg atgatgatga tgaaatcttc  1380
attgttgata gattgaagga attgatcaag ttcaagggtt accaagttgc tccagctgaa  1440
ttggaagctt tgttgatttc tcacccatct atcgatgatg ccgctgttgt tgctatgaag  1500
gatgaagttg ctgatgaagt tccagttgct ttcgttgcta gatctcaagg ttctcaattg  1560
actgaagatg atgtcaagtc ttacgttaac aagcaagttg ttcactacaa gagaattaag  1620
atggttttct tcatcgaagt tatcccaaag gctgtttctg gtaagatttt gagaaaggat  1680
ttgagagcta agttggaaac catgtgttct aagtaa                             1716
```

```
SEQ ID NO: 125         moltype = AA  length = 561
FEATURE                Location/Qualifiers
source                 1..561
                       mol_type = protein
                       organism = Citrus clementina
SEQUENCE: 125
MSISIATKKP ELSLDISSPA PPAPSNEKIA THIFKSKLPD IPISNHLPLH TYCFQDRLSD  60
DPCLIVGLTG KTYSYAETHL ICRKTAAGLS NLGIKKGDVI MILLQNCAEF VFSFMGASMI  120
GAVTTTANPF YTSAEILKQF RTSGAKLIIT MSQYVDRLPK TDKDFTVITI DAPPENCLHF  180
TVLSEADEDQ IPEVAIEPDD PVALPFSSGT TGLPKGVVLT HKSLITSVAQ QVDGENPNLY  240
LTNGDVVLCV LPLFHIYSLN SVLLCSLRAG AGVLLMQKFE IGALLELIQR HRVSVAAVVP  300
PLVLALAKNP MVADYDLSSI RVVLSGAAPL GKELEDALRS RVPQAILGQG YGMTEAGPVL  360
SMCLGFAKQP FPTKSGSCGT VVRNAELKVI DPEIGASLPH NQPGEICIRG PQIMKGYLND  420
PEATAATIDV EGWLHTGDIG YVDDDDEVFI VDRVKEIIKF KGFQVPPAEI EALLLSHPSI  480
GDAAVVPQKD EVAGEVPVAF VVRSNGFELT EEAIKEYIAK QVVFYKRLHK IYFVHAIPKS  540
PSGKILRKDL RAKLASSMPL N                                             561

SEQ ID NO: 126         moltype = DNA  length = 1686
FEATURE                Location/Qualifiers
misc_feature           1..1686
                       note = coding sequence for SEQ ID NO:125
source                 1..1686
                       mol_type = other DNA
                       organism = synthetic construct
SEQUENCE: 126
atgtccatct ctatcgccac taagaagcca gaattgtctt tggatatctc ttctccagct  60
ccaccagctc catccaacga aaagatcgcc acccacattt tcaagtctaa gttgccagat  120
atcccaatct ccaaccactt gccattgcac acttactgtt tccaagatag attgtctgac  180
gacccatgtt tgatcgttgg tttgactggt aagacttact cttacgccga aactcacttg  240
atctgtagaa agaccgctgc cggtttgtct aacttgggta tcaagaaggg tgacgttatc  300
atgatcttgt tgcaaaactg tgccgaattc gttttctctt tcatgggtgc ttccatgatc  360
ggtgctgtca ctactactgc caacccattc tacacttctg ctgaaatctt gaagcaattc  420
agaacctctg gtgccaagtt gattatcact atgtctcaat acgtcgacag attgccaaag  480
actgacaagg atttcactgt tatcactatc gatgccccac cagaaaactg tttgcacttc  540
actgttttgt ctgaagctga tgaagatcaa atcccagaag ttgccatcga accagacgat  600
ccagttgctt tgccattctc ttctggtacc actggtttgc caaagggtgt tgttttgact  660
cataagagct tgatcacctc tgttgctcaa caagttgacg gtgaaaaccc aaacttgtac  720
ttgactaacg gtgacgttgt tttgtgtgtt ttgccattgt tccacattta ctctttgaac  780
tctgttttgt tgtgttcttt gagagctggt gctggtgttt tgttgatgca aaagttcgaa  840
atcggtgctt tgttggaatt gatccaaaga cacagagttt ctgttgctgc tgttgttcca  900
ccattggttt tggctttggc caagaaccca atggttgctg attacgactt gtcatctatc  960
agagttgttt tgtccggtgc tgctccattg ggtaaggaat tggaagatgc tttgagatct  1020
agagtcccac aagctatctt gggtcaaggt tacggtatga ctgaagctgg tccagttttg  1080
tctatgtgtt tgggtttcgc taagcaacca ttcccaacta agtctggttc ttgtggtacc  1140
gttgttagaa acgctgaatt gaaggttatt gacccagaaa ttggtgcctc cttgccacac  1200
aaccaaccag gtgaaatttg tatcagaggt ccacaaatta tgaagggtta cttgaacgat  1260
ccagaagcta ctgctgctac tatcgacgtt gaaggttggt tgcacactgg tgacatcggt  1320
tacgttgatg atgatgatga agttttcatc gtcgatagag tcaaggaaat catcaagttc  1380
aagggtttcc aagttccacc agctgaaatt gaagccttgt tgttgtctca cccatctatt  1440
ggtgatgctg ctgttgttcc acaaaaggat gaagttgcgg gtgaagttcc agttgcgttc  1500
gttgttcgtt cgaacggctt cgaattgacc gaggaagcca ttaaggaata catcgctaag  1560
caagttgttt tctacaagag attgcacaag atttacttcg ttcacgctat tccaaagtct  1620
ccatccggta agattttgag aaaggatttg agagccaagt tggcctcttc tatgccattg  1680
aactaa                                                              1686

SEQ ID NO: 127         moltype = AA  length = 365
FEATURE                Location/Qualifiers
source                 1..365
                       mol_type = protein
                       organism = Angelica archangelica
SEQUENCE: 127
MSAPTTITAL AQEKTLNLAF VRDEDERPKV AYNQFSNEIP IISLAGMDDD TGRRPQICRK  60
IVEAFEDWGI FQVVDHGIDG TLISEMTRLS REFFALPAEE KLRYDTTGGK RGGFTISTHL  120
QGDDVKDWRE FVTYFSYPID DRDYSRWPDK PQGWRSTTEV YSEKLMVLGA KLLEVLSEAM  180
GLEKEALTKA CVNMEQKVLI NYYPTCPEPD LTLGVRRHTD PGTITILLQD MVGGLQATRD  240
GGKTWITVQP VEGAFVVNLG DHGHYLSNGR FKNADHQAVV NSTSSRLSIA TFQNPAQNAI  300
VYPLRIREGE KAVLDEAITY AEMYKKNMTK HIEVATLKKL AKEKRLQEEK AKLETESKSA  360
DGISA                                                               365

SEQ ID NO: 128         moltype = DNA  length = 1098
FEATURE                Location/Qualifiers
misc_feature           1..1098
                       note = coding sequence for SEQ ID NO:127
source                 1..1098
                       mol_type = other DNA
                       organism = synthetic construct
SEQUENCE: 128
atgtccgctc caactactat cactgctttg gctcaagaaa agactttgaa cttggctttc  60
```

```
gttagagatg aagatgaaag accaaaggtt gcttacaacc aattctctaa cgaaatccca  120
atcatctctt tggctggtat ggacgacgac actggtagga ggccacaaat ctgtagaaag  180
atcgttgaag ctttcgaaga ttggggtatc ttccaagttg ttgaccacgg tatcgacggt  240
actttgatct ctgaaatgac tagattgtct agagaattct tcgctttgcc agctgaagaa  300
aagttgagat acgacactac tggtggtaag agaggtggtt tcactatctc tactcacttg  360
caaggtgacg acgttaagga ctggagagaa ttcgttactt acttctctta cccaatcgac  420
gacagagact actctagatg gccagacaag ccacaaggtt ggagatctac tactgaagtt  480
tactctgaaa agttgatggt tttgggtgct aagttgttgg aagttttgtc tgaagctatg  540
ggtttggaaa aggaagcttt gactaaggct tgtgttaaca tggaacaaaa ggttttgatc  600
aactactacc caacttgtcc agaaccagac ttgactttgg gtgttaggag acacactgac  660
ccaggtacta tcactatctt gttgcaagac atggttggtg gtttgcaagc tactagagat  720
ggtggtaaga cttggatcac tgttcaacca gttgaaggtg ctttcgttgt taacttgggt  780
gaccacggtc actacttgtc taacggtaga ttcaagaacg ctgaccacca agctgttgtt  840
aactctactt cttctagatt gtctatcgct actttccaaa acccagctca aaacgctatc  900
gtttacccat tgagaatcag agaaggtgaa aaggctgttt tggacgaagc tatcacttac  960
gctgaaatgt acaagaagaa catgactaag cacatcgaag ttgctacttt gaagaagttg  1020
gctaaggaaa agagattgca agaagaaaag gctaagttgg aaactgaatc taagtctgct  1080
gacggtatct ctgcttaa                                                1098

SEQ ID NO: 129         moltype = AA  length = 514
FEATURE                Location/Qualifiers
source                 1..514
                       mol_type = protein
                       organism = Cynara cardunculus var. scolymus
SEQUENCE: 129
MSQVHETLTP AVIAAVVLSS VFLYLLFKKK QNHRLPPSPP SLPIIGHLHH LGPLIHQSFH  60
HLSTRYGPLI HLRLGSVPCI VASTPDLARD FLKTNELAFS SRKHSLAIDH ITYGVAFAFA  120
PYGPYWKFIK KMSTVELLGN QNLGHFLPIR THEIQELLQT LTEKAKRRES VNLTEELLKL  180
TNNVICQMMM SIRCSGTNSE ADEAKNLVRE VTQIFGEFNV SDFIWFCKNI DLQGFKKRYT  240
DTHKRYDALL EKIIFEREEK RRKEGKREDG KGKDFLDMLL DVLEDAKAEI KITRDHIKAL  300
ILDFFTAATD TTAIALEWML VELISNPKVL EIAREEIDQV VGNERLVQES DAPNLPYIQA  360
IIKEALRLHP PIPMLIRKSI EDVSVQGYDI PAGTMLFVNI WSIGRNPKYW ESPLEFKPHR  420
FLEDDPVKKS LDIKGQSFQL LPFGTGRRGC PGINLAMREL PVVIAGLIQC FEWNVNGKQV  480
LDMDERAGLT APRAADFVCV PSVRENSPMM FTST                              514

SEQ ID NO: 130         moltype = DNA  length = 1545
FEATURE                Location/Qualifiers
misc_feature           1..1545
                       note = coding sequence for SEQ ID NO:129
source                 1..1545
                       mol_type = other DNA
                       organism = synthetic construct
SEQUENCE: 130
atgtcccaag ttcacgaaac tttgactcca gctgttatcg ctgctgttgt tttgtcatct  60
gttttcttgt acttgttgtt caagaagaag caaaaccaca gattgccacc atctccacca  120
tctttgccaa tcatcggtca cttgcaccac ttgggtccat tgatccacca atctttccac  180
cacttgtcta ctagatacgg tccattgatc cacttgagat tgggttctgt tccatgtatc  240
gttgcttcta ctccagactt ggctagagac ttcttgaaaa ctaacgaatt ggctttctct  300
tctagaaagc actctttggc tatcgaccac atcacttacg gtgttgcttt cgctttcgct  360
ccatacggtc catactggaa gttcatcaag aagatgtcta ctgttgaatt gttgggtaac  420
caaaacttgg gtcacttctt gccaatcaga actcacgaaa tccaagaatt gttgcaaact  480
ttgactgaaa aggctaagag aagagaatct gttaacttga ctgaagaatt gttgaagttg  540
actaacaacg ttatctgtca aatgatgatg tctatcagat gttctggtac taactctgaa  600
gctgacgaag ctaagaactt ggttagagaa gttactcaaa tcttcggtga attcaacgtt  660
tctgacttca tctggttctg taagaacatc gacttgcaag gtttcaagaa gagatacact  720
gacactcaca agagatacga cgctttgttg gaaaagatca tcttcgaaag agaagaaaag  780
agaagaaagg aaggtaagag agaagatggt aagggtaagg acttcttgga catgttgttg  840
gacgttttgg aagatgctaa ggctgaaatc aagatcacta gagatcacat caaggctttg  900
atcttggact tcttcactgc tgctactgac actactgcta tcgctttgga atggatgttg  960
gttgaattga tctctaaccc aaaggttttg gaaatcgcta gagaagaaat cgaccaagtt  1020
gttggtaacg aaagattggt tcaagaatct gacgctccaa acttgccata catccaagct  1080
atcatcaagg aagctttgag attgcaccca ccaatcccaa tgttgatcag aaagtctatc  1140
gaagatgttt ctgttcaagg ttacgacatc ccagctggta ctatgttgtt cgttaacatc  1200
tggtctatcg gtagaaaccc aaagtactgg gaatctccat tggaattcaa gccacacaga  1260
ttcttggaag atgacccagt taagaagtct ttggacatca agggtcaatc tttccaattg  1320
ttgccattcg gtactggtag aagaggttgt ccaggtatca acttggctat gagagaattg  1380
ccagttgtta tcgctggttt gatccaatgt ttcgaatgga acgttaacgg taagcaagtt  1440
ttggacatgg acgaaagagc tggtttgact gctccaagag ctgctgactt cgtttgtgtt  1500
ccatctgtta gagaaaactc tccaatgatg ttcacttcta cttaa                  1545

SEQ ID NO: 131         moltype = AA  length = 507
FEATURE                Location/Qualifiers
source                 1..507
                       mol_type = protein
                       organism = Perilla frutescens var. crispa
SEQUENCE: 131
MSALYAALFL LSAAVVRSVL DRKRGRPPYP PGPFPLPIIG HLHLLGPRLH QTFHDLSQRY  60
GPLMQLRLGS IRCVIAASPE LAKECLKTHE LVFSSRKHST AIDIVTYDSS FAFSPYGPYW  120
KFIKKLCTYE LLGARNLAHF QPIRTLEVKS FLQILMRKGE SGESFNVTEE LVKLTSNVIS  180
```

```
HMMLSIRCSE TESEAEAART VIREVTQIFG EFDVSDIIWL CKNFDFQGIR KRSEDIQRRY  240
DALLEKIITD REKQRRTHGG GGGGGEAKDF LDMFLDIMES GKAEVKFTRE HLKALILDFF  300
TAGTDTTAIV CEWAIAEVIN NPNVLKKAQE EIANIVGFDR ILQESDAPNL PYLQALIKET  360
FRLHPPIPML ARKSISDCVI DGYMIPANTL LFVNLWSMGR NPKIWDYPTA FQPERFLEKE  420
KAAIDVKGQH FELLPFGTGR RGCPGMLLAI QEVVIIIGTM IQCFDWKLPD GSGHVDMAER  480
PGLTAPRETD LFCRVVPRVD PLVVSTQ                                      507

SEQ ID NO: 132         moltype = DNA  length = 1524
FEATURE                Location/Qualifiers
misc_feature           1..1524
                       note = coding sequence for SEQ ID NO:131
source                 1..1524
                       mol_type = other DNA
                       organism = synthetic construct
SEQUENCE: 132
atgtccgctt tgtacgctgc tttgttcttg ttgtctgctg ctgttgttag atctgttttg  60
gacagaaaga gaggtagacc accataccca ccaggtccat tcccattgcc aatcatcggt  120
cacttgcact tgttgggtcc aagattgcac caaactttcc acgacttgtc tcaaagatac  180
ggtccattga tgcaattgag attgggttct atcagatgtg ttatcgctgc ttctccagaa  240
ttggctaagg aatgtttgaa aactcacgaa ttggttttct cttctagaaa gcactctact  300
gctatcgaca tcgttactta cgactcttct ttcgctttct ctccatacgg tccatactgg  360
aagttcatca agaagttgtg tacttacgaa ttgttgggtg ctagaaactt ggctcacttc  420
caaccaatca gaactttgga agttaagtct ttcttgcaaa tcttgatgag aaagggtgaa  480
tctggtgaat ctttcaacgt tactgaagaa ttggttaagt tgacttctaa cgttatctct  540
cacatgatgt tgtctatcag atgttctgaa actgaatctg aagctgaagc tgctagaact  600
gttatcagag aagttactca aatcttcggt gaattcgacg tttctgacat catctggttg  660
tgtaagaact tcgacttcca aggtatcaga aagagatctg aagatatcca aagaagatac  720
gacgctttgt tggaaaagat catcactgac agagaaaagc aaagaagaac tcacggtggt  780
ggtggtggtg gtggtgaagc taaggacttc ttggacatgt tcttggacat catggaatct  840
ggtaaggctg aagttaagtt cactagagaa cacttgaagg ctttgatctt ggacttcttc  900
actgctggta ctgacactac tgctatcgtt tgtgaatggg ctatcgctga agttatcaac  960
aacccaaacg ttttgaagaa ggctcaagaa gaaatcgcta acatcgttgg tttcgacaga  1020
atcttgcaag aatctgacgc tccaaacttg ccatacttgc aagctttgat caaggaaact  1080
ttcagattgc acccaccaat cccaatgttg gctagaaagt ctatctctga ctgtgttatc  1140
gacggttaca tgatcccagc taacactttg ttgttcgtta acttgtggtc tatgggtaga  1200
aacccaaaga tctgggacta cccaactgct ttccaaccag aaagattctt ggaaaaggaa  1260
aaggctgcta tcgacgttaa gggtcaacac ttcgaattgt tgccattcgg tactggtaga  1320
agaggttgtc caggtatgtt gttggctatc caagaagttg ttatcatcat cggtactatg  1380
atccaatgtt tcgactggaa gttgccagac ggttctggtc acgttgacat ggctgaaaga  1440
ccaggtttga ctgctccaag agaaactgac ttgttctgta gagttgttcc aagagttgac  1500
ccattggttg tttctactca ataa                                         1524

SEQ ID NO: 133         moltype = AA  length = 515
FEATURE                Location/Qualifiers
source                 1..515
                       mol_type = protein
                       organism = Dahlia pinnata
SEQUENCE: 133
MSNTLLVLQM VIPAIIAFVI FHLLFFKSKP NRRLPPSPPS LPIIGHLHHL GPLIHQSFNR  60
LSARYGPLIH LRLGSVSCVV ADAPDLAQEL LQKNDLAFAN RKHTLAIDHV TYGVAFAFAP  120
YGPYWRFIKK MSTVELLGIQ NLGHFLPIRT QEIHGLLLTL TEKSKQNESV NMTNELLKLS  180
NNIICQMMMG IRCSGNKTEA EEAKNLVREV TTIFGEFNVS DFIWFCKKLD LQGFKKRYED  240
IRTRYDALLE RIIFAREEMR KEGKGMEDGK GKDFLDMLLD VLEDDKAEIK ITRNHIKALI  300
LDFVTAGTDT TAVIIEWTLV ELIKNPMVME KAKQELDEVV GNTRLVEESD APKLPYIQAI  360
IKEAFRLHPP IPMIIRKSNE NVSVKSGYEI PAGSILFVNN WSIGRNPKYW ESPLEFKPDR  420
FLKEGVLKPS LDIRGQNFQI LPFGTGRRSC PGINMAMRQL PVVVAILIQC FEWTVNDKQV  480
LNMDERGGLT TPRATDLVCF PLLRKNSPHS MFTSV                             515

SEQ ID NO: 134         moltype = DNA  length = 1548
FEATURE                Location/Qualifiers
misc_feature           1..1548
                       note = coding sequence for SEQ ID NO:133
source                 1..1548
                       mol_type = other DNA
                       organism = synthetic construct
SEQUENCE: 134
atgtccaaca ctttgttggt tttgcaaatg gttatcccag ctatcatcgc tttcgttatc  60
ttccacttgt tgttcttcaa gtctaagcca aacagaagat tgccaccatc tccaccatct  120
ttgccaatca tcggtcactt gcaccacttg ggtccattga tccaccaatc tttcaacaga  180
ttgtctgcta gatacggtcc attgatccac ttgagattgg gttctgtttc ttgtgttgtt  240
gctgacgctc cagacttggc tcaagaattg ttgcaaaaga acgacttggc tttcgctaac  300
agaaagcaca ctttggctat cgaccacgtt acttacggtg ttgctttcgc tttcgctcca  360
tacggtccat actggagatt catcaagaag atgtctactg ttgaattgtt gggtatccaa  420
aacttgggtc acttcttgcc aatcagaact caagaaatcc acggtttgtt gttgactttg  480
actgaaaagt ctaagcaaaa cgaatctgtt aacatgacta acgaattgtt gaagttgtct  540
aacaacatca tctgtcaaat gatgatgggt atcagatgtt ctggtaacaa gactgaagct  600
gaagaagcta agaacttggt tagagaagtt actactatct tcggtgaatt caacgtttct  660
gacttcatct ggttctgtaa gaagttggac ttgcaaggtt tcaagaagag atacgaagat  720
atcagaacta gatacgacgc tttgttggaa agaatcatct tcgctagaga agaaatgaga  780
```

```
aaggaaggta agggtatgga agatggtaag ggtaaggact tcttggacat gttgttggac  840
gttttggaag atgacaaggc tgaaatcaag atcactagaa accacatcaa ggctttgatc  900
ttggacttcg ttactgctgg tactgacact actgctgtta tcatcgaatg gactttggtt  960
gaattgatca agaacccaat ggttatggaa aaggctaagc aagaattgga cgaagttgtt  1020
ggtaacacta gattggttga agaatctgac gctccaaagt tgccatacat ccaagctatc  1080
atcaaggaag ctttcagatt gcacccacca atcccaatga tcatcagaaa gtctaacgaa  1140
aacgtttctg ttaagtctgg ttacgaaatc ccagctggtt ctatcttgtt cgttaacaac  1200
tggtctatcg gtagaaaccc aaagtactgg gaatctccat tggaattcaa gccagacaga  1260
ttcttgaagg aaggtgtttt gaagccatct ttggacatca gaggtcaaaa cttccaaatc  1320
ttgccattcg gtactggtag aagatcttgt ccaggtatca acatggctat gagacaattg  1380
ccagttgttg ttgctatctt gatccaatgt ttcgaatgga ctgttaacga caagcaagtt  1440
ttgaacatgg acgaaagagg tggtttgact actccaagag ctactgactt ggtttgtttc  1500
ccattgttga gaaagaactc tccacactct atgttcactt ctgtttaa              1548

SEQ ID NO: 135         moltype = AA  length = 515
FEATURE                Location/Qualifiers
source                 1..515
                       mol_type = protein
                       organism = Callistephus chinensis
SEQUENCE: 135
MSNIFEVFQS VSPAIIAIFF ISSLFIYLVL IRNQKSLSLP PSPPALPIIG HLHHLGPLIH  60
HSFHDLSTRY GPLIHLRLGS VPCVVASTPD LARDFLKTNE LAFSSRKHSL AIDHVTYGVS  120
FAFAPYGPYW KFIKKTSIVE LLGNQNLSNF LPIRTQEVHE LLQTLMVKSK KNESVNLSEE  180
LLKLTNNVIC QMMMSIRCSG TNNEADEAKN LVREVTKIFG EFNISDFICL FKNIDLQGFK  240
KRYVDTHTRY NALLEKMIFE REEKRKQKKS EDGKGKDFLD ILLDVLEDEN AEIKITRDHI  300
KALILDFFTA ATDTTAISIE WTLVELTNNP KVLENARKEI AEVVGDERLV QESDIPNLPY  360
IQAIIKETLR MHPPIPMVIR KSIDNVTVQG YDIRAGTMLF VNIWSIGRNP LYWESPLEFK  420
PHRFLDGHAR NLDVKGQCFQ LLPFGTGRRG CPGISLAMRE LPVVIAGLIQ CFEWNANDKE  480
VLSMDERAGL TAPRAVDLEF VPLMRQNCPN IFVSA                            515

SEQ ID NO: 136         moltype = DNA  length = 1548
FEATURE                Location/Qualifiers
misc_feature           1..1548
                       note = coding sequence for SEQ D NO 135
source                 1..1548
                       mol_type = other DNA
                       organism = synthetic construct
SEQUENCE: 136
atgtccaaca tcttcgaagt tttccaatct gtttctccag ctatcatcgc tatcttcttc  60
atctcttctt tgttcatcta cttggttttg atcagaaacc aaaagtcttt gtctttgcca  120
ccatctccac cagctttgcc aatcatcggt cacttgcacc acttgggtcc attgatccac  180
cactctttcc acgacttgtc tactagatac ggtccattga tccacttgag attgggttct  240
gttccatgtg ttgttgcttc tactccagac ttggctagag acttcttgaa aactaacgaa  300
ttggctttct cttctagaaa gcactctttg gctatcgacc acgttactta cggtgtttct  360
ttcgctttcg ctccatacgg tccatactgg aagttcatca agaaaacttc tatcgttgaa  420
ttgttgggta accaaaactt gtctaacttc ttgccaatca gaactcaaga agttcacgaa  480
ttgttgcaaa ctttgatggt taagtctaag aagaacgaat ctgttaactt gtctgaagaa  540
ttgttgaagt tgactaacaa cgttatctgt caaatgatga tgtctatcag atgttctggt  600
actaacaacg aagctgacga agctaagaac ttggttagag aagttactaa gatcttcggt  660
gaattcaaca tctctgactt catctgtttg ttcaagaaca tcgacttgca aggtttcaag  720
aagagatacg ttgacactca cactagatac aacgctttgt tggaaaagat gatcttcgaa  780
agagaagaaa agagaaagca aaagaagtct gaagatggta agggtaagga cttcttggac  840
atcttgttgg acgttttgga agatgaaaac gctgaaatca agatcactag agatcacatc  900
aaggctttga tcttggactt cttcactgct gctactgaca ctactgctat ctctatcgaa  960
tggactttgg ttgaattgac taacaaccca aaggttttgg aaaacgctag aaaggaaatc  1020
gctgaagttg ttggtgacga aagattggtt caagaatctg acatcccaaa cttgccatac  1080
atccaagcta tcatcaagga aactttgaga atgcacccac caatcccaat ggttatcaga  1140
aagtctatcg acaacgttac tgttcaaggt tacgacatca gagctggtac tatgttgttc  1200
gttaacatct ggtctatcgg tagaaaccca ttgtactggg aatctccatt ggaattcaag  1260
ccacacagat tcttggacgg tcacgctaga aacttggacg ttaagggtca atgtttccaa  1320
ttgttgccat tcggtactgg tagaagaggt tgtccaggta tctctttggc tatgagagaa  1380
ttgccagttg ttatcgctgg tttgatccaa tgtttcgaat ggaacgctaa cgacaaggaa  1440
gttttgtcta tggacgaaag agctggtttg actgctccaa gagctgttga cttggaattc  1500
gttccattga tgagacaaaa ctgtccaaac atcttcgttt ctgcttaa              1548

SEQ ID NO: 137         moltype = AA  length = 356
FEATURE                Location/Qualifiers
source                 1..356
                       mol_type = protein
                       organism = Apium graveolens
SEQUENCE: 137
MSAPSTITAL SQEKTLNLDF VRDEDERPKV AYNQFSNEVP IISLAGLDDD SNGRRAEICR  60
KIVEAFEEWG IFQVVDHGID SGLISEMSRL SREFFALPAE EKLVYDTTGE KKGGFTISTH  120
LQGDDVRDWR EFVTYFSYPI SARDYSRWPK KPEGWRSTTE VYSEKLMVLG AKLLEVLSEA  180
MGLEKEALTK ACVEMEQKVL INYYPTCPEP DLTLGVRRHT DPGTITILLQ DMVGGLQATR  240
DGGKTWITVQ PVEGAFVVNL GDHGHYLSNG RFRNADHQAV VNSTSTRLSI ATFQNPAQNA  300
IVYPLKIREG EKAILDEAIT YAEMYKKNMT KHIAVATQKK LAKEKRLQDE KAKMKI      356

SEQ ID NO: 138         moltype = DNA  length = 1071
```

```
FEATURE                Location/Qualifiers
misc_feature           1..1071
                       note = coding sequence for SEQ ID NO: 137
source                 1..1071
                       mol_type = other DNA
                       organism = synthetic construct
SEQUENCE: 138
atgtccgctc catctactat cactgctttg tctcaagaaa agactttgaa cttggacttc  60
gttagagatg aagatgaaag accaaaggtt gcttacaacc aattctctaa cgaagttcca  120
atcatctctt tggctggttt ggacgacgac tctaacggta gaagagctga aatctgtaga  180
aagatcgttg aagctttcga agaatggggt atcttccaag ttgttgacca cggtatcgac  240
tctggtttga tctctgaaat gtctagattg tctagagaat tcttcgcttt gccagctgaa  300
gaaaagttgg tttacgacac tactggtgaa aagaagggtg gtttcactat ctctactcac  360
ttgcaaggtg acgacgttag agactggaga gaattcgtta cttacttctc ttacccaatc  420
tctgctagag actactctag atggccaaag aagccagaag gttggagatc tactactgaa  480
gtttactctg aaaagttgat ggttttgggt gctaagttgt tggaagtttt gtctgaagct  540
atgggtttgg aaaaggaagc tttgactaag gcttgtgttg aaatggaaca aaaggttttg  600
atcaactact acccaacttg tccagaacca gacttgactt tgggtgttag gagacacact  660
gacccaggta ctatcactat cttgttgcaa gacatggttg gtggtttgca agctactaga  720
gatggtggta agacttggat cactgttcaa ccagttgaag gtgctttcgt tgttaacttg  780
ggtgaccacg gtcactactt gtctaacggt agattcagaa acgctgacca ccaagctgtt  840
gttaactcta cttctactag attgtctatc gctactttcc aaaacccagc tcaaaacgct  900
atcgtttacc cattgaagat cagagaaggt gaaaaggcta tcttggacga agctatcact  960
tacgctgaaa tgtacaagaa gaacatgact aagcacatcg ctgttgctac tcaaaagaag  1020
ttggctaagg aaaagagatt gcaagacgaa aaggctaaga tgaagatcta a           1071

SEQ ID NO: 139         moltype = AA  length = 521
FEATURE                Location/Qualifiers
source                 1..521
                       mol_type = protein
                       organism = Medicago truncatula
SEQUENCE: 139
MSEPLLLAFT LFLSSLICYI IFQPILNRHK NLPPSPLFKL PIIGHMHMLG PLLHHSFDRL  60
SQKYGPIFSL NFGSVLCVVA STPHYAKQIL QINEHAFNCR NESTAIKRLT YEASLAFAPY  120
GEYWRFIKKL SMNELLGSRS ISSFQHLRLQ ETHNLLKLFA DKAKNYEAVN VTQELLKLSN  180
NVISKMMLGE AEEARDVVRD VTEIFGEFNV SDFIWLFKKL DLQGFGKRIE DLFMRFDTLV  240
ERIISKREEL RKNKGRKENK GEQGAEFRDF LDILLDCAED QNSEIKVQRV HIKALIMDFF  300
TAGTDTTSIS TEWALVELMN NPSLLQKARE EIDNVVGKNR LVDESDGPNL PYIQAIIKET  360
FRLHPPVPMV TRRCVTQCKI ENYVIPENSL IFVNNWAMGR NSAYWDKPLE FNPERFLKNS  420
TNSNGVIDVR GQNFQILPFG SGRRMCPGVT LAMQEVPALL GAIIQCFDFN FVGPKGEILK  480
GGDIVIDVNE RPGLTAPRVH DLVCVPVERF ACGGPLQSLG C                     521

SEQ ID NO: 140         moltype = DNA  length = 1566
FEATURE                Location/Qualifiers
misc_feature           1..1566
                       note = coding sequence for SEQ ID NO: 139
source                 1..1566
                       mol_type = other DNA
                       organism = synthetic construct
SEQUENCE: 140
atgtccgaac cattgttgtt ggctttcact ttgttcttgt catctttgat ctgttacatc  60
atcttccaac caatcttgaa cagacacaag aacttgccac catctccatt gttcaagttg  120
ccaatcatcg gtcacatgca catgttgggt ccattgttgc accactcttt cgacagattg  180
tctcaaaagt acggtccaat cttctctttg aacttcggtt ctgttttgtg tgttgttgct  240
tctactccac actacgctaa gcaaatcttg caaatcaacg aacacgcttt caactgtaga  300
aacgaatcta ctgctatcaa gagattgact tacgaagctt ctttggcttt cgctccatac  360
ggtgaatact ggagattcat caagaagttg tctatgaacg aattgttggg ttctagatct  420
atctcttctt tccaacactt gagattgcaa gaaactcaca acttgttgaa gttgttcgct  480
gacaaggcta agaactacga agctgttaac gttactcaag aattgttgaa gttgtctaac  540
aacgttatct ctaagatgat gttgggtgaa gctgaagaag ctagagatgt tgttagagat  600
gttactgaaa tcttcggtga attcaacgtt tctgacttca tctggttgtt caagaagttg  660
gacttgcaag gtttcggtaa gagaatcgaa gatttgttca tgagattcga cactttggtt  720
gaaagaatca tctctaagag agaagaattg agaaagaaca agggtagaaa ggaaaacaag  780
ggtgaacaag gtgctgaatt cagagacttc ttggacatct tgttggactg tgctgaagat  840
caaaactctg aaatcaaggt tcaaagagtt cacatcaagg ctttgatcat ggacttcttc  900
actgctggta ctgacactac ttctatctct actgaatggg ctttggttga attgatgaac  960
aacccatctt tgttgcaaaa ggctagagaa gaaatcgaca acgttgttgg taagaacaga  1020
ttggttgacg aatctgacgg tccaaacttg ccatacatcc aagctatcat caaggaaact  1080
ttcagattgc acccaccagt tccaatggtt actagaagat gtgttactca atgtaagatc  1140
gaaaactacg ttatcccaga aaactctttg atcttcgtta acaactgggc tatgggtaga  1200
aactctgctt actgggacaa gccattggaa ttcaacccag aaagattctt gaagaactct  1260
actaactcta acggtgttat cgacgttaga ggtcaaaact tccaaatctt gccattcggt  1320
tctggtagaa gaatgtgtcc aggtgttact ttggctatgc aagaagttcc agctttgttg  1380
ggtgctatca tccaatgttt cgacttcaac ttcgttggtc caaagggtga aatcttgaag  1440
ggtggtgaca tcgttatcga cgttaacgaa agaccaggtt tgactgctcc aagagttcac  1500
gacttggttt gtgttccagt tgaaagattc gcttgtggtg gtccattgca atctttgggt  1560
tgttaa                                                             1566

SEQ ID NO: 141         moltype = AA  length = 366
```

```
FEATURE                Location/Qualifiers
source                 1..366
                       mol_type = protein
                       organism = Cuminum cyminum
SEQUENCE: 141
MSAPTTITAL AQEKTLNSDF VRDEDERPKV AYNQFSTEIP IISLAGIDDD SKGRRPEVCR  60
KIVEAFEDWG IFQVVDHGVD SALISEMSRL SREFFALPAE EKLRYDTTGG KRGGFTISTH  120
QQGDDVRDWR EFVTYFSYPV DARDYSRWPE KPEGWRSVTE VYSEKLMVLG AKLLEVLSEA  180
MGLDKGALTK ACVNMEQKVL INYYPTCPEP DLTLGVRRHT DPGTITILLQ DMVGGLQATR  240
DGGKTWITVQ PVEGVFVVNL GDHGHYLSNG RFKNADHQAV VNSTSSRLSI ATFQNPAQNA  300
IVYPLKIREG EKPILEEAIT YAEMYKKNMT KHIEVATQKK LAKEKRLQEE KAKLETKTKS  360
ADGILA                                                           366

SEQ ID NO: 142         moltype = DNA  length = 1101
FEATURE                Location/Qualifiers
misc_feature           1..1101
                       note = coding sequence for SEQ ID NO: 141
source                 1..1101
                       mol_type = other DNA
                       organism = synthetic construct
SEQUENCE: 142
atgtccgctc caactactat cactgctttg gctcaagaaa agactttgaa ctctgacttc  60
gttagagatg aagatgaaag accaaaggtt gcttacaacc aattctctac tgaaatccca  120
atcatctctt tggctggtat cgacgacgac tctaagggta ggaggccaga agtttgtaga  180
aagatcgttg aagctttcga agattggggt atcttccaag ttgttgacca cggtgttgac  240
tctgctttga tctctgaaat gtctagattg tctagagaat tcttcgcttt gccagctgaa  300
gaaaagttga gatacgacac tactggtggt aagagaggtg gtttcactat ctctactcac  360
caacaaggtg acgacgttag agactggaga gaattcgtta cttacttctc ttacccagtt  420
gacgctagag actactctag atggccagaa aagccagaag gttggagatc tgttactgaa  480
gtttactctg aaaagttgat ggttttgggt gctaagttgt tggaagtttt gtctgaagct  540
atgggtttgg acaagggtgc tttgactaag gcttgtgtta acatggaaca aaaggttttg  600
atcaactact acccaacttg tccagaacca gacttgactt tgggtgttag gagacacact  660
gacccaggta ctatcactat cttgttgcaa gacatggttg gtggtttgca agctactagg  720
gacggtggta agacttggat cactgttcaa ccagttgaag gtgttttcgt tgttaacttg  780
ggtgaccacg gtcactactt gtctaacggt agattcaaga acgctgacca ccaagctgtt  840
gttaactcta cttcttctag attgtctatc gctactttcc aaaacccagc tcaaaacgct  900
atcgtttacc cattgaagat cagagaaggt gaaaagccaa tcttggaaga agctatcact  960
tacgctgaaa tgtacaagaa gaacatgact aagcacatcg aagttgctac tcaaaagaag  1020
ttggctaagg aaaagagatt gcaagaagaa aaggctaagt tggaaactaa gactaagtct  1080
gctgacggta tcttggctta a                                          1101

SEQ ID NO: 143         moltype = AA  length = 356
FEATURE                Location/Qualifiers
source                 1..356
                       mol_type = protein
                       organism = Aethusa cynapium
SEQUENCE: 143
MSAPTTITAL SQEKSLNLDF VRDEDERPKV AYNQFSNEIP IISLAGMDDD SNGRRPEICR  60
KIVEAFEDWG IFQVVDHGID KGLISQMSRL SREFFALPAE EKLRYDTTGG KRGGFTISTH  120
LQGDDVKDWR EFVTYFSYPI EDRDYSRWPE KPEGWRSTTE VYSEKLMVLG AKLLEVLSEA  180
MGLEKEALTK ACVNMEQKVL INYYPTCPEP DLTLGVRRHT DPGTITILLQ DMVGGLQATR  240
DGGKTWITVQ PVEGAFVVNL GDHGHYLSNG RFKNADHQAV VNSTSSRLSI ATFQNPAQNA  300
IVYPLKIREG EKAILDEAIT YAEMYKKNMT KHIEVAALKK LAKEKRLQDE KAKLEM      356

SEQ ID NO: 144         moltype = DNA  length = 1071
FEATURE                Location/Qualifiers
misc_feature           1..1071
                       note = coding sequence for SEQ ID NO: 143
source                 1..1071
                       mol_type = other DNA
                       organism = synthetic construct
SEQUENCE: 144
atgtccgctc caactactat cactgctttg tctcaagaaa agtctttgaa cttggacttc  60
gttagagatg aagatgaaag accaaaggtt gcttacaacc aattctctaa cgaaatccca  120
atcatctctt tggctggtat ggacgacgac tctaacggta ggaggccaga aatctgtaga  180
aagatcgttg aagctttcga agattggggt atcttccaag ttgttgacca cggtatcgac  240
aagggtttga tctctcaaat gtctagattg tctagagaat tcttcgcttt gccagctgaa  300
gaaaagttga gatacgacac tactggtggt aagagaggtg gtttcactat ctctactcac  360
ttgcaaggtg acgacgttaa ggactggaga gaattcgtta cttacttctc ttacccaatc  420
gaagatagag actactctag atggccagaa aagccagaag gttggagatc tactactgaa  480
gtttactctg aaaagttgat ggttttgggt gctaagttgt tggaagtttt gtctgaagct  540
atgggtttgg aaaaggaagc tttgactaag gcttgtgtta acatggaaca aaaggttttg  600
atcaactact acccaacttg tccagaacca gacttgactt tgggtgttag gagacacact  660
gacccaggta ctatcactat cttgttgcaa gacatggttg gtggtttgca agctactagg  720
gacggtggta agacttggat cactgttcaa ccagttgaag gtgctttcgt tgttaacttg  780
ggtgaccacg gtcactactt gtctaacggt agattcaaga acgctgacca ccaagctgtt  840
gttaactcta cttcttctag attgtctatc gctactttcc aaaacccagc tcaaaacgct  900
atcgtttacc cattgaagat cagagaaggt gaaaaggcta tcttggacga agctatcact  960
tacgctgaaa tgtacaagaa gaacatgact aagcacatcg aagttgctgc tttgaagaag  1020
```

```
ttggctaagg aaaagagatt gcaagacgaa aaggctaagt tggaaatgta a          1071

SEQ ID NO: 145          moltype = AA  length = 366
FEATURE                 Location/Qualifiers
source                  1..366
                        mol_type = protein
                        organism = Conium maculatum
SEQUENCE: 145
MSAPTTITAL AQEKTLNLAF VRDEDERPKV AYNEFSNEIP IISLAGLEND SDGRRPEICR  60
KIVEAFENWG IFQVVDHGID SALISEMSRL SREFFALPAE EKLRYDTTGG KRGGFTISTH  120
LQGDDVRDWR EFVTYFSYPI DARDYSRWPD KPEGWRSITE VYSERLMVLG AKLLEVLSEA  180
MGLEKEALTK ACVNMEQKVL INYYPTCPEP DLTLGVRRHT DPGTITVLLQ DMVGGLQATR  240
DGGKTWITVQ PVEGAFVVNL GDHGHYLSNG RFKNADHQAV VNSSSSRLSI ATFQNPAQNA  300
IVYPLKIREG EKAILDEAIT YAEMYKKNMT KHIEVATLKK LAKEKRLQDE KANMEKKSKS  360
AHGISA                                                            366

SEQ ID NO: 146          moltype = DNA  length = 1101
FEATURE                 Location/Qualifiers
misc_feature            1..1101
                        note = coding sequence for SEQ ID NO: 145
source                  1..1101
                        mol_type = other DNA
                        organism = synthetic construct
SEQUENCE: 146
atgtccgctc caactactat cactgctttg gctcaagaaa agactttgaa cttggctttc  60
gttagagatg aagatgaaag accaaaggtt gcttacaacg aattctctaa cgaaatccca  120
atcatctctt tggctggttt ggaaaacgac tctgacggta gaaggccaga aatctgtaga  180
aagatcgttg aagctttcga aaactggggt atcttccaag ttgttgacca cggtatcgac  240
tctgctttga tctctgaaat gtctagattg tctagagaat tcttcgcttt gccagctgaa  300
gaaaagttga gatacgacac tactggtggt aagagaggtg gtttcactat ctctactcac  360
ttgcaaggtg acgacgttag agactggaga gaattcgtta cttacttctc ttacccaatc  420
gacgctagag actactctag atggccagac aagccagaag gttggagatc tatcactgaa  480
gtttactctg aaagattgat ggttttgggt gctaagttgt tggaagtttt gtctgaagct  540
atgggtttgg aaaaggaagc tttgactaag gcttgtgtta acatggaaca aaaggttttg  600
atcaactact acccaacttg tccagaacca gacttgactt tgggtgttag aaggcacact  660
gacccaggta ctatcactgt tttgttgcaa gacatggttg gtggtttgca agctactaga  720
gatggtggta agacttggat cactgttcaa ccagttgaag gtgctttcgt tgttaacttg  780
ggtgaccacg gtcactactt gtctaacggt agattcaaga acgctgacca ccaagctgtt  840
gttaactctt cttcttctag attgtctatc gctactttcc aaaacccagc tcaaaacgct  900
atcgtttacc cattgaagat cagagaaggt gaaaaggcta tcttggacga agctatcact  960
tacgctgaaa tgtacaagaa gaacatgact aagcacatcg aagttgctac tttgaagaag  1020
ttggctaagg aaaagagatt gcaagacgaa aaggctaaca tggaaaagaa gtctaagtct  1080
gctcacggta tctctgctta a                                           1101

SEQ ID NO: 147          moltype = AA  length = 535
FEATURE                 Location/Qualifiers
source                  1..535
                        mol_type = protein
                        organism = Camellia sinensis
SEQUENCE: 147
MSFDLISIAT LFFVIISTTI LLLSINHFKK PPHLRRRLSL PPTPFALPII GHLHLLGPII  60
HRSFHDLSSR YGPLFHLRLG SVPCFVVSTP ELAKEFLLTH ELKFSSRRDS IAIQRLTYDS  120
AFAFAPYGPY WKFLKKLCTC DLLGARSINH FLPTRTRELH CFVRLLIDKA VACEPVNITK  180
ELSTLANNII SQMMIGVRCS GTTGEAEEAT TLAREVTKIF GEFNVSDFMW VIRNFDLQGF  240
RKRVEDIYTR YDALLERIIT NREEVREKNV QERKLGVGEG HHVKDFLDLL LDVLEEDHSE  300
INFSRDNIKG LILDFFTAGT DTSSIAIEWA LAELINNPRV LQKAQEEIDN VVGKHRLVSE  360
SDGPNLPYIQ AIIREALRLH PPVPLITRKS IEDCMIQGYN IPANSMLFVN VWSLARNPKY  420
WDSPLDFLPE RFLRPEKGGP VGPTDVKGQH FQLLPFGTGR RGCPGTSLAM QELPAMLAAM  480
IQCFEWKVVN QSGDVMNGDG ALDMTEQPGM TAPRAHDLVC MPIPRIDQLY ALLDP      535

SEQ ID NO: 148          moltype = DNA  length = 1608
FEATURE                 Location/Qualifiers
misc_feature            1..1608
                        note = coding sequence for SEQ ID NO:147
source                  1..1608
                        mol_type = other DNA
                        organism = synthetic construct
SEQUENCE: 148
atgtccttcg acttgatctc tatcgctact ttgttcttcg ttatcatctc tactactatc  60
ttgttgttgt ctatcaacca cttcaagaag ccaccacact tgagaagaag attgtctttg  120
ccaccaactc cattcgcttt gccaatcatc ggtcacttgc acttgttggg tccaatcatc  180
cacagatctt tccacgactt gtcatctaga tacggtccat tgttccactt gagattgggt  240
tctgttccat gtttcgttgt ttctactcca gaattggcta aggaattctt gttgactcac  300
gaattgaagt tctcttctag aagagactct atcgctatcc aaagattgac ttacgactct  360
gctttcgctt tcgctccata cggtccatac tggaagttct tgaagaagtt gtgtacttgt  420
gacttgttgg gtgctagatc tatcaaccac ttcttgccaa ctagaactag agaattgcac  480
tgtttcgtta gattgttgat cgacaaggct gttgcttgtg aaccagttaa catcactaag  540
gaattgtcta ctttggctaa caacatcatc tctcaaatga tgatcggtgt tagatgttct  600
ggtactactg gtgaagctga agaagctact actttggcta gagaagttac taagatcttc  660
```

```
ggtgaattca acgtttctga cttcatgtgg gttatcagaa acttcgactt gcaaggtttc  720
agaaagagag ttgaagatat ctacactaga tacgacgctt tgttggaaag aatcatcact  780
aacagagaag aagttagaga aaagaacgtt caagaaagaa agttgggtgt tggtgaaggt  840
caccacgtta aggacttctt ggacttgttg ttggacgttt tggaagaaga tcactctgaa  900
atcaacttct ctagagacaa catcaagggt ttgatcttgg acttcttcac tgctggtact  960
gacacttctt ctatcgctat cgaatgggct ttggctgaat tgatcaacaa cccaagagtt  1020
ttgcaaaagg ctcaagaaga aatcgacaac gttgttggta agcacagatt ggtttctgaa  1080
tctgacggtc caaacttgcc atacatccaa gctatcatca gagaagcttt gagattgcac  1140
ccaccagttc cattgatcac tagaaagtct atcgaagatt gtatgatcca aggttacaac  1200
atcccagcta actctatgtt gttcgttaac gtttggtctt tggctagaaa cccaaagtac  1260
tgggactctc cattggactt cttgccagaa agattcttga ggccagaaaa gggtggtcca  1320
gttggtccaa ctgacgttaa gggtcaacac ttccaattgt tgccattcgg tactggtaga  1380
agaggttgtc caggtacttc tttggctatg caagaattgc cagctatgtt ggctgctatg  1440
atccaatgtt tcgaatggaa ggttgttaac caatctggtg acgttatgaa cggtgacggt  1500
gctttggaca tgactgaaca accaggtatg actgctccaa gagctcacga cttggtttgt  1560
atgccaatcc caagaatcga ccaattgtac gctttgttgg acccataa              1608

SEQ ID NO: 149          moltype = AA  length = 517
FEATURE                 Location/Qualifiers
source                  1..517
                        mol_type = protein
                        organism = Saussurea medusa
SEQUENCE: 149
MSQVLQTLTP AVIAAVLLSS LFLYLLIKKN QNHRLPPSPP SLPIIGHLHH LGPLIHQSFH  60
HLSTKYGPLI HLRLGSVTCV VASTPDLARD FLKTNELAFS SRKHSLAIDH ITYGVAFAFA  120
PYGPYWKFIK KMSTVELLGN QNLGHFLPIR TQEIHELLHT LMNKAKKRES VNLTEELLKL  180
TNNVICQMMM SIRCSGTNSE ADEAKNLVRE VTQIFGEFNV SDFIWFCKNI DLQGFKKRYE  240
DTHRRYDVLL EKIILEREEE RRKEGKREDG NKGKDFLDML LDVLEDGKAE IQITRDHIKA  300
LILDFFTAAT DTTAIALEWM LVELIRNPKV LEIAREEIDH IIGNERLVQE SDIPNLPYIQ  360
AIIKETLRLH PPIPMLIRKS IENVSVQGYD IPAGTMLFVN IWSIGRNPKY WESPLEFKPH  420
RFLEEDNALK SSFDIKGQNF QLLPFGTGRR GCPGINLAMK ELPVVIAGLI QCFEWNINEK  480
QVLDMDERAG LTAPRAADFV CVPSIREDSP KSFITST                          517

SEQ ID NO: 150          moltype = DNA  length = 1554
FEATURE                 Location/Qualifiers
misc_feature            1..1554
                        note = coding sequence for SEQ ID NO: 149
source                  1..1554
                        mol_type = other DNA
                        organism = synthetic construct
SEQUENCE: 150
atgtcccaag ttttgcaaac tttgactcca gctgttatcg ctgctgtttt gttgtcatct  60
ttgttcttgt acttgttgat caagaagaac caaaaccaca gattgccacc atctccacca  120
tctttgccaa tcatcggtca cttgcaccac ttgggtccat tgatccacca atctttccac  180
cacttgtcta ctaagtacgg tccattgatc cacttgagat tgggttctgt tacttgtgtt  240
gttgcttcta ctccagactt ggctagagac ttcttgaaaa ctaacgaatt ggctttctct  300
tctagaaagc actctttggc tatcgaccac atcacttacg gtgttgcttt cgctttcgct  360
ccatacggtc catactggaa gttcatcaag aagatgtcta ctgttgaatt gttgggtaac  420
caaaacttgg gtcacttctt gccaatcaga actcaagaaa tccacgaatt gttgcacact  480
ttgatgaaca aggctaagaa gagagaatct gttaacttga ctgaagaatt gttgaagttg  540
actaacaacg ttatctgtca aatgatgatg tctatcagat gttctggtac taactctgaa  600
gctgacgaag ctaagaactt ggttagagaa gttactcaaa tcttcggtga attcaacgtt  660
tctgacttca tctggttctg taagaacatc gacttgcaag gtttcaagaa gagatacgaa  720
gatactcaca gaagatacga cgttttgttg gaaaagatca tcttggaaag agaagaagaa  780
agaagaaagg aaggtaagag agaagatggt aacaagggta aggacttctt ggacatgttg  840
ttggacgttt tggaagatgg taaggctgaa atccaaatca ctagagatca catcaaggct  900
ttgatcttgg acttcttcac tgctgctact gacactactg ctatcgcttt ggaatggatg  960
ttggttgaat tgatcagaaa cccaaaggtt ttggaaatcg ctagagaaga aatcgaccac  1020
atcatcggta acgaaagatt ggttcaagaa tctgacatcc caaacttgcc atacatccaa  1080
gctatcatca aggaaacttt gagattgcac ccaccaatcc caatgttgat cagaaagtct  1140
atcgaaaacg tttctgttca aggttacgac atcccagctg gtactatgtt gttcgttaac  1200
atctggtcta tcggtagaaa cccaaagtac tgggaatctc cattggaatt caagccacac  1260
agattcttgg aagaagataa cgctttgaag tcatctttcg acatcaaggg tcaaaacttc  1320
caattgttgc cattcggtac tggtagaaga ggttgtccag gtatcaactt ggctatgaag  1380
gaattgccag ttgttatcgc tggtttgatc caatgtttcg aatggaacat caacgaaaag  1440
caagttttgg acatggacga aagagctggt ttgactgctc caagagctgc tgacttcgtt  1500
tgtgttccat ctatcagaga agattctcca aagtctttca tcacttctac ttaa        1554

SEQ ID NO: 151          moltype = AA  length = 510
FEATURE                 Location/Qualifiers
source                  1..510
                        mol_type = protein
                        organism = Plectranthus barbatus
SEQUENCE: 151
MSDHVEAALF AAIFLLSAAL LNHLLTGKRR QNAYPPGPFP LPIIGHLHLL GPRLHHTFHD  60
LTQRYGPLMQ VRLGSIRCVI AATPELAKEF LKTSELVFSA RKHSTAIDIV TYESSFAFSP  120
YGPYWKYIKK LCTYELLGAR NLNHFLPIRT IEVKTFLEAL MQKGKTGERL NVTEELVKLT  180
SNVISQMMLS IRCSGTEGET EAVRTVIREV TQIFGEFDVA DIIWFCKNFD FQGIRKRSED  240
IQRRYDALLE KIITDREKQR RTQHGGEAKD FLDMFLDIMK SGKAEVNFTR DHLKALILDF  300
```

```
FTAGTDTTAI VVGWAIAELI NNPNVLKKAQ AEIDKVVGLH RILQESDGPN LPYLNAVIKE  360
TFRLHPPIPM LSRKSISDCV IDGYTIPANT LLFVNIWSMG RNPKIWDNPM AFRPERFLEK  420
EKTGIDIKGQ HFELLPFGTG RRGCPGMLLA IREVVVIIGT VIQCFDWKLP VDDVSGLVDM  480
TERPGLTAPR ADDLICRVVP RVDPLVVSGH                                 510

SEQ ID NO: 152         moltype = DNA  length = 1533
FEATURE                Location/Qualifiers
misc_feature           1..1533
                       note = coding sequence for SEQ ID NO: 151
source                 1..1533
                       mol_type = other DNA
                       organism = synthetic construct
SEQUENCE: 152
atgtccgacc acgttgaagc tgctttgttc gctgctatct tcttgttgtc tgctgctttg  60
ttgaaccact tgttgactgg taagagaagg caaaacgctt acccaccagg tccattccca  120
ttgccaatca tcggtcactt gcacttgttg ggtccaagat tgcaccacac tttccacgac  180
ttgactcaaa gatacggtcc attgatgcaa gttagattgg gttctatcag atgtgttatc  240
gctgctactc cagaattggc taaggaattc ttgaaaactt ctgaattggt tttctctgct  300
agaaagcact ctactgctat cgacatcgtt acttacgaat cttctttcgc tttctctcca  360
tacggtccat actggaagta catcaagaag ttgtgtactt acgaattgtt gggtgctaga  420
aacttgaacc acttcttgcc aatcagaact atcgaagtta agactttctt ggaagctttg  480
atgcaaaagg gtaagactgg tgaaagattg aacgttactg aagaattggt taagttgact  540
tctaacgtta tctctcaaat gatgttgtct atcagatgtt ctggtactga aggtgaaact  600
gaagctgtta gaactgttat cagagaagtt actcaaatct tcggtgaatt cgacgttgct  660
gacatcatct ggttctgtaa gaacttcgac ttccaaggta tcagaaagag atctgaagat  720
atccaaagaa gatacgacgc tttgttggaa aagatcatca ctgacagaga aaagcaaaga  780
agaactcaac acggtggtga agctaaggac ttcttggaca tgttcttgga catcatgaag  840
tctggtaagg ctgaagttaa cttcactaga gatcacttga aggctttgat cttggacttc  900
ttcactgctg gtactgacac tactgctatc gttgttggtt gggctatcgc tgaattgatc  960
aacaacccaa acgttttgaa gaaggctcaa gctgaaatcg acaaggttgt tggtttgcac  1020
agaatcttgc aagaatctga cggtccaaac ttgccatact tgaacgctgt tatcaaggaa  1080
actttcagat tgcacccacc aatcccaatg ttgtctagaa agtctatctc tgactgtgtt  1140
atcgacggtt acactatccc agctaacact ttgttgttcg ttaacatctg gtctatgggt  1200
agaaacccaa agatctggga caacccaatg gctttcagac cagaaagatt cttggaaaag  1260
gaaaagactg gtatcgacat caagggtcaa cacttcgaat tgttgccatt cggtactggt  1320
agaagaggtt gtccaggtat gttgttggct atcagagaag ttgttgttat catcggtact  1380
gttatccaat gtttcgactg gaagttgcca gttgacgacg tttctggttt ggttgacatg  1440
actgaaagac caggtttgac tgctccaaga gctgacgact tgatctgtag agttgttcca  1500
agagttgacc cattggttgt ttctggtcac taa                             1533

SEQ ID NO: 153         moltype = AA  length = 506
FEATURE                Location/Qualifiers
source                 1..506
                       mol_type = protein
                       organism = Scutellaria baicalensis
SEQUENCE: 153
MSEVTLNVAL LLLSAAVCLM VFTGKRRRRL PNPPGPFPLP LIGNLNLVSP RLHHTFHMLA  60
QRYGPIMKFR LGSIPCLVVS TPELAKDILK THELIFSSRV KSTAIDIVTY GVSFAFSPYG  120
PYWKYIKKLC TYELLGSRML NHFEPLRALE VREFLKDVMA MGKAGKSFNV TEELMKLTSN  180
VMSNMMLSIR AAESEEQAEV ARTLIREVSQ LFGEFDFGDM LWFCKSFDFQ GIKKRSKDIK  240
VRYDALLEKI LTDRENVRRQ NGVVEPKDML DMFLDIMEGG KTDVEFTREH LKAVILDFLT  300
AGTDTTAITV EWVLAELMNS PKAMKKAQDE MDRVVGERRM MAESDAPNLP YFLAIIKETF  360
RLHPPIPLII RRSIEDCVID GYHIPADTLA FINVWSMGRN EKYWDSPLSF RPERFLEGDN  420
AAIDIKGMHF ELLPFGSGRR GCPGMLSAIQ EVLIIAGTVI QCFDWEQADG SGRVDMSERP  480
GLTTPREIDL VCRVVPRVDE RVISGH                                     506

SEQ ID NO: 154         moltype = DNA  length = 1521
FEATURE                Location/Qualifiers
misc_feature           1..1521
                       note = coding sequence for SEQ ID NO:153
source                 1..1521
                       mol_type = other DNA
                       organism = synthetic construct
SEQUENCE: 154
atgtccgaag ttactttgaa cgttgctttg ttgttgttgt ctgctgctgt ttgtttgatg  60
gttttcactg gtaagagaag aagaagattg ccaaacccac caggtccatt cccattgcca  120
ttgatcggta acttgaactt ggtttctcca agattgcacc acactttcca catgttggct  180
caaagatacg gtccaatcat gaagttcaga ttgggttcta tcccatgttt ggttgtttct  240
actccagaat tggctaagga catcttgaaa actcacgaat tgatcttctc ttctagagtt  300
aagtctactg ctatcgacat cgttacttac ggtgtttctt tcgctttctc tccatacggt  360
ccatactgga agtacatcaa gaagttgtgt acttacgaat tgttgggttc tagaatgttg  420
aaccacttcg aaccattgag agctttggaa gttagagaat tcttgaagga cgttatggct  480
atgggtaagg ctggtaagtc tttcaacgtt actgaagaat tgatgaagtt gacttctaac  540
gttatgtcta acatgatgtt gtctatcaga gctgctgaat ctgaagaaca agctgaagtt  600
gctagaactt tgatcagaga agtttctcaa ttgttcggtg aattcgactt cggtgacatg  660
ttgtggttct gtaagtcttt cgacttccaa ggtatcaaga agagatctaa ggacatcaag  720
gttagatacg acgctttgtt ggaaaagatc ttgactgaca gagaaaacgt taggagacaa  780
aacggtgttg ttgaaccaaa ggacatgttg gacatgttct tggacatcat ggaaggtggt  840
aagactgacg ttgaattcac tagagaacac ttgaaggctg ttatcttgga cttcttgact  900
```

```
gctggtactg acactactgc tatcactgtt gaatgggttt tggctgaatt gatgaactct  960
ccaaaggcta tgaagaaggc tcaagacgaa atggacagag ttgttggtag agaaagaatg  1020
atggctgaat ctgacgctcc aaacttgcca tacttcttgg ctatcatcaa ggaaactttc  1080
agattgcacc caccaatccc attgatcatc agaagatcta tcgaagattg tgttatcgac  1140
ggttaccaca tcccagctga cactttggct ttcatcaacg tttggtctat gggtagaaac  1200
gaaaagtact gggactctcc attgtctttc agaccagaaa gattcttgga aggtgacaac  1260
gctgctatcg acatcaaggg tatgcacttc gaattgttgc cattcggttc tggtagaaga  1320
ggttgtccag gtatgttgtc tgctatccaa gaagttttga tcatcgctgg tactgttatc  1380
caatgtttcg actgggaaca agctgacggt tctggtagag ttgacatgtc tgaaagacca  1440
ggtttgacta ctccaagaga aatcgacttg gtttgtagag ttgttccaag agttgacgaa  1500
agagttatct ctggtcacta a                                            1521

SEQ ID NO: 155          moltype = AA  length = 510
FEATURE                 Location/Qualifiers
source                  1..510
                        mol_type = protein
                        organism = Dorcoceras hygrometricum
SEQUENCE: 155
MSDLVQITLS AALLLLSAAF LHTIFATKRR RLSPPPGPLA LPIIGHLHLL GPRLHQTFHD  60
LSLRHGPIFN LRLGSVACAV VSTPELAKEC LKTHELVFSS RKHSTAIDIV TYDSSFAFSP  120
YGPYWKYIKK LCTYELLGAR NLLHFQPIRT LEVNSFVGTL MNKAESGESF NVTEELVKLT  180
SNVISHMMLG IRCSGTEGEA EAARTVIREV TQIFGEFDVA DIIWFCKNFD FQGIRKRSED  240
IQRRYDALLE KIITDREELR RSHGGAAGEA RDFLDMFLDI MEGGKSEVTF TREHLKALIL  300
DFFTAGTDTT AIVTEWAISE LINNPKVLEK AQQEIDKVIG SGRLVQESDA PNLPYLMAVI  360
KETFRLHPPI PMLSRKSISD CVIDGYDVPA KSLLFVNIWS MGRNPKIWES PLEFRPERFL  420
EREKSSIDIK GQHFELLPFG TGRRGCPGML LGIQEVVIII GTMVQCFDWK LSDGSGQVDM  480
TERPGLTAPR AHDLFCRVVP RINPVVVSGN                                   510

SEQ ID NO: 156          moltype = DNA  length = 1533
FEATURE                 Location/Qualifiers
misc_feature            1..1533
                        note = coding sequence for SEQ ID NO: 155
source                  1..1533
                        mol_type = other DNA
                        organism = synthetic construct
SEQUENCE: 156
atgtccgact tggttcaaat cactttgtct gctgctttgt tgttgttgtc tgctgctttc  60
ttgcacacta tcttcgctac taagagaaga agattgtctc caccaccagg tccattggct  120
ttgccaatca tcggtcactt gcacttgttg ggtccaagat tgcaccaaac tttccacgac  180
ttgtctttga gacacggtcc aatcttcaac ttgagattgg gttctgttgc ttgtgctgtt  240
gtttctactc cagaattggc taaggaatgt ttgaaaactc acgaattggt tttctcttct  300
agaaagcact ctactgctat cgacatcgtt acttacgact cttctttcgc tttctctcca  360
tacggtccat actggaagta catcaagaag ttgtgtactt acgaattgtt gggtgctaga  420
aacttgttgc acttccaacc aatcagaact ttggaagtta actctttcgt tggtactttg  480
atgaacaagg ctgaatctgg tgaatctttc aacgttactg aagaattggt taagttgact  540
tctaacgtta tctctcacat gatgttgggt atcagatgtt ctggtactga aggtgaagct  600
gaagctgcta gaactgttat cagagaagtt actcaaatct tcggtgaatt cgacgttgct  660
gacatcatct ggttctgtaa gaacttcgac ttccaaggta tcagaaagag atctgaagat  720
atccaaagaa gatacgacgc tttgttggaa aagatcatca ctgacagaga agaattgaga  780
agatctcacg gtggtgctgc tggtgaagct agagacttct tggacatgtt cttggacatc  840
atggaaggtg gtaagtctga agttactttc actagagaac acttgaaggc tttgatcttg  900
gacttcttca ctgctggtac tgacactact gctatcgtta ctgaatgggc tatctctgaa  960
ttgatcaaca acccaaaggt tttggaaaag gctcaacaag aaatcgacaa ggttatcggt  1020
tctggtagat tggttcaaga atctgacgct ccaaacttgc catacttgat ggctgttatc  1080
aaggaaactt tcagattgca cccaccaatc ccaatgttgt ctagaaagtc tatctctgac  1140
tgtgttatcg acggttacga cgttccagct aagtctttgt tgttcgttaa catctggtct  1200
atgggtagaa acccaaagat ctgggaatct ccattggaat tcagaccaga aagattcttg  1260
gaaagagaaa agtcatctat cgacatcaag ggtcaacact tcgaattgtt gccattcggt  1320
actggtagaa gaggttgtcc aggtatgttg ttgggtatcc aagaagttgt tatcatcatc  1380
ggtactatgg ttcaatgttt cgactggaag ttgtctgacg gttctggtca agttgacatg  1440
actgaaagac caggtttgac tgctccaaga gctcacgact tgttctgtag agttgttcca  1500
agaatcaacc cagttgttgt ttctggtaac taa                              1533

SEQ ID NO: 157          moltype = AA  length = 507
FEATURE                 Location/Qualifiers
source                  1..507
                        mol_type = protein
                        organism = Antirrhinum majus
SEQUENCE: 157
MSSTLVYSTL FILSTLLLTL LTRTRRKTRP PGPLALPLIG HLHLLGPKLH HTFHQFSQRY  60
GPLIQLYLGS VPCVVASTPE LAREFLKTHE LDFSSRKHST AIDIVTYDSS FAFAPYGPYW  120
KFIKKLCTYE LLGARNLSHF QPIRALEVNS FLRILYEKTE QKQSVNVTEE LVKLTSNVIS  180
NMMLGIRCSG TEGEAEVART VIREVTQIFG EFDVSEIVWF CKNLDLQGIR KRSEDIRRRY  240
DALLEKIISD RERLRLRGGG GGGGGEVKDF LDMLLDVMES EKSEVEFTRE HLKALILDFF  300
TAGTDTTAIT TEWAIAELIS NPNVLKKAQE EMDKVIGSQR LLQESDAPNL PYLNAIIKET  360
FRLHPPIPML TRKSISDVVV NGYTIPAKTL LFVNLWSMGR NPNYWENPME FRPERFLEKG  420
TGSIDVKGQH FELLPFGTGR RGCPGMLLGM QELFSIIGAM VQCFDWKLPD GVKSVDMTER  480
PGLTAPRAND LVCQLVPRID PVVVSGP                                      507
```

```
SEQ ID NO: 158         moltype = DNA  length = 1524
FEATURE                Location/Qualifiers
misc_feature           1..1524
                       note = coding sequence for SEQ ID NO: 157
source                 1..1524
                       mol_type = other DNA
                       organism = synthetic construct
SEQUENCE: 158
atgtcctcta ctttggttta ctctactttg ttcatcttgt ctactttgtt gttgactttg  60
ttgactagaa ctagaagaaa gactagacca ccaggtccat tggctttgcc attgatcggt  120
cacttgcact tgttgggtcc aaagttgcac cacactttcc accaattctc tcaaagatac  180
ggtccattga tccaattgta cttgggttct gttccatgtg ttgttgcttc tactccagaa  240
ttggctagag aattcttgaa aactcacgaa ttggacttct cttctagaaa gcactctact  300
gctatcgaca tcgttactta cgactcttct ttcgctttcg ctccatacgg tccatactgg  360
aagttcatca agaagttgtg tacttacgaa ttgttgggtg ctagaaactt gtctcacttc  420
caaccaatca gagctttgga agttaactct ttcttgagaa tcttgtacga aaagactgaa  480
caaaagcaat ctgttaacgt tactgaagaa ttggttaagt tgacttctaa cgttatctct  540
aacatgatgt tgggtatcag atgttctggt actgaaggtg aagctgaagt tgctagaact  600
gttatcagag aagttactca aatcttcggt gaattcgacg tttctgaaat cgtttggttc  660
tgtaagaact tggacttgca aggtatcaga aagagatctg aagatatcag aagaagatac  720
gacgctttgt tggaaaagat catctctgac agagaaagat tgagattgag aggtggtggt  780
ggtggtggtg gtggtgaagt taaggacttc ttggacatgt tgttggacgt tatggaatct  840
gaaaagtctg aagttgaatt cactagagaa cacttgaagg ctttgatctt ggacttcttc  900
actgctggta ctgacactac tgctatcact actgaatggg ctatcgctga attgatctct  960
aacccaaacg ttttgaagaa ggctcaagaa gaaatggaca aggttatcgg ttctcaaaga  1020
ttgttgcaag aatctgacgc tccaaacttg ccatacttga acgctatcat caaggaaact  1080
ttcagattgc acccaccaat cccaatgttg actagaaagt ctatctctga cgttgttgtt  1140
aacggttaca ctatcccagc taagactttg ttgttcgtta acttgtggtc tatgggtaga  1200
aacccaaact actgggaaaa cccaatggaa ttcagaccag aaagattctt ggaaaagggt  1260
actggttcta tcgacgttaa gggtcaacac ttcgaattgt tgccattcgg tactggtaga  1320
agaggttgtc caggtatgtt gttgggtatg caagaattgt tctctatcat cggtgctatg  1380
gttcaatgtt tcgactggaa gttgccagac ggtgttaagt ctgttgacat gactgaaaga  1440
ccaggtttga ctgctccaag agctaacgac ttggtttgtc aattggttcc aagaatcgac  1500
ccagttgttg tttctggtcc ataa                                         1524

SEQ ID NO: 159         moltype = AA  length = 511
FEATURE                Location/Qualifiers
source                 1..511
                       mol_type = protein
                       organism = Erythranthe lewisii
SEQUENCE: 159
MSNQTMDLPE ICLYAVILFV STLLLILGIYK RKRSHIPSPP GPFALPVIGH LHLLGPRIHH  60
TFHDLSQRYG PLFQLSLGSV RCVVVSTPEL AREFLKTHEL VFSSRKHTTA IDIVTYESSF  120
AFSPYGPYWK YIKKLCTYEL LGARNLANFE PVRNVEIKDF LKVMSNKANT GEIVNVTEEL  180
VKLTSNVISH MMLGIRCSGT EGEAEAARNV IRDVTQIFGE FDVSDIIWFC KNFDLQGIRR  240
RSEDIQKRYD GLLEKIITDR EKTRGGGGGG VKDFLDMLLD VMDSKNSDVK FTREHLKALI  300
LDFFTAGTDT TAIAVEWSIA ELLRNPKVIK KAQQEIDNVV GSQRLLQESD APKLPYIMAI  360
IKETFRLHPP IPMISRKSVS DCAINGCMIR ANTLLFVNIW SIGRNPMYWE RPMEFRPERF  420
LDPGCGSIDV KGQNFELMPF GTGRRGCPGM LLAMQELVAI IGAMVQCFEW QLPDDSQDVD  480
MTERPGLTAP RANDLFCRVV PRVDVAVVSG N                                 511

SEQ ID NO: 160         moltype = DNA  length = 1536
FEATURE                Location/Qualifiers
misc_feature           1..1536
                       note = coding sequence for SEQ ID NO: 159
source                 1..1536
                       mol_type = other DNA
                       organism = synthetic construct
SEQUENCE: 160
atgtccaacc aaactatgga cttgccagaa atctgtttgt acgctgttat cttgttcgtt  60
tctactttgt tgatcttggg tatctacaag agaaagagat ctcacatccc atctccacca  120
ggtccattcg ctttgccagt tatcggtcac ttgcacttgt tgggtccaag aatccaccac  180
actttccacg acttgtctca aagatacggt ccattgttcc aattgtcttt gggttctgtt  240
agatgtgttg ttgtttctac tccagaattg gctagagaat tcttgaaaac tcacgaattg  300
gtttctctt  ctagaaagca cactactgct atcgacatcg ttacttacga atcttctttc  360
gctttctctc catacggtcc atactggaag tacatcaaga agttgtgtac ttacgaattg  420
ttgggtgcta gaaacttggc taacttcgaa ccagttagaa acgttgaaat caaggacttc  480
ttgaaggtta tgtctaacaa ggctaacact ggtgaaatcg ttaacgttac tgaagaattg  540
gttaagttga cttctaacgt tatctctcac atgatgttgg gtatcagatg ttctggtact  600
gaaggtgaag ctgaagctgc tagaaacgtt atcagagatg ttactcaaat cttcggtgaa  660
ttcgacgttt ctgacatcat ctggttctgt aagaacttcg acttgcaagg tatcagaaga  720
agatctgaag atatccaaaa gagatacgac ggtttgttgg aaaagatcat cactgacaga  780
gaaaagacta gaggtggtgg tggtggtggt gttaaggact tcttggacat gttgttggac  840
gttatggact ctaagaactc tgacgttaag ttcactagag aacacttgaa ggctttgatc  900
ttggacttct tcactgctgg tactgacact actgctatcg ctgttgaatg gtctatcgct  960
gaattgttga gaaacccaaa ggttatcaag aaggctcaac aagaaatcga caacgttgtt  1020
ggttctcaaa gattgttgca agaatctgac gctccaaagt tgccatacat catggctatc  1080
atcaaggaaa ctttcagatt gcacccacca atcccaatga tctctagaaa gtctgtttct  1140
gactgtgcta tcaacggttg tatgatcaga gctaacactt tgttgttcgt taacatctgg  1200
```

-continued

```
tctatcggta gaaacccaat gtactgggaa agaccaatgg aattcagacc agaaagattc  1260
ttggacccag gttgtggttc tatcgacgtt aagggtcaaa acttcgaatt gatgccattc  1320
ggtactggta gaagaggttg tccaggtatg ttgttggcta tgcaagaatt ggttgctatc  1380
atcggtgcta tggttcaatg tttcgaatgg caattgccag acgactctca agacgttgac  1440
atgactgaaa gaccaggttt gactgctcca agagctaacg acttgttctg tagagttgtt  1500
ccaagagttg acgttgctgt tgtttctggt aactaa                           1536
```

METHOD FOR THE BIOSYNTHESIS OF DIOSMIN AND/OR HESPERIDIN IN A MICROORGANISM

CROSS-REFERENCE TO RELATED APPLICATIONS

This application is a divisional of U.S. application Ser. No. 17/429,459, filed Aug. 9, 2021, now U.S. Pat. No. 11,987,829, which is the U.S. national stage application of International Patent Application No. PCT/EP2020/053503, filed Feb. 11, 2020.

The Sequence Listing for this application is labeled "Seq-List.xml" which was created on May 17, 2024 and is 331,375 bytes. The entire content of the sequence listing is incorporated herein by reference in its entirety.

FIELD OF THE INVENTION

The present invention relates to a method for producing diosmin and hesperidin.

TECHNOLOGICAL BACKGROUND

Daflon is a mixture of flavonoids with vasotonic and vascular-protective effects. This mixture is mainly composed of ~85% diosmin, ~8% hesperidin and traces of various flavones and the respective oxidized forms thereof.

The current method for producing the medicament is acid/base extraction, from the peel of small oranges, of a mixture of flavonoids mainly containing hesperidin (94%) and a mixture of isonaringin (~3%), neoponcirin (~2%) and hesperetin (<1%). This mixture then undergoes controlled oxidation via a chemical process, transforming about 90% of the hesperidin into diosmin, and minor flavonoids in their oxidized form.

Thus, the production of Daflon is associated with the supply of purified extract of orange flavonoids, which may vary as a result of climatic variations, fluctuations in currency movements and the difficulty of being supplied from dozens of sites in several countries (mainly Mexico, the countries of the Mediterranean basin and China).

It would thus be valuable to have available an alternative method for producing Daflon which is not dependent on the vagaries of being supplied with purified extract of orange flavonoids. Thus, there is an unsatisfied need for a process for the biosynthesis of diosmin and hesperidin.

SUMMARY OF THE INVENTION

The inventors have developed a method for the biosynthesis of diosmin and hesperidin in a recombinant microorganism.

Thus, the present invention relates to a recombinant microorganism comprising:

- a heterologous nucleic acid sequence coding for a flavanone 7-O-beta-D-glucosyltransferase (UGT) which is capable of adding a glucose in position 7 of hesperetin and/or diosmetin; and
- a heterologous nucleic acid sequence coding for a 6"-O-rhamnosyltransferase (RhaT) which is capable of transferring a rhamnose into position 6 of the glucose of hesperetin-7-O-glucoside and/or of diosmetin-7-O-glucoside; and
- a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose.

Preferably, the flavanone 7-O-beta-D-glucosyltransferase (UGT) is an enzyme from *Citrus sinensis, Citrus clementina, Arabidopsis thaliana, Scutellaria baicalensis* or *Homo sapiens*. In particular, the flavanone 7-O-beta-D-glucosyltransferase (UGT) may be an enzyme from *Arabidopsis thaliana, Scutellaria baicalensis* or *Homo sapiens*, preferably from *Arabidopsis thaliana* or *Scutellaria baicalensis*. Preferably, the flavanone 7-O-beta-D-glucosyltransferase (UGT) is from *Citrus sinensis* or *Scutellaria baicalensis.*

The flavanone 7-O-beta-D-glucosyltransferase may be selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity. In particular, it may be selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity. Preferably, the flavanone 7-O-beta-D-glucosyltransferase is selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity.

Preferably, 6"-O-rhamnosyltransferase (RhaT) is a plant enzyme, preferably of the genus *Citrus* or *Petunia hybrida*, preferably *Citrus sinensis, Citrus maxima*, or *Citrus clementina*, more preferably *Citrus sinensis* or *Citrus clementina*. Preferably, 6"-O-rhamnosyltransferase is selected from enzymes comprising a sequence chosen from SEQ ID NOs: 103, 105 and polypeptides comprising a sequence having at least 60, 70, 80, 85, 90 or 95% sequence identity with one of these sequences and having 6"-O-rhamnosyltransferase activity. More particularly preferably, 6"-O-rhamnosyltransferase is selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity.

Preferably, UDP-glucose 4,6-dehydratase/UDP-4-keto-6-deoxy-D-glucose 3,5-epimerase/UDP-4-keto-L-rhamnose-reductase (RHM) is a plant enzyme, preferably from *Citrus sinensis* or *Arabidopsis thaliana*. Preferably, UDP-glucose 4,6-dehydratase/UDP-4-keto-6-deoxy-D-glucose 3,5-epimerase/UDP-4-keto-L-rhamnose-reductase is selected from enzymes comprising a sequence chosen from SEQ ID NOs:

107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity. More particularly preferably, UDP-glucose 4,6-dehydratase/UDP-4-keto-6-deoxy-D-glucose 3,5-epimerase/UDP-4-keto-L-rhamnose-reductase is selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In one embodiment, the microorganism according to the invention also comprises:

- a heterologous nucleic acid sequence coding for a tyrosine ammonia lyase (TAL); and/or a heterologous nucleic acid sequence coding for a phenylalanine ammonia lyase (PAL) and a heterologous nucleic acid sequence coding for a cinnamate 4-hydroxylase (C4H);
- a heterologous nucleic acid sequence coding for a 4-coumaroyl-CoA ligase (4CL);
- a heterologous nucleic acid sequence coding for a naringenin-chalcone synthase (CHS);
- a heterologous nucleic acid sequence coding for a chalcone isomerase (CHI);
- a heterologous nucleic acid sequence coding for a flavonoid 3'-monooxygenase (F3'H);
- a heterologous nucleic acid sequence coding for an O-methyl-transferase (OMT), and
- optionally, a heterologous nucleic acid sequence coding for a 4-methoxybenzoate O-demethylase which is capable of converting tyrosine into L-DOPA and also p-coumaric acid into caffeic acid; or a heterologous nucleic acid sequence coding for a p-coumarate 3-hydroxylase which is capable of converting p-coumaric acid into caffeic acid.

Preferably, the microorganism comprises:

- a heterologous nucleic acid sequence coding for a tyrosine ammonia lyase (TAL) comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity, and preferably a tyrosine ammonia lyase (TAL) comprising a sequence chosen from SEQ ID NO: 41 and polypeptides comprising a sequence having at least 60, 70, 80, 85, 90 or 95% sequence identity with this sequence and having tyrosine ammonia lyase activity; and
- a heterologous nucleic acid sequence coding for a 4-coumaroyl-CoA ligase (4CL) comprising a sequence chosen from SEQ ID NOs: 123, 125, 43, 45, 47 and 49 and polypeptides comprising a sequence having at least 60, 70, 80, 85, 90 or 95% sequence identity with one of these sequences and having 4-coumarate-CoA ligase activity, preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity, and in particular a heterologous nucleic acid sequence coding for a 4-coumaroyl-CoA ligase (4CL) comprising a sequence selected from SEQ ID NO: 45 and polypeptides comprising a sequence having at least 60, 70, 80, 85, 90 or 95% sequence identity with this sequence and having 4-coumarate-CoA ligase activity; and
- a heterologous nucleic acid sequence coding for a chalcone synthase (CHS) comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and
- a heterologous nucleic acid sequence coding for a chalcone isomerase (CHI) comprising a sequence chosen from SEQ ID NOs: 61 and 59 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, the microorganism comprises a heterologous nucleic acid sequence coding for a flavonoid 3'-monooxygenase (F3'H) from *Callistephus chinensis, Perilla frutescens* var. *crispa, Petunia×hybrida, Gerbera hybrida, Citrus sinensis, Arabidopsis thaliana, Pilosella officinarum, Osteospermum* hybrid cultivar, *Phanerochaete chrysosporium, Citrus clementina* or *Streptomyces avermitilis*, in particular from *Callistephus chinensis, Perilla frutescens* var. *crispa, Petunia×hybrida, Gerbera hybrida, Citrus sinensis, Arabidopsis thaliana* or *Pilosella officinarum*, preferably an enzyme comprising a sequence chosen from SEQ ID NOs: 7, 1, 3, 5, 9, 11, 13, 15, 17, 19, 21 and 121 and polypeptides comprising a sequence having at least 60, 70, 80, 85, 90 or 95% sequence identity with one of these sequences and having flavonoid 3'-monooxygenase activity, preferably selected from enzymes having the SEQ ID NOs: 7, 11, 17 and 121 and polypeptides having at least 60, 70, 80, 85, 90 or 95% identity with one of these sequences and having flavonoid 3'-monooxygenase activity.

More particularly preferably, the microorganism comprises a heterologous nucleic acid sequence coding for a flavonoid 3'-monooxygenase (F3'H) comprising a sequence chosen from SEQ ID NOs: 7, 17 and 121 and polypeptides having at least 60, 70, 80, 85, 90 or 95% identity with one of these sequences and having flavonoid 3'-monooxygenase activity, preferably a flavonoid 3'-monooxygenase (F3'H) comprising a sequence chosen from SEQ ID NO: 7 and polypeptides having at least 60, 70, 80, 85, 90 or 95% identity with this sequence and having flavonoid 3'-monooxygenase activity.

Preferably, the microorganism comprises a heterologous nucleic acid sequence coding for an O-methyl-transferase (OMT) from *Citrus*, in particular *Citrus clementina* or *Citrus sinensis*, from *Homo sapiens* or from *Arabidopsis thaliana*, preferably an enzyme comprising a sequence chosen from SEQ ID NOs: 119, 117, 87 and 89 and polypeptides comprising a sequence having at least 60, 70, 80, 85, 90 or 95% sequence identity with one of these sequences and having O-methyltransferase activity. More particularly preferably, it comprises a heterologous nucleic acid sequence coding for an O-methyltransferase (OMT) comprising a sequence chosen from SEQ ID NOs: 119, 117 and 89 and polypeptides comprising a sequence having at least 60, 70, 80, 85, 90 or 95% sequence identity with one of these sequences and having O-methyltransferase activity, preferably a sequence chosen from SEQ ID NOs: 119 and 117 and polypeptides comprising a sequence having at least 60, 70, 80, 85, 90 or 95% sequence identity with one of these sequences and having O-methyltransferase activity.

Preferably, the microorganism comprises:

- a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77, and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and
- a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity; and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

The microorganism may also comprise a heterologous nucleic acid sequence coding for a flavone synthase (FNS), in particular a flavone synthase which is capable of producing luteolin from eriodictyol, preferably from *Arabidopsis thaliana, Petroselinum crispum, Zea mays, Lonicera japonica, Lonicera macranthoides, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*. The flavone synthase (FNS) may be selected from enzymes comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity. In particular, the FNS may be an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity, and preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

Moreover, it may also comprise:

- a heterologous nucleic acid sequence coding for a cytochrome P450 reductase (CPR); and/or
- a heterologous or endogenous nucleic acid sequence coding for an S-adenosylmethionine synthetase (SAMT).

Preferably, the CPR comprises a sequence chosen from SEQ ID NOs: 25, 23, 27, 29 and 31 and polypeptides comprising a sequence having at least 60, 70, 80, 85, 90 or 95% sequence identity with one of these sequences and having cytochrome P450 reductase activity, preferably a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly a sequence chosen from SEQ ID NO: 25 and polypeptides comprising a sequence having at least 60, 70, 80, 85, 90 or 95% sequence identity with this sequence and having cytochrome P450 reductase activity.

Preferably, the microorganism is a yeast or a bacterium, preferably a yeast of the genus *Saccharomyces*, in particular *Saccharomyces cerevisiae*, or a bacterium such as *Escherichia coli*.

The present invention also relates to the use of a microorganism as described in the present document for producing diosmin and/or hesperidin.

In addition, the invention relates to a method for producing diosmin and/or hesperidin comprising the cultivation of a microorganism as described in the present document, and optionally the harvesting of diosmin and/or hesperidin.

Preferably, during the use of the microorganism according to the invention for producing diosmin and/or hesperidin there is no naringenin, apigenin, eriodictyol, luteolin, hesperetin and/or diosmetin supplied to the culture medium.

DETAILED DESCRIPTION OF THE INVENTION

The pathways for the biosynthesis of hesperetin in the peel of small oranges are poorly understood. The inventors thus explored several biosynthetic pathways and succeeded in developing the biosynthesis of diosmin and of hesperidin in a recombinant microorganism.

Definition

The term "microorganism" refers to a unicellular organism. Preferably, the microorganism is a bacterium or a yeast.

The term "recombinant microorganism" refers to a microorganism which is not found in nature and which contains a genome modified following insertion, modification or deletion of one or more heterologous genetic elements.

The term "recombinant nucleic acid" refers to a nucleic acid which has been modified and does not exist in a natural microorganism. For example, this term may denote a coding sequence or gene which is operatively linked to a promoter which is not the natural promoter. This may also denote a coding sequence in which the introns have been deleted for genes comprising exons and introns.

The term "heterologous" means that the gene has been introduced by genetic engineering into the cell. It may be present therein in episomal or chromosomal form. The origin of the gene may be different from that of the cell into which it is introduced. However, the gene may also originate from the same species as the cell into which it is introduced, but it is considered as heterologous on account of its unnatural environment. For example, the gene or the nucleic acid sequence is heterologous since it is under the control of a promoter other than its natural promoter, it is introduced into a position different from that in which it is naturally located. The host cell may contain a copy of the endogenous gene prior to the introduction of the heterologous gene or it may not contain an endogenous copy. Moreover, the nucleic acid sequence may be heterologous in the sense that the coding sequence has been optimized for expression in the host microorganism. Preferably, in the present document, a heterologous nucleic acid sequence codes for a protein which is heterologous to the host cell, i.e. which is not naturally present in the yeast.

As used herein, the term "native" or "endogenous", relative to the host microorganism, refers to a genetic element or to a protein that is naturally present in said microorganism.

The term "gene" denotes any nucleic acid coding for a protein. The term "gene" covers DNA, such as cDNA or gDNA, and also RNA. The gene may first be prepared via recombinant, enzymatic and/or chemical techniques, and subsequently replicated in a host cell or a system in vitro. The gene typically comprises an open reading frame coding for a desired protein. The gene may contain additional sequences such as a transcription terminator or a signal peptide.

As a result of degeneracy of the genetic code, several nucleic acids may code for a particular polypeptide. Thus, the codons in the coding sequence for a given polypeptide may be modified such that optimum expression in a particular microorganism is obtained, for example by using suitable codon translation tables for this microorganism. The nucleic acids may also be optimized according to a preferable GC content for the particular yeast and/or to reduce the number of repeat sequences. In certain embodiments, the heterologous nucleic acids were codon-optimized for expression in the microorganism concerned. Codon optimization may be performed via routine processes known in the art (see, for example, Welch, M., et al. (2011), Methods in Enzymology 498:43-66).

The term "operatively linked" denotes a configuration in which a control sequence is placed in a suitable position relative to a coding sequence, such that the control sequence controls the expression of the coding sequence.

The term "control sequences" denotes the nucleic acid sequences required for the expression of a gene. The control sequences may be native or heterologous. Control sequences that are well known and currently used by those skilled in the art will be preferred. Such control sequences comprise, but without being limited thereto, a leader, a polyadenylation sequence, a propeptide sequence, a promoter, a signal peptide sequence and a transcription terminator. Preferably, the control sequences comprise a promoter and a transcription terminator.

The term "expression cassette" denotes a nucleic acid construct comprising a coding region, i.e. a gene, and a regulating region, i.e. a region comprising one or more control sequences, which are operatively linked. Preferably, the control sequences are suitable for use in the host microorganism.

As used herein, the term "expression vector" denotes a DNA or RNA molecule which comprises an expression cassette. Preferably, the expression vector is a linear or circular double-stranded DNA molecule. The vector may also comprise an origin of replication, a selection marker, etc.

For the purposes of the present invention, the term "percentage of identity" between two nucleic acid sequences or amino acid sequences is intended to denote a percentage of nucleotides or of amino acid residues that are identical between the two sequences to be compared, obtained after the best alignment, this percentage being purely statistical and the differences between the two sequences being distributed randomly and over their entire length. The best alignment or optimum alignment is the alignment for which the percentage of identity between the two sequences to be compared, as calculated below, is the highest. Sequence comparisons between two nucleic acid or amino acid sequences are conventionally performed by comparing these sequences after they have been optimally aligned, said comparison being performed by segment or by comparison window to identify and compare the local regions with sequence similarity. The alignment for the purposes of determining the percentage of amino acid sequence identity may be performed in various ways that are well known in the field, for example by using computer software available on the Internet, such as blast.ncbi.nlm.Nih.gov/or www.ebi.ac.uk/Tools/emboss/). A person skilled in the art can determine the appropriate parameters for measuring the alignment, including any algorithm necessary to obtain a maximum alignment over the entire length of the sequences compared. For the purposes of the present invention, the values of the percentage of amino acid sequence identity refer to values generated using the EMBOSS Needle pair sequence alignment program which creates an optimum global alignment of two sequences by means of the Needleman-Wunsch algorithm, in which all the search parameters are defined by default Notation matrix=BLOSUM62, Open gap=10, Extended gap=0.5, end gap penalty=false, open end gap=10 and extended end gap=0.5. In certain embodiments, all the percentages of identity mentioned in the present patent application may be set at at least 60%, at least 70%, at least 80%, at least 85%, preferably at at least 90% identity, more preferably at at least 95% identity. In particular, the embodiments in which all the percentages of sequence identity of the enzymes are at least 80% or at least 85%, preferably at least 90% or at least 95% sequence identity are considered as described.

In one embodiment, the polypeptides may contain 1, 2, 3, 4, 5, 6, 7, 8, 9 or 10 additions, substitutions or deletions relative to the sequences described in the SEQ ID NOs. In particular, these additions, substitutions or deletions are introduced at the N-terminal end, the C-terminal end or at both ends.

The polypeptides may optionally be in the form of a fusion protein.

The terms "overexpression" and "increased expression" as used herein are used interchangeably and mean that the expression of a gene or of an enzyme is increased relative to an unmodified microorganism, for example a wild-type microorganism or a microorganism not comprising the genetic modifications described herein. The term "wild-type" refers to an unmodified microorganism existing in nature. The increased expression of an enzyme is usually obtained by increasing the expression of the gene coding for said enzyme. In embodiments in which the gene or the enzyme is not naturally present in the microorganism of the invention, i.e. a heterologous gene or enzyme, the terms "overexpression" and "expression" may be used interchangeably. To increase the expression of a gene, a person skilled in the art can use any known technique such as increasing the number of copies of the gene in the microorganism, by using a promoter inducing a high level of expression of the gene, i.e. a strong promoter, by using elements which stabilize the corresponding messenger RNA or sequences which sequester the ribosomal binding site (RBS) and the sequences surrounding same. In particular, overexpression may be obtained by increasing the number of copies of the gene in the microorganism. One or more copies of the gene may be introduced into the genome via recombination processes, known to those skilled in the art, including the replacement of the genes or multi-copy integration (see, for example, the international patent application WO 2015/092013). Preferably, an expression cassette comprising the gene, preferably placed under the control of a strong promoter, is integrated into the genome. As a variant, the gene may be carried by an expression vector, preferably a plasmid, comprising an expression cassette with the gene of interest preferably placed under the control of a strong promoter. The expression vector may be present in the microorganism in one or more copies, depending on the nature of the origin of replication. Overexpression of the gene may also be obtained by using a promoter which induces a high level of expression of the gene. For example, the promoter of an endogenous gene may be replaced with a stronger promoter, i.e. a promoter which induces a higher level of expression. The endogenous gene under the control of a promoter which is not the natural promoter is termed a heterologous nucleic acid. The promoters that are suitable for use in the present invention are known to those skilled in the art and may be constitutive or inducible, and may be endogenous or heterologous.

The term "comprising" also means "consisting of" or "consisting essentially of". The term "consisting essentially of" means that the sequence may contain 1, 2, 3, 4, 5, 6, 7, 8, 9 or 10 additions, substitutions or deletions relative to the sequences described in the SEQ ID NOs.

Recombinant Microorganisms

The microorganism according to the present invention may be a eukaryotic or prokaryotic microorganism.

In a first embodiment, the microorganism is a eukaryote. Preferably, it is a yeast of the Saccharomycesles, Sporidiobolales and Schizosaccharomycesles orders. The yeast may be selected, for example, from *Pichia, Kluyveromyces, Saccharomyces, Schizosaccharomyces, Candida, Lipomyces, Rhodotorula, Rhodosporidium, Yarrowia*, or *Debaryomyces*. In one embodiment, the yeast is chosen from *Pichia pastoris, Kluyveromyces lactis, Kluyveromyces marxianus, Saccharomyces cerevisiae, Saccharomyces carlsbergensis, Saccharomyces diastaticus, Saccharomyces douglasii, Saccharomyces kluyveri, Saccharomyces norbensis, Saccharomyces oviformis, Schizosaccharomyces pombe, Candida albicans, Candida tropicalis, Rhodotorula glutinis, Rhodosporidium toruloides, Yarrowia lipolytica, Debaryomyces hansenii* and *Lipomyces starkeyi*. In a preferred embodiment, the microorganism is a *Saccharomyces* yeast, preferably a *Saccharomyces cerevisiae* yeast. Alternatively, the microorganism may be a fungus, preferably a filamentous fungus. Preferably, it is chosen from *Aspergillus, Trichoderma, Neurospora, Podospora, Endothia, Mucor, Cochiobolus* or *Pyricularia*. Preferentially, the fungus is chosen from *Aspergillus nidulans, Aspergillus niger, Aspergillus awomari, Aspergillus oryzae, Aspergillus terreus, Neurospora crassa, Trichoderma reesei* and *Trichoderma viride.*

In a second embodiment, the microorganism is a prokaryote. Preferably, it is a bacterium, notably chosen from the phylum Acidobacteria, Actinobacteria, Aquificae, Bacterioidetes, Chlamydiae, Chlorobi, Chloroflexi, Chrysiogenetes, Cyanobacteria, Deferribacteres, *Deinococcus-Thermus*, Dictyoglomi, Fibrobacteres, Firmicutes, Fusobacteria, Gemmatimonadetes, Nitrospirae, Planctomycetes, Proteobacteria, Spirochaetes, Thermodesulfobacteria, Thermomicrobia, Thermotogae or Verrucomicrobia. Preferably, the bacterium belongs to the genus *Acaryochloris, Acetobacter, Actinobacillus, Agrobacterium, Alicyclobacillus, Anabaena, Anacystis, Anaerobiospirillum, Aquifex, Arthrobacter, Arthrospira, Azobacter, Bacillus, Brevibacterium, Burkholderia, Chlorobium, Chromatium, Chlorobaculum, Clostridium, Corynebacterium, Cupriavidus, Cyanothece, Enterobacter, Deinococcus, Erwinia, Escherichia, Geobacter, Gloeobacter, Gluconobacter, Hydrogenobacter, Klebsiella, Lactobacillus, Lactococcus, Mannheimia, Mesorhizobium, Methylobacterium, Microbacterium, Microcystis, Nitrobacter, Nitrosomonas, Nitrospina, Nitrospira, Nostoc, Phormidium, Prochlorococcus, Pseudomonas, Ralstonia, Rhizobium, Rhodobacter, Rhodococcus, Rhodopseudomonas, Rhodospirillum, Salmonella, Scenedesmun, Serratia, Shigella, Staphylococcus, Streptomyces, Synechoccus, Synechocystis, Thermosynechococcus, Trichodesmium* or *Zymomonas*. More preferably, the bacterium is chosen from the species *Agrobacterium tumefaciens, Anaerobiospirillum succiniciproducens, Actinobacillus succinogenes, Aquifex aeolicus, Aquifex pyrophilus, Bacillus subtilis, Bacillus amyloliquefacines, Brevibacterium ammoniagenes, Brevibacterium immariophilum, Clostridium pasteurianum, Clostridium ljungdahlii, Clostridium acetobutylicum, Clostridium beigerinckii, Corynebacterium glutamicum, Cupriavidus necator, Cupriavidus metallidurans, Enterobacter sakazakii, Escherichia coli, Gluconobacter oxydans, Hydrogenobacter thermophilus, Klebsiella oxytoca, Lactococcus lactis, Lactobacillus plantarum, Mannheimia succiniciproducens, Mesorhizobium loti, Pseudomonas aeruginosa, Pseudomonas mevalonii, Pseudomonas pudica, Pseudomonas putida, Pseudomonas fluorescens, Rhizobium etli, Rhodobacter capsulatus, Rhodobacter sphaeroides, Rhodospirillum rubrum, Salmonella enterica, Salmonella typhi, Salmonella typhimurium, Shigella dysenteriae, Shigella flexneri, Shigella Streptomyces coelicolor, Zymomonas mobilis, sonnei, Staphylococcus aureus, Acaryochloris marina, Anabaena variabilis, Arthrospira platensis, Arthrospira maxima, Chlorobium tepidum, Chlorobaculum* sp., Cyanothece sp., Gloeobacter *violaceus, Microcystis aeruginosa, Nostoc punctiforme, Prochlorococcus marinus, Synechococcus elongatus, Synechocystis* sp., *Thermosynechococcus elongatus, Trichodesmium erythraeum* and *Rhodopseudomonas palustris*. In a preferred embodiment, the microorganism is an *Escherichia coli* bacterium, for example *E. coli* BL21, *E. coli* BL21 (DE3), *E. coli* MG1655 or *E. coli* W31 10 and derivatives thereof. In an alternative embodiment, the microorganism is a bacterium of the *Streptomyces* genus, in particular *Streptomyces venezuelae.*

The microorganisms may have been modified to increase the production of tyrosine and/or phenylalanine, preferably tyrosine. Notably, the genes responsible for the feedback inhibition of the production of tyrosine and/or phenylalanine, preferably of tyrosine, may be inactivated. Alternatively or cumulatively, the pathway for the biosynthesis of tyrosine and/or phenylalanine, preferably of tyrosine, may be optimized, notably by redirecting the flow of carbon from other metabolic pathways toward that of tyrosine and/or phenylalanine, preferably of tyrosine. These modifications and these genes are well known to those skilled in the art (see U.S. Pat. No. 8,809,028; Pandey et al., 2016, Biotechnol. Adv., 34, 634-662).

Thus, in one embodiment, the microorganism produces large amounts of tyrosine and/or of phenylalanine, in particular from a simple carbon source such as glucose.

Modifications Enabling the Production of Hesperidin and/or Diosmin

The recombinant microorganism according to the present invention was modified to produce hesperidin and/or diosmin. Notably, to enable the microorganism to synthesize hesperidin and/or diosmin from hesperetin and/or from diosmetin, respectively, the microorganism was modified to introduce the enzymes required for the glycosylation of hesperetin and/or of diosmetin in position 7 and for the transfer of a rhamnose in position 6 of the glucose of hesperetin-7-O-glucoside and/or diosmetin-7-O-glucoside.

In a first embodiment, the recombinant microorganism is capable of producing hesperetin and/or diosmetin: in particular, it has been modified for this purpose. In an alternative embodiment, hesperetin and/or diosmetin may be provided to the microorganism, for example by adding these compounds to the culture medium.

In one particular embodiment, the microorganism produces hesperidin. Diosmin may then be prepared from hesperidin by chemical conversion, notably by oxidation.

In a preferred embodiment, the microorganism produces hesperidin and diosmin.

Thus, the recombinant microorganism comprises:

a. a heterologous nucleic acid sequence coding for a flavanone 7-O-beta-D-glucosyltransferase (UGT) which is capable of adding a glucose in position 7 of hesperetin and/or diosmetin;

b. a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside; and c. a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose.

In one embodiment, the flavanone 7-O-beta-D-glucosyltransferase (UGT), 6"-O-rhamnosyltransferase (RhaT) and UDP-glucose 4,6-dehydratase/UDP-4-keto-6-deoxy-D-glucose 3,5-epimerase/UDP-4-keto-L-rhamnose-reductase (RHM) are enzymes that are heterologous to the microorganism.

UGT: Flavanone 7-O-Beta-Glucosyltransferase

UGT is an enzyme which performs the transfer of a glucose into position 7 of hesperetin and/or diosmetin. The name of UGT is UDP-glucose: flavanone 7-O-beta-D-glucosyltransferase or flavanone 7-O-beta-D-glucosyltransferase. It is also referred to by the following names: uridine diphosphoglucose-flavanone 7-O-glucosyltransferase, naringenin 7-O-glucosyltransferase, and hesperetin 7-O-glucosyl-transferase. This enzyme belongs to the class EC 2.4.1.185.

The inventors had to identify and select enzymes that are capable of accepting hesperetin and/or diosmetin as a substrate and of adding a glucose in position 7 of these compounds. Preferably, the enzyme is selected so as to have a preference for glycosylation in position 7 of hesperetin and/or diosmetin. In a preferred embodiment, the enzyme is specific for position 7 of hesperetin and/or diosmetin.

The microorganism thus comprises a heterologous nucleic acid sequence coding for a flavanone 7-O-beta-D-glucosyltransferase (UGT) which is capable of adding a glucose in position 7 of hesperetin and diosmetin.

The term "7-O-beta-glycosyltransferase activity" refers to a UGT enzyme which is capable of adding a glucose in position 7 of a flavonoid. To determine whether there is 7-O-beta-glycosyltransferase activity, an enzymatic test may be performed, which consists of the in vitro incubation of the flavanone 7-O-beta-D-glucosyltransferase enzyme in the presence of NAD (P) H, $O_2$, and of a flavonoid, under optimum conditions (pH, ions, etc.), and observation by UPLC-MS and comparison with the standard expected for the appearance of a flavonoid containing an additional glucose in position 7. Preferably, the flavonoid is hesperetin or diosmetin and the flavonoid containing an additional glucose in position 7 is their form with an additional glucose in position 7, i.e. hesperetin 7-O-glucoside and diosmetin 7-O-glucoside.

This enzyme is present only in higher eukaryotes, in particular in plants. For example, the enzyme may originate from plants of the genus *Citrus*, in particular *Citrus maxima, Citrus sinensis, Citrus clementina, Citrus mitis* and *Citrus×paradisi, Lysium*, in particular *Lysium barbarum, Petunia*, in particular *Petunia×hybrida, Arabidopsis*, in particular *Arabidopsis thaliana*, or *Scutellaria*, in particular *Scutellaria baicalensis.*

In one embodiment, the UGT is an enzyme from *Arabidopsis thaliana, Scutellaria baicalensis* or *Homo sapiens*. Preferably, the UGT is an enzyme from *Arabidopsis thaliana* or from *Scutellaria baicalensis.*

In a preferred embodiment, the UGT is an enzyme from *Citrus sinensis*, from *Citrus clementina*, from *Arabidopsis thaliana*, from *Scutellaria baicalensis* or from *Homo sapiens*, preferably from *Citrus sinensis* or from *Scutellaria baicalensis.*

In a particular embodiment, the UGT is selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity, notably with hesperetin and/or diosmetin as substrate.

In a preferred embodiment, the UGT is selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity. More particularly preferably, the UGT is selected from enzymes comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity.

Thus, the UGT may be from *Arabidopsis thaliana*. The nucleic acid sequences coding for this enzyme and protein sequences are described in NCBI under the reference numbers NM_119576 and NP_567995.1, respectively, and more particularly in SEQ ID NO: 91. The protein is also described in UniProtKB/Swiss Prot under the reference number UGT73B1.

Alternatively, the UGT is from *Scutellaria baicalensis*. In a first aspect, the nucleic acid sequences coding for a first UGT and protein sequences are described in NCBI under the reference numbers KU712253 and AMK52071.1, respectively, and more particularly in SEQ ID. NO: 93. The protein is described in UniProtKB/Swiss Prot under the reference number A0A140DPB7. In a second aspect, the nucleic acid sequences coding for a second UGT and protein sequences are described in NCBI under the reference numbers KU712254 and AMK52072.1, respectively, and more particularly in SEQ ID NO: 95. The protein is described in UniProtKB/Swiss Prot under the reference number A0A140DPB8. In a third aspect, the nucleic acid sequences coding for a third UGT and protein sequences are described in NCBI under the reference numbers KU712255 and AMK52073.1, respectively, and more particularly in SEQ ID NO: 97. The protein is described in UniProtKB/Swiss Prot under the reference number A0A140DPB9.

Moreover, the UGT may be from *Homo sapiens*. In a first aspect, the UGT is UGT1A6 (UDP glucuronosyltransferase family 1 member A6). The protein is described in UniProtKB/Swiss Prot under the reference number P19224. The consensus coding sequence is described in NCBI under the number CCDS2507.1. The sequence of this enzyme is described in SEQ ID NO: 99. In a second aspect, the UGT is UGT1A7 (UDP glucuronosyltransferase family 1 member A7). The protein is described in UniProtKB/Swiss Prot under the reference number Q9HAW7. The consensus coding sequence is described in NCBI under the number CCDS2506.1. The sequence of this enzyme is described in SEQ ID NO: 101.

The UGT may also be from *Citrus*, in particular from *Citrus sinensis* or *Citrus clementina*. In particular, the UGT from *Citrus sinensis* is described in SEQ ID NO: 113. A nucleotide sequence coding for this enzyme is described in SEQ ID NO: 114. The UGT from *Citrus clementina* is described in SEQ ID NO: 115. A nucleotide sequence coding for this enzyme is described in SEQ ID NO: 116.

In a preferred embodiment, the UGT is selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity.

RhaT: 6-O-Rhamnosyltransferase

RhaT is an enzyme which performs the transfer of a rhamnose into position 6 of the glucose of hesperetin-7-O-glucoside and/or diosmetin-7-O-glucoside. RhaT is a 6-O-rhamnosyltransferase. This enzyme belongs to the class EC 2.4.1.B53.

The inventors had to identify and select enzymes that are capable of accepting hesperetin-7-O-glucoside and/or diosmetin-7-O-glucoside as a substrate and of adding a rhamnose in position 6 of the glucose of these compounds.

The microorganism thus comprises a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside. This enzyme is present only in higher eukaryotes, in particular in plants.

The term "6-O-rhamnosyltransferase activity" means the addition of a rhamnose in position 6 of the glucose by the enzyme RhaT. To determine whether there is 6-O-rhamnosyltransferase activity, an enzymatic test may be performed, which consists of the in vitro incubation of the 6-O-rhamnosyltransferase enzyme in the presence of NAD (P) H, $O_2$, and of a flavonoid, under optimum conditions (pH, ions, etc.), and observation by UPLC-MS and comparison with the standard expected for the appearance of a flavonoid in which a rhamnose is added in position 6 of the glucose. Preferably, the flavonoid is hesperetin 7-O-glucoside or diosmetin 7-O-glucoside and the flavonoids in which a rhamnose is added in position 6 of the glucose are hesperidin and diosmin.

Preferably, this enzyme is an enzyme produced by a plant of the genus *Citrus* or *Petunia hybrida*, preferably of the species *Citrus sinensis, Citrus maxima*, or *Citrus clementina*. Preferably, the enzyme is an enzyme originating from *Citrus sinensis* or *Citrus clementina.*

In a particular embodiment, the 6-O-rhamnosyltransferase is selected from enzymes comprising a sequence chosen from SEQ ID NOs: 103, 105 and polypeptides comprising a sequence having at least 60, 70, 80, 85, 90 or 95% sequence identity with one of these sequences and having 6-O-rhamnosyltransferase activity.

Thus, the RhaT may be from *Citrus clementina*. It is described in the GenBank database from NCBI under the number XM_006420965 for the nucleic acid sequence and under the number XP_006421028 for the protein sequence, and more particularly in SEQ ID NO: 103. The protein is described in UniProtKB/Swiss Prot under the reference number V4RJL6.

The RhaT may also be from *Citrus sinensis*. It is described in the GenBank database from NCBI under the number DQ119035 for the nucleic acid sequence and under the number ABA18631.1 for the protein sequence, and more particularly in SEQ ID NO: 105. The protein is described in UniProtKB/Swiss Prot under the reference number A7ISD3.

In a particular embodiment, the RhaT is from *Citrus sinensis* and is an enzyme comprising the sequence SEQ ID NO: 105 or a polypeptide comprising a sequence having at least 60, 70, 80, 85, 90 or 95% sequence identity therewith and having 6"-O-rhamnosyltransferase activity.

In a preferred embodiment, the RhaT is selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity.

RHM: UDP-glucose 4,6-dehydratase/UDP-4-keto-6-deoxy-D-glucose 3,5-epimerase/UDP-4-keto-L-rhamnose-reductase RHM is a trifunctional enzyme UDP-glucose 4,6-dehydratase/UDP-4-keto-6-deoxy-D-glucose 3,5-epimerase/UDP-4-keto-L-rhamnose-reductase. This enzyme is capable of producing UDP-rhamnose from UDP-glucose. This enzyme belongs to the class EC 4.2.1.76. UDP-rhamnose is necessary for 6-O-rhamnosyltransferase (RhaT) activity.

The microorganism thus comprises a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose. This enzyme is present only in higher eukaryotes, in particular in plants.

The term "UDP-glucose 4,6-dehydratase/UDP-4-keto-6-deoxy-D-glucose 3,5-epimerase/UDP-4-keto-L-rhamnose-reductase activity" means the transformation of UDP-glucose into UDP-rhamnose. To determine whether there is UDP-glucose 4,6-dehydratase/UDP-4-keto-6-deoxy-D-glucose 3,5-epimerase/UDP-4-keto-L-rhamnose-reductase activity, an enzymatic test may be performed, which consists of the in vitro incubation of the UDP-glucose enzyme, NAD (P) H and $O_2$, under optimum conditions (pH, ions, etc.), and observation by UPLC-MS and comparison with the standard expected for the appearance of a UDP-rhamnose.

Preferably, this enzyme is an enzyme produced by a plant of the genus *Citrus*, in particular *Citrus sinensis*, or by *Arabidopsis thaliana*.

In a particular embodiment, the UDP-glucose 4,6-dehydratase/UDP-4-keto-6-deoxy-D-glucose 3,5-epimerase/UDP-4-keto-L-rhamnose-reductase is selected from enzymes comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity.

The RHM may be from *Citrus sinensis*. It is described in the GenBank database from NCBI under the number XM_006477756 for the nucleic acid sequence and under the number XP_006477819.1 for the protein sequence, and more particularly in SEQ ID NO: 107.

The RHM may also be from *Arabidopsis thaliana*. In a first aspect, the protein is described in the GenBank database from NCBI under the number AY081471 for the nucleic acid sequence and under the number AAM10033.1 for the protein sequence, and more particularly in SEQ ID NO: 109. The protein is described in UniProtKB/Swiss Prot under the reference number Q9SYM5. In a second aspect, the protein is described in the GenBank database from NCBI under the number AJ565874 for the nucleic acid sequence and under the number CAD92667.1 for the protein sequence, and more particularly in SEQ ID NO: 111. The protein is described in UniProtKB/Swiss Prot under the reference number Q9LPG6.

In a particular embodiment, the RHM is an enzyme comprising a sequence chosen from SEQ ID NOs: 107 and 109 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity.

In a preferred embodiment, the RHM is selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Combination of Enzymes

In a particular embodiment, the recombinant microorganism comprises:

- a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity, and most particularly preferably comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity, in particular comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity;
- a heterologous nucleic acid sequence coding for a 6-O-rhamnosyltransferase (RhaT) of the genus *Citrus* or *Petunia hybrida*, preferably *Citrus sinensis, Citrus maxima*, or *Citrus clementina*, even more preferably *Citrus sinensis* or *Citrus clementina*, preferably a 6-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6-O-rhamnosyltransferase activity, and preferably an RhaT comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and
- a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity, and preferably an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In another particular embodiment, the recombinant microorganism comprises a heterologous nucleic acid sequence coding for a 6-O-rhamnosyltransferase (RhaT) and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) as defined in the preceding embodiment and a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs:

91, 93, 95 and 97 and polypeptides comprising a sequence having at least 60, 70, 80, 85, 90 or 95% sequence identity with one of these sequences and having flavanone 7-O-beta-D-glucosyltransferase activity.

In a preferred embodiment, the microorganism comprises:

- a heterologous nucleic acid sequence coding for a flavanone 7-O-beta-D-glucosyltransferase (UGT) selected from enzymes comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, and more particularly preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and
- a heterologous nucleic acid sequence coding for a 6"-O-rhamnosyltransferase selected from enzymes comprising a sequence chosen from SEQ ID NOs: 103 and polypeptides comprising a sequence having at least 60, 70, 80, 85, 90 or 95% sequence: identity with this sequence and having 6"-O-rhamnosyltransferase activity; and
- a heterologous nucleic acid sequence coding for a UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In a particular embodiment, the enzymes described above are enzymes from higher eukaryotes, preferably plant enzymes. In a particular embodiment, the enzymes originate from plants of the same genus, for example of the same species.

Modifications Enabling the Production of Hesperetin and/or Diosmetin

As indicated previously, either hesperetin and/or diosmetin are supplied to the microorganism, or the microorganism is capable of producing hesperetin and/or diosmetin. In particular, the microorganism is capable or has been modified to be capable of producing hesperetin and/or diosmetin. The inventors thus also developed a biosynthetic pathway enabling the microorganism to produce hesperetin and/or diosmetin.

From Naringenin/Apigenin to Hesperetin/Diosmetin

Hesperetin and/or diosmetin may be obtained from naringenin and apigenin.

Several biosynthetic strategies were possible. To prepare hesperetin and/or diosmetin, it is necessary to make two modifications: methylation of the hydroxyl in position 4' and hydroxylation of position 3'. Thus, to increase the specificity of methylation of the hydroxyl in position 4', it appears logical to first perform methylation of the hydroxyl group already present before adding a second hydroxyl group in position 3'. On the contrary, the inventors arrived at the conclusion that it was necessary first to perform the hydroxylation and then the methylation, despite the risk of the problem of methylation specificity due to the introduction of the second hydroxyl.

F3'H: Flavonoid 3'-monooxygenase

Flavonoid 3'-monooxygenase (F3'H) is an enzyme which performs the addition of a hydroxyl group in position 3' of naringenin and/or apigenin. This enzyme belongs to the class EC 1.14.14.82. It is also known as flavone 3'-hydroxylase.

The inventors had to identify and select enzymes that are capable of accepting naringenin and/or apigenin as a substrate and of adding a hydroxyl group in position 3' of these compounds. Preferably, the enzyme is selected so as to have a preference for hydroxylation in position 3' of naringenin and/or apigenin. In a preferred embodiment, the enzyme is specific for the 3' position of naringenin and/or apigenin, in particular relative to the 5' position so as to avoid a double hydroxylation in positions 3' and 5', and preferably also to avoid hydroxylation in position 5'.

Flavonoid 3'-monooxygenase (F3'H) is an enzyme which performs the addition of a hydroxyl group in position 3' of naringenin and/or apigenin. This enzyme belongs to the class EC 1.14.14.82. It is also known as flavonoid 3'-hydroxylase.

The term "flavonoid 3'-monooxygenase activity" means the transformation of a flavonoid into a 3'-hydroxylated flavonoid by a CPR-dependent F3'H enzyme. To determine whether there is flavonoid 3'-monooxygenase activity, an enzymatic test may be performed, which consists of the in vitro incubation of the flavonoid 3'-monooxygenase enzyme in the presence of NAD (P) H, $O_2$, and of a flavonoid, under optimum conditions (pH, ions, etc.), and observation by UPLC-MS and comparison with the standard expected for the appearance of a 3'-hydroxylated flavonoid. Preferably, the flavonoid is naringenin or apigenin and the 3'-hydroxylated flavonoid is the 3'-hydroxylated form thereof, i.e. eriodictyol or luteolin.

The microorganism may thus comprise a heterologous nucleic acid sequence coding for a flavonoid 3'-monooxygenase (F3'H) which is capable of adding a hydroxyl in position 3' of naringenin and/or apigenin.

In one embodiment, the F3'H is a plant enzyme, notably from plants of the genus *Allium, Arabidopsis, Brassica, Callistephus, Columnea, Citrus, Dianthus, Gentiana, Gerbera, Glycine, Fragaria, Ipomoea, Malus, Matthiola, Osteospermum, Oryza, Phanerochaete, Perilla, Petroselinum, Pelargonium, Pilosella, Petunia, Sinningia, Sorghum, Torenia, Vitis* or *Zea*, for example *Allium cepa, Arabidopsis thaliana, Brassica napus, Columnea hybrida, Callistephus chinensis, Citrus sinensis, Citrus clementina, Dianthus caryophyllus, Fragaria vesca, Fragaria×ananassa, Gerbera hybrida, Glycine max, Gentiana triflora, Ipomoea nil, Ipomoea purpurea, Ipomoea tricolor, Matthiola incana, Malus domestica, Osteospermum* hybrid cultivar, *Oryza sativa, Phanerochaete chrysosporium, Pilosella officinarum, Petroselinum crispum, Pelargonium×hortorum, Perilla frutescens* var. *crispa, Petunia×hybrida, Sinningia cardinalis, Sorghum bicolor, Torenia* sp, *Torenia* hybrid cultivar, *Vitis vinifera* or *Zea mays*. In a more specific embodiment, the F3'H is an enzyme from plants of the genus *Allium, Brassica, Callistephus, Columnea, Citrus, Dianthus, Gentiana, Gerbera, Glycine, Fragaria, Ipomoea, Malus, Matthiola, Osteospermum, Oryza, Phanerochaete, Perilla, Petroselinum, Pelargonium, Pilosella, Petunia, Sinningia, Sorghum, Torenia, Vitis* or *Zea*, for example *Allium cepa,*

*Brassica napus, Columnea hybrida, Callistephus chinensis, Citrus sinensis, Citrus clementina, Dianthus caryophyllus, Fragaria vesca, Fragaria×ananassa, Gerbera hybrida, Glycine max, Gentiana triflora, Ipomoea nil, Ipomoea purpurea, Ipomoea tricolor, Matthiola incana, Malus domestica, Osteospermum* hybrid cultivar, *Oryza sativa, Phanerochaete chrysosporium, Pilosella officinarum, Petroselinum crispum, Pelargonium×hortorum, Perilla frutescens* var. *crispa, Petunia×hybrida, Sinningia cardinalis, Sorghum bicolor, Torenia* sp, *Torenia* hybrid cultivar, *Vitis vinifera* or *Zea mays.*

Preferably, the F3'H is an enzyme from *Perilla frutescens* var. *crispa, Petunia×hybrida, Callistephus chinensis, Gerbera hybrida, Citrus clementina, Osteospermum hybrid cultivar, Phanerochaete chrysosporium, Streptomyces avermitilis, Citrus sinensis, Arabidopsis thaliana* or *Pilosella officinarum*. In particular, the F3'H may be an enzyme from *Perilla frutescens* var. *crispa, Petunia×hybrida, Callistephus chinensis, Gerbera hybrida, Citrus sinensis* and *Pilosella officinarum.*

In a particular embodiment, the F3'H is selected from enzymes comprising a sequence chosen from SEQ ID NOs: 1, 3, 5, 7, 9, 11, 13, 15, 17, 19, 21 and 121, in particular from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17, 19 and 121, in particular from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, notably with naringenin and/or apigenin as substrate and with hydroxylation in position 3'. In a particular embodiment, the F3'H is an enzyme comprising a sequence selected from SEQ ID NOs: 5, 7 and 17 and polypeptides comprising a sequence having at least 60, 70, 80, 85, 90 or 95% identity with one of these sequences and having flavonoid 3'-monooxygenase activity.

In a preferred embodiment, the F3'H is an enzyme comprising a sequence selected from SEQ ID NOs: 7, 11, 17 and 121 and polypeptides comprising a sequence having at least 60, 70, 75, 80, 85, 90 or 95% identity with one of these sequences and having flavonoid 3'-monooxygenase activity. Most particularly preferably, the F3'H may be an enzyme comprising a sequence selected from SEQ ID NOs: 7, 17 and 121 and polypeptides comprising a sequence having at least 60, 70, 75, 80, 85, 90 or 95% identity with one of these sequences and having flavonoid 3'-monooxygenase activity.

Thus, the F3'H may be from *Perilla frutescens* var. *crispa*. The nucleic acid sequences coding for this enzyme and protein sequences are described in NCBI under the reference numbers AB045593.1 and BAB59005.1, respectively, and more particularly in SEQ ID NOs: 2 and 1.

The F3'H may be from *Phanerochaete chrysosporium*. The nucleic acid sequences coding for this enzyme and protein sequences are described in NCBI under the reference numbers AB597870.1 and BAL05157.1, respectively, and more particularly in SEQ ID NOs: 4 and 3.

The F3'H may be from *Petunia×hybrida*. The nucleic acid sequences coding for this enzyme and protein sequences are described in NCBI under the reference numbers AF155332.1 and AAD56282.1, respectively, and more particularly in SEQ ID NOs: 6 and 5.

The F3'H may be from *Callistephus chinensis*. In one embodiment, the nucleic acid sequences coding for this enzyme and protein sequences are described in NCBI under the reference numbers AF313488.1 and AAG49298.1, respectively, and more particularly in SEQ ID NOs: 8 and 7. In another embodiment, the nucleic acid sequences coding for this enzyme and protein sequences are described in NCBI under the reference numbers AF313489.1 and AAG49299.1, respectively, and more particularly in SEQ ID NOs: 10 and 9.

The F3'H may be from *Gerbera hybrida*. The nucleic acid sequences coding for this enzyme and protein sequences are described in NCBI under the reference numbers DQ218417.1 and ABA64468.1, respectively, and more particularly in SEQ ID NOs: 12 and 11.

The F3'H may be from *Osteospermum hybrid* cultivar. The nucleic acid sequences coding for this enzyme and protein sequences are described in NCBI under the reference numbers DQ250711.1 and ABB29899.1, respectively, and more particularly in SEQ ID NOs: 14 and 13.

The F3'H may be from *Citrus clementina*. The nucleic acid sequences coding for this enzyme and protein sequences are described in NCBI under the reference numbers XM 006440673.1 and XP_006440736.1, respectively, and more particularly in SEQ ID NOs: 16 and 15.

The F3'H may be from *Citrus sinensis*. The nucleic acid sequences coding for this enzyme and protein sequences are described in NCBI under the reference numbers XM_006477592.2 et XP_006477655.1, respectively, and more particularly in SEQ ID NOs: 18 and 17.

The F3'H may be from *Pilosella officinarum*. The nucleic acid sequences coding for this enzyme and protein sequences are described in NCBI under the reference numbers DQ319866.2 and ABC47161.1, respectively, and more particularly in SEQ ID NOs: 20 and 19.

The F3'H may be from *Streptomyces avermitilis*. The nucleic acid sequences coding for this enzyme and protein sequences are described in NCBI under the reference numbers SAV_4539 et WP_010985964.1, respectively, and more particularly in SEQ ID NOs: 22 and 21.

The F3'H may be from *Arabidopsis thaliana*. A nucleic acid sequence coding for this enzyme and the protein sequence are described in NCBI under the reference numbers NM 120881.2 and NP_196416.1, respectively, and more particularly in SEQ ID NOs: 122 and 121.

Preferably, the F3'H is an enzyme comprising a sequence selected from SEQ ID NOs: 7, 11, 17 and 121 and polypeptides comprising a sequence having at least 75%, at least 80%, at least 85%, at least 90% or at least 95% identity with one of these sequences and having flavonoid 3'-monooxygenase activity. Most particularly preferably, the F3'H is an enzyme comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity.

According to a preferred embodiment, the F3'H is an enzyme comprising a sequence chosen from SEQ ID NO: 7 and polypeptides comprising a sequence having at least 75%, at least 80%, at least 85%, at least 90% or at least 95% sequence identity with the sequence SEQ ID NO: 7 and having flavonoid 3'-monooxygenase activity.

According to another particular embodiment, the F3'H is an enzyme comprising a sequence chosen from SEQ ID NO: 17 and polypeptides comprising a sequence having at least 75%, at least 80%, at least 85%, at least 90% or at least 95% sequence identity with the sequence SEQ ID NO: 17 and having flavonoid 3'-monooxygenase activity.

According to another particular embodiment, the F3'H is an enzyme comprising a sequence chosen from SEQ ID NO: 121 and polypeptides comprising a sequence having at least 70%, at least 75%, at least 80%, at least 85%, at least 90% or at least 95% sequence identity with the sequence SEQ ID NO: 121 and having flavonoid 3'-monooxygenase activity.

According to another particular embodiment, the F3'H is an enzyme comprising a sequence chosen from SEQ ID NO: 11 and polypeptides comprising a sequence having at least 75%, at least 80%, at least 85%, at least 90% or at least 95% sequence identity with the sequence SEQ ID NO: 11 and having flavonoid 3'-monooxygenase activity.

CPR: Cytochrome P450 Reductase

Flavonoid 3'-monooxygenase (F3'H) requires the presence of NADPH to perform the addition of the hydroxyl group.

Thus, in a preferred embodiment, the microorganism comprises a heterologous nucleic acid coding for a cytochrome P450 reductase, an NADPH-cytochrome P450 reductase. This enzyme belongs to the class EC 1.6.2.4.

Cytochrome P450 reductase originates from a eukaryote, notably from a yeast, for example of the genus Saccharomycesles, or from a plant, for example a plant of the genus *Arabidopsis, Ammi, Avicennia, Camellia, Camptotheca, Catharanthus, Citrus, Glycine, Helianthus, Lotus, Mesembryanthemum, Phaseolus, Physcomitrella, Pinus, Populus, Ruta, Saccharum, Solanum, Vigna, Vitis* or *Zea.*

In a preferred embodiment, the cytochrome P450 reductase originates from a eukaryote, for example from yeast, in particular from *Saccharomyces cerevisiae*, or from a plant, for example from *Catharanthus roseus* or *Arabidopsis thaliana.*

In a particular embodiment, the cytochrome P450 reductase is selected from enzymes comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity. In a very particular embodiment, the cytochrome P450 reductase may be selected from enzymes comprising a sequence chosen from SEQ ID NO: 25 and polypeptides comprising a sequence having at least 60, 70, 80, 85, 90 or 95% sequence identity with this sequence and having cytochrome P450 reductase activity.

For example, the cytochrome P450 reductase may be from *Catharanthus roseus*. It is described in the GenBank database from NCBI under the number X69791.1 for the nucleic acid sequence and under the number CAA49446.1 for the protein sequence, and more particularly in SEQ ID NOs: 24 and 23, respectively. The protein is described in UniProtKB/Swiss Prot under the reference number Q05001.

The cytochrome P450 reductase may be from *Saccharomyces cerevisiae*. It is described in the GenBank database from NCBI under the number NM_001179172.1 for the nucleic acid sequence and under the number NP_011908.1 for the protein sequence, and more particularly in SEQ ID NOs: 26 and 25, respectively. The protein is described in UniProtKB/Swiss Prot under the reference number P16603.

The cytochrome P450 reductase may be chimeric. It is described in the article by Aigrain et al. (2009, EMBO Reports, 10, 742-747). The nucleic acid sequence coding for this enzyme and the protein sequence are described in SEQ ID NOs: 28 and 27, respectively.

Moreover, the cytochrome P450 reductase may be from *Arabidopsis thaliana*. When the cytochrome P450 originates from *Arabidopsis thaliana*, it may be named ATR. It is described in the GenBank database from NCBI under the number NM_118585.4 for the nucleic acid sequence and under the number NP_194183.1 for the protein sequence, and more particularly in SEQ ID NOs: 30 and 29, respectively. The protein is described in UniProtKB/Swiss Prot under the reference number Q9SB48.

In addition, the cytochrome P450 reductase may be from *Arabidopsis thaliana* and may be described in the GenBank database from NCBI under the number NM_179141.2 for the nucleic acid sequence and under the number NP_849472.2 for the protein sequence, and more particularly in SEQ ID NOs: 32 and 31, respectively. The protein is described in UniProtKB/Swiss Prot under the reference number Q9SUM3.

In one embodiment, a new copy of a sequence coding for CPR as defined above is introduced into the yeast. In another embodiment, when the yeast is *Saccharomyces cerevisiae* and when the CPR originates from the same yeast, the promoter of the endogenous gene coding for CPR is replaced with a strong promoter. Thus, the expression of the CPR is increased relative to the wild-type yeast; the CPR is thus overexpressed in the modified yeast.

In one particular embodiment, the F3'H and the CPR are from the same origin, the same species.

OMT: O-methyltransferase

O-methyltransferases (OMT) are a very large family of enzymes having targets that are difficult to define. The inventors had to identify and select O-methyltransferases that are capable of methylating eriodictyol and/or luteolin in position 4' (para position).

Preferably, the enzyme was selected so as to have a preference for methylation in position 4' of eriodictyol and/or luteolin. In a preferred embodiment, the enzyme is specific for position 4' of eriodictyol and/or luteolin. The term "specific" means that the methyl group introduced by the enzyme onto eriodictyol and/or luteolin is found in position 4' in 60% of the cases, the remainder being introduced into position 3', preferably in 70% of the cases, and even more preferably in 80% of the cases.

The term "4'-O-methyltransferase activity" means the transformation of a 4'-hydroxyflavonoid into a 4'-methoxyflavonoid by a 4'-O-methyltransferase enzyme. To determine whether there is 4'-O-methyltransferase activity, an enzymatic test may be performed, which consists of the in vitro incubation of a mixture composed of the 4'-O-methyltransferase enzyme, a 4'-hydroxyflavonoid and S-adenosyl-L-methionine, under optimum conditions (pH, temperature, ions, etc.). After a certain incubation time, the appearance of the 4'-methoxyflavonoid is observed in UPLC-MS in comparison with the expected standard.

In the present case, the 4'-hydroxyflavonoid is eriodictyol or luteolin, which will be transformed, respectively, into their 4'-methoxyflavonoid form, i.e. into hesperetin or diosmetin.

The microorganism may thus comprise a heterologous nucleic acid sequence coding for an O-methyltransferase which is capable of methylating eriodictyol and/or luteolin in position 4'.

This enzyme is present only in higher eukaryotes, in particular in plants.

In one embodiment, the O-methyltransferase (OMT) is an enzyme from *Arabidopsis thaliana*. In another embodiment, the O-methyltransferase (OMT) originates from a higher eukaryote, preferably from a mammal. In particular, the O-methyltransferase (OMT) is of human origin (*Homo sapiens*).

In a particular embodiment, the OMT is selected from enzymes comprising a sequence chosen from SEQ ID NOs: 87 and 89 and polypeptides comprising a sequence having at least 60, 70, 80, 85, 90 or 95% identity with one of these sequences and having O-methyltransferase activity, notably with eriodictyol and/or luteolin as substrate and with methylation in position 4'.

In one embodiment, the OMT is selected from the enzyme comprising a sequence chosen from SEQ ID NO: 89 and polypeptides comprising a sequence having at least 60, 70, 80, 85, 90 or 95% identity with this sequence and having O-methyltransferase activity.

In another embodiment, the OMT is selected from the enzyme comprising a sequence chosen from SEQ ID NO: 87 and polypeptides comprising a sequence having at least 60, 70, 80, 85, 90 or 95% identity with this sequence and having O-methyltransferase activity.

Thus, the OMT may be from *Arabidopsis thaliana*. The nucleic acid sequences coding for this enzyme and protein sequences are described in NCBI under the reference numbers NM_118755.4 and NP_567739.1, respectively. The protein is also described in UniProtKB/Swiss Prot under the reference number Q9C5D7, and more particularly in SEQ ID NO: 87.

Alternatively, the OMT is from *Homo sapiens*. The nucleic acid sequences coding for this enzyme and protein sequences are described in NCBI under the reference numbers NM_007310.2 and NP_009294.1, respectively. The protein is also described in UniProtKB/Swiss Prot under the reference number P21964, and more particularly in SEQ ID NO: 89.

The OMT from *Homo sapiens* has the advantage of accepting eriodictyol and luteolin as substrate for the methylation, whereas the OMT from *Arabidopsis thaliana* has a strong preference for eriodictyol. Conversely, if the synthesis of hesperetin is to be favored relative to that of diosmetin, the OMT from *Arabidopsis thaliana* might have an advantage.

In a preferred embodiment, the OMT is an OMT from *Citrus*, in particular *Citrus clementina* or *Citrus sinensis*. In a particularly preferred embodiment, the OMT is selected from an enzyme comprising a sequence chosen from SEQ ID NOs 117 and 119 and polypeptides comprising a sequence having at least 60, 70, 80, 85, 90 or 95% identity with one of these sequences and having O-methyltransferase activity.

Preferably, the OMT is selected from an enzyme comprising a sequence chosen from SEQ ID NO: 117 and polypeptides comprising a sequence having at least 60, 70, 80, 85, 90 or 95% identity with this sequence and having O-methyltransferase activity.

Alternatively, the OMT is selected from an enzyme comprising a sequence chosen from SEQ ID NO: 119 and polypeptides comprising a sequence having at least 60, 70, 80, 85, 90 or 95% identity with this sequence and having O-methyltransferase activity.

The OMTs from *Citrus* and from *Arabidopsis thaliana* described above have the advantage of specifically methylating eriodictyol in position 4'.

During the design of the microorganism, the inventors observed that this methylation step constituted one of the limiting steps. Surprisingly, despite the presence of the cofactor S-adenosyl-L-methionine in the microorganism, in particular the yeast, the addition of an enzyme which increases the synthesis of this cofactor made it possible to dispel the limiting aspect of this step. Thus, in a preferred embodiment, the microorganism also comprises a heterologous or endogenous sequence coding for an enzyme which synthesizes S-adenosyl-L-methionine, an S-adenosylmethionine synthetase (SAMT). This enzyme belongs to the class EC 2.5.1.6.

In one embodiment, the microorganism comprises a heterologous nucleic acid sequence coding for an O-methyltransferase (OMT), which is in particular capable of methylating eriodictyol and/or luteolin in position 4' and a heterologous or endogenous nucleic acid sequence coding for an S-adenosylmethionine synthetase (SAMT).

In one embodiment, the SAMT originates from a yeast, in particular from *Saccharomyces cerevisiae*, most particularly when the microorganism is a yeast.

In a particular embodiment, the S-adenosylmethionine synthetase is an enzyme comprising a sequence chosen from SEQ ID NO: 81 and a polypeptide comprising a sequence having at least 60, 70, 80, 85, 90 or 95% identity with this sequence and having S-adenosylmethionine synthetase activity.

For example, the S-adenosylmethionine synthase may be from *Saccharomyces cerevisiae*. It is described in the GenBank database from NCBI under the number NM_001180810.3 for the nucleic acid sequence and under the number NP_010790.3 for the protein sequence. The protein is described in UniProtKB/Swiss Prot under the reference number P19358.

In one embodiment, a new copy of a sequence coding for SAMT as defined above is introduced into the microorganism. In another embodiment, when the microorganism is *Saccharomyces cerevisiae*, the promoter of the endogenous gene coding for SAMT is replaced with a strong promoter. Thus, the expression of the SAMT is increased relative to the wild-type microorganism; the SAMT is thus overexpressed in the modified microorganism.

Thus, in a preferred embodiment, the microorganism comprises a heterologous nucleic acid sequence coding for an O-methyltransferase which is capable of methylating eriodictyol and/or luteolin in position 4' and a heterologous or endogenous nucleic acid sequence coding for an S-adenosylmethionine synthetase (SAMT) which is capable of producing S-adenosyl-L-methionine.

FNS: Flavone Synthase

Diosmetin may be produced from luteolin. It may also be obtained from eriodictyol, either by transforming it into luteolin and then preparing diosmetin from luteolin, or by transforming it into hesperetin and then preparing diosmetin from hesperetin. The enzyme that is capable of transforming eriodictyol into luteolin and/or hesperetin into diosmetin is a flavone synthase (FNS). In a particular embodiment, the flavone synthase is also capable of transforming eriodictyol into luteolin.

Thus, the microorganism may comprise a heterologous nucleic acid sequence coding for a flavone synthase, in particular a flavone synthase which is capable of producing luteolin from eriodictyol and/or diosmetin from hesperetin.

The term "flavone synthase activity" means the transformation of a flavanone into flavone by an FNSI enzyme (CPR-independent) or an FNSII enzyme (CPR-dependent).

To determine if there is flavone synthase activity, an enzymatic test may be performed, which consists of the in vitro incubation in the case of FNSI of a mixture composed of the flavone synthase enzyme (FNSI), a flavanone, 2-oxoglutarate and $O_2$, under optimum conditions (pH, temperature, ions, etc.) and in the case of FNSII of a mixture composed of the enzyme FNSII, a flavanone, NAD (P) H and $O_2$, under optimum conditions (pH, temperature, ions, etc.). After a certain incubation time, the appearance of the flavone corresponding to the flavanone is observed in UPLC-MS in comparison with the expected standard. Preferably, the flavanone is eriodictyol or hesperetin, which will be transformed, respectively, into their flavone form, i.e. into luteolin or diosmetin.

Thus, in a particular embodiment, the microorganism comprises a heterologous nucleic acid sequence coding for an O-methyltransferase (OMT), which is in particular capable of methylating eriodictyol and/or luteolin in position 4'; and a heterologous nucleic acid sequence coding for a flavone synthase, in particular a flavone synthase which is capable of producing luteolin from eriodictyol and/or diosmetin from hesperetin.

Preferably, the flavone synthase is an enzyme originating from a plant, for example of the genus *Aethusa, Angelica, Antirrhinum, Apium, Arabidopsis, Callistephus, Camellia, Conium, Cuminum, Cynara, Dahlia, Dorcoceras, Erythranthe, Lonicera, Medicago, Oryza, Perilla, Petroselinum, Plectranthus, Populus, Saussurea, Scutellaria* or *Zea*, in particular of the genus *Arabidopsis, Lonicera, Medicago, Oryza, Petroselinum, Populus* or *Zea*, notably of *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular of *Arabidopsis thaliana, Lonicera japonica, Lonicera macranthoides, Medicago truncatula, Oryza sativa, Petroselinum crispum, Populus deltoides* or *Zea mays*, preferably of *Petroselinum crispum*, or of the genus *Lonicera* for instance *Lonicera japonica* and *Lonicera macranthoides*.

In a particular embodiment, the flavone synthase (FNS) is selected from enzymes comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity. In particular, the flavone synthase (FNS) is selected from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity. Preferably, the FNS is selected from enzymes comprising a sequence chosen from SEQ ID NO: 37 and polypeptides comprising a sequence having at least 60, 70, 80, 85, 90 or 95% sequence identity with this sequence and having flavone synthase activity.

There are two types of flavone synthase (FNS): flavone synthase 1 (FNSI) and flavone synthase 2 (FNSII). Starting with a flavanone and 2-oxoglutarate, FNSI is capable of producing the corresponding flavone. The enzyme FNSI belongs to the class EC 1.14.11.22. FNSII belongs to the P450 group and requires the presence of a cytochrome P450 reductase. The enzyme FNSII belongs to the class EC 1.14.13.

In one embodiment, the FNS is a type I flavone synthase. In another embodiment, the FNS is a type II flavone synthase. In an additional embodiment, the microorganism comprises a type I flavone synthase and a type II flavone synthase.

In a preferred embodiment, the microorganism comprises a heterologous nucleic acid sequence coding for a type I flavone synthase (FNSI). The advantage of FNSI is that it functions without cytochrome P450 reductase.

The FNSI may be a flavone synthase from a plant such as *Petroselinum crispum, Oryza sativa, Populus deltoides, Medicago truncatula, Apium graveolens, Cuminum cyminum, Aethusa cynapium, Angelica archangelica*, or *Conium maculatum*, in particular from *Petroselinum crispum, Oryza sativa, Populus deltoides* or *Medicago truncatula*, preferably from *Petroselinum crispum.*

The FNSI may be an enzyme comprising a sequence chosen from SEQ ID NOs: 37, 127, 137, 141, 143 and 145 and polypeptides comprising a sequence having at least 60, 70, 80, 85, 90 or 95% sequence identity with one of these sequences and having flavone synthase activity. In a particular aspect, the FNSI may be an enzyme comprising a sequence chosen from SEQ ID NO: 37 and a polypeptide comprising a sequence having at least 60, 70, 80, 85, 90 or 95% sequence identity with this sequence and having flavone synthase activity.

For example, the FNSI may be from *Petroselinum crispum*. It is described in the GenBank database from NCBI under the number AY817680.1 for the nucleic acid sequence and under the number AAX21541.1 for the protein sequence. The protein is described in UniProtKB/Swiss Prot under the reference number Q7XZQ8. The amino acid and nucleic acid sequences are described in SEQ ID NOs: 37 and 38, respectively.

The FNSI may also be from *Angelica archangelica*. It is described in the GenBank database from NCBI under the number DQ683352.1 for the nucleic acid sequence and under the number ABG78793.1 for the protein sequence. The amino acid and nucleic acid sequences are described in SEQ ID NOs: 127 and 128, respectively.

The FNSI may also be from *Apium graveolens*. It is described in the GenBank database from NCBI under the number AY817676.1 for the nucleic acid sequence and under the number AAX21537.1 for the protein sequence. The amino acid and nucleic acid sequences are described in SEQ ID NOs: 137 and 138, respectively.

The FNSI may also be from *Cuminum cyminum*. It is described in the GenBank database from NCBI under the number DQ683349.1 for the nucleic acid sequence and under the number ABG78790.1 for the protein sequence. The amino acid and nucleic acid sequences are described in SEQ ID NOs: 141 and 142, respectively.

The FNSI may also be from *Aethusa cynapium*. It is described in the GenBank database from NCBI under the number DQ683350.1 for the nucleic acid sequence and under the number DQ683350.1 for the protein sequence. The amino acid and nucleic acid sequences are described in SEQ ID NOs: 143 and 144, respectively.

The FNSI may also be from *Conium maculatum*. It is described in the GenBank database from NCBI under the number DQ683354.1 for the nucleic acid sequence and under the number ABG78795.1 for the protein sequence. The amino acid and nucleic acid sequences are described in SEQ ID NOs: 145 and 146, respectively.

In another embodiment, the microorganism comprises a heterologous nucleic acid sequence coding for a type II flavone synthase (FNSII).

The FNSII may be a flavone synthase from a plant, for example from *Arabidopsis thaliana, Zea mays*, of the genus *Lonicera* for instance *Lonicera japonica* and *Lonicera macranthoides, Callistephus chinensis, Medicago truncatula, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular a flavone synthase from *Arabidopsis thaliana, Zea mays* or of the genus *Lonicera*, for instance *Lonicera japonica* and *Lonicera macranthoides*.

In a particular embodiment, the flavone synthase (FNSII) is selected from enzymes comprising a sequence chosen from SEQ ID NOs: 33, 35, 129, 131, 133, 135, 139, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33 and 35 and polypeptides comprising a sequence having at least 60, 70, 80, 85, 90 or 95% sequence identity with one of these sequences and having flavone synthase activity.

In one embodiment, the flavone synthase FNS is an FNSII originating from *Lonicera japonica*. In this embodiment, the enzyme may be an enzyme described in the GenBank database from NCBI under the number KU127576.1 for the nucleic acid sequence and under the number AMQ91109.1 for the protein sequence, and more particularly in SEQ ID NOs: 34 and 33, respectively.

In another embodiment, the flavone synthase FNS is an FNSII originating from *Lonicera macranthoides*. The nucleic acid sequences coding for this enzyme and protein sequences are described in NCBI under the reference numbers KU127580.1 and AMQ91113.1, respectively, and more particularly in SEQ ID NOs: 36 and 35, respectively.

In another embodiment, the flavone synthase FNS is an FNSII originating from *Cynara cardunculus* var *scolymus*. The nucleic acid sequences coding for this enzyme and protein sequences are described in NCBI under the reference numbers JN825735.1 and AFG31000.1, respectively, and more particularly in SEQ ID NOs: 130 and 129, respectively.

In another embodiment, the flavone synthase FNS is an FNSII originating from *Perilla frutescens* var *crispa*. The nucleic acid sequences coding for this enzyme and protein sequences are described in NCBI under the reference numbers AB045592.1 and BAB59004.1, respectively, and more particularly in SEQ ID NOs: 132 and 131, respectively.

In another embodiment, the flavone synthase FNS is an FNSII originating from *Dahlia pinnata*. The nucleic acid sequences coding for this enzyme and protein sequences are described in NCBI under the reference numbers AB769842.1 and BAM72335.1, respectively, and more particularly in SEQ ID NOs: 134 and 133, respectively.

In another embodiment, the flavone synthase FNS is an FNSII originating from *Callistephus chinensis*. The nucleic acid sequences coding for this enzyme and protein sequences are described in NCBI under the reference numbers AF188612.1 and AAF04115.1, respectively, and more particularly in SEQ ID NOs: 136 and 135, respectively.

In another embodiment, the flavone synthase FNS is an FNSII originating from *Medicago truncatula*. The nucleic acid sequences coding for this enzyme and protein sequences are described in NCBI under the reference numbers DQ354373.1 and ABC86159.1, respectively, and more particularly in SEQ ID NOs: 140 and 139, respectively.

In another embodiment, the flavone synthase FNS is an FNSII originating from *Camellia sinensis*. The nucleic acid sequences coding for this enzyme and protein sequences are described in NCBI under the reference numbers FJ169499.1 and ACH99109.1, respectively, and more particularly in SEQ ID NOs: 148 and 147, respectively.

In another embodiment, the flavone synthase FNS is an FNSII originating from *Saussurea medusa*. The nucleic acid sequences coding for this enzyme and protein sequences are described in NCBI under the reference numbers KF170286.1 and AGV40781.1, respectively, and more particularly in SEQ ID NOs: 150 and 149, respectively.

In another embodiment, the flavone synthase FNS is an FNSII originating from *Plectranthus barbatus*. The nucleic acid sequences coding for this enzyme and protein sequences are described in NCBI under the reference numbers KF606861.1 and AHJ89438.1, respectively, and more particularly in SEQ ID NOs: 152 and 151, respectively.

In another embodiment, the flavone synthase FNS is an FNSII originating from *Scutellaria baicalensis*. The nucleic acid sequences coding for this enzyme and protein sequences are described in NCBI under the reference numbers KT963454.1 and AMW91729.1, respectively, and more particularly in SEQ ID NOs: 154 and 153, respectively.

In another embodiment, the flavone synthase FNS is an FNSII originating from *Dorcoceras hygrometricum*. The nucleic acid sequences coding for this enzyme and protein sequences are described in NCBI under the reference numbers KV013332.1 and KZV23934.1, respectively, and more particularly in SEQ ID NOs: 156 and 155, respectively.

In another embodiment, the flavone synthase FNS is an FNSII originating from *Antirrhinum majus*. The nucleic acid sequences coding for this enzyme and protein sequences are described in NCBI under the reference numbers AB028151.1 and BAA84071.1, respectively, and more particularly in SEQ ID NOs: 158 and 157, respectively.

In another embodiment, the flavone synthase FNS is an FNSII originating from *Erythranthe lewisii*. The nucleic acid sequences coding for this enzyme and protein sequences are described in NCBI under the reference numbers KX710102.1 and AOR81894.1, respectively, and more particularly in SEQ ID NOs: 160 and 159, respectively.

In a particular embodiment, the microorganism comprises a heterologous nucleic acid sequence coding for a type II flavone synthase (FNSII) and a type I flavone synthase, for example a sequence chosen from SEQ ID NOs: 33, 35, 129, 131, 133, 135, 139, 147, 149, 151, 153, 155, 157 and 159 and polypeptides comprising a sequence having at least 60, 70, 80, 85, 90 or 95% sequence identity with one of these sequences and having flavone synthase activity, and an enzyme comprising a sequence chosen from SEQ ID NOs: 37, 127, 137, 141, 143 and 145 and a polypeptide comprising a sequence having at least 60, 70, 80, 85, 90 or 95% sequence identity with this sequence and having flavone synthase activity, preferably a sequence chosen from SEQ ID NOs: 33 and 35 and polypeptides comprising a sequence having at least 60, 70, 80, 85, 90 or 95% sequence identity with one of these sequences and having flavone synthase activity and an enzyme comprising a sequence chosen from SEQ ID NO: 37 and a polypeptide comprising a sequence having at least 60, 70, 80, 85, 90 or 95% sequence identity with this sequence and having flavone synthase activity.

The type II FNSs, FNSII, require the presence of a cytochrome P450 reductase (CPR). If the microorganism does not comprise cytochrome P450 reductase, it will thus be necessary to introduce a heterologous cytochrome P450 reductase. If the microorganism already comprises one, it is possible to envisage either the overexpression of an endogenous cytochrome P450 reductase (for example by replacing the promoter with a strong promoter or by adding one or more copies of the coding sequence) or by also introducing a heterologous cytochrome P450 reductase.

In a particular embodiment, the type II FNS and the CPR are from the same origin, the same species.

Combination of Enzymes

Thus, besides the enzymes required for the biosynthesis of hesperidin and/or diosmin from hesperetin and/or diosmetin, respectively, as described previously, the microorganism preferably comprises enzymes for producing hesperetin and/or diosmetin from naringenin and/or apigenin.

In a first particular embodiment, the recombinant microorganism comprises:

- a heterologous nucleic acid sequence coding for a flavanone 7-O-beta-D-glucosyltransferase (UGT) which is capable of adding a glucose in position 7 of hesperetin and/or diosmetin; preferably a flavanone 7-O-beta-D-glucosyltransferase (UGT) from *Arabidopsis thaliana, Citrus sinensis, Citrus clementina, Scutellaria baicalensis* or *Homo sapiens*, preferably from *Citrus sinensis* or *Scutellaria baicalensis*; preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113, 115, 91, 93, 95 and 97 and polypeptides comprising a sequence having at least 60, 70, 80, 85, 90 or 95% sequence identity with one of these sequences and having flavanone 7-O-beta-D-glucosyltransferase activity;
- a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside; preferably an RhaT of the genus *Citrus* or *Petunia hybrida*, preferably *Citrus sinensis, Citrus maxima*, or *Citrus clementina*, even more preferably *Citrus sinensis* or *Citrus clementina*, preferably a 6-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6-O-rhamnosyltransferase activity;
- a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing a UDP-rhamnose; preferably an RHM from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;
- a heterologous nucleic acid sequence coding for a flavonoid 3'-monooxygenase (F3'H) which is capable of hydroxylating naringenin and/or apigenin in position 3'; in particular which is capable of hydroxylating naringenin and/or apigenin in position 3'; preferably from *Perilla frutescens* var. *crispa, Petunia×hybrida, Callistephus chinensis, Gerbera hybrida, Citrus sinensis, Citrus clementina, Osteospermum* hybrid cultivar, *Phanerochaete chrysosporium, Streptomyces avermitilis* or *Pilosella officinarum*, in particular from *Perilla frutescens* var. *crispa, Petunia×hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19, 21 and 121 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17, 19 and 121 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 7, 11, 17 and 121 and polypeptides comprising a sequence having at least 60, 70, 80, 85, 90 or 95% sequence identity with one of these sequences and having flavonoid 3'-monooxygenase activity;
- optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity;
- a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NOs: 117, 119 and 89 and polypeptides comprising a sequence having at least 60, 70, 80, 85, 90 or 95% sequence identity with one of these sequences and having O-methyltransferase activity; and
- optionally, a heterologous nucleic acid sequence coding for a flavone synthase (FNS) which is capable of producing a flavone from a flavanone, in particular which is capable of transforming naringenin into apigenin, and/or eriodictyol into luteolin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In another particular embodiment, the recombinant microorganism comprises:

a heterologous nucleic acid sequence coding for a flavanone 7-O-beta-D-glucosyltransferase (UGT) which is capable of adding a glucose in position 7 of hesperetin and/or diosmetin; preferably a flavanone 7-O-beta-D-glucosyltransferase (UGT) from *Arabidopsis thaliana, Scutellaria baicalensis* or *Homo sapiens*, preferably from *Arabidopsis thaliana* or *Scutellaria baicalensis*; preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity;

a heterologous nucleic acid sequence coding for a 6-O-rhamnosyltransferase (RhaT) which is capable of transferring a rhamnose into position 6 of the glucose of hesperetin-7-O-glucoside and/or diosmetin-7-O-glucoside; preferably an RhaT of the genus *Citrus* or *Petunia hybrida*, preferably *Citrus sinensis, Citrus maxima*, or *Citrus clementina*, even more preferably *Citrus sinensis* or *Citrus clementina*, preferably a 6-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6-O-rhamnosyltransferase activity;

a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing a UDP-rhamnose; preferably an RHM from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

a heterologous nucleic acid sequence coding for a flavonoid 3'-monooxygenase (F3'H) which is capable of hydroxylating naringenin and/or apigenin in position 3'; in particular which is capable of hydroxylating naringenin and/or apigenin in position 3'; preferably from *Perilla frutescens* var. *crispa, Petunia×hybrida, Callistephus chinensis, Gerbera hybrida, Citrus sinensis* and *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity;

optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity; and optionally, a heterologous nucleic acid sequence coding for a flavone synthase (FNS) which is capable of producing a flavone from a flavanone, in particular capable of transforming naringenin into apigenin, and/or eriodictyol into luteolin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity.

In a preferred embodiment, the microorganism comprises:

a heterologous nucleic acid sequence coding for a flavanone 7-O-beta-D-glucosyltransferase selected from enzymes comprising a sequence chosen from SEQ ID NOs: 113, 115 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, and most particularly preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and a heterologous nucleic acid sequence coding for a 6"-O-rhamnosyltransferase selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity; and a heterologous nucleic acid sequence coding for a flavonoid 3'-monooxygenase (F3'H) selected from enzymes comprising a sequence chosen from SEQ ID NOs: 7, 11, 17 and 121 and polypeptides comprising a sequence having at least 60, 70, 80, 85, 90 or 95% sequence identity with one of these sequences and having flavonoid 3'-monooxygenase activity, preferably a flavonoid 3'-monooxygenase (F3'H) comprising a sequence chosen from SEQ ID NOs: 7, 17 and 121 and polypeptides having at least 60, 70, 80, 85, 90 or 95% identity with one of these sequences and having flavonoid 3'-monooxygenase activity, and most particularly preferably a flavonoid 3'-monooxygenase (F3'H) comprising a sequence chosen from SEQ ID NO: 7 and polypeptides having at least 60, 70, 80, 85, 90 or 95% identity with this sequence and having flavonoid 3'-monooxygenase activity;

optionally, a heterologous nucleic acid sequence coding for a cytochrome P450 reductase (CPR) comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and most particularly preferably from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and a heterologous nucleic acid sequence coding for an O-methyltransferase (OMT) which is capable of methylating eriodictyol and/or luteolin in position 4' and comprising a sequence chosen from SEQ ID NOs: 117, 119 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NOs: 117 and 119 and polypeptides comprising a sequence having at least 60, 70, 80, 85, 90 or 95% sequence identity with one of these sequences and having O-methyltransferase activity; and optionally, a heterologous nucleic acid sequence coding for a flavone synthase (FNS) which is capable of producing a flavone from a flavanone, in particular which is capable of transforming naringenin into apigenin, and/or eriodictyol into luteolin, preferably of transforming eriodictyol into luteolin and comprising a sequence chosen from SEQ ID NO: 37 and a polypeptide comprising a sequence having at least 60, 70, 80, 85, 90 or 95% sequence identity with this sequence and having flavone synthase activity.

Preferably, the microorganism comprises each of these heterologous nucleic acid sequences.

In another particular embodiment, the recombinant microorganism comprises:

a heterologous nucleic acid sequence coding for a flavanone 7-O-beta-D-glucosyltransferase (UGT) which is capable of adding a glucose in position 7 of hesperetin and/or diosmetin;

- a heterologous nucleic acid sequence coding for a 6"-O-rhamnosyltransferase (RhaT) which is capable of transferring a rhamnose into position 6 of the glucose of hesperetin-7-O-glucoside and/or diosmetin-7-O-glucoside;
- a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose;
- a heterologous nucleic acid sequence coding for a flavonoid 3'-monooxygenase (F3'H) which is capable of hydroxylating naringenin and/or apigenin in position 3';
- a heterologous nucleic acid sequence coding for a cytochrome P450 reductase;
- a heterologous nucleic acid sequence coding for an O-methyltransferase which is capable of methylating eriodictyol and/or luteolin in position 4'; and
- a heterologous nucleic acid sequence coding for a flavone synthase (FNS) which is capable of producing a flavone from a flavanone, in particular which is capable of transforming naringenin into apigenin, eriodictyol into luteolin and/or hesperetin into diosmetin, preferably of transforming eriodictyol into luteolin.

In another particular embodiment, the recombinant microorganism also comprises a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

Each enzyme may be chosen from the enzymes described above.

Up to Naringenin and Apigenin

Various pathways for the biosynthesis of naringenin and apigenin are known in plants, in particular from glucose, tyrosine or phenylalanine. Microorganisms, notably *E. coli* and *Saccharomyces cerevisiae*, have been modified to produce naringenin and/or apigenin (Hwang E I, et al. 2003. Appl. Environ. Microbiol. 2003, 69 (5): 2699-2706; Jiang H1, et al. 2005. Appl. Environ. Microbiol. 2005, 71 (6): 2962-9; Pandey et al., 2016, Biotechnol. Adv., 34, 634-662).

For example, the pathway for the biosynthesis of naringenin and apigenin may be that described in FIG. 1.

In a first embodiment, the microorganism comprises the enzymes required for the synthesis of naringenin and/or apigenin from tyrosine.

In a second embodiment, the microorganism comprises the enzymes required for the synthesis of naringenin and/or apigenin from phenylalanine.

In a third embodiment, the microorganism comprises the enzymes required for the synthesis of naringenin and/or apigenin from tyrosine and phenylalanine.

TAL: Tyrosine Ammonia Lyase

TAL is a tyrosine ammonia lyase. This enzyme is capable of producing p-coumaric acid from tyrosine. This enzyme belongs to the class EC 4.3.1.23.

The term "phenylalanine ammonia lyase activity" means the transformation of phenylalanine into trans-cinnamic acid by means of the enzyme phenylalanine ammonia lyase. To determine whether there is phenylalanine ammonia lyase activity, an enzymatic test may be performed, which consists of the in vitro incubation of a mixture composed of the phenylalanine ammonia lyase enzyme and phenylalanine, under optimum conditions (pH, temperature, ions, etc.). After a certain incubation time, the appearance of trans-cinnamic acid is observed in UPLC-MS in comparison with the expected standard.

A tyrosine ammonia lyase (TAL) may also have phenylalanine ammonia lyase (PAL) activity as defined above and/or dihydroxyphenylalanine ammonia-lyase (DAL) activity.

The microorganism may thus comprise a heterologous nucleic acid sequence coding for a tyrosine ammonia lyase.

Preferably, this enzyme is an enzyme produced by a bacterium of the genus *Rhodobacter* or a bacterium of the genus Flavobacteriaceae. In a particular embodiment, this enzyme is produced by a *Rhodobacter capsulatus* or *Rhodobacter sphaeroides* bacterium. In another particular embodiment, this enzyme is produced by a *Flavobacterium johnsoniae* bacterium. In another embodiment, this enzyme is an enzyme produced by a yeast, in particular a yeast of the genus *Rhodotorula*, for example *Rhodotorula glutinis*. Other organisms also produce such an enzyme, for example *Camellia sinensis, Fragaria×ananassa, Ralstonia metallidurans* or *Zea mays*.

In a particular embodiment, the tyrosine ammonia lyase is selected from enzymes comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity.

In one embodiment, the TAL is from *Flavobacterium johnsoniae*. It is described in the GenBank database from NCBI under the number KR095306.1 for the nucleic acid sequence and under the number AKE50827.1 for the protein sequence, and more particularly in SEQ ID NOs: 40 and 39.

In a particularly preferred embodiment, the TAL is from *Rhodotorula glutinis*. It is described in the GenBank database from NCBI under the number KF765779.1 for the nucleic acid sequence and under the number AGZ04575.1 for the protein sequence, and more particularly in SEQ ID NOs: 42 and 41, respectively.

In a particularly preferred embodiment, the tyrosine ammonia lyase is selected from the enzyme comprising a sequence chosen from SEQ ID NO: 41 and polypeptides comprising a sequence having at least 60, 70, 80, 85, 90 or 95% sequence identity with this sequence and having tyrosine ammonia lyase activity.

4CL: 4-Coumarate-CoA Ligase

4CL is a 4-coumarate-CoA ligase. This enzyme is capable of producing 4-coumaroyl-CoA from p-coumaric acid and Coenzyme A and of producing caffeoyl-CoA from caffeic acid and Coenzyme A. This enzyme belongs to the class EC 6.2.1.12.

The term "4-coumarate-CoA ligase activity" means the transformation of p-coumaric acid into p-coumaroyl-CoA or of caffeic acid into caffeoyl-CoA by the enzyme 4-coumarate CoA ligase. To determine whether there is 4-coumarate CoA ligase activity, an enzymatic test may be performed, which consists of the in vitro incubation of a mixture composed of the 4-coumarate CoA ligase enzyme, p-coumaric acid or caffeic acid, ATP and CoA under optimum conditions (pH, temperature, ions, etc.). After a certain incubation time, the appearance of p-coumaroyl-CoA or of caffeoyl-CoA is observed on the UV spectrophotometer at a wavelength of 333 nm and 346 nm, respectively, in comparison with the expected standard.

The microorganism may thus comprise a heterologous nucleic acid sequence coding for a 4-coumarate-CoA ligase.

Preferably, this enzyme is an enzyme produced by a plant, for example *Abies, Arabidopsis, Agastache, Amorpha, Brassica, Citrus, Cathaya, Cedrus, Crocus, Larix, Festuca, Glycine, Juglans, Keteleeria, Lithospermum, Lolium, Lotus, Lycopersicon, Malus, Medicago, Mesembryanthemum, Nicotiana, Nothotsuga, Oryza, Phaseolus, Pelargonium, Petroselinum, Physcomitrella, Picea, Prunus, Pseudolarix, Pseudotsuga, Rosa, Rubus, Ryza, Saccharum, Suaeda, Pinus, Populus, Solanum, Thellungiella, Triticum, Tsuga, Vitis* or *Zea*. Alternatively, this enzyme is an enzyme produced by a microorganism, for example *Aspergillus, Mycosphaerella, Mycobacterium, Neisseria, Neurospora, Streptomyces, Rhodobacter* or *Yarrowia*.

In a preferred embodiment, this enzyme is an enzyme produced by a plant, preferably *Arabidopsis thaliana, Citrus clementina* or *Petroselinum crispum*, in particular *Arabidopsis thaliana* or *Petroselinum crispum*, or by a bacterium, preferably of the genus *Streptomyces*, in particular *Streptomyces clavuligerus*.

In a particular embodiment, the 4-coumarate-CoA ligase is selected from enzymes comprising a sequence chosen from SEQ ID NOs: 43, 45, 47, 49, 123 and 125 and polypeptides comprising a sequence having at least 60, 70, 80, 85, 90 or 95% sequence identity with one of these sequences and having 4-coumarate-CoA ligase activity.

In another particular embodiment, the 4-coumarate-CoA ligase is an enzyme comprising a sequence selected from SEQ ID NOs: 43, 45, 47 and 49, preferably SEQ ID NOs: 45 and 49 and polypeptides comprising a sequence having at least 60, 70, 80, 85, 90 or 95% sequence identity with one of these sequences and having 4-coumarate-CoA ligase activity.

In a first particular embodiment, the 4CL is from *Arabidopsis thaliana*. It is described in the GenBank database from NCBI under the number AY099747.1 for the nucleic acid sequence and under the number AAM20598.1 for the protein sequence, and more particularly in SEQ ID NOs: 44 and 43, respectively.

In a second particular embodiment, the 4CL is from *Petroselinum crispum*. It is described in the GenBank database from NCBI under the number X13324.1 or X13325.1 for the nucleic acid sequence and under the number CAA31696.1 or CAA31697.1 for the protein sequence, respectively. The proteins are described in UniProtKB/Swiss Prot under the reference numbers P14912 and P14913, respectively, and more particularly in SEQ ID NOs: 46 and 45, 48 and 47, respectively. Preferably, the 4CL is from *Petroselinum crispum* and is described in the GenBank database from NCBI under the number X13324.1 for the nucleic acid sequence and under the number CAA31696.1 for the protein sequence, and in UniProtKB/Swiss Prot under the reference number P14912, and more particularly in SEQ ID NOs: 46 and 45, respectively.

In a third particular embodiment, the 4CL is from *Streptomyces clavuligerus*. It is described in the GenBank database from NCBI under the number CP016559.1 for the nucleic acid sequence and under the number ANW18832.1 for the protein sequence, and more particularly in SEQ ID NOs: 50 and 49, respectively.

In a fourth particular embodiment, the 4CL is from *Arabidopsis thaliana*. A nucleotide sequence and the protein sequence of this enzyme are described, respectively, in SEQ ID NOs: 124 and 123.

In a fifth particular embodiment, the 4CL is from *Citrus clementina* and a nucleotide sequence and the protein sequence of this enzyme are described, respectively, in SEQ ID NOs: 126 and 125.

In a preferred embodiment, the 4CL is an enzyme comprising a sequence selected from SEQ ID NOs: 45, 123 and 125, preferably SEQ ID NOs: 123 and 45 and polypeptides comprising a sequence having at least 60, 70, 80, 85, 90 or 95% sequence identity with one of these sequences and having 4-coumarate-CoA ligase activity. Most particularly preferably, the 4CL is an enzyme comprising a sequence selected from SEQ ID NO: 45 and polypeptides comprising a sequence having at least 60, 70, 80, 85, 90 or 95% sequence identity with this sequence and having 4-coumarate-CoA ligase activity.

CHS: Chalcone Synthase

CHS is a chalcone synthase. This enzyme is capable of producing naringenin-chalcone from 4-coumaroyl-CoA and from malonyl-CoA and of producing eriodictyol-chalcone from caffeoyl-CoA and from malonyl-CoA. This enzyme belongs to the class EC 2.3.1.74.

The term "chalcone synthase activity" means the transformation of p-coumaroyl-CoA and of malonyl-CoA into naringenin chalcone or of caffeoyl-CoA and of malonyl-CoA-into eriodictyol chalcone by means of the chalcone synthase enzyme. To determine whether there is chalcone synthase activity, an enzymatic test may be performed, which consists of the in vitro incubation of a mixture composed of the chalcone synthase enzyme, coumaroyl-CoA or caffeoyl-CoA and malonyl-CoA, under optimum conditions (pH, temperature, ions, etc.). After a certain incubation time, the appearance of naringenin chalcone or of eriodictyol chalcone, respectively, is observed in HPLC-MS in comparison with the expected standard.

The microorganism thus comprises a heterologous nucleic acid sequence coding for a chalcone synthase.

This enzyme may be an enzyme produced by a plant, notably of the genus *Arabidopsis, Avena, Cosmos, Citrus, Daucus, Fagopyrum, Freesia, Glycine, Glycyrrhiza, Humulus, Hypericum, Hordeum, Juglans, Medicago, Phaseolus, Physcomitrella, Plagiochasma, Petroselinum, Pueraria, Rubus, Secale, Scutellaria, Silene, Sinapis, Spinacia, Stellaria, Triticum, Tulipa, Verbena, Vitis* or *Xanthisma*, for example *Arabidopsis thaliana, Avena sativa, Cosmos sulphureus, Citrus sinensis, Daucus carota, Fagopyrum esculentum, Freesia* hybrid cultivar, *Glycine max, Glycyrrhiza echinata, Humulus lupulus, Hypericum androsaemum, Hordeum vulgare, Juglans* sp., *Medicago sativa, Phaseolus vulgaris, Physcomitrella patens, Plagiochasma appendiculatum, Petroselinum crispum, Pueraria montana* var. *lobata, Rubus idaeus, Secale cereale, Scutellaria baicalensis, Silene* sp., *Sinapis alba, Spinacia oleracea, Stellaria longipes, Triticum aestivum, Tulipa* hybrid cultivar, *Verbena* sp., *Vitis vinifera* or *Xanthisma gracile*.

Preferably, this enzyme is an enzyme produced by a plant, for example of the genus *Citrus*, in particular *Citrus sinensis*, or *Hordeum vulgare* or by a bacterium, preferably of the genus *Streptomyces*, in particular *Streptomyces clavuligerus*.

In a particular embodiment, the chalcone synthase is selected from enzymes comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity.

In a particularly preferred embodiment, the chalcone synthase is an enzyme comprising a sequence chosen from SEQ ID NO: 53 and polypeptides comprising a sequence having at least 60, 70, 80, 85, 90 or 95% sequence identity with this sequence and having chalcone synthase activity.

In a first particular embodiment, the CHS is from *Hordeum vulgare*. It is described in the GenBank database from NCBI under the number Y09233.1 for the nucleic acid sequence and under the number CAA70435.1 for the protein sequence, and more particularly in SEQ ID NOs: 52 and 51, respectively. The protein is described in UniProtKB/Swiss Prot under the reference number Q96562.

In a second particular embodiment, the CHS is from *Citrus sinensis*. It is described in the GenBank database from NCBI under the number AB009351.1 for the nucleic acid sequence and under the number BAA81664.1 for the protein sequence, and more particularly in SEQ ID NOs: 54 and 53, respectively.

In a third particular embodiment, the CHS is from *Citrus sinensis*. It is described in the GenBank database from NCBI under the number XM_006489733.1 for the nucleic acid sequence and under the number XP_006489796.1 for the protein sequence, and more particularly in SEQ ID NOs: 56 and 55, respectively.

In a fourth particular embodiment, the CHS is from *Streptomyces clavuligerus*. It is described in the GenBank database from NCBI under the number CP016559.1 for the nucleic acid sequence and under the number ANW16917.1 for the protein sequence, and more particularly in SEQ ID NOs: 58 and 57, respectively.

Since the reaction catalyzed by chalcone synthase requires the presence of malonyl-CoA, the microorganism can be modified to increase the synthesis of malonyl-CoA.

CHI: Chalcone Isomerase

CHI is a chalcone isomerase. It is capable of producing naringenin from naringenin chalcone and of producing eriodictyol from eriodictyol chalcone. This enzyme belongs to the class EC 5.5.1.6.

The term "chalcone isomerase activity" means the transformation of naringenin chalcone or of eriodictyol chalcone into naringenin or eriodictyol by a chalcone isomerase enzyme. To determine whether there is chalcone isomerase activity, an enzymatic test may be performed, which consists of the in vitro incubation of a mixture composed of the chalcone isomerase enzyme, naringenin chalcone or eriodictyol chalcone under optimum conditions (pH, temperature, ions, etc.). After a certain incubation time, the appearance of naringenin or of eriodictyol, respectively, is observed in HPLC-MS in comparison with the expected standard.

The microorganism thus comprises a heterologous nucleic acid sequence coding for a chalcone isomerase.

This enzyme may originate from a plant, notably of the genus *Arabidopsis, Ginkgo, Oncidium, Perilla, Citrus* or *Trigonella*, for example *Arabidopsis thaliana, Ginkgo biloba, Oncidium* Gower Ramsey, *Perilla frutescens, Citrus Sinensis* or *Trigonella* foenum-graecum.

Preferably, this enzyme is an enzyme produced by a plant, for example *Arabidopsis thaliana* or by a bacterium, preferably of the genus *Streptomyces*, in particular *Streptomyces clavuligerus.*

In a particular embodiment, the chalcone isomerase is selected from enzymes comprising a sequence chosen from SEQ ID NOs: 59 and 61 and polypeptides comprising a sequence having at least 60, 70, 80, 85, 90 or 95% sequence identity with one of these sequences and having chalcone isomerase activity.

In a preferred embodiment, the chalcone isomerase is selected from enzymes comprising a sequence chosen from SEQ ID NO: 61 and polypeptides comprising a sequence having at least 60, 70, 80, 85, 90 or 95% sequence identity with this sequence and having chalcone isomerase activity.

In a first particular embodiment, the CHI is from *Streptomyces clavuligerus*. It is described in the GenBank database from NCBI under the number CP016559.1 for the nucleic acid sequence and under the number ANW16918.1 for the protein sequence, and more particularly in SEQ ID NOs: 60 and 59, respectively.

In a second particular embodiment, the CHI is from *Arabidopsis thaliana*. It is described in the GenBank database from NCBI under the number NM_115370.4 for the nucleic acid sequence and under the number NP_191072.1 for the protein sequence, and more particularly in SEQ ID NOs: 62 and 61, respectively.

FNS: Flavone Synthase

Apigenin may be prepared from naringenin using a flavone synthase (FNS). It is capable of producing apigenin from naringenin.

The microorganism may thus comprise a heterologous nucleic acid sequence coding for a flavone synthase, which is in particular capable of producing apigenin from naringenin and/or a heterologous nucleic acid sequence coding for a flavone synthase, which is in particular capable of producing luteolin from eriodictyol, and/or a heterologous nucleic acid sequence coding for a flavone synthase, which is in particular capable of producing diosmetin from hesperetin.

The FNS may be chosen from those described previously.

Starting with Phenylalanine

Alternatively or in addition, the microorganism may also comprise the enzymes required for the synthesis of p-coumaric acid from phenylalanine.

In this context, the microorganism may also comprise a heterologous nucleic acid sequence coding for a phenylalanine ammonia lyase (PAL) and a heterologous nucleic acid sequence coding for a cinnamate 4-hydroxylase (C4H).

The PAL belongs to the class EC 4.3.1.24. It is capable of producing cinnamic acid from phenylalanine.

The term "phenylalanine ammonia lyase activity" means the transformation of phenylalanine into trans-cinnamic acid by means of the enzyme phenylalanine ammonia lyase. To determine whether there is phenylalanine ammonia lyase activity, an enzymatic test may be performed, which consists of the in vitro incubation of a mixture composed of the phenylalanine ammonia lyase enzyme and phenylalanine, under optimum conditions (pH, temperature, ions, etc.). After a certain incubation time, the appearance of trans-cinnamic acid is observed in UPLC-MS in comparison with the expected standard.

Several enzymes have already been described in the prior art. Preferably, the enzyme originates from a plant, example a plant of the genus *Arabidopsis, Agastache, Ananas, Asparagus, Brassica, Bromheadia, Bambusa, Beta, Betula, Citrus, Cucumis, Camellia, Capsicum, Cassia, Catharanthus, Cicer, Citrullus, Coffea, Cucurbita, Cynodon, Daucus, Dendrobium, Dianthus, Digitalis, Dioscorea, Eucalyptus, Gallus, Ginkgo, Glycine, Hordeum, Helianthus, Ipomoea, Lactuca, Lithospermum, Lotus, Lycopersicon, Medicago, Malus, Manihot, Medicago, Mesembryanthemum, Nicotiana, Olea, Oryza, Phaseolus, Pinus, Populus, Pisum, Persea, Petroselinum, Phalaenopsis, Phyllostachys,*

*Physcomitrella, Picea, Pyrus, Prunus, Quercus, Raphanus, Rehmannia, Rubus, Solanum, Sorghum, Sphenostylis, Stellaria, Stylosanthes, Triticum, Trifolium, Vaccinium, Vigna, Vitis, Zea* or *Zinnia*. For example, mention may be made of those from *Arabidopsis thaliana* or from *Petroselinum crispum*. In a preferred embodiment, the PAL is from *Citrus sinensis*.

In addition, phenylalanine ammonia lyase (PAL) may also have tyrosine ammonia lyase (TAL) activity and/or dihydroxyphenylalanine ammonia-lyase (DAL) activity as defined below.

In a particular embodiment, the phenylalanine ammonia lyase (PAL) is selected from enzymes comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity.

In a preferred embodiment, the PAL is selected from enzymes comprising a sequence chosen from SEQ ID NOs: 65 and 77 and polypeptides comprising a sequence having at least 60, 70, 80, 85, 90 or 95% sequence identity with one of these sequences and having phenylalanine ammonia lyase activity. Most particularly preferably, the PAL is selected from enzymes comprising a sequence chosen from SEQ ID NOs: 65 and polypeptides comprising a sequence having at least 60, 70, 80, 85, 90 or 95% sequence identity with this sequence and having phenylalanine ammonia lyase activity.

In a particular embodiment, the PAL from *Citrus sinensis* is described in the GenBank database from NCBI under the number XM_006481431.2 for the nucleic acid sequence and under the number XP_006481494.1 for the protein sequence, and more particularly in SEQ ID NOs: 64 and 63, respectively.

In another particular embodiment, the PAL from *Citrus sinensis* is described in the GenBank database from NCBI under the number XM_006488000.2 for the nucleic acid sequence and under the number XP_006488063.1 for the protein sequence, and more particularly in SEQ ID NOs: 66 and 65, respectively.

In another particular embodiment, the PAL from *Arabidopsis thaliana* is described in the GenBank database from NCBI under the number NM_115186.4 for the nucleic acid sequence and under the number NP_190894.1 for the protein sequence, and more particularly in SEQ ID NOs: 78 and 77, respectively.

Optionally, if biosynthesis starting with tyrosine and phenylalanine is envisaged, the PAL and the TAL may be replaced or supplemented with a phenylalanine/tyrosine ammonia lyase (PTAL). PTAL belongs to the class EC 4.3.1.25.

C4H belongs to the class EC 1.14.13.11. It is capable of producing p-coumaric acid from cinnamic acid.

The term "trans-cinnamate 4-monooxygenase activity" means the transformation of trans-cinnamic acid into p-coumaric acid by a trans-cinnamate 4-monooxygenase enzyme (CPR-dependent). To determine whether there is trans-cinnamate 4-monooxygenase activity, an enzymatic test may be performed, which consists of the in vitro incubation of a mixture composed of the trans-cinnamate 4-monooxygenase enzyme, cinnamic acid, NADPH, $H^+$ and $O_2$, under optimum conditions (pH, temperature, ions, etc.). After a certain incubation time, the appearance of the 4-hydroxycinnamate (p-coumaric acid) is observed in UPLC-MS in comparison with the expected standard.

Several enzymes have already been described in the prior art. Preferably, the enzyme originates from a plant, for example a plant of the genus *Arabidopsis, Ammi, Avicennia, Camellia, Camptotheca, Catharanthus, Citrus, Glycine, Helianthus, Lotus, Mesembryanthemum, Physcomitreila, Phaseolus, Pinus, Populus, Ruta, Saccharum, Solanum, Vitis, Vigna* or *Zea*. In a preferred embodiment, the cinnamate 4-hydroxylase (C4H) is from *Citrus sinensis* or from *Arabidopsis thaliana*.

In a particular embodiment, the cinnamate 4-hydroxylase (C4H) is selected from enzymes comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity.

In a preferred embodiment, the C4H is selected from enzymes comprising a sequence chosen from SEQ ID NO: 79 and polypeptides comprising a sequence having at least 60, 70, 80, 85, 90 or 95% sequence identity with this sequence and having cinnamate 4-hydroxylase activity.

In a particular embodiment, the C4H from *Citrus sinensis* is described in the GenBank database from NCBI under the number NM_001288840.1 for the nucleic acid sequence and under the number NP_001275769.1 for the protein sequence, and more particularly in SEQ ID NOs: 68 and 67, respectively.

In another particular embodiment, the C4H from *Citrus sinensis* is described in the GenBank database from NCBI under the number NM_001288895.1 for the nucleic acid sequence and under the number NP_001275824.1 for the protein sequence, and more particularly in SEQ ID NOs: 70 and 69, respectively.

In another particular embodiment, the C4H from *Arabidopsis thaliana* is described in the GenBank database from NCBI under the number NM_128601.3 for the nucleic acid sequence and under the number NP_180607.1 for the protein sequence, and more particularly in SEQ ID NOs: 80 and 79, respectively.

Proceeding Via Caffeic Acid

In an additional embodiment, the biosynthesis of eriodictyol may also comprise the synthesis of L-DOPA (3,4-dihydroxy-L-phenylalanine) from tyrosine and then of caffeic acid from L-DOPA (3,4-dihydroxy-L-phenylalanine). To do this, the following enzymes are necessary. To convert tyrosine into L-DOPA (3,4-dihydroxy-L-phenylalanine), two subunits are necessary, HpaB and HpaC.

HpaB is a 4-hydroxyphenylacetate 3-monooxygenase oxygenase subunit (HpaB).

Preferably, this enzyme is an enzyme produced by a bacterium, preferably *Escherichia coli*.

In a particular embodiment, the 4-hydroxyphenylacetate 3-monooxygenase oxygenase (HpaB) is an enzyme comprising a sequence chosen from SEQ ID NO: 83 and polypeptides comprising a sequence having at least 60, 70, 80, 85, 90 or 95% sequence identity with this sequence and having 4-hydroxyphenylacetate 3-monooxygenase activity.

In a particular embodiment, the HpaB is from *Escherichia coli*. It is described in the GenBank database from NCBI under the number CAQ34705.1 for the protein sequence, and more particularly in SEQ ID NO: 83. A nucleic acid sequence coding for this enzyme is described in SEQ ID NO: 84. The protein is described in UniProtKB/Swiss Prot under the reference number A0A140NG21.

HpaC is a 4-hydroxyphenylacetate 3-monooxygenase reductase subunit. The microorganism may thus comprise a heterologous nucleic acid sequence coding for a 4-hydroxyphenylacetate 3-monooxygenase reductase subunit (HpaC).

The term "p-coumarate 3-hydroxylase activity" means the transformation of p-coumaric acid into caffeic acid and/or of L-tyrosine into L-DOPA using an enzymatic complex composed of HpaB (4-hydroxyphenylacetate 3-hydroxylase oxidase) and HpaC (4-hydroxyphenylacetate 3-hydroxylase reductase). To determine whether there is p-coumarate 3-hydroxylase activity, an enzymatic test may be performed, which consists of the in vitro incubation of a mixture composed of the enzymes HpaB, HpaC, p-coumaric acid or L-tyrosine, FAD and NADH under optimum conditions (pH, temperature, ions, etc.). After a certain incubation time, the appearance of caffeic acid or of L-DOPA is observed in HPLC-MS in comparison with the expected standard.

Preferably, this enzyme is an enzyme produced by a bacterium, preferably *Escherichia coli.*

In a particular embodiment, the 4-hydroxyphenylacetate 3-monooxygenase reductase (HpaC) is an enzyme comprising a sequence chosen from SEQ ID NO: 85 and polypeptides comprising a sequence having at least 60, 70, 80, 85, 90 or 95% sequence identity with this sequence and having 4-hydroxyphenylacetate 3-monooxygenase activity.

In a particular embodiment, the HpaC is from *Escherichia coli*. It is described in the GenBank database from NCBI under the number CAQ34704.1 for the protein sequence, and more particularly in SEQ ID NO: 85. A nucleic acid sequence coding for this enzyme is described in SEQ ID NO: 86. The protein is described in UniProtKB/Swiss Prot under the reference number A0A140NG67.

Together, HpaB and HpaC are capable of producing L-DOPA (3,4-dihydroxy-L-phenylalanine) from tyrosine.

Thus, the microorganism may comprise a heterologous nucleic acid sequence coding for a 4-hydroxyphenylacetate 3-monooxygenase oxygenase (HpaB) and a heterologous nucleic acid sequence coding for 4-hydroxyphenylacetate 3-monooxygenase reductase (HpaC).

Moreover, this pathway also requires the presence of an enzyme that is capable of synthesizing caffeic acid from L-DOPA (3,4-dihydroxy-L-phenylalanine), a dihydroxyphenylalanine ammonia-lyase (DAL). This enzyme belongs to the class EC 4.3.1.11.

The term "dihydroxyphenylalanine ammonia lyase activity" means the transformation of L-DOPA into trans-caffeic acid by means of a dihydroxyphenylalanine ammonia lyase enzyme. To determine whether there is dihydroxyphenylalanine ammonia lyase activity, an enzymatic test may be performed, which consists of the in vitro incubation of a mixture composed of the dihydroxyphenylalanine ammonia lyase enzyme and L-DOPA (levodopa) under optimum conditions (pH, temperature, ions, etc.). After a certain incubation time, the appearance of trans-caffeic acid is observed in UPLC-MS in comparison with the expected standard.

In addition, dihydroxyphenylalanine ammonia lyase (DAL) may also have tyrosine ammonia lyase (TAL) activity and/or phenylalanine ammonia-lyase (PAL) activity.

The microorganism may thus comprise a heterologous nucleic acid sequence coding for a 4-hydroxyphenylacetate 3-monooxygenase oxygenase subunit (HpaB), a heterologous nucleic acid sequence coding for a 4-hydroxyphenylacetate 3-monooxygenase reductase subunit (HpaC) and a heterologous nucleic acid sequence coding for a dihydroxyphenylalanine ammonia-lyase (DAL).

As an alternative to the use of HpaB and HpaC or in combination therewith, it is possible to use an enzyme for converting tyrosine into L-DOPA and an enzyme for converting p-coumaric acid into caffeic acid.

These are, respectively, a 4-methoxybenzoate O-demethylase, also known as 4-methoxybenzoate monooxygenase (O-demethylating) which has L-tyrosine hydroxylase activity, belonging to the class EC 1.14.99.15, and a p-coumarate 3-hydroxylase having p-coumarate 3-hydroxylase activity, belonging to the class EC 1.14.13.

These various enzymes both form part of the cytochrome P450 (CYP) family.

The term "L-tyrosine hydroxylase activity" means the transformation of p-coumaric acid into caffeic acid and/or of L-tyrosine into L-DOPA using a p-coumarate 3-hydroxylase enzyme (CPR-dependent). To determine whether there is L-tyrosine hydroxylase activity, an enzymatic test may be performed, which consists of the in vitro incubation of a mixture composed of the p-coumarate 3-hydroxylase enzyme, p-coumaric acid or L-tyrosine and the necessary cofactors, under optimum conditions (pH, temperature, ions, etc.). After a certain incubation time, the appearance of caffeic acid or of L-DOPA is observed in HPLC-MS in comparison with the expected standard.

The term "p-coumarate 3-hydroxylase activity" means the transformation of p-coumaric acid into caffeic acid and/or of L-tyrosine into L-DOPA using a p-coumarate 3-hydroxylase enzyme (CPR-dependent). To determine whether there is p-coumarate 3-hydroxylase activity, an enzymatic test may be performed, which consists of the in vitro incubation of a mixture composed of the p-coumarate 3-hydroxylase enzyme, p-coumaric acid or L-Tyrosine under optimum conditions (pH, temperature, ions, etc.). After a certain incubation time, the appearance of caffeic acid or of L-DOPA is observed in HPLC-MS in comparison with the expected standard.

The recombinant microorganism may thus comprise a heterologous nucleic acid sequence coding for a 4-methoxybenzoate O-demethylase (CYP) which is capable of converting tyrosine into L-DOPA and also p-coumaric acid into caffeic acid.

In one embodiment, the 4-methoxybenzoate O-demethylase is a bacterial enzyme, notably from *Rhodopseudomonas palustris, Pseudomonas putida* or *Escherichia coli*, a plant enzyme, notably from *Beta vulgaris*, a mammalian enzyme, notably from *Oryctolagus cuniculus* or a fungal enzyme, notably from *Rhodotorula glutinis*. In a particular embodiment, the 4-methoxybenzoate O-demethylase is an enzyme from *Rhodopseudomonas palustris, Saccharothrix espanaensis* or *Beta vulgaris*.

In a particular embodiment, the 4-methoxybenzoate O-demethylase is selected from enzymes comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity.

The 4-methoxybenzoate O-demethylase may also be from *Beta vulgaris*. The nucleic acid sequences coding for this enzyme and the protein sequences are described in SEQ ID NOs: 74 and 73, respectively. The protein is described in UniProtKB/Swiss Prot under the reference number P0DKI2.

In addition, the 4-methoxybenzoate O-demethylase may be from *Saccharothrix espanaensis*. The nucleic acid sequences coding for this enzyme and protein sequences are described in NCBI under the reference numbers NC_005296.1 and WP_011157377.1, respectively, and more particularly in SEQ ID NOs: 76 and 75. The protein is described in UniProtKB/Swiss Prot under the reference number Q6N8N2.

In one embodiment, the microorganism may comprise a heterologous nucleic acid sequence coding for a 4-methoxybenzoate O-demethylase and a heterologous nucleic acid sequence coding for a dihydroxyphenylalanine ammonia-lyase (DAL).

The recombinant microorganism may thus comprise a heterologous nucleic acid sequence coding for a coumarate 3-hydroxylase (Coum3H) which is capable of converting p-coumaric acid into caffeic acid.

In one embodiment, the coumarate 3-hydroxylase is a bacterial enzyme, notably from *Saccharothrix*.

In a particular embodiment, the 4-methoxybenzoate O-demethylase is selected from the enzyme comprising a sequence chosen from SEQ ID NO: 71 and polypeptides comprising a sequence having at least 60, 70, 80, 85, 90 or 95% sequence identity with one of these sequences and having coumarate 3-hydroxylase activity.

The nucleic acid sequence coding for this enzyme and the protein sequence are described in NCBI under the reference numbers DQ357071.1 and ABC88666.1, respectively, and more particularly in SEQ ID NOs: 72 and 71.

In one embodiment, the microorganism may comprise a heterologous nucleic acid sequence coding for a coumarate 3-hydroxylase and a heterologous nucleic acid sequence coding for a dihydroxyphenylalanine ammonia-lyase (DAL).

Additional Combination of Enzymes

Thus, besides the enzymes required for the biosynthesis of hesperidin and/or diosmin from naringenin and/or apigenin as described previously, the microorganism preferably comprises enzymes for producing naringenin and/or apigenin from tyrosine and/or phenylalanine, preferably from tyrosine.

Thus, according to particular embodiments, the microorganism comprises

- a heterologous nucleic acid sequence coding for a flavanone 7-O-beta-D-glucosyltransferase (UGT) which is capable of adding a glucose in position 7 of hesperetin and/or diosmetin,
- a heterologous nucleic acid sequence coding for a 6"-O-rhamnosyltransferase (RhaT) which is capable of transferring a rhamnose into position 6 of the glucose of hesperetin-7-O-glucoside and/or diosmetin-7-O-glucoside,
- a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) which is capable of producing UDP-rhamnose,
- a heterologous nucleic acid sequence coding for an O-methyltransferase (OMT) which is capable of methylating eriodictyol and/or luteolin in position 4',
- a heterologous nucleic acid sequence coding for an F3'H enzyme,
- and optionally a heterologous nucleic acid sequence coding for an FNS enzyme and a heterologous nucleic acid sequence coding for a CPR enzyme,
- and also comprises
- a heterologous nucleic acid sequence coding for a tyrosine ammonia lyase (TAL), a heterologous nucleic acid sequence coding for a 4-coumaroyl-CoA ligase (4CL), a heterologous nucleic acid sequence coding for a chalcone synthase (CHS) and a heterologous nucleic acid sequence coding for a chalcone isomerase (CHI).

In one embodiment, the microorganism comprises:

- a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 117 and 119 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 117 and polypeptides comprising a sequence having at least 60, 70, 80, 85, 90 or 95% sequence identity with this sequence and having O-methyltransferase activity; and
- a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 121 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and
- optionally, a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and
- optionally, a heterologous nucleic acid sequence coding for a flavone synthase (FNS) and comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, in particular for a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity; and a heterologous nucleic acid sequence coding for a 4-coumaroyl-CoA ligase (4CL) from *Arabidopsis thaliana, Citrus clementina, Petroselinum crispum* or *Streptomyces clavuligerus*; in particular a 4CL comprising a sequence chosen from SEQ ID NOs: 123, 125, 45, 43, 47 and 49 and polypeptides comprising a sequence having at least 60, 70, 80, 85, 90 or 95% sequence identity with one of these sequences and having 4-coumarate-CoA ligase activity; preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity; most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity, and a heterologous nucleic acid sequence coding for a chalcone synthase (CHS) from *Citrus sinensis, Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity; preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, in this embodiment, the microorganism comprises one of the combinations of enzymes UGT, RhaT and RHM described above, in particular the flavanone 7-O-beta-D-glucosyltransferase selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and the 6"-O-rhamnosyltransferase selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and the UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Preferably, in this embodiment, the microorganism also comprises:

a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity; and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

In another embodiment, the microorganism comprises:

a heterologous nucleic acid sequence coding for an O-methyltransferase (OMT) comprising a sequence chosen from SEQ ID NOs: 117 and 119 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 117 and polypeptides comprising a sequence having at least 60, 70, 80, 85, 90 or 95% sequence identity with this sequence and having O-methyltransferase activity; and a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and optionally, a heterologous nucleic acid sequence coding for a cytochrome P450 reductase (CPR) and comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, preferably chosen from enzymes comprising a sequence chosen from SEQ ID NO: 25 and polypeptides comprising a sequence having at least 60, 70, 80, 85, 90 or 95% sequence identity with this sequence and having cytochrome P450 reductase activity; and optionally, a heterologous nucleic acid sequence coding for a flavone synthase (FNS) and comprising a sequence chosen from SEQ ID NO: 37 and a polypeptide comprising a sequence having at least 60, 70, 80, 85, 90 or 95% sequence identity with this sequence and having flavone synthase activity; and

- a heterologous nucleic acid sequence coding for a tyrosine ammonia lyase (TAL) comprising a sequence chosen from SEQ ID NOs: 41 and polypeptides comprising a sequence having at least 60, 70, 80, 85, 90 or 95% sequence identity with this sequence and having tyrosine ammonia lyase activity;
- a heterologous nucleic acid sequence coding for a 4-coumaroyl-CoA ligase (4CL) comprising a sequence selected from SEQ ID NOs: 123, 125 and 45 and polypeptides comprising a sequence having at least 60, 70, 80, 85, 90 or 95% sequence identity with these sequences and having 4-coumarate-CoA ligase activity, most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity; and
- a heterologous nucleic acid sequence coding for a chalcone synthase (CHS) comprising a sequence chosen from SEQ ID NO: 53 and polypeptides comprising a sequence having at least 60, 70, 80, 85, 90 or 95% sequence identity with this sequence and having chalcone synthase activity; and
- a heterologous nucleic acid sequence coding for a chalcone isomerase (CHI) comprising a sequence chosen from SEQ ID NO: 61 and polypeptides comprising a sequence having at least 60, 70, 80, 85, 90 or 95% sequence identity with this sequence and having chalcone isomerase activity.

Preferably, in this embodiment, the microorganism comprises one of the combinations of enzymes UGT, RhaT and RHM described above, in particular the flavanone 7-O-beta-D-glucosyltransferase selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity; and the 6"-O-rhamnosyltransferase selected from enzymes comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and the UDP-glucose 4,6-dehydratase/UDP-4-keto-6-deoxy-D-glucose 3,5-epimerase/UDP-4-keto-L-rhamnose-reductase selected from enzymes comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Preferably, in this embodiment, the microorganism also comprises a heterologous nucleic acid sequence coding for a phenylalanine ammonia lyase (PAL) and a heterologous nucleic acid sequence coding for a cinnamate 4-hydroxylase (C4H) as described in the preceding embodiment.

Optionally, in these various embodiments, the microorganism also comprises a heterologous or endogenous nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

In another particular embodiment, the microorganism comprises:

- a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity, and preferably a UGT comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;
- a heterologous nucleic acid sequence coding for a 6"-O-rhamnosyltransferase (RhaT) of the genus *Citrus* or *Petunia hybrida*, preferably *Citrus sinensis, Citrus maxima*, or *Citrus clementina*, even more preferably *Citrus sinensis* or *Citrus clementina*, preferably a 6"-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity, and preferably an RhaT comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity, and preferably an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia×hybrida, Callistephus chinensis, Gerbera hybrida, Citrus sinensis, Citrus clementina, Osteospermum hybrid* cultivar, *Phanerochaete chrysosporium, Streptomyces avermitilis* or *Pilosella officinarum*, in particular from *Perilla frutescens* var. *crispa, Petunia×hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity, more particularly preferably an F3'H comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;

optionally, a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NO: 89 and polypeptides comprising a sequence having at least 60, 70, 80, 85, 90 or 95% sequence identity with this sequence and having O-methyltransferase activity;

optionally, a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity; and optionally, a heterologous nucleic acid sequence coding for a flavone synthase (FNS) which is capable of transforming naringenin into apigenin, eriodictyol into luteolin, and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity, preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity, and more particularly preferably a CHS comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and more particularly preferably a CHI comprising a sequence chosen from SEQ ID NO: 61 and polypeptides comprising a sequence having at least 60, 70, 80, 85, 90 or 95% sequence identity with this sequence and having chalcone isomerase activity.

In another particular embodiment, the microorganism comprises heterologous nucleic acid sequences coding for the enzymes UGT, RhaT, RHM, F3'H, OMT, 4CL, CHS and CHI, and optionally for the enzymes CPR, FNS and SAMT, as described in the preceding embodiment and also comprises:

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, in particular a PAL comprising a sequence chosen from SEQ ID NO: 65 and polypeptides comprising a sequence having at least 60, 70, 80, 85, 90 or 95% sequence identity with this sequence and having phenylalanine ammonia lyase activity, and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, in particular a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity.

In a third particular embodiment, the microorganism comprises heterologous nucleic acid sequences coding for the enzymes UGT, RhaT, RHM, F3'H, OMT, 4CL, CHS and CHI, and optionally for the enzymes CPR, FNS and SAMT, as described in the preceding embodiment and also comprises:

a heterologous nucleic acid sequence coding for a dihydroxyphenylalanine ammonia-lyase (DAL) which is capable of producing caffeic acid from L-DOPA (3,4-dihydroxy-L-phenylalanine);

a heterologous nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a heterologous nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a heterologous nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydroxylase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity.

In another particular embodiment, the microorganism comprises heterologous nucleic acid sequences coding for the enzymes UGT, RhaT, RHM, F3'H, OMT, 4CL, CHS and CHI, and optionally for the enzymes CPR, FNS and SAMT, as described in the preceding embodiment and also comprises:

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

optionally, a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, preferably a PAL comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, preferably a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity;

optionally, a heterologous nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a heterologous nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a heterologous nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence chosen from SEQ ID NO: 71 and polypeptides comprising a sequence having at least 60, 70, 80, 85, 90 or 95% sequence identity with one of these sequences and having p-coumarate 3-hydroxylase activity;

optionally, a heterologous nucleic acid sequence coding for a dihydroxyphenylalanine ammonia-lyase (DAL) which is capable of producing caffeic acid from L-DOPA (3,4-dihydroxy-L-phenylalanine).

In another particular embodiment, the microorganism comprises:

a heterologous nucleic acid sequence coding for a flavanone 7-O-beta-D-glucosyltransferase (UGT) selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;

a heterologous nucleic acid sequence coding for a 6"-O-rhamnosyltransferase (RhaT) comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

a heterologous nucleic acid sequence coding for a phenylalanine ammonia lyase (PAL)' comprising a sequence chosen from SEQ ID NO: 65 and polypeptides comprising a sequence having at least 60, 70, 80, 85, 90 or 95% sequence identity with this sequence and having phenylalanine ammonia lyase activity;

a heterologous nucleic acid sequence coding for a cinnamate 4-hydroxylase (C4H), comprising a sequence chosen from SEQ ID NO: 79 and polypeptides comprising a sequence having at least 60, 70, 80, 85, 90 or 95% sequence identity with this sequence and having cinnamate 4-hydroxylase activity;

a heterologous nucleic acid sequence coding for a tyrosine ammonia lyase (TAL) comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) comprising a sequence selected from SEQ ID NO: 45 or 123 and polypeptides comprising a sequence having at least 60, 70, 80, 85, 90 or 95% sequence identity with one of these sequences and having 4-coumarate-CoA ligase activity, preferably a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a flavonoid 3'-monooxygenase (F3'H) comprising a sequence chosen from SEQ ID NO: 7 and polypeptides comprising a sequence having at least 60, 70, 80, 85, 90 or 95% sequence identity with the sequence SEQ ID NO: 7 and having flavonoid 3'-monooxygenase activity;

a heterologous nucleic acid sequence coding for a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a heterologous nucleic acid sequence coding for a cytochrome P450 reductase (CPR) comprising a sequence chosen from SEQ ID NO: 25 and polypeptides comprising a sequence having at least 60, 70, 80, 85, 90 or 95% sequence identity with one of these sequences and having cytochrome P450 reductase activity; and a heterologous nucleic acid sequence coding for an O-methyltransferase (OMT) which is capable of methylating eriodictyol and/or luteolin in position 4' and comprising a sequence chosen from SEQ ID NOs: 117 and 119 and polypeptides comprising a sequence having at least 60, 70, 80, 85, 90 or 95% sequence identity with one of these sequences and having O-methyltransferase activity, and preferably an OMT comprising a sequence chosen from SEQ ID NO: 117 and polypeptides comprising a sequence having at least 60, 70, 80, 85, 90 or 95% sequence identity with this sequence and having O-methyltransferase activity.

Preferably, the microorganism also comprises a heterologous or endogenous nucleic acid sequence coding for an S-adenosylmethionine synthetase (SAMT), in particular an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity.

The origin of the enzymes or of a set of enzymes may be chosen so that their origin is the same or is similar. For example, the enzymes or the set of enzymes may be obtained from bacteria, for example from bacteria of the same genus or of the same species. In another example, the enzymes or the set of enzymes may be obtained from plants, for example from plants of the same genus or of the same species. The reason for this is that these common origins enable the enzymes to function together optimally.

In one embodiment, the microorganisms comprise a metabolic pathway for the biosynthesis of tyrosine. Notably, the microorganisms may have been modified to have increased production of tyrosine relative to a wild-type strain. Notably, the microorganisms may have been modified so that the carbon flow is redirected toward tyrosine biosynthesis. In addition, the microorganisms may have been modified to reduce or suppress the tyrosine biosynthesis feedback inhibitions.

In another embodiment, the microorganisms comprise a metabolic pathway for the biosynthesis of phenylalanine. Notably, the microorganisms may have been modified to have increased production of phenylalanine relative to a wild-type strain. Notably, the microorganisms may have been modified so that the carbon flow is redirected toward phenylalanine biosynthesis. In addition, the microorganisms may have been modified to reduce or suppress the phenylalanine biosynthesis feedback inhibitions.

In another embodiment, the microorganisms comprise a metabolic pathway for the biosynthesis of phenylalanine and tyrosine. Notably, the microorganisms may have been modified to have increased production of phenylalanine and tyrosine relative to a wild-type strain. Notably, the microorganisms may have been modified so that the carbon flow is redirected toward phenylalanine and tyrosine biosynthesis. In addition, the microorganisms may have been modified to reduce or suppress the phenylalanine and tyrosine biosynthesis feedback inhibitions.

Recombinant Nucleic Acid and Expression Cassette

Each nucleic acid sequence coding for an enzyme as described previously is included in an expression cassette. Preferably, the coding nucleic acid sequences have been optimized for expression in the host microorganism. The coding nucleic acid sequence is operatively linked to the elements required for the expression of the gene, notably for transcription and translation. These elements are chosen so as to be functional in the host recombinant microorganism. These elements may include, for example, transcription promoters, transcription activators, terminator sequences, and start and stop codons. The methods for selecting these elements as a function of the host cell in which expression is desired are well known to those skilled in the art.

Preferably, the promoter is a strong promoter. The promoter may optionally be inducible.

For example, if the microorganism is prokaryotic, the promoter may be selected from the following promoters: LacI, LacZ, pLacT, ptac, pARA, pBAD, the RNA polymerase promoters of bacteriophage T3 or T7, the polyhedrin promoter, the PR or PL promoter of lambda phage. In one particular embodiment, the promoter is pLac. If the microorganism is eukaryotic and in particular a yeast, the promoter may be selected from the following promoters: the promoter pTDH3, the promoter pTEF1, the promoter pTEF2, the promoter pCCW12, the promoter pHHF2, the promoter pHTB2 and the promoter pRPL18B. Examples of inducible promoters that may be used in yeast are the promoters tetO-2, GAL10, GAL10-CYC1 and PHO5.

All or part of the expression cassettes comprising the nucleic acid sequences coding for the enzymes as described or a combination of some of them may be included in a common expression vector or in different expression vectors.

The present invention thus relates to a vector comprising two nucleic acid sequences chosen from a heterologous nucleic acid sequence coding for a flavanone 7-O-beta-D-glucosyltransferase (UGT), a heterologous nucleic acid sequence coding for a 6"-O-rhamnosyltransferase (RhaT) and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM); preferably, a vector comprises these three sequences.

In particular, the present invention thus relates to a vector comprising two nucleic acid sequences chosen from (i) a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113, 115, 91, 93, 95 and 97 or from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity, preferably selected from enzymes comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;

(ii) a heterologous nucleic acid sequence coding for a 6"-O-rhamnosyltransferase (RhaT) of the genus *Citrus* or *Petunia hybrida*, preferably *Citrus sinensis, Citrus maxima* or *Citrus clementina*, even more preferably *Citrus sinensis* or *Citrus clementina*, preferably a 6"-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity, and preferably an RhaT comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity, and preferably an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In particular, the vector may comprise two nucleic acid sequences chosen from (i) a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 91, 93, 95 and 97 and polypeptides comprising a sequence having at least 60, 70, 80, 85, 90 or 95% sequence identity with one of these sequences and having flavanone 7-O-beta-D-glucosyltransferase activity;

(ii) a heterologous nucleic acid sequence coding for a 6"-O-rhamnosyltransferase (RhaT) of the genus *Citrus* or *Petunia hybrida*, preferably *Citrus sinensis, Citrus maxima* or *Citrus clementina*, even more preferably *Citrus sinensis* or *Citrus clementina*, preferably a 6"-O-rhamnosyltransferase (RhaT) comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NOs: 107 and 109 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

Preferably, the vector comprises two nucleic acid sequences chosen from (i) a heterologous nucleic acid sequence coding for a flavanone 7-O-beta-D-glucosyltransferase (UGT) selected from enzymes comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity; preferably a flavanone 7-O-beta-D-glucosyltransferase (UGT) comprising a sequence chosen from SEQ ID NO: 113 and polypeptides comprising a sequence having at least 60, 70, 80, 85, 90 or 95% sequence identity with this sequence and having flavanone 7-O-beta-D-glucosyltransferase activity;

(ii) a heterologous nucleic acid sequence coding for a 6"-O-rhamnosyltransferase (RhaT) comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) comprising a sequence chosen from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity.

In a preferred embodiment, the microorganism comprises all three.

The coding nucleic acid sequences and the enzyme sequences are as described above. The term "comprising a nucleic acid sequence" also means comprising an expression cassette comprising the nucleic acid sequence.

Optionally, the vector may also comprise one or more nucleic acid sequences chosen from: a nucleic acid sequence coding for an O-methyltransferase (OMT), a nucleic acid sequence coding for an F3'H, a nucleic acid sequence coding for a CPR, a nucleic acid sequence coding for an FNS, a nucleic acid sequence coding for an SAMT, a nucleic acid sequence coding for a TAL, a nucleic acid sequence coding for a 4CL, a nucleic acid sequence coding for a CHS, a nucleic acid sequence coding for a CHI, a nucleic acid sequence coding for a PAL, a nucleic acid sequence coding for a C4H, a nucleic acid sequence coding for an HpaB, and a nucleic acid sequence coding for a DAL, each of these enzymes being as defined above, and also combinations thereof.

Preferably, the vector also comprises one or more sequences chosen from a nucleic acid sequence coding for an OMT, a nucleic acid sequence coding for an F3'H, a nucleic acid sequence coding for a CPR, a nucleic acid sequence coding for an FNS, a nucleic acid sequence coding for a TAL, a nucleic acid sequence coding for a 4CL, a nucleic acid sequence coding for a CHS, a nucleic acid sequence coding for a CHI, a nucleic acid sequence coding for a PAL and a nucleic acid sequence coding for a C4H.

In particular, the vector may also comprise one or more nucleic acid sequences chosen from:

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia×hybrida, Callistephus chinensis, Gerbera hybrida, Citrus sinensis, Arabidopsis thaliana, Citrus clementina, Osteospermum hybrid cultivar, Phanerochaete chrysosporium, Streptomyces avermitilis* or *Pilosella officinarum*, in particular from *Perilla frutescens* var. *crispa, Petunia×hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19, 21 and 121 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17, 19 and 121 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7, 17 and 121 and polypeptides comprising a sequence having at least 60, 70, 80, 85, 90 or 95% sequence identity with this sequence and having flavonoid 3'-monooxygenase activity, and preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity;

a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and preferably a CPR comprising a sequence chosen from SEQ ID NO: 25 and polypeptides comprising a sequence having at least 60, 70, 80, 85, 90 or 95% sequence identity with this sequence and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NOs: 117, 119 and 89 and polypeptides comprising a sequence having at least 60, 70, 80, 85, 90 or 95% sequence identity with this sequence and having O-methyltransferase activity;

a heterologous nucleic acid sequence coding for a flavone synthase (FNS) which is capable of transforming naringenin into apigenin, eriodictyol into luteolin, and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum*

*crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Citrus clementina, Petroselinum crispum* or *Streptomyces clavuligerus*; a 4CL comprising a sequence chosen from SEQ ID NOs: 43, 45, 47, 49, 123 and 125 and polypeptides comprising a sequence having at least 60, 70, 80, 85, 90 or 95% sequence identity with one of these sequences and having 4-coumarate-CoA ligase activity, preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity, and in particular a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity, and preferably a CHS comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, preferably a PAL comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, and preferably a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity;

a nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence SEQ ID NO: 71 and polypeptides comprising a sequence having at least 60, 70, 80, 85, 90 or 95% sequence identity with one of these sequences and having p-coumarate 3-hydroxylase activity, and a nucleic acid sequence coding for a dihydroxyphenylalanine ammonia-lyase (DAL).

In particular, the vector may also comprise one or more nucleic acid sequences chosen from:

a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia×hybrida, Callistephus chinensis, Gerbera hybrida, Citrus sinensis* and *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity;

a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity;

a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising the sequence SEQ ID NO: 89 and polypeptides comprising a sequence having at least 60, 70, 80, 85, 90 or 95% sequence identity with this sequence and having O-methyltransferase activity;

a heterologous nucleic acid sequence coding for a flavone synthase (FNS) which is capable of transforming naringenin into apigenin, eriodictyol into luteolin and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;

a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;

a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity;

- a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity;
- a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity; and
- a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine;
- a nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence SEQ ID NO: 71 and polypeptides comprising a sequence having at least 60, 70, 80, 85, 90 or 95% sequence identity with one of these sequences and having p-coumarate 3-hydroxylase activity, and
- a nucleic acid sequence coding for a dihydroxyphenylalanine ammonia-lyase (DAL).

Preferably, the vector may also comprise one or more nucleic acid sequences chosen from:

- a heterologous nucleic acid sequence coding for a flavonoid 3'-monooxygenase (F3'H) comprising a sequence chosen from SEQ ID NOs: 7, 11, 17 and 121 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 7, 17 and 121 and polypeptides comprising a sequence having at least 60, 70, 80, 85, 90 or 95% sequence identity with one of these sequences and having flavonoid 3'-monooxygenase activity, and most particularly preferably an F3'H comprising a sequence selected from SEQ ID NO: 7 and polypeptides comprising a sequence having at least 60, 70, 80, 85, 90 or 95% sequence identity with this sequence and having flavonoid 3'-monooxygenase activity;
- a heterologous nucleic acid sequence coding for a cytochrome P450 reductase (CPR) comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and most particularly preferably from enzymes comprising a sequence chosen from SEQ ID NO: 25 and polypeptides comprising a sequence having at least 60, 70, 80, 85, 90 or 95% sequence identity with this sequence and having cytochrome P450 reductase activity;
- a heterologous nucleic acid sequence coding for an O-methyltransferase (OMT) which is capable of methylating eriodictyol and/or luteolin in position 4' and comprising a sequence chosen from SEQ ID NOs: 117 and 119 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NO: 117 and polypeptides comprising a sequence having at least 60, 70, 80, 85, 90 or 95% sequence identity with this sequence and having O-methyltransferase activity;
- a heterologous nucleic acid sequence coding for a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;
- a heterologous or endogenous nucleic acid sequence coding for an S-adenosylmethionine synthetase (SAMT) comprising a sequence chosen from SEQ ID NO: 81 and a polypeptide having at least 60, 70, 80, 85, 90 or 95% sequence identity with this sequence and having S-adenosylmethionine synthetase activity;
- a heterologous nucleic acid sequence coding for a tyrosine ammonia lyase (TAL) which is capable of producing p-coumaric acid from tyrosine and comprising a sequence chosen from SEQ ID NO: 41 and polypeptides comprising a sequence having at least 60, 70, 80, 85, 90 or 95% sequence identity with this sequence and having tyrosine ammonia lyase activity;
- a heterologous nucleic acid sequence coding for a 4-coumarate-CoA ligase (4CL) which is capable of producing coumaryl-CoA from p-coumaric acid and Coenzyme A and comprising a sequence chosen from SEQ ID NOs: 123, 125 and 45 and polypeptides comprising a sequence having at least 60, 70, 80, 85, 90 or 95% sequence identity with one of these sequences and having 4-coumarate-CoA ligase activity, preferably comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA and comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone and comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a phenylalanine ammonia lyase (PAL) and comprising a sequence chosen from SEQ ID NOs: 65 and 77 and polypeptides comprising a sequence having at least 60, 70, 80, 85, 90 or 95% sequence identity with one of these sequences and having phenylalanine ammonia lyase activity, preferably comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H) and comprising a sequence chosen from SEQ ID NO: 79 and polypeptides comprising a sequence having at least 60, 70, 80, 85, 90 or 95% sequence identity with this sequence and having cinnamate 4-hydroxylase activity, which are capable of producing p-coumaric acid from phenylalanine.

In a particular embodiment, the vector comprises:

a nucleic acid sequence coding for an O-methyltransferase, in particular which is capable of methylating eriodictyol and/or luteolin in position 4' and a heterologous nucleic acid sequence coding for a flavonoid 3'-monooxygenase (F3'H), in particular which is capable of adding a hydroxyl in position 3' of naringenin and/or apigenin; or a nucleic acid sequence coding for an O-methyltransferase (OMT), in particular which is capable of methylating eriodictyol and/or luteolin in position 4'; a heterologous nucleic acid sequence coding for a flavonoid 3'-monooxygenase (F3'H), in particular which is capable of adding a hydroxyl in position 3' of naringenin and/or apigenin; and a heterologous nucleic acid sequence coding for a cytochrome P450 reductase; or a heterologous nucleic acid sequence coding for an O-methyltransferase (OMT), in particular which is capable of methylating eriodictyol and/or luteolin in position 4'; and a heterologous nucleic acid sequence coding for a flavone synthase (FNS), which is capable of transforming naringenin into apigenin, eriodictyol into luteolin and/or hesperetin into diosmetin, preferably of transforming eriodictyol into luteolin; or a heterologous nucleic acid sequence coding for an O-methyltransferase which is capable of methylating eriodictyol and/or luteolin in position 4'; a heterologous nucleic acid sequence coding for a flavonoid 3'-monooxygenase (F3'H) which is capable of hydroxylating in position 3' of naringenin and/or apigenin; a heterologous nucleic acid sequence coding for a cytochrome P450 reductase; and a heterologous nucleic acid sequence coding for flavone synthase (FNS) which is capable of transforming naringenin into apigenin, eriodictyol into luteolin and/or hesperetin into diosmetin, preferably of transforming eriodictyol into luteolin.

The vector may thus comprise several nucleic acid sequences chosen therefrom, notably 1, 2, 3, 4, 5, 6, 7, 8, 9 or 10 nucleic acid sequences chosen therefrom.

The vector may notably comprise combinations of particular coding sequences as described above.

The vectors comprise coding sequences that are heterologous insofar as the coding sequences may be optimized for the host microorganism, may be under the control of a heterologous promoter and/or may combine coding sequences which do not originate from the same original organism and/or which are not present in the same arrangement.

The vector may be any DNA sequence in which it is possible to insert foreign nucleic acids, the vectors making it possible to introduce foreign DNA into the host microorganism. For example, the vector may be a plasmid, a phagemid, a cosmid, an artificial chromosome, notably a YAC, or a BAC.

The expression vectors may comprise nucleic acid sequences coding for selection markers. The selection markers may be genes for resistance to one or more antibiotics or auxotrophic genes. The auxotrophic gene may be, for example, URA3, LEU2, HIS3 or TRP1. The antibiotic-resistance gene may preferably be, for example, a gene for resistance to ampicillin, kanamycin, hygromycin, geneticin and/or nourseothricin.

The introduction of vectors into a host microorganism is a process that is widely known to those skilled in the art. Several methods are notably described in "Current Protocols in Molecular Biology", 13.7.1-13.7.10; or in Ellis T. et al., Integrative Biology, 2011, 3 (2), 109-118.

The host microorganism may be transiently or stably transformed/transfected and the nucleic acid, the cassette or the vector may be contained therein in episomal form or in a form incorporated into the genome of the host microorganism.

The expression vector may also comprise one or more sequences allowing the targeted insertion of the vector, of the expression cassette or of the nucleic acid into the genome of the host microorganism.

All or part of the expression cassettes comprising the nucleic acid sequences coding for the enzymes as described above or a combination of some of them may be inserted into the/a chromosome of the recombinant microorganism.

Conversely, all or part of the expression cassettes comprising the nucleic acid sequences coding for the enzymes as described or a combination of some of them may be conserved in episomal form, notably in plasmid form.

Optionally, the microorganism may comprise several copies of nucleic acid sequences coding for an enzyme as described previously. Notably, it may comprise 2 to 10 copies, for example 2, 3, 4, 5, 6, 7, 8, 9 or 10 copies of a nucleic acid sequence coding for an enzyme as described previously.

The present invention relates to a method for preparing a microorganism according to the present invention, comprising the introduction of nucleic acid sequences coding for a flavanone 7-O-beta-D-glucosyltransferase (UGT), in particular which is capable of adding a glucose in position 7 of hesperetin and diosmetin; for a 6''-O-rhamnosyltransferase (RhaT), in particular which is capable of transferring a rhamnose in position 6 of the glucose of hesperetin-7-O-glucoside and/or diosmetin-7-O-glucoside; and for a UDP-glucose 4,6-dehydratase/UDP-4-keto-6-deoxy-D-glucose 3,5-epimerase/UDP-4-keto-L-rhamnose-reductase (RHM), in particular which is capable of producing UDP-rhamnose in the microorganism and the selection of microorganisms comprising said nucleic acid sequences.

The method may also comprise the introduction of one or more nucleic acid sequences chosen from:

- a heterologous nucleic acid sequence coding for a flavonoid 3'-monooxygenase (F3'H) which is capable of hydroxylating naringenin and/or apigenin in position 3'; preferably from *Perilla frutescens* var. *crispa, Petunia×hybrida, Callistephus chinensis, Gerbera hybrida, Citrus sinensis, Citrus clementina, Osteospermum* hybrid cultivar, *Phanerochaete chrysosporium, Streptomyces avermitilis* or *Pilosella officinarum*, in particular from *Perilla frutescens* var. *crispa, Petunia×hybrida, Callistephus chinensis, Gerbera hybrida, Citrus sinensis* or *Pilosella officinarum*, preferably an F3'H comprising a sequence chosen from SEQ ID NOs: 1, 3, 5, 7, 9, 11, 13, 15, 17, 19 and 21 and polypeptides comprising a sequence having at least 60, 70, 80, 85, 90 or 95% sequence identity with one of these sequences and having flavonoid 3'-monooxygenase activity, preferably selected from enzymes comprising a sequence chosen from SEQ ID NOs: 1, 5, 7, 11, 17 and 19 and polypeptides comprising a sequence having at least 60, 70, 80, 85, 90 or 95% sequence identity with one of these sequences and having flavonoid 3'-monooxygenase activity, in particular an F3'H comprising a sequence selected from SEQ ID NOs: 5, 7 and 17 and polypeptides comprising a sequence having at least 60, 70, 80, 85, 90 or 95% sequence identity with this sequence and having flavonoid 3'-monooxygenase activity, preferably an F3'H comprising a sequence chosen from SEQ ID NOs: 7 and polypeptides comprising a sequence having at least 60, 70, 80, 85, 90 or 95% sequence identity with the sequence SEQ ID NO: 7 and having flavonoid 3'-monooxygenase activity;
- a heterologous nucleic acid sequence coding for a cytochrome P450 reductase (CPR); preferably a CPR from *Saccharomyces cerevisiae*, or from a plant, for example from *Catharanthus roseus* or *Arabidopsis thaliana*; preferably a CPR comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25, 29 and 31 and polypeptides comprising a sequence having at least 60, 70, 80, 85, 90 or 95% sequence identity with one of these sequences and having cytochrome P450 reductase activity, and particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity;
- a heterologous nucleic acid sequence coding for an O-methyltransferase (OMT) which is capable of methylating eriodictyol and/or luteolin in position 4'; preferably an OMT from *Arabidopsis thaliana* or *Homo sapiens*, preferably an OMT comprising a sequence chosen from SEQ ID NOs: 87 and 89 and polypeptides comprising a sequence having at least 60, 70, 80, 85, 90 or 95% sequence identity with one of these sequences and having O-methyltransferase activity, notably with eriodictyol and/or luteolin as substrate and with methylation in position 4', preferably selected from the enzyme comprising a sequence chosen from SEQ ID NO: 89 and polypeptides comprising a sequence having at least 60, 70, 80, 85, 90 or 95% sequence identity with this sequence and having O-methyltransferase activity;
- a heterologous nucleic acid sequence coding for a flavone synthase (FNS) which is capable of transforming naringenin into apigenin, eriodictyol into luteolin, and/or hesperetin into diosmetin, preferably of transforming eriodictyol into luteolin; preferably an FNS from *Arabidopsis thaliana, Lonicera japonica, Lonicera macranthoides, Medicago truncatula, Oryza sativa, Petroselinum crispum, Populus deltoides, Zea mays, Callistephus chinensis, Apium graveolens, Medicago truncatula, Cuminum cyminum, Aethusa cynapium, Angelica archangelica, Conium maculatum, Camellia sinensis, Cynara cardunculus* var *scolymus, Saussurea medusa, Plectranthus barbatus, Scutellaria baicalensis, Dorcoceras hygrometricum, Antirrhinum majus, Perilla frutescens* var *crispa, Dahlia pinnata* or *Erythranthe lewisii*, in particular from *Arabidopsis thaliana, Lonicera japonica, Lonicera macranthoides, Medicago truncatula, Oryza sativa, Petroselinum crispum, Populus deltoides* or *Zea mays*, preferably from *Lonicera japonica, Lonicera macranthoides* and *Petroselinum crispum*; preferably an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, preferably from enzymes comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity;
- a heterologous or endogenous nucleic acid sequence coding for an S-adenosylmethionine synthetase (SAMT), in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity;
- a heterologous nucleic acid sequence coding for a tyrosine ammonia lyase (TAL) which is capable of producing p-coumaric acid from tyrosine; preferably from *Rhodotorula glutinis* or *Flavobacterium johnsoniae*; in particular a TAL comprising a sequence chosen from SEQ ID NOs: 39 and 41 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumarate-CoA ligase (4CL) which is capable of producing coumaryl-CoA from p-coumaric acid and Coenzyme A; preferably from *Arabidopsis thaliana, Petroselinum crispum* or *Streptomyces clavuligerus*; a 4CL comprising a sequence chosen from SEQ ID NOs: 43, 45, 47 and 49 and polypeptides comprising a sequence having at least 60, 70, 80, 85, 90 or 95% sequence identity with one of these sequences and having 4-coumarate-CoA ligase activity, and preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity;

a heterologous nucleic acid sequence coding for a chalcone synthase (CHS) which is capable of producing naringenin-chalcone from 4-coumaroyl-CoA and malonyl-CoA; preferably from *Citrus sinensis, Hordeum vulgare* or *Streptomyces clavuligerus*, in particular a CHS comprising a sequence chosen from SEQ ID NOs: 51, 53, 55 and 57 and polypeptides comprising a sequence having at least 60, 70, 80, 85, 90 or 95% sequence identity with one of these sequences and having chalcone synthase activity, preferably from enzymes comprising a sequence chosen from SEQ ID NOs: 53 and 55 and polypeptides comprising a sequence having at least 60, 70, 80, 85, 90 or 95% sequence identity with one of these sequences and having chalcone synthase activity, and more particularly preferably a CHS comprising a sequence chosen from SEQ ID NO: 53 and polypeptides comprising a sequence having at least 60, 70, 80, 85, 90 or 95% sequence identity with this sequence and having chalcone synthase activity;

a heterologous nucleic acid sequence coding for a chalcone isomerase (CHI) which is capable of producing naringenin from naringenin chalcone; preferably from *Arabidopsis thaliana* or *Streptomyces clavuligerus*, in particular a CHI comprising a sequence chosen from SEQ ID NOs: 59 and 61 and polypeptides comprising a sequence having at least 60, 70, 80, 85, 90 or 95% sequence identity with one of these sequences and having chalcone isomerase activity, and preferably a CHI comprising a sequence chosen from SEQ ID NO: 61 and polypeptides comprising a sequence having at least 60, 70, 80, 85, 90 or 95% sequence identity with this sequence and having chalcone isomerase activity;

a heterologous nucleic acid sequence coding for a phenylalanine ammonia lyase (PAL), in particular a PAL comprising a sequence chosen from SEQ ID NOs: 63, 65 and 77 and polypeptides comprising a sequence having at least 60, 70, 80, 85, 90 or 95% sequence identity with one of these sequences and having phenylalanine ammonia lyase activity, in particular a PAL comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, which are capable of producing p-coumaric acid from phenylalanine, in particular a C4H comprising a sequence chosen from SEQ ID NO: 79 and polypeptides comprising a sequence having at least 60, 70, 80, 85, 90 or 95% sequence identity with this sequence and having cinnamate 4-hydroxylase activity;

a nucleic acid sequence coding for a 4-hydroxyphenylacetate 3-monooxygenase oxygenase subunit (HpaB), preferably comprising a sequence chosen from SEQ ID NO: 83 and polypeptides comprising a sequence having at least 60, 70, 80, 85, 90 or 95% sequence identity therewith and having 4-hydroxyphenylacetate 3-monooxygenase oxygenase activity, and a nucleic acid sequence coding for a 4-hydroxyphenylacetate 3-monooxygenase reductase subunit (HpaC), preferably comprising a sequence chosen from SEQ ID NO: 85 and polypeptides comprising a sequence having at least 60, 70, 80, 85, 90 or 95% sequence identity therewith and having 4-hydroxyphenylacetate 3-monooxygenase reductase activity; or a nucleic acid sequence coding for a 4-methoxybenzoate O-demethylase which is capable of converting tyrosine into L-DOPA and also p-coumaric acid into caffeic acid, preferably comprising a sequence chosen from SEQ ID NOs: 73 and 75 and polypeptides comprising a sequence having at least 60, 70, 80, 85, 90 or 95% sequence identity with one of these sequences and having L-tyrosine hydrolase activity; or a heterologous nucleic acid sequence coding for a p-coumarate 3-hydroxylase which is capable of converting p-coumaric acid into caffeic acid, preferably comprising a sequence SEQ ID NO: 71 and polypeptides comprising a sequence having at least 60, 70, 80, 85, 90 or 95% sequence identity with one of these sequences and having p-coumarate 3-hydroxylase activity, and a nucleic acid sequence coding for a dihydroxyphenylalanine ammonia-lyase (DAL).

According to a preferred embodiment, the method comprises the introduction of:

(i) a heterologous nucleic acid sequence coding for a flavanone 7-O-beta-D-glucosyltransferase (UGT) from *Arabidopsis thaliana, Scutellaria baicalensis* or *Homo sapiens*, preferably from *Arabidopsis thaliana* or from *Scutellaria baicalensis*, preferably a flavanone 7-O-beta-D-glucosyltransferase (UGT) selected from enzymes comprising a sequence chosen from SEQ ID NOs: 113, 115, 91, 93, 95, 97, 99 and 101 and polypeptides comprising a sequence having at least 60, 70, 80, 85, 90 or 95% sequence identity with one of these sequences and having flavanone 7-O-beta-D-glucosyltransferase activity; in particular a flavanone 7-O-beta-D-glucosyltransferase (UGT) comprising a sequence chosen from SEQ ID NOs: 113 and 95 and polypeptides comprising a sequence having at least 60, 70, 80, 85, 90 or 95% sequence identity with one of these sequences and having flavanone 7-O-beta-D-glucosyltransferase activity;

(ii) a heterologous nucleic acid sequence coding for a 6"-O-rhamnosyltransferase (RhaT) of the genus *Citrus* or *Petunia hybrida*, preferably *Citrus sinensis, Citrus maxima*, or *Citrus clementina*, even more preferably *Citrus sinensis* or *Citrus clementina*, preferably an RhaT comprising a sequence chosen from SEQ ID NOs: 103 and 105 and polypeptides comprising a sequence having at least 60, 70, 80, 85, 90 or 95% sequence identity with one of these sequences and having 6"-O-rhamnosyltransferase activity, in particular a 6"-O-rhamnosyltransferase (RhaT) comprising a sequence chosen from SEQ ID NO: 103 and polypeptides comprising a sequence having at least 60, 70, 80, 85, 90 or 95% sequence identity with this sequence and having 6"-O-rhamnosyltransferase activity; and (iii) a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) from *Citrus sinensis* or from *Arabidopsis thaliana*, preferably an RHM comprising a sequence chosen from SEQ ID NOs: 107, 109 and 111 and polypeptides comprising a sequence having at least 60, 70, 80, 85, 90 or 95% sequence identity with one of these sequences and having UDP-glucose 4,6-dehydratase/UDP-4-keto-6-deoxy-D-glucose 3,5-epimerase/UDP-4-keto-L-rhamnose-reductase activity, in particular an RHM comprising a sequence selected from SEQ ID NO: 107 and polypeptides comprising a sequence having at least 60, 70, 80, 85, 90 or 95% sequence identity with this sequence and having UDP-glucose 4,6-dehydratase/UDP-4-keto-6-deoxy-D-glucose 3,5-epimerase/UDP-4-keto-L-rhamnose-reductase activity;

and of at least one nucleic acid sequence chosen from:

a heterologous nucleic acid sequence coding for an O-methyltransferase (OMT) which is capable of methylating eriodictyol and/or luteolin in position 4'; preferably an OMT from *Citrus clementina, Citrus sinensis, Arabidopsis thaliana* or *Homo sapiens*, preferably an OMT comprising a sequence chosen from SEQ ID NOs: 117, 119, 87 and 89 and polypeptides comprising a sequence having at least 60, 70, 80, 85, 90 or 95% sequence identity with one of these sequences and having O-methyltransferase activity, notably with eriodictyol and/or luteolin as substrate and methylation in position 4', preferably an OMT comprising a sequence chosen from SEQ ID NOs: 117 and 119 and polypeptides comprising a sequence having at least 60, 70, 80, 85, 90 or 95% sequence identity with one of these sequences and having O-methyltransferase activity, and most particularly preferably an OMT comprising a sequence chosen from SEQ ID NO: 117 and polypeptides comprising a sequence having at least 60, 70, 80, 85, 90 or 95% sequence identity with this sequence and having O-methyltransferase activity;

a heterologous nucleic acid sequence coding for a flavonoid 3'-monooxygenase (F3'H) which is capable of hydroxylating naringenin and/or apigenin in position 3' and comprising a sequence selected from SEQ ID NOs: 7, 11, 17 and 121 and polypeptides comprising a sequence having at least 75%, at least 80%, at least 85%, at least 90% or at least 95% identity with one of these sequences and having flavonoid 3'-monooxygenase activity, preferably an enzyme comprising a sequence selected from SEQ ID NOs: 7, 17 and 121 and polypeptides comprising a sequence having at least 75%, at least 80%, at least 85%, at least 90% or at least 95% identity with one of these sequences and having flavonoid 3'-monooxygenase activity, and most particularly preferably an enzyme comprising a sequence selected from SEQ ID NO: 7 and polypeptides comprising a sequence having at least 75%, at least 80%, at least 85%, at least 90% or at least 95% identity with this sequence and having flavonoid 3'-monooxygenase activity; and a heterologous nucleic acid sequence coding for a cytochrome P450 reductase (CPR) and comprising a sequence chosen from SEQ ID NOs: 23, 25, 27, 29 and 31 and polypeptides comprising a sequence having at least 60, 70, 80, 85, 90 or 95% sequence identity with one of these sequences and having cytochrome P450 reductase activity, preferably from enzymes comprising a sequence chosen from SEQ ID NOs: 23, 25 and 29 and polypeptides comprising a sequence having at least 60, 70, 80, 85, 90 or 95% sequence identity with one of these sequences and having cytochrome P450 reductase activity, and particularly a CPR comprising a sequence chosen from SEQ ID NO: 25 and polypeptides comprising a sequence having at least 60, 70, 80, 85, 90 or 95% sequence identity with this sequence and having cytochrome P450 reductase activity; and a heterologous nucleic acid sequence coding for an FNS comprising a sequence chosen from SEQ ID NOs: 33, 35, 37, 127, 129, 131, 133, 135, 137, 139, 141, 143, 145, 147, 149, 151, 153, 155, 157 and 159 and polypeptides comprising a sequence having at least 60, 70, 80, 85, 90 or 95% sequence identity with one of these sequences and having flavone synthase activity, in particular a flavone synthase (FNS) and comprising a sequence chosen from SEQ ID NOs: 33, 35 and 37 and polypeptides comprising a sequence having at least 60, 70, 80, 85, 90 or 95% sequence identity with one of these sequences and having flavone synthase activity, preferably a flavone synthase (FNS) comprising a sequence chosen from SEQ ID NO: 37 and a polypeptide comprising a sequence having at least 60, 70, 80, 85, 90 or 95% sequence identity with this sequence and having flavone synthase activity; and a nucleic acid sequence coding for an S-adenosylmethionine synthetase (SAMT); in particular from *Saccharomyces cerevisiae*, for example an SAMT comprising a sequence chosen from SEQ ID NO: 81 and a polypeptide comprising a sequence having at least 60, 70, 80, 85, 90 or 95% sequence identity with this sequence and having S-adenosylmethionine synthetase activity, and a heterologous nucleic acid sequence coding for a tyrosine ammonia lyase (TAL) from *Rhodotorula glutinis* or *Flavobacterium johnsoniae*; in particular a TAL comprising a sequence chosen from SEQ ID NOs: 41 and 39 and polypeptides comprising a sequence having at least 60, 70, 80, 85, 90 or 95% sequence identity with one of these sequences and having tyrosine ammonia lyase activity; preferably a TAL comprising a sequence chosen from SEQ ID NO: 41 and polypeptides comprising a sequence having at least 60, 70, 80, 85, 90 or 95% sequence identity with this sequence and having tyrosine ammonia lyase activity;

a heterologous nucleic acid sequence coding for a 4-coumaroyl-CoA ligase (4CL) from *Arabidopsis thaliana, Citrus clementina, Petroselinum crispum* or *Streptomyces clavuligerus*; in particular a 4CL comprising a sequence chosen from SEQ ID NOs: 123, 125, 45, 43, 47 and 49 and polypeptides comprising a sequence having at least 60, 70, 80, 85, 90 or 95% sequence identity with one of these sequences and having 4-coumarate-CoA ligase activity; preferably a 4CL comprising a sequence selected from SEQ ID NOs: 123, 125 and 45 and polypeptides comprising a sequence having at least 60, 70, 80, 85, 90 or 95% sequence identity with one of these sequences and having 4-coumarate-CoA ligase activity; most particularly preferably a 4CL comprising a sequence selected from SEQ ID NO: 45 and polypeptides comprising a sequence having at least 60, 70, 80, 85, 90 or 95% sequence identity with this sequence and having 4-coumarate-CoA ligase activity, and a heterologous nucleic acid sequence coding for a chalcone synthase (CHS) from *Citrus sinensis, Hordeum vulgare* or *Streptomyces clavuligerus*, in particular a CHS comprising a sequence chosen from SEQ ID NOs: 53, 51, 55 and 57 and polypeptides comprising a sequence having at least 60, 70, 80, 85, 90 or 95% sequence identity with one of these sequences and having chalcone synthase activity, preferably a CHS comprising a sequence chosen from SEQ ID NO: 53 and polypeptides comprising a sequence having at least 60, 70, 80, 85, 90 or 95% sequence identity with this sequence and having chalcone synthase activity; and a heterologous nucleic acid sequence coding for a chalcone isomerase (CHI) from *Arabidopsis thaliana* or *Streptomyces clavuligerus*, in particular a CHI comprising a sequence chosen from SEQ ID NOs: 61 and 59 and polypeptides comprising a sequence having at least 60, 70, 80, 85, 90 or 95% sequence identity with one of these sequences and having chalcone isomerase activity; preferably a CHI comprising a sequence chosen from SEQ ID NO: 61 and polypeptides comprising a sequence having at least 60, 70, 80, 85, 90 or 95% sequence identity with this sequence and having chalcone isomerase activity.

Preferably, the method comprises the introduction of all these sequences.

Preferably, the method also comprises the introduction of:

a heterologous nucleic acid sequence coding for a phenylalanine ammonia lyase (PAL), in particular a PAL comprising a sequence chosen from SEQ ID NOs: 63, 65 and 77, preferably SEQ ID NOs: 65 and 77 and polypeptides comprising a sequence having at least 60, 70, 80, 85, 90 or 95% sequence identity with one of these sequences and having phenylalanine ammonia lyase activity, and more particularly preferably a phenylalanine ammonia lyase (PAL) comprising a sequence chosen from SEQ ID NO: 65 and polypeptides comprising a sequence having at least 60, 70, 80, 85, 90 or 95% sequence identity with this sequence and having phenylalanine ammonia lyase activity; and a heterologous nucleic acid sequence coding for a cinnamate 4-hydroxylase (C4H), in particular a C4H comprising a sequence chosen from SEQ ID NOs: 67, 69 and 79 and polypeptides comprising a sequence having at least 60, 70, 80, 85, 90 or 95% sequence identity with one of these sequences and having cinnamate 4-hydroxylase activity, and most particularly preferably a cinnamate 4-hydroxylase (C4H) comprising a sequence chosen from SEQ ID NO: 79 and polypeptides comprising a sequence having at least 60, 70, 80, 85, 90 or 95% sequence identity with this sequence and having cinnamate 4-hydroxylase activity.

Preferably, the method comprises the introduction of combinations of particular coding sequences as described above.

Production of Diosmin and/or Hesperidin

The present invention relates to the use of a microorganism according to the present invention for producing diosmin and/or hesperidin. In a first preferred embodiment, the invention relates to the use of a microorganism according to the present invention for producing diosmin. In a second preferred embodiment, the invention relates to the use of a microorganism according to the present invention for producing hesperidin. In a preferred embodiment, the invention relates to the use of a microorganism according to the present invention for producing diosmin and hesperidin.

The present invention also relates to a method for producing diosmin and/or hesperidin, comprising the cultivation of a microorganism according to the present invention, notably under conditions allowing or that are favourable for the production of diosmin and/or hesperidin and optionally the recovery and/or purification of the diosmin and/or hesperidin produced.

The conditions for cultivating the microorganism according to the invention may be adapted according to the conventional techniques that are well known to those skilled in the art.

The microorganism is cultivated in a suitable culture medium. The term "suitable culture medium" generally denotes a culture medium providing the nutrients that are essential for or beneficial to the maintenance and/or growth of said microorganism, such as carbon sources; nitrogen sources such as ammonium sulfate; phosphorus sources, for example monobasic potassium phosphate; trace elements, for example copper, iodide, iron, magnesium, zinc or molybdate salts; vitamins and other growth factors such as amino acids or other growth promoters. An antifoam may be added if need be. According to the invention, this suitable culture medium may be chemically defined or complex. The culture medium may thus be identical or similar in composition to that of a synthetic medium, as defined by Verduyn et al., (Yeast. 1992. 8:501-17), adapted by Visser et al., (Biotechnology and Bioengineering. 2002. 79:674-81), or commercially available such as the YNB medium (Yeast Nitrogen Base, MP Biomedicals or Sigma-Aldrich). Notably, the culture medium may comprise a simple carbon source, such as glucose, fructose, xylose, ethanol, glycerol, galactose, sucrose, cellulose, cellobiose, starch, glucose polymers, molasses, or byproducts of these sugars.

Preferably, the production of diosmin and/or hesperidin by the microorganism according to the invention is obtained without supplying naringenin, apigenin, eriodictyol, luteolin, hesperetin and/or diosmetin to the culture medium, preferably without supplying naringenin, apigenin, eriodictyol, luteolin, hesperetin and diosmetin to the culture medium.

According to the invention, any cultivation method for the industrial-scale production of molecules of interest may be envisioned. Advantageously, the cultivation is performed in bioreactors, notably in batch, fed-batch, chemostat and/or continuous cultivation mode. Controlled feeding with vitamins during the process may also be beneficial to the productivity (Alfenore et al., Appl. Microbiol. Biotechnol. 2002. 60:67-72).

The cultivation is generally performed in bioreactors, with possible solid and/or liquid preculturing steps in Erlenmeyer flasks, with a suitable culture medium.

In general, the conditions for cultivating the microorganisms according to the invention are readily adaptable by a person skilled in the art, as a function of the microorganism. For example, the cultivation temperature is notably, for yeasts, between 20° C. and 40° C., preferably between 28° C. and 35° C., and more particularly about 30° C. for *S. cerevisiae.*

The microorganism according to the present invention may be cultivated for 1 to 30 days and preferably for 1 to 10 days.

A microorganism according to the present invention is capable of producing diosmin and/or hesperidin in a minimum amount of 1 mg/l of culture medium, preferably 10, 20, 25, 30, 35, 40, 45, 50, 55, 60, 65, 70, 75, 80, 85, 90, 95 or 100 mg/l of culture medium, optionally 150, 200, 250, 300, 350, 400, 450, 500, 600, 700, 800, 900 or 1000 mg/l of culture medium.

DESCRIPTION OF THE FIGURES

FIG. 1: Description of the metabolic pathways for producing hesperidin and diosmin.

FIG. 2: Production of eriodictyol from naringenin by the strain FL_405 (F3'H4+CPR2). Control strain: CF235. Observation of disappearance of the naringenin peak and appearance of an eriodictyol peak in the strain FL-405.

FIG. 3: Production of luteolin from apigenin by the strain FL_405 (F3'H4+CPR2). Control strain: CF235. Observation of disappearance of the apigenin peak and appearance of a luteolin peak in the strain FL-405.

FIG. 4: Production of apigenin from naringenin by the strain SC744 (FNSII1+CPR2). Control strain: CF234. Observation of disappearance of the naringenin peak and appearance of an apigenin peak in the strain.

FIG. 5: Production of luteolin from eriodictyol SC744 (FNSII1+CPR2). Control strain: CF234. Observation of disappearance of the eriodictyol peak and appearance of a luteolin peak in the strain.

FIG. 6: Production of eriodictyol and luteolin by the strain SC1500. Control strain: CF237. Observation of the eriodictyol and luteolin peaks.

FIG. 7: Production of hesperetin from eriodictyol by the strains SC 1612 (MET+SAM) and SC 1614 (MET+SAM). Control strain: CF235. Observation of disappearance of the eriodictyol peak and appearance of a hesperetin peak in the strains.

FIG. 8: Production of diosmetin from luteolin by the strains SC 1612 (MET+SAM) and SC 1614 (MET+SAM). Control strain: CF235. Observation of disappearance of the luteolin peak and appearance of a diosmetin peak in the strains.

FIG. 9: Production of diosmetin from hesperetin by the strain SC744 (FNSII+CPR). Control strain: CF234. Observation of disappearance of the hesperetin peak and appearance of a diosmetin peak in the strain.

FIG. 10: Production of hesperetin from eriodictyol by *E. coli* EC26 (MET+SAM). Control strain: *E. coli* MH1. Observation of disappearance of the eriodictyol peak and appearance of a hesperetin peak in the strain.

FIG. 11: Production of diosmetin from luteolin by *E. coli* EC26 (MET+SAM). Control strain: *E. coli* MH1. Observation of disappearance of the luteolin peak and appearance of a diosmetin peak in the strain.

FIG. 12: Production of diosmetin from hesperetin by *E. coli* EC30 (FNSII). Control strain: *E. coli* MH1. Observation of disappearance of the hesperetin peak and appearance of a diosmetin peak in the strain.

FIG. 13: Production of hesperetin and diosmetin by the strain SC1508. Control strain: CF237. Observation of the hesperetin and diosmetin peaks.

FIG. 14: Production of hesperidin from hesperetin by the strain FL 547 (GT+RHM+RHAT). Control strain: CF 233. Observation of disappearance of the hesperetin peak and appearance of the hesperidin peak.

FIG. 15: Production of diosmin from diosmetin by the strain FL 547 (GT+RHM+RHAT). Control strain: CF 233. Observation of disappearance of the diosmetin peak and appearance of the diosmin peak.

FIG. 16: Production of hesperidin from hesperetin by *E. coli* EC38, EC45 and EC47 (GT+RHM+RHAT). Control strain: *E. coli* MH1. Observation of disappearance of the hesperetin peak and appearance of the hesperidin peak.

FIG. 17: Production of diosmin from diosmetin by *E. coli* EC38, EC45 and EC47 (GT+RHM+RHAT). Control strain: *E. coli* MH1. Observation of disappearance of the diosmetin peak and appearance of the diosmin peak.

FIG. 18: Production of hesperidin and diosmin by the strains SC1509, SC1530, SC1529, SC1568 and SC2410. Control strain: CF237. Observation of the hesperidin and diosmin peaks.

FIG. 19: Production of eriodictyol and luteolin by the strains SC2424, SC2425, SC2426, SC2427, SC2428 and SC1500. Control strain: CF237.

FIG. 20: Production of hesperetin and homoeriodictyol by the strains SC2147, SC2151, SC1612 and SC1614. Control strain: CF235.

FIG. 21: Production of diosmetin and chrysoeriol by the strains SC2147, SC2151, SC1612 and SC1614. Control strain: CF235.

FIG. 22: Production of hesperetin from eriodictyol by *E. coli* EC41 (MET+SAM). Control strain: *E. coli* MH1. Observation of disappearance of the eriodictyol peak and appearance of a hesperetin peak in the strain.

FIG. 23: Production of hesperetin from eriodictyol by *E. coli* EC43 (MET+SAM): Control strain: *E. coli* MH1. Observation of disappearance of the eriodictyol peak and appearance of a hesperetin peak in the strain.

FIG. 24: Production of diosmetin from luteolin by *E. coli* EC43 (MET+SAM). Control strain: *E. coli* MH1. Observation of disappearance of the luteolin peak and appearance of a diosmetin peak in the strain.

FIG. 25: Production of hesperetin and diosmetin by the strain SC2408. Control strain: CF237. Observation of the hesperetin and diosmetin peaks.

FIG. 26: Production of hesperetin and diosmetin by the strain SC2409. Control strain: CF237. Observation of the hesperetin and diosmetin peaks.

FIG. 27: Production of hesperetin and diosmetin by the strains SC2408, SC2409 and SC1508. Control strain: CF237.

FIG. 28: Production of hesperidin and diosmin by the strains SC1579, SC1584, SC1621 and SC1626.

FIG. 29: Production of diosmetin from naringenin by the strains SC2429 to SC2434, SC2436 to SC2444, SC2446 to SC2454, SC2456 to SC2464 and SC2466.

TABLE 1

SEQUENCE DESCRIPTION

| SEQ ID NO | Description |
|---|---|
| 39 | Amino acid sequence of tyrosine ammonia lyase from *Flavobacterium johnsoniae* |
| 40 | Nucleic acid sequence coding for tyrosine ammonia lyase from *Flavobacterium johnsoniae* |
| 41 | Amino acid sequence of tyrosine ammonia lyase from *Rhodotorula glutinis* |
| 42 | Nucleic acid sequence coding for tyrosine ammonia lyase from *Rhodotorula glutinis* |
| 43 | Amino acid sequence of 4-coumarate-CoA ligase from *Arabidopsis thaliana* |
| 44 | Nucleic acid sequence coding for 4-coumarate-CoA ligase from *Arabidopsis thaliana* |
| 45 | Amino acid sequence of 4-coumarate-CoA ligase from *Petroselinum crispum* |

TABLE 1-continued

SEQUENCE DESCRIPTION

| SEQ ID NO | Description |
|---|---|
| 46 | Nucleic acid sequence coding for 4-coumarate-CoA ligase from *Petroselinum crispum* |
| 47 | Amino acid sequence of 4-coumarate-CoA ligase from *Petroselinum crispum* |
| 48 | Nucleic acid sequence coding for 4-coumarate-CoA ligase from *Petroselinum crispum* |
| 49 | Amino acid sequence of 4-coumarate-CoA ligase from *Streptomyces clavuligerus* |
| 50 | Nucleic acid sequence coding for 4-coumarate-CoA ligase from *Streptomyces clavuligerus* |
| 51 | Amino acid sequence of chalcone synthase from *Hordeum vulgare* |
| 52 | Nucleic acid sequence coding for chalcone synthase from *Hordeum vulgare* |
| 53 | Amino acid sequence of chalcone synthase from *Citrus sinensis* |
| 54 | Nucleic acid sequence coding for chalcone synthase from *Citrus sinensis* |
| 55 | Amino acid sequence of chalcone synthase from *Citrus sinensis* |
| 56 | Nucleic acid sequence coding for chalcone synthase from *Citrus sinensis* |
| 57 | Amino acid sequence of chalcone synthase from *Streptomyces clavuligerus* |
| 58 | Nucleic acid sequence coding for chalcone synthase from *Streptomyces clavuligerus* |
| 59 | Amino acid sequence of chalcone isomerase from *Streptomyces clavuligerus* |
| 60 | Nucleic acid sequence coding for chalcone isomerase from *Streptomyces clavuligerus* |
| 61 | Amino acid sequence of chalcone isomerase from *Arabidopsis thaliana* |
| 62 | Nucleic acid sequence coding for chalcone isomerase from *Arabidopsis thaliana* |
| 33 | Amino acid sequence of flavone synthase from *Lonicera japonica* |
| 34 | Nucleic acid sequence coding for flavone synthase from *Lonicera japonica* |
| 35 | Amino acid sequence of flavone synthase from *Lonicera macranthoides* |
| 36 | Nucleic acid sequence coding for flavone synthase from *Lonicera macranthoides* |
| 37 | Amino acid sequence of flavone synthase from *Petroselinum crispum* |
| 38 | Nucleic acid sequence coding for flavone synthase from *Petroselinum crispum* |
| 1 | Amino acid sequence of flavonoid 3'-monooxygenase from *Perilla frutescens* var. *crispa* |
| 2 | Nucleic acid sequence coding for flavonoid 3'-monooxygenase from *Perilla frutescens* var. *crispa* |
| 3 | Amino acid sequence of flavonoid 3'-monooxygenase from *Phanerochaete chrysosporium* |
| 4 | Nucleic acid sequence coding for flavonoid 3'-monooxygenase from *Phanerochaete chrysosporium* |
| 5 | Amino acid sequence of flavonoid 3'-monooxygenase from *Petunia* x *hybrida* |
| 6 | Nucleic acid sequence coding for flavonoid 3'-monooxygenase from *Petunia* x *hybrida* |
| 7 | Amino acid sequence of flavonoid 3'-monooxygenase from *Callistephus chinensis* |
| 8 | Nucleic acid sequence coding for flavonoid 3'-monooxygenase from *Callistephus chinensis* |
| 9 | Amino acid sequence of flavonoid 3'-monooxygenase from *Callistephus chinensis* |
| 10 | Nucleic acid sequence coding for flavonoid 3'-monooxygenase from *Callistephus chinensis* |
| 11 | Amino acid sequence of flavonoid 3'-monooxygenase from *Gerbera hybrida* |
| 12 | Nucleic acid sequence coding for flavonoid 3'-monooxygenase from *Gerbera hybrida* |
| 13 | Amino acid sequence of flavonoid 3'-monooxygenase from *Osteospermum hybrid cultivar* |
| 14 | Nucleic acid sequence coding for flavonoid 3'-monooxygenase from *Osteospermum hybrid cultivar* |
| 15 | Amino acid sequence of flavonoid 3'-monooxygenase from *Citrus clementina* |
| 16 | Nucleic acid sequence coding for flavonoid 3'-monooxygenase from *Citrus clementina* |
| 17 | Amino acid sequence of flavonoid 3'-monooxygenase from *Citrus sinensis* |
| 18 | Nucleic acid sequence coding for flavonoid 3'-monooxygenase from *Citrus sinensis* |
| 19 | Amino acid sequence of flavonoid 3'-monooxygenase from *Pilosella officinarum* |
| 20 | Nucleic acid sequence coding for flavonoid 3'-monooxygenase from *Pilosella officinarum* |
| 21 | Amino acid sequence of flavonoid 3'-monooxygenase from *Streptomyces avermitilis* |
| 22 | Nucleic acid sequence coding for flavonoid 3'-monooxygenase from *Streptomyces avermitilis* |
| 23 | Amino acid sequence of cytochrome P450 reductase from *Catharanthus roseus* |
| 24 | Nucleic acid sequence coding for cytochrome P450 reductase from *Catharanthus roseus* |
| 25 | Amino acid sequence of cytochrome P450 reductase from *Saccharomyces cerevisiae* |
| 26 | Nucleic acid sequence coding for cytochrome P450 reductase from *Saccharomyces cerevisiae* |
| 27 | Amino acid sequence of chimeric cytochrome P450 reductase |
| 28 | Nucleic acid sequence coding for chimeric cytochrome P450 reductase |
| 29 | Amino acid sequence of cytochrome P450 reductase from *Arabidopsis thaliana* |
| 30 | Nucleic acid sequence coding for cytochrome P450 reductase from *Arabidopsis thaliana* |
| 31 | Amino acid sequence of cytochrome P450 reductase from *Arabidopsis thaliana* |
| 32 | Nucleic acid sequence coding for cytochrome P450 reductase from *Arabidopsis thaliana* |
| 63 | Amino acid sequence of phenylalanine ammonia lyase from *Citrus sinensis* |
| 64 | Nucleic acid sequence coding for phenylalanine ammonia lyase from *Citrus sinensis* |
| 65 | Amino acid sequence of phenylalanine ammonia lyase from *Citrus sinensis* |
| 66 | Nucleic acid sequence coding for phenylalanine ammonia lyase from *Citrus sinensis* |
| 67 | Amino acid sequence of cinnamate 4-hydroxylase from *Citrus sinensis* |
| 68 | Nucleic acid sequence coding for cinnamate 4-hydroxylase from *Citrus sinensis* |
| 69 | Amino acid sequence of cinnamate 4-hydroxylase from *Citrus sinensis* |
| 70 | Nucleic acid sequence coding for cinnamate 4-hydroxylase from *Citrus sinensis* |
| 71 | Amino acid sequence of coumarate 3-hydroxylase from *Saccharothrix espanaensis* |
| 72 | Nucleic acid sequence coding for coumarate 3-hydroxylase from *Saccharothrix espanaensis* |
| 73 | Amino acid sequence of 4-methoxybenzoate O-demethylase from *Beta vulgaris* |
| 74 | Nucleic acid sequence coding for 4-methoxybenzoate O-demethylase from *Beta vulgaris* |
| 75 | Amino acid sequence of 4-methoxybenzoate O-demethylase from *Rhodopseudomonas palustris* |
| 76 | Nucleic acid sequence coding for 4-methoxybenzoate O-demethylase from *Rhodopseudomonas palustris* |
| 77 | Amino acid sequence of phenylalanine ammonia lyase from *Arabidopsis thaliana* |
| 78 | Nucleic acid sequence coding for phenylalanine ammonia lyase from *Arabidopsis thaliana* |
| 79 | Amino acid sequence of cinnamate 4-hydroxylase from *Arabidopsis thaliana* |
| 80 | Nucleic acid sequence coding for cinnamate 4-hydroxylase from *Arabidopsis thaliana* |
| 81 | Amino acid sequence of S-adenosylmethionine synthetase from *Saccharomyces cerevisiae* |
| 82 | Nucleic acid sequence coding for S-adenosylmethionine synthetase from *Saccharomyces cerevisiae* |

TABLE 1-continued

SEQUENCE DESCRIPTION

| SEQ ID NO | Description |
|---|---|
| 83 | Amino acid sequence of 4-hydroxyphenylacetate 3-monooxygenase oxygenase from *Escherichia coli* |
| 84 | Nucleic acid sequence coding for 4-hydroxyphenylacetate 3-monooxygenase oxygenase from *Escherichia coli* |
| 85 | Amino acid sequence of 4-hydroxyphenylacetate 3-monooxygenase reductase from *Escherichia coli* |
| 86 | Nucleic acid sequence coding for 4-hydroxyphenylacetate 3-monooxygenase reductase from *Escherichia coli* |
| 87 | Amino acid sequence of O-methyltransferase from *Arabidopsis thaliana* |
| 88 | Nucleic acid sequence coding for O-methyltransferase from *Arabidopsis thaliana* |
| 89 | Amino acid sequence of O-methyltransferase from *Homo sapiens* |
| 90 | Nucleic acid sequence coding for O-methyltransferase from *Homo sapiens* |
| 91 | Amino acid sequence of flavanone 7-O-beta-D-glucosyltransferase from *Arabidopsis thaliana* |
| 92 | Nucleic acid sequence coding for flavanone 7-O-beta-D-glucosyltransferase from *Arabidopsis thaliana* |
| 93 | Amino acid sequence of flavanone 7-O-beta-D-glucosyltransferase from *Scutellaria baicalensis* |
| 94 | Nucleic acid sequence coding for flavanone 7-O-beta-D-glucosyltransferase from *Scutellaria baicalensis* |
| 95 | Amino acid sequence of flavanone 7-O-beta-D-glucosyltransferase from *Scutellaria baicalensis* |
| 96 | Nucleic acid sequence coding for flavanone 7-O-beta-D-glucosyltransferase from *Scutellaria baicalensis* |
| 97 | Amino acid sequence of flavanone 7-O-beta-D-glucosyltransferase from *Scutellaria baicalensis* |
| 98 | Nucleic acid sequence coding for flavanone 7-O-beta-D-glucosyltransferase from *Scutellaria baicalensis* |
| 99 | Amino acid sequence of flavanone 7-O-beta-D-glucosyltransferase from *Homo sapiens* |
| 100 | Nucleic acid sequence coding for flavanone 7-O-beta-D-glucosyltransferase from *Homo sapiens* |
| 101 | Amino acid sequence of flavanone 7-O-beta-D-glucosyltransferase from *Homo sapiens* |
| 102 | Nucleic acid sequence coding for flavanone 7-O-beta-D-glucosyltransferase from *Homo sapiens* |
| 103 | Amino acid sequence of 6-O-rhamnosyltransferase from *Citrus clementina* |
| 104 | Nucleic acid sequence coding for 6-O-rhamnosyltransferase from *Citrus clementina* |
| 105 | Amino acid sequence of 6-O-rhamnosyltransferase from *Citrus sinensis* |
| 106 | Nucleic acid sequence coding for 6-O-rhamnosyltransferase from *Citrus sinensis* |
| 107 | Amino acid sequence of UDP-glucose 4,6-dehydratase/UDP-4-keto-6-deoxy-D-glucose 3,5-epimerase/UDP-4-keto-L-rhamnose-reductase from *Citrus sinensis* |
| 108 | Nucleic acid sequence coding for UDP-glucose 4,6-dehydratase/UDP-4-keto-6-deoxy-D-glucose 3,5-epimerase/UDP-4-keto-L-rhamnose-reductase from *Citrus sinensis* |
| 109 | Amino acid sequence of UDP-glucose 4,6-dehydratase/UDP-4-keto-6-deoxy-D-glucose 3,5-epimerase/UDP-4-keto-L-rhamnose-reductase from *Arabidopsis thaliana* |
| 110 | Nucleic acid sequence coding for UDP-glucose 4,6-dehydratase/UDP-4-keto-6-deoxy-D-glucose 3,5-epimerase/UDP-4-keto-L-rhamnose-reductase from *Arabidopsis thaliana* |
| 111 | Amino acid sequence of UDP-glucose 4,6-dehydratase/UDP-4-keto-6-deoxy-D-glucose 3,5-epimerase/UDP-4-keto-L-rhamnose-reductase from *Arabidopsis thaliana* |
| 112 | Nucleic acid sequence coding for UDP-glucose 4,6-dehydratase/UDP-4-keto-6-deoxy-D-glucose 3,5-epimerase/UDP-4-keto-L-rhamnose-reductase from *Arabidopsis thaliana* |
| 113 | Amino acid sequence of flavanone 7-O-beta-D-glucosyltransferase from *Citrus sinensis* |
| 114 | Nucleic acid sequence coding for flavanone 7-O-beta-D-glucosyltransferase from *Citrus sinensis* |

TABLE 1-continued

SEQUENCE DESCRIPTION

| SEQ ID NO | Description |
|---|---|
| 115 | Amino acid sequence of flavanone 7-O-beta-D-glucosyltransferase from *Citrus clementina* |
| 116 | Nucleic acid sequence coding for flavanone 7-O-beta-D-glucosyltransferase from *Citrus clementina* |
| 117 | Amino acid sequence of O-methyltransferase from *Citrus clementina* |
| 118 | Nucleic acid sequence coding for O-methyltransferase from *Citrus clementina* |
| 119 | Amino acid sequence of O-methyltransferase from *Citrus sinensis* |
| 120 | Nucleic acid sequence coding for O-methyltransferase from *Citrus sinensis* |
| 121 | Amino acid sequence of flavonoid 3'-monooxygenase from *Arabidopsis thaliana* |
| 122 | Nucleic acid sequence coding for flavonoid 3'-monooxygenase from *Arabidopsis thaliana* |
| 123 | Amino acid sequence of a 4-coumarate-CoA ligase from *Arabidopsis thaliana* |
| 124 | Nucleic acid sequence coding for a 4-coumarate-CoA ligase from *Arabidopsis thaliana* |
| 125 | Amino acid sequence of a 4-coumarate-CoA ligase from *Citrus clementina* |
| 126 | Nucleic acid sequence coding for 4-coumarate-CoA ligase from *Citrus clementina* |
| 127 | Amino acid sequence of flavone synthase from *Angelica archangelica* |
| 128 | Nucleic acid sequence coding for flavone synthase from *Angelica archangelica* |
| 129 | Amino acid sequence of flavone synthase from *Cynara cardunculus* var. *scolymus* |
| 130 | Nucleic acid sequence coding for flavone synthase from *Cynara cardunculus* var. *scolymus* |
| 131 | Amino acid sequence of flavone synthase from *Perilla frutescens* var. *crispa* |
| 132 | Nucleic acid sequence coding for flavone synthase from *Perilla frutescens* var. *crispa* |
| 133 | Amino acid sequence of flavone synthase from *Dahlia pinnata* |
| 134 | Nucleic acid sequence coding for flavone synthase from *Dahlia pinnata* |
| 135 | Amino acid sequence of flavone synthase from *Callistephus chinensis* |
| 136 | Nucleic acid sequence coding for flavone synthase from *Callistephus chinensis* |
| 137 | Amino acid sequence of flavone synthase from *Apium graveolens* |
| 138 | Nucleic acid sequence coding for flavone synthase from *Apium graveolens* |
| 139 | Amino acid sequence of flavone synthase from *Medicago truncatula* |
| 140 | Nucleic acid sequence coding for flavone synthase from *Medicago truncatula* |
| 141 | Amino acid sequence of flavone synthase from *Cuminum cyminum* |
| 142 | Nucleic acid sequence coding for flavone synthase from *Cuminum cyminum* |
| 143 | Amino acid sequence of flavone synthase from *Aethusa cynapium* |
| 144 | Nucleic acid sequence coding for flavone synthase from *Aethusa cynapium* |
| 145 | Amino acid sequence of flavone synthase from *Conium maculatum* |
| 146 | Nucleic acid sequence coding for flavone synthase from *Conium maculatum* |
| 147 | Amino acid sequence of flavone synthase from *Camellia sinensis* |
| 148 | Nucleic acid sequence coding for flavone synthase from *Camellia sinensis* |
| 149 | Amino acid sequence of flavone synthase from *Saussurea medusa* |
| 150 | Nucleic acid sequence coding for flavone synthase from *Saussurea medusa* |
| 151 | Amino acid sequence of flavone synthase from *Plectranthus barbatus* |
| 152 | Nucleic acid sequence coding for flavone synthase from *Plectranthus barbatus* |
| 153 | Amino acid sequence of flavone synthase from *Scutellaria baicalensis* |

TABLE 1-continued

| SEQUENCE DESCRIPTION | |
|---|---|
| SEQ ID NO | Description |
| 154 | Nucleic acid sequence coding for flavone synthase from *Scutellaria baicalensis* |
| 155 | Amino acid sequence of flavone synthase from *Dorcoceras hygrometricum* |
| 156 | Nucleic acid sequence coding for flavone synthase from *Dorcoceras hygrometricum* |
| 157 | Amino acid sequence of flavone synthase from *Antirrhinum majus* |
| 158 | Nucleic acid sequence coding for flavone synthase from *Antirrhinum majus* |
| 159 | Amino acid sequence of flavone synthase from *Erythranthe lewisii* |
| 160 | Nucleic acid sequence coding for flavone synthase from *Erythranthe lewisii* |

EXAMPLES

Materials and Methods

Strains

The yeasts used in the examples were obtained from *Saccharomyces cerevisiae* FY1679-28A (Tettelin et al., 1995 doi.org/10.1016/S1067-2389 (06) 80008-7). This yeast is quadruply auxotrophic for uracil, tryptophan, histidine and leucine. The bacterial strains used in the examples were obtained from *Escherichia coli* MH1.

Standards

The standards were acquired from the supplier Extrasynthèse, France (naringenin, apigenin, eriodictyol, luteolin, hesperetin, hesperidin, diosmetin and diosmin).

Gene Cloning

The genes optimized to express in the yeast were synthesized by Eurofins Genomics, Ebersberg, Germany or Biomatik, Cambridge, Canada or Twist Biosciences, San Francisco, USA or DC Biosciences, Dundee, UK. By PCR, the gene cpr2 (SEQ ID NO: 26) from *S. cerevisiae* was amplified from the genomic DNA.

The genes obtained by synthesis or by PCR comprise at the 5' and 3' ends a BbsI (GAAGAC) or BsaI (GGTCTC) restriction site.

All the genes, promoters and terminators were restriction-cloned in the vector pSBK for expression in the yeast or in the vector pSB1K3 for expression in *E. coli*. The promoters and terminators (Wargner et al., 2015 DOI: 10.1016/j.fgb.2015.12.001) were recovered by PCR from the genomic DNA of the yeast *S. cerevisiae* or of *E. coli*.

The vector pSBK comprises a URA or LEU or TRP or HIS selection marker for the yeast and the vector pSB1K3 comprises a kanamycin-resistance marker.

Culture Conditions

The strains were cultivated in 1 ml of minimum nitrogen base medium (Dutscher, Brumath, Fr) supplemented with glucose at 20 g/l for the yeasts and in 1 ml of M9 supplemented with glucose at 4 $g \cdot l^{-1}$ for *E. coli* in 24-well plates (Starlab, Orsay, Fr) at 30° C. for 72 hours with continuous stirring at 200 rpm. In certain cases, naringenin or apigenin was added at a concentration of 100 $mg \cdot l^{-1}$ to determine the activity of the F3'Hs, naringenin or eriodictyol was added at a concentration of 100 $mg \cdot l^{-1}$ to determine the activity of the FNSIIs, eriodictyol or luteolin was added at a concentration of 100 $mg \cdot l^{-1}$ to determine the activity of the METs, hesperetin or diosmetin was added at a concentration of 100 $mg \cdot l^{-1}$ to determine the activity of the GTs, and hesperetin 7-O-glucoside and/or diosmetin 7-O-glucoside was added to determine the activity of the RHMs and RHATs.

Each strain was inoculated at an OD of 0.2 using a 24-hour preculture cultivated under the same conditions.

Analytical Method

Preparation of the samples: The 1 mL cultures are frozen at −80° C. and then lyophilized for 12 hours at 0.10 mbar. The samples are then taken up in 1 mL of dimethyl sulfoxide (DMSO), stirred for 30 seconds at 1000 rpm and then centrifuged for 5 minutes at 3000 rpm at room temperature. After centrifugation, a known volume of supernatant is added to a known volume of a mixture of internal standards dissolved in methanol.

The final concentrations of the internal standards are:

Diosmin C13 0.5 mg/L

Diosmetin C13 0.015 mg/L

Analysis by UHPLC-TQ: The samples were analysed using a Vanquish-H UHPLC machine (Thermo) coupled to a Quantis triple-quadrupole MS (Thermo). The column is a Waters Acquity UPLC® USST3 column (8 μm 2.1×100 mm) combined with an HSST3 1.8 μm 2.1×5 mm precolumn.

The mobile phase A is a 0.1% solution of formic acid in LC/MS-grade water and the mobile phase B is a 0.1% solution of formic acid in pure LC/MS-grade acetonitrile. The column temperature is 50° C. and the temperature of the sample changer is 10° C.

Two chromatographic conditions were used for detecting the flavonoids of interest:

TABLE 2

| Chromatographic conditions method 1 | | | |
|---|---|---|---|
| Time (min) | Flow rate (ml/min) | Mobile phase A (%) | Mobile phase B (%) |
| 0 | 0.5 | 73 | 27 |
| 8 | 0.5 | 73 | 27 |

TABLE 3

| Chromatographic conditions method 2 | | | |
|---|---|---|---|
| Time (min) | Flow rate (ml/min) | Mobile phase A (%) | Mobile phase B (%) |
| 0 | 0.5 | 83 | 17 |
| 3.75 | 0.5 | 83 | 17 |
| 4 | 0.5 | 73 | 27 |
| 8.5 | 0.5 | 73 | 27 |
| 11.0 | 0.5 | 50 | 50 |
| 13.0 | 0.5 | 0 | 100 |
| 13.5 | 0.5 | 83 | 17 |
| 15.0 | 0.5 | 83 | 17 |

The ions monitored and the fragmentation conditions for the molecules of interest are:

TABLE 4

| For method 1 | | | | | | | |
|---|---|---|---|---|---|---|---|
| Molecules | Retention time (min) | Polarity | Precursor ion | Daughter ion | Collision energy | Lens RF (V) | Reference internal standard |
| Naringenin | 3.3 | Negative | 271.0 | 119.0 | 27 | 169 | Diosmetin |
| | | | | 150.9 | 18 | 169 | C13 |
| Apigenin | 3.5 | Negative | 269.0 | 117.1 | 35 | 201 | Diosmetin |
| | | | | 150.9 | 24 | 201 | C13 |
| Eriodictyol | 1.9 | Negative | 287.1 | 135.1 | 26 | 147 | Diosmetin |
| | | | | 150.9 | 14 | 147 | C13 |
| Luteolin | 2.1 | Negative | 285.0 | 133.0 | 34 | 213 | Diosmetin C13 |

TABLE 5

| For method 2 | | | | | | | |
|---|---|---|---|---|---|---|---|
| Molecules | Retention time (min) | Polarity | Precursor ion | Daughter ion | Collision energy | Lens RF (V) | Reference internal standard |
| Naringenin | 7.8 | Negative | 271.0 | 119.0 | 27 | 169 | Diosmetin |
| | | | | 150.9 | 18 | 169 | C13 |
| Apigenin | 8.2 | Negative | 269.0 | 117.1 | 35 | 201 | Diosmetin |
| | | | | 150.9 | 24 | 201 | C13 |
| Eriodictyol | 6.2 | Negative | 287.1 | 135.1 | 26 | 147 | Diosmetin |
| | | | | 150.9 | 14 | 147 | C13 |
| Luteolin | 6.6 | Negative | 285.0 | 133.0 | 34 | 213 | Diosmetin |
| | | | | 150.9 | 25 | 213 | C13 |
| Hesperetin | 8.7 | Negative | 301.0 | 164.0 | 24 | 169 | Diosmetin |
| | | | | 150.9 | 17 | 169 | C13 |
| Diosmetin | 9.1 | Negative | 299.0 | 256.0 | 30 | 192 | Diosmetin |
| | | | | 284.1 | 21 | 192 | C13 |
| Hesperetin 7-O-glucoside | 4.9 | Negative | 463.2 | 286.0 | 32 | 141 | Diosmin |
| | | | | 301.1 | 15 | 141 | C13 |
| Hesperidin | 3.9 | Negative | 609.2 | 286.0 | 42 | 211 | Diosmin |
| | | | | 301.1 | 25 | 211 | C13 |
| Diosmetin 7-O-glucoside | 5.0 | Negative | 461.1 | 284.0 | 36 | 194 | Diosmin |
| | | | | 299.1 | 10 | 194 | C13 |
| Diosmin | 4.0 | Negative | 607.2 | 284.0 | 50 | 274 | Diosmin |
| | | | | 299.0 | 25 | 274 | C13 |

F3'H

Constructs for each of the F3'Hs were made in a vector bearing the URA selection marker (Table 6). Constructs including each SAM2 and only one of the various CPRs were created in a vector bearing the LEU selection marker (Table 7). Two vectors including only the URA or LEU selection marker were also created as controls. The marker genes make it possible to detect and to select the cells that have incorporated the gene of interest.

TABLE 6

| List of the various F3'H constructs tested | | |
|---|---|---|
| Names | Assembled genes | Markers |
| FL 23 | F3'H from *Perilla frutescens* var. *crispa* (SEQ ID NO: 2) | URA |
| FL 24 | F3'H from *Phanerochaete chrysosporium* (SEQ ID NO: 4) | URA |
| FL 25 | F3'H from *Petunia* x *hybrida* (SEQ ID NO: 6) | URA |
| FL 26 | F3'H from *Callistephus chinensis* (SEQ ID NO: 8) | URA |
| FL 27 | F3'H from *Callistephus chinensis* (SEQ ID NO: 10) | URA |

TABLE 6-continued

| List of the various F3'H constructs tested | | |
|---|---|---|
| Names | Assembled genes | Markers |
| FL 28 | F3'H from *Gerbera hybrida* (SEQ ID NO: 12) | URA |
| FL 29 | F3'H from *Osteospermum hybrid cultivar* (SEQ ID NO: 14) | URA |
| FL 30 | F3'H from *Citrus clementina* (SEQ ID NO: 16) | URA |
| FL 31 | F3'H from *Citrus sinensis* (SEQ ID NO: 18) | URA |
| FL 32 | F3'H from *Pilosella officinarum* (SEQ ID NO: 20) | URA |
| FL 1031 | F3'H from *Arabidopsis thaliana* (SEQ ID NO: 122) | URA |
| TT URA | — | URA |

TABLE 7

| List of constructs made with the various CPRs | | |
|---|---|---|
| Names | Assembled genes | Markers |
| FL 121 (CPR + SAM) | CPR from *Catharanthus roseus* (SEQ ID NO: 24), SAM from *Saccharomyces cerevisiae* (SEQ ID NO: 82) | LEU |

TABLE 7-continued

List of constructs made with the various CPRs

| Names | Assembled genes | Markers |
|---|---|---|
| FL 274 (CPR + SAM) | chimeric CPR (SEQ ID NO: 28), SAM from *Saccharomyces cerevisiae* (SEQ ID NO: 82) | LEU |
| FL 275 (ATR + SAM) | ATR from *Arabidopsis thaliana* (SEQ ID NO: 30), SAM from *Saccharomyces cerevisiae* (SEQ ID NO: 82) | LEU |
| FL 401 (CPR + SAM) | CPR from *Saccharomyces cerevisiae* (SEQ ID NO: 26), SAM from *Saccharomyces cerevisiae* (SEQ ID NO: 82) | LEU |
| FL 463 (ATR + SAM) | ATR from *Arabidopsis thaliana* (SEQ ID NO: 32), SAM from *Saccharomyces cerevisiae* (SEQ ID NO: 82) | LEU |
| TT LEU | — | LEU |

Several strains were created with, respectively, all the F3'Hs listed in Table 6 so that they could each be tested with the constructs of Table 7.

These various assemblies make it possible to check the enzymatic activity of the F3'Hs and also make it possible to determine the most efficient F3'H-CPR pairs.

For example, the strain FL 405 contains the constructs FL 26 and FL 401.

The control strain (without the genes) containing the constructs TT URA and TT LEU is called CF235.

FNSII

For each of the following FNSIIs, constructs in a TRP vector were prepared (Table 8). The same vectors with the LEU selection marker each containing SAM2 and a different CPR were used to test the FNSIIs (Table 9).

TABLE 8

Constructs including the various FNSIIs tested

| Names | Assembled genes | Markers |
|---|---|---|
| FL 620 (TAL + 4CL + CHS + CHI + FNSII) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Lonicera japonica* (SEQ ID NO: 34) | TRP |
| FL 621 (TAL + 4CL + CHS + CHI + FNSII) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Lonicera macranthoides* (SEQ ID NO: 36) | TRP |
| FL 112 (TAL + 4CL + CHS + CHI + FNSII) | TAL from *Flavobacetrium jonhsoniae* (SEQ ID NO: 40), 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Petroselinum crispum* (SEQ ID NO: 38) | TRP |
| TT TRP | — | TRP |

TABLE 9

List of constructs made with the various CPRs

| Names | Assembled genes | Markers |
|---|---|---|
| FL 121 (CPR + SAM) | CPR from *Catharanthus roseus* (SEQ ID NO: 24), SAM from *Saccharomyces cerevisiae* (SEQ ID NO: 82) | LEU |

TABLE 9-continued

List of constructs made with the various CPRs

| Names | Assembled genes | Markers |
|---|---|---|
| FL 274 (CPR + SAM) | Chimeric CPR (SEQ ID NO: 28), SAM from *Saccharomyces cerevisiae* (SEQ ID NO: 82) | LEU |
| FL 275 (ATR + SAM) | ATR from *Arabidopsis thaliana* (SEQ ID NO: 30), SAM from *Saccharomyces cerevisiae* (SEQ ID NO: 82) | LEU |
| FL 401 (CPR + SAM) | CPR from *Saccharomyces cerevisiae* (SEQ ID NO: 26), SAM from *Saccharomyces cerevisiae* (SEQ ID NO: 82) | LEU |
| FL 463 (ATR + SAM) | ATR from *Arabidopsis thaliana* (SEQ ID NO: 32), SAM from *Saccharomyces cerevisiae* (SEQ ID NO: 82) | LEU |
| TT LEU | — | LEU |

Several strains were created with, respectively, each of the constructs of the FNSIIs listed in Table 8 and each of the constructs of the CPRs of Table 9.

These various assemblies make it possible to check the enzymatic activity of the FNSIIs and also make it possible to determine the most efficient FNSIIs.

For example, the strain SC 744 contains the constructs FL 620 and FL 401.

The control strain (without the genes) containing the constructs TT TRP and TT LEU is called CF234.

Similar constructs were made to test the FNSIIs of SEQ ID NOs: 127, 129, 131, 133, 135, 137, 139, 141, 143, 145, 147, 149, 151, 153, 155, 157 and 159.

Yeast Up to Eriodictyol/Luteolin

Strains including the pathway up to eriodictyol and luteolin were also tested:

- the strain SC1500 comprises the constructs FL 26, FL 602, FL 808 and FL 822;
- the strain SC2424 comprising the constructs FL 1031+FL 602+FL 822+TT HIS;
- the strain SC2425 comprising the constructs FL 26+FL 602+FL 822+TT HIS;
- the strain SC2426 comprising the constructs FL 31+FL 602+FL 822+TT HIS;
- the strain SC2427 comprises the constructs FL 1031, FL 602, FL 808 and FL 822; and
- the strain SC2428 comprising the constructs FL 31+FL 602+FL 808+FL 822.

TABLE 10

Lists of constructs used for the strains including the pathway up to eriodictyol and luteolin

| Names | Assembled genes | Markers |
|---|---|---|
| FL 26 (F3'H) | F3'H from *Callistephus chinensis* (SEQ ID NO: 8) | URA |
| FL 1031 (F3'H) | F3'H from *Arabidopsis thaliana* (SEQ ID NO: 122) | URA |
| FL 31 (F3'H) | F3'H from *Citrus sinensis* (SEQ ID NO: 18) | URA |
| FL 602 (TAL + 4CL + CHS + CHI + FNS) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliana* (SEQ ID NO: 62) FNSII from *Petroselinum crispum* (SEQ ID NO: 38) | TRP |
| FL 808 (PAL + C4H) | PAL from *Arabidopsis thaliana* (SEQ ID NO: 78), C4H from *Arabidopsis thaliana* (SEQ ID NO: 80), | HIS |

TABLE 10-continued

Lists of constructs used for the strains including the pathway up to eriodictyol and luteolin

| Names | Assembled genes | Markers |
|---|---|---|
| FL 822 (CPR + CAF) | CPR from *Catharanthus roseus* (SEQ ID NO: 24), CAF from *Rhodopseudomonas palustris* (SEQ ID NO: 76) | LEU |
| TT HIS | | HIS |

The control strain (without the genes) containing the constructs TT URA, TT TRP, TT HIS and TT LEU is called CF237.

MET:

In order to test each of the METs, constructs were made and are presented in Table 11. The marker genes make it possible to detect and to select the cells that have incorporated the gene of interest.

TABLE 11

List of constructs made to test the various METs

| Names | Assembled genes | Markers |
|---|---|---|
| FL 121 (CPR + SAM) | CPR from *Catharanthus roseus* (SEQ ID NO: 24), SAM from *Saccharomyces cerevisiae* (SEQ ID NO: 82) | LEU |
| FL 266 (F3'H + MET) | F3'H from *Callistephus chinensis* (SEQ ID NO: 8), MET from *Arabidopsis thaliana* (SEQ ID NO: 88) | URA |
| FL 268 (F3'H + MET) | F3'H from *Callistephus chinensis* (SEQ ID NO: 8), MET from *Homo sapiens* (SEQ ID NO: 90) | URA |
| FL 469 (F3'H + MET) | F3'H from *Callistephus chinensis* (SEQ ID NO: 8) MET from *Citrus clementina* (SEQ ID NO: 118) | URA |
| FL 475 (F3'H + MET) | F3'H from *Callistephus chinensis* (SEQ ID NO: 8) MET from *Citrus sinensis* (SEQ ID NO: 120) | URA |

Four strains SC1612, SC1614, SC2147 and SC2151 were created, with FL 121 and FL 266 for SC1612, FL 121 and FL 268 for SC1614, FL 475 and FL 121 for SC2147 and FL 469 and FL 121 for SC2151 for the conversion of eriodictyol into hesperetin in order to determine which MET is the most efficient.

The control strain (without the genes) containing the constructs TT LEU and TT URA is called CF235.

F3'H, MET, FNS, CPR: Production of Diosmetin from Naringenin

TABLE 12

List of constructs used to test the enzymes in *Saccharomyces cerevisiae* (SC)

| Names | Assembled genes | Markers |
|---|---|---|
| FL 121 (CPR + SAM) | CPR from *Catharanthus roseus* (SEQ ID NO: 24), SAM from *Saccharomyces cerevisiae* (SEQ ID NO: 82) | LEU |
| TT LEU | — | LEU |
| FL_26 (F3'H) | F3'H from *Callistephus chinensis* (SEQ ID NO: 8), | URA |
| FL 1031 (F3'H) | F3'H from *Arabidopsis thaliana* (SEQ ID NO: 122), | URA |

TABLE 12-continued

List of constructs used to test the enzymes in *Saccharomyces cerevisiae* (SC)

| Names | Assembled genes | Markers |
|---|---|---|
| FL 1111 (FNS + MET) | FNSII from *Petroselinum crispum* (SEQ ID NO: 33) MET from *Citrus clementina* (SEQ ID NO: 118) | TRP |
| FL 1112 (FNS + MET) | FNSII from *Angelica archangelica* (SEQ ID NO: 128) MET from *Citrus clementina* (SEQ ID NO: 118) | TRP |
| FL 1113 (FNS + MET) | FNSII from *Cynara cardunculus* var. *scolymus* (SEQ ID NO: 130) MET from *Citrus clementina* (SEQ ID NO: 118) | TRP |
| FL 1114 (FNS + MET) | FNSII from *Perilla frutescens* var. *crispa* (SEQ ID NO: 132) MET from *Citrus clementina* (SEQ ID NO: 118) | TRP |
| FL 1115 (FNS + MET) | FNSII from *Dahlia pinnata* (SEQ ID NO: 134) MET from *Citrus clementina* (SEQ ID NO: 118) | TRP |
| FL 1116 (FNS + MET) | FNSII from *Petroselinum crispum* (SEQ ID NO: 33) MET from *Citrus sinensis* (SEQ ID NO: 120) | TRP |
| FL 1118 (FNS + MET) | FNSII from *Cynara cardunculus* var. *scolymus* (SEQ ID NO: 130) MET from *Citrus sinensis* (SEQ ID NO: 120) | TRP |
| FL 1119 (FNS + MET) | FNSII from *Perilla frutescens* var. *crispa* (SEQ ID NO: 132) MET from *Citrus sinensis* (SEQ ID NO: 120) | TRP |
| FL 1120 (FNS + MET) | FNSII from *Dahlia pinnata* (SEQ ID NO: 134) MET from *Citrus sinensis* (SEQ ID NO: 120) | TRP |

The following strains were constructed:

C2429: FL 1111+FL 1031+FL 121
SC2430: FL 1112+FL 1031+FL 121
SC2431: FL 1113+FL 1031+FL 121
SC2432: FL 1114+FL 1031+FL 121
SC2433: FL 1115+FL 1031+FL 121
SC2439: FL 1111+FL 1031+TT LEU
SC2440: FL 1112+FL 1031+TT LEU
SC2441: FL 1113+FL 1031+TT LEU
SC2442: FL 1114+FL 1031+TT LEU
SC2443: FL 1115+FL 1031+TT LEU
SC2434: FL 1116+FL 1031+FL 121
SC2436: FL 1118+FL 1031+FL 121
SC2437: FL 1119+FL 1031+FL 121
SC2438: FL 1120+FL 1031+FL 121
SC2444: FL 1116+FL 1031+TT LEU
SC2446: FL 1118+FL 1031+TT LEU
SC2447: FL 1119+FL 1031+TT LEU
SC2448: FL 1120+FL 1031+TT LEU
SC2449: FL 1111+FL 26+FL 121
SC2450: FL 1112+FL 26+FL 121
SC2451: FL 1113+FL 26+FL 121
SC2452: FL 1114+FL 26+FL 121
SC2453: FL 1115+FL 26+FL 121
SC2459: FL 1111+FL 26+TT LEU
SC2460: FL 1112+FL 26+TT LEU
SC2461: FL 1113+FL 26+TT LEU
SC2462: FL 1114+FL 26+TT LEU
SC2463: FL 1115+FL 26+TT LEU
SC2454: FL 1116+FL 26+FL 121

SC2456: FL 1118+FL 26+FL 121

SC2457: FL 1119+FL 26+FL 121

SC2458: FL 1120+FL 26+FL 121

SC2464: FL 1116+FL 26+TT LEU

SC2466: FL 1118+FL 26+TT LEU

SC2467: FL 1119+FL 26+TT LEU

SC2468: FL 1120+FL 26+TT LEU

The control strain (without the genes) containing the constructs TT URA, TT TRP, TT HIS and TT LEU is called CF237.

*E. coli* Up to Hesperetin/Diosmetin

TABLE 13

List of constructs used to test the enzymes in *E. coli*

| Names | Assembled genes |
|---|---|
| EC26 (SAM + MET) | SAM from *Saccharomyces cerevisiae* (SEQ ID NO: 82)<br>MET from *Homo sapiens* (SEQ ID NO: 90) |
| EC41 (SAM + MET) | SAM from *Saccharomyces cerevisiae* (SEQ ID NO: 82)<br>MET from *Citrus clementina* (SEQ ID NO: 118) |
| EC43 (SAM + MET) | SAM from *Saccharomyces cerevisiae* (SEQ ID NO: 82)<br>MET from *Citrus sinensis* (SEQ ID NO: 120) |
| EC30 (FNSII) | FNSII from *Petroselinum crispum* (SEQ ID NO: 38) |

Yeast Up to Hesperetin/Diosmetin

Three strains including the pathway up to hesperetin/diosmetin were also tested. The strain SC1508 comprises the constructs FL 121+FL 268+FL: 602+FL 808 of Table 14. The strain SC2408 comprises the constructs FL 121+FL 469+FL 602+FL 808 of Table 14. The strain SC2409 comprises the constructs FL 121+FL 475+FL 602+FL 808 of Table 14.

TABLE 14

List of constructs used in the examples

| Names | Assembled genes | Markers |
|---|---|---|
| FL 121 (CPR + SAM) | CPR from *Catharanthus roseus* (SEQ ID NO: 24),<br>SAM from *Saccharomyces cerevisiae* (SEQ ID NO: 82) | LEU |
| FL 268 (F3'H + MET) | F3'H from *Catllistephus chinensis* (SEQ ID NO: 8),<br>MET from *Homo sapiens* (SEQ ID NO: 90) | URA |
| FL 469 (F3'H + MET) | F3'H from *Callistephus chinensis* (SEQ ID NO: 8)<br>MET from *Citrus clementina* (SEQ ID NO: 118) | URA |
| FL 475 (F3'H + MET) | F3'H from *Callistephus chinensis* (SEQ ID NO: 8)<br>MET from *Citrus sinensis* (SEQ ID NO: 120) | URA |
| FL 602 (TAL + 4CL + CHS + CHI + FNSII) | TAL from *Rhodotorula glutinis* (SEQ ID NO: 42),<br>4CL from *Petroselinum crispum* (SEQ ID NO: 46),<br>CHS from *Citrus sinensis* (SEQ ID NO: 54),<br>CHI from *Arabidopsis thaliona* (SEQ ID NO: 62)<br>FNSII from *Petroselinum crispum* (SEQ ID NO: 38) | TRP |
| FL 808 (PAL + C4H) | PAL from *Arabidopsis thaliona* (SEQ ID NO: 78),<br>C4H from *Arabidopsis thaliona* (SEQ ID NO: 80), | HIS |
| TT LEU | — | LEU |
| TT URA | — | URA |
| TT TRP | — | TRP |
| TT HIS | — | HIS |

The control strain (without the genes) containing the constructs TT LEU, TT URA, TT TRP and TT HIS is called CF237.

GT

In order to test each of the GTs, constructs were made and are presented in Table 15. The marker genes make it possible to detect and to select the cells that have incorporated the gene of interest.

TABLE 15

List of constructs used to test the various GTs

| Names | Assembled genes | Markers |
|---|---|---|
| FL 545 (F3'H + MET + GT + RHM + RHAT) | F3'H from *Callistephus chinensis* (SEQ ID NO: 8),<br>MET from *Citrus sinensis* (SEQ ID NO: 120),<br>GT from *Arabidopsis thaliana* (SEQ ID NO: 92),<br>RHM from *Citrus sinensis* (SEQ ID NO: 108)<br>RHAT from *Citrus clementina* (SEQ ID NO: 104) | URA |
| FL 546 (F3'H + MET + GT + RHM + RHAT) | F3'H from *Callistephus chinensis* (SEQ ID NO: 8),<br>MET from *Citrus sinensis* (SEQ ID NO: 120),<br>GT from *Scutellaria baicalensis* (SEQ ID NO: 94),<br>RHM from *Citrus sinensis* (SEQ ID NO: 108)<br>RHAT from *Citrus clementina* (SEQ ID NO: 104) | URA |
| FL 547 (F3'H + MET + GT + RHM + RHAT) | F3'H from *Callistephus chinensis* (SEQ ID NO: 8),<br>MET from *Citrus sinensis* (SEQ ID NO: 120),<br>GT from *Scutellaria baicalensis* (SEQ ID NO: 96),<br>RHM from *Citrus sinensis* (SEQ ID NO: 108)<br>RHAT from *Citrus clementina* (SEQ ID NO: 104) | URA |
| FL 548 (F3'H + MET + GT + RHM + RHAT) | F3'H from *Callistephus chinensis* (SEQ ID NO: 8),<br>MET from *Citrus sinensis* (SEQ ID NO: 120),<br>GT from *Scutellaria baicalensis* (SEQ ID NO: 98),<br>RHM from *Citrus sinensis* (SEQ ID NO: 108<br>RHAT from *Citrus clementina* (SEQ ID NO: 104) | URA |
| FL 549 (F3'H + MET + GT + RHM + RHAT) | F3'H from *Callistephus chinensis* (SEQ ID NO: 8),<br>MET from *Citrus sinensis* (SEQ ID NO: 120),<br>GT from *Homo sapiens* (SEQ ID NO: 100),<br>RHM from *Citrus sinensis* (SEQ ID NO: 108)<br>RHAT from *Citrus clementina* (SEQ ID NO: 104) | URA |
| FL 550 (F3'H + MET + GT + RHM + RHAT) | F3'H from *Callistephus chinensis* (SEQ ID NO: 8),<br>MET from *Citrus sinensis* (SEQ ID NO: 120),<br>GT from *Homo sapiens* (SEQ ID NO: 102),<br>RHM from *Citrus sinensis* (SEQ ID NO: 108)<br>RHAT from *Citrus clementina* (SEQ ID NO: 104) | URA |
| FL 554 (F3'H + MET + GT + UDPRHA + RHAT) | F3'H from *Callistephus chinensis* (SEQ ID NO: 8),<br>MET from *Citrus sinensis* (SEQ ID NO: 120),<br>GT from *Citrus sinensis* (SEQ ID NO: 114),<br>UDPRHA from *Citrus sinensis* (SEQ ID NO: 108),<br>RHAT from *Citrus clementina* (SEQ ID NO: 104) | URA |
| FL 556 (F3'H + MET + GT + UDPRHA + RHAT) | F3'H from *Callistephus chinensis* (SEQ ID NO: 8),<br>MET from *Citrus sinensis* (SEQ ID NO: 120),<br>GT from *Citrus clementina* (SEQ ID NO: 116),<br>UDPRHA from *Citrus sinensis* (SEQ ID NO: 108),<br>RHAT from *Citrus clementina* (SEQ ID NO: 104) | URA |
| TT URA | — | URA |

The various constructs with the various GTs make it possible to check the enzymatic activity of the GTs and also make it possible to determine the most efficient GTs.

The control strain (without the genes) containing the construct TT URA is called CF233.

RHM

In order to test each of the RHMs, constructs were made and are presented in Table 16.

TABLE 16

| List of constructs used to test the various RHMs | | |
|---|---|---|
| Names | Assembled genes | Markers |
| FL 545 (F3'H + MET + GT + RHM + RHAT) | F3'H from *Callistephus chinensis* (SEQ ID NO: 8), MET from *Citrus sinensis* (SEQ ID NO: 120), GT from *Arabidopsis thaliana* (SEQ ID NO: 98), RHM from *Citrus sinensis* (SEQ ID NO: 108), RHAT from *Citrus clementina* (SEQ ID NO: 104) | URA |
| FL 512 (F3'H + MET + GT + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 98), RHM from *Arabidopsis thaliana* (SEQ ID NO: 110), RHAT from *Citrus clementina* (SEQ ID NO: 104) | URA |
| TT URA | — | URA |

The various constructs with the various RHMs make it possible to check the enzymatic activity of the RHMs and also make it possible to determine the most efficient RHMs.

The control strain (without the genes) containing the construct TT URA is called CF233.

RHAT

In order to test each of the RHATs, constructs were made and are presented in Table 17.

TABLE 17

| List of constructs used to test the various RHATs | | |
|---|---|---|
| Names | Assembled genes | Markers |
| FL 512 (F3'H + MET + GT3 + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 92), RHM from *Arabidopsis thaliana* (SEQ ID NO: 110) RHAT from *Citrus clementina* (SEQ ID NO: 104) | URA |
| FL 165 (F3'H + MET + GT + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 92), RHM from *Arabidopsis thaliana* (SEQ ID NO: 110) RHAT from *Citrus sinensis* (SEQ ID NO: 106) | URA |
| TT URA[2] | — | URA |

The various assemblies made with the various RHATs make it possible to check the enzymatic activity of the RHATs and also make it possible to determine the most efficient RHATs.

The control strain (without the genes) containing the construct TT URA is called CF233.

*E. coli* Up to Hesperidin/Diosmin

TABLE 18

| List of strains created to test the pathway in *E. coli* | |
|---|---|
| Names | Assembled genes |
| EC38 (GT + RHM + RHAT) | GT from *Arabidopsis thaliona* (SEQ ID NO: 92), RHM from *Citrus sinensis* (SEQ ID NO: 108) RHAT from *Citrus clementina* (SEQ ID NO: 104) |
| EC45 (GT + UDPRHA + RHAT) | GT from *Citrus sinensis* (SEQ ID NO: 114), UDPRHA from *Citrus sinensis* (SEQ ID NO: 108), RHAT from *Citrus clementina* (SEQ ID NO: 104) |
| EC47 (GT + UDPRHA + RHAT) | GT from *Citrus clementina* (SEQ ID NO: 116), UDPRHA from *Citrus sinensis* (SEQ ID NO: 108), RHAT from *Citrus clementina* (SEQ ID NO: 104) |

Yeast Up to Hesperidin/Diosmin

Nine strains including the full pathway were also created.

The strain SC1509 comprises the constructs FL 121+FL 511+FL 602+FL 808.

The strain SC1530 comprises the constructs FL 121+FL 603+FL 602+FL 808.

The strain SC1529 comprises the constructs FL 121+FL 554+FL 602+FL 808.

The strain SC1568 comprises the constructs FL 121+FL 556+FL 602+FL 808.

The strain SC2410 comprises the constructs FL 121+FL 1100+FL 602+FL 808.

The strain SC1579 comprises the constructs FL 401+FL 547+FL 602+FL 828.

The strain SC1584 comprises the constructs FL 401+FL 554+FL 602+FL 828.

The strain SC1621 comprises the constructs FL 401+FL 556+FL 602+FL 828.

The strain SC1626 comprises the constructs FL 401+FL 603+FL 602+FL 828.

TABLE 19

| Lists of constructs used to create the strains up to hesperidin/diosmin | | |
|---|---|---|
| Names | Assembled genes | Markers |
| FL 121 (CPR + SAM) | CPR from *Catharanthus roseus* (SEQ ID NO: 24), SAM from *Saccharomyces cerevisiae* (SEQ ID NO: 82) | LEU |
| FL 401 (CPR + SAM) | CPR from *Saccharomyces cerevisiae* (SEQ ID NO: 26), SAM from *Saccharomyces cerevisiae* (SEQ ID NO: 82) | LEU |
| FL 547 (F3'H + MET + GT + RHM + RHAT) | F3'H from *Callistephus chinensis* (SEQ ID NO: 8), MET from *Citrus sinensis* (SEQ ID NO: 120), GT from *Scutellaria baicalensis* (SEQ ID NO: 96), RHM from *Citrus sinensis* (SEQ ID NO: 108) RHAT from *Citrus clementina* (SEQ ID NO: 104) | URA |
| FL 511 (F3'H + MET + GT + RHM + RHAT) | F3'H from *Callistephus chinensis* (SEQ ID NO: 8), MET from *Homo sapiens* (SEQ ID NO: 90), GT from *Arabidopsis thaliana* (SEQ ID NO: 92), RHM from *Citrus sinensis* (SEQ ID NO: 108) RHAT from *Citrus clementina* (SEQ ID NO: 104) | URA |
| FL 603 (F3'H + MET + GT + UDPRHA + RHAT) | F3'H from *Callistephus chinensis* (SEQ ID NO: 8), MET from *Citrus clementina* (SEQ ID NO: 118), GT from *Citrus sinensis* (SEQ ID NO: 114), UDPRHA from *Citrus sinensis* (SEQ ID NO: 108), RHAT from *Citrus clementina* (SEQ ID NO: 104) | URA |
| FL 554 (F3'H + MET + GT + UDPRHA + RHAT) | F3'H from *Callistephus chinensis* (SEQ ID NO: 8), MET from *Citrus sinensis* (SEQ ID NO: 120), GT from *Citrus sinensis* (SEQ ID NO: 114), UDPRHA from *Citrus sinensis* (SEQ ID NO: 108), RHAT from *Citrus clementina* (SEQ ID NO: 104) | URA |

TABLE 19-continued

| Lists of constructs used to create the strains up to hesperidin/diosmin | | |
|---|---|---|
| Names | Assembled genes | Markers |
| FL 556 (F3'H + MET + GT + UDPRHA + RHAT) | F3'H from *Callistephus chinensis* (SEQ ID NO: 8), MET from *Citrus sinensis* (SEQ ID NO: 120), GT from *Citrus clementina* (SEQ ID NO: 116), UDPRHA from *Citrus sinensis* (SEQ ID NO: 108), RHAT from *Citrus clementina* (SEQ ID NO: 104) | URA |
| FL 1100 (F3'H + MET + GT + UDPRHA + RHAT) | F3'H from *Callistephus chinensis* (SEQ ID NO: 8), MET from *Citrus clementina* (SEQ ID NO: 118), GT from *Citrus clementina* (SEQ ID NO: 116), UDPRHA from *Citrus sinensis* (SEQ ID NO: 108), RHAT from *Citrus clementina* (SEQ ID NO: 104) | URA |
| FL 602 (TAL + 4CL + CHS + CHI + FNS) | TAL from *Rhodotorula glutinis* (SEQ ID NO: 42), 4CL from *Petroselinum crispum* (SEQ ID NO: 46), CHS from *Citrus sinensis* (SEQ ID NO: 54), CHI from *Arabidopsis thaliona* (SEQ ID NO: 62) FNSII from *Petroselinum crispum* (SEQ ID NO: 38) | TRP |
| FL 808 (PAL + C4H) | PAL from *Arabidopsis thaliona* (SEQ ID NO: 78), C4H from *Arabidopsis thaliona* (SEQ ID NO: 80), | HIS |
| FL 828 (PAL + C4H) | PAL from *Citrus sinensis* (SEQ ID NO: 66), C4H from *Arabidopsis thaliona* (SEQ ID NO: 80), | HIS |
| TT LEU | — | LEU |
| TT URA | — | URA |
| TT TRP | — | TRP |
| TT HIS | — | HIS |

The control strain (without the genes) containing the constructs TT LEU, TT URA, TT TRP and TT HIS is called CF237.

Results

F3'H

Tables 20 and 21 below show the production of eriodictyol (Table 20) and of luteolin (Table 21) obtained by cultivating the strains comprising the F3'Hs listed in Table 6 and the constructs of Table 7, in the presence of naringenin and apigenin, respectively.

TABLE 20

| Concentration of eriodictyol (in mg · $l^{-1}$) | | | | | | |
|---|---|---|---|---|---|---|
| F3'H (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 2 (FL23) | 35.5 ± 2.9 | 42.1 ± 4.3 | 49.9 ± 4.2 | 43.6 ± 4.2 | 38.8 ± 4.1 | 43.3 ± 5.1 |
| 4 (FL24) | 1 ± 0.8 | 6.4 ± 0.5 | 4.0 ± 0.5 | 4.7 ± 0.3 | 5.1 ± 0.4 | 5.3 ± 0.4 |
| 6 (FL25) | 115.2 ± 3.2 | 76.8 ± 4.2 | 42.3 ± 2.6 | 70.2 ± 8.6 | 71.1 ± 8.7 | 71.3 ± 7.4 |
| 8 (FL26) | 108.3 ± 4.0 | 71.1 ± 7.1 | 89.2 ± 9.5 | 87.4 ± 5.0 | 75.8 ± 5.2 | 90.0 ± 6.1 |
| 10 (FL27) | 28.8 ± 1.2 | 57.7 ± 2.6 | 69.3 ± 10.6 | 79.1 ± 4.2 | 52.3 ± 0.5 | 69.7 ± 2.3 |
| 12 (FL28) | 108.0 ± 2.0 | 7.0 ± 1.4 | 9.1 ± 5.9 | 4.6 ± 0.3 | 7.4 ± 2.8 | 9.2 ± 0.6 |
| 14 (FL29) | 119.9 ± 1.1 | 39.9 ± 4.7 | 56.1 ± 16.3 | 64.8 ± 4.1 | 36.8 ± 4.4 | 46.1 ± 5.5 |
| 16 (FL30) | <QL | 76.3 ± 2.6 | 70.9 ± 6.2 | 70.4 ± 4.4 | 58.5 ± 10.9 | 76.9 ± 1.7 |
| 18 (FL31) | 107.3 ± 8.0 | 82.3 ± 17.2 | 102.2 ± 7.1 | 98.8 ± 5.9 | 96.6 ± 4.7 | 101.3 ± 4.0 |
| 20 (FL32) | 33.7 ± 4.0 | 68.9 ± 2.7 | 81.5 ± 3.4 | 63.6 ± 3.7 | 69.5 ± 0.9 | 69.7 ± 1.1 |
| 122 (FL1031) | 4.8 ± 0.3 | 60.5 ± 3.4 | 34.4 ± 2.8 | 25.8 ± 5.8 | 59.0 ± 1.7 | 40.0 ± 9.5 |

QL: below the quantification limit

The various strains are indeed capable of producing eriodictyol from naringenin, in different concentrations according to the F3'Hs and the CPR used (see FIG. 2).

TABLE 21

| Concentration of luteolin (in mg · $l^{-1}$) | | | | | | |
|---|---|---|---|---|---|---|
| F3'H (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 2 (FL23) | 3.5 ± 0.1 | 11.7 ± 0.7 | 9.1 ± 2.1 | 11.01 ± 0.4 | 10.8 ± 1.7 | 10.2 ± 1.4 |
| 4 (FL24) | <QL | <QL | <QL | <QL | <QL | <QL |
| 6 (FL25) | 10.2 ± 0.9 | 12.8 ± 0.7 | 7.8 ± 1.4 | 11.9 ± 0.8 | 10.1 ± 1.2 | 12.9 ± 1.4 |
| 8 (FL26) | 9.5 ± 0.4 | 13.2 ± 1.1 | 8.2 ± 0.7 | 10.9 ± 0.7 | 12.2 ± 0.4 | 12.1 ± 0.7 |
| 10 (FL27) | <QL | 2.5 ± 0.3 | <QL | 0.5 ± 0 | 2.7 ± 0.1 | 2.77 ± 0.4 |
| 12 (FL28) | 12.1 ± 0.4 | 13.3 ± 1.2 | 14.7 ± 1.8 | 14.1 ± 1.7 | 12.5 ± 3.8 | 15.3 ± 0.9 |
| 14 (FL29) | 1.5 ± 0.1 | 0.6 ± 0.04 | 1.1 ± 0.2 | 0.8 ± 0.03 | 0.7 ± 0.06 | 1.0 ± 0.08 |
| 16 (FL30) | 0.5 ± 0.02 | 1.3 ± 0.1 | 2.5 ± 1.5 | 1.6 ± 0.1 | 1.5 ± 0.5 | 2.0 ± 0.1 |
| 18 (FL31) | 12.2 ± 0.7 | 13.2 ± 0.8 | 13.7 ± 1.2 | 12.7 ± 0.4 | 14.0 ± 1.8 | 12.7 ± 0.6 |
| 20 (FL32) | 1.2 ± 0.2 | 9.9 ± 1.4 | 2.8 ± 0.4 | 4.3 ± 0.1 | 11.0 ± 0.9 | 9.3 ± 1.8 |
| 122 (FL1031) | 0.4 ± 0.1 | 10.9 ± 0.1 | 3.0 ± 0.6 | 3.0 ± 0.9 | 11.4 ± 0.4 | 9.5 ± 1.6 |

QL: below the quantification limit

The various strains are indeed capable of producing luteolin from apigenin, in different concentrations according to the F3'Hs and the CPR used (see FIG. 3).

FNS

Tables 22 and 23 below show the production of apigenin (Table 22) and of luteolin (Table 23) obtained by cultivating the strains comprising the FNSIIs listed in Table 8 and the constructs of Table 9, in the presence of naringenin and eriodictyol, respectively.

TABLE 22

| Concentration of apigenin (in mg · $l^{-1}$) | | | | | | |
|---|---|---|---|---|---|---|
| FNSII (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 34 (FL620) | 11.6 ± 0.3 | 34.7 ± 1.0 | 47.6 ± 5.7 | 37.7 ± 1.6 | 50.5 ± 1.5 | 51.3 ± 3.4 |
| 36 (FL621) | 3.5 ± 0.1 | 35.6 ± 0.2 | 14.9 ± 1.3 | 16.4 ± 1.4 | 29.8 ± 3.9 | 33.2 ± 1.5 |
| 38 (FL112) | 2.9 ± 0.1 | 40.7 ± 1.2 | 41.4 ± 1.5 | 34.2 ± 1.7 | 38.0 ± 0.9 | 43.5 ± 0.0 |

TABLE 23

| Concentration of luteolin (in mg · $l^{-1}$) | | | | | | |
|---|---|---|---|---|---|---|
| FNSII (SEQ ID No) | WITHOUT CPR (TT LEU) | CPR (SEQ ID No 24; FL121) | CPR (SEQ ID No 26; FL401) | CPR (SEQ ID No 28; FL274) | ATR (SEQ ID No 30; FL275) | ATR (SEQ ID No 32; FL463) |
| 34 (FL620) | 2.5 ± 0.2 | 1.4 ± 0.3 | 7.8 ± 1.4 | 4.5 ± 0.9 | 4.5 ± 2.9 | 8.5 ± 0.8 |
| 36 (FL621) | 0.2 ± 0.2 | 1.5 ± 0.1 | 1.3 ± 0.2 | 0.9 ± 0.1 | 1.3 ± 0.3 | 1.2 ± 0.2 |
| 38 (FL112) | 0.2 ± 0.0 | 4.5 ± 1.9 | 2.3 ± 0.5 | 2.6 ± 1.2 | 1.4 ± 0.0 | 1.6 ± 0.0 |

The various strains are indeed capable of producing apigenin and luteolin from naringenin and eriodictyol, in different concentrations according to the FNS used (FIGS. 4 and 5).

Similar results were obtained with the FNSIIs of SEQ ID NOs: 127, 129, 131, 133, 135, 137, 139, 141, 143, 145, 147, 149, 151, 153, 155, 157 and 159.

F3'H, MET, FNS, CPR: Production of Diosmetin from Naringenin

The results for the production of diosmetin from naringenin by the strains SC2429 to SC2434, SC2436 to SC2444, SC2446 to SC2454, SC2456 to SC2464 and SC2466 to SC2468 are presented in FIG. 29.

All the strains are capable of producing diosmetin from naringenin. The production of diosmetin is largely increased by adding a CPR.

Yeast Up to Eriodictyol/Luteolin

The strains SC2424, SC2425, SC2426, SC2427, SC1500 and SC2428 contain all the enzymes of the pathway up to eriodictyol and luteolin and are capable of producing luteolin and eriodictyol from glucose.

The results for the strain SC1500 correspond to FIG. 6, in which the eriodictyol and luteolin peaks are observed. Similar results are obtained for the strains SC2424, SC2425, SC2426, SC2427 and SC2428. The production of eriodictyol and of luteolin for each of the strains SC2424, SC2425, SC2426, SC2427, SC1500 and SC2428 is presented in FIG. 19.

It should be noted that the addition of the enzymes PAL and C4H to the biosynthetic pathway makes it possible to obtain markedly higher eriodictyol and luteolin concentrations. These concentrations may be up to six times higher than the concentrations obtained with the strains containing the same enzymes with the exception of PAL and C4H (cf. FIG. 19, for example by comparing the strain SC2425 without PAL/C4H and the strain SC1500 with PAL/C4H or the strain SC2426 without PAL/C4H and the strain SC2428 with PAL/C4H).

MET

The results for the production of hesperetin and diosmetin from eriodictyol and luteolin by the strains SC1612, SC1614, SC2147 and SC2151 are presented, respectively, in FIGS. 7, 8, 20 and 21.

The yeast strains SC1612, SC1614, SC2147 and SC2151 are indeed capable of producing hesperetin and/or diosmetin.

Starting with eriodictyol, the strains SC2147, SC2151 and SC1612 are capable of specifically producing hesperetin, i.e. of specifically methylating the hydroxyl in position 4' of eriodictyol (FIG. 20). The strain SC1614 produces, for its part, a mixture of hesperetin and of homoeriodictyol.

In a noteworthy manner, the strain SC2151 is moreover capable of producing about 40 mg/L of hesperetin (FIG. 20). The strains SC2147, SC1612 and SC1614, for their part, are capable of producing diosmetin from luteolin (FIG. 21).

FNSII

The results for the production of diosmetin from hesperetin by the strain SC744 are presented in FIG. 9.

The yeast strain SC744 is indeed capable of producing diosmetin from hesperetin.

*E. coli* Up to Hesperetin/Diosmetin

The results for the production of hesperetin from eriodictyol by the strains EC26, EC41 and EC43 are presented in FIGS. 10, 22 and 23 and the production of diosmetin from luteolin by the strains EC26 and EC43 are presented in FIGS. 11 and 24.

The *E. coli* strains EC26, EC41 and EC43 are indeed capable of producing hesperetin and/or diosmetin.

The results for the production of diosmetin from hesperetin by the strain EC30 are presented in FIG. 12.

The *E. coli* strain EC30 is indeed capable of producing diosmetin from hesperetin.

Yeast Up to Hesperetin/Diosmetin

The results for the production of hesperetin and diosmetin from glucose by the strains SC1508, SC2408 and SC2409 are presented in FIGS. 13, 25 and 26.

The yeast strains SC1508, SC2408 and SC2409 containing all the enzymes of the pathway up to hesperetin and diosmetin are capable of producing hesperetin and/or diosmetin from glucose (FIG. 27). In a noteworthy manner, the strain SC2408 produces about 25 mg/L of hesperetin and about 5 mg/L of diosmetin.

GT

TABLE 24

Concentration of hesperetin, hesperetin 7-O-glucoside and hesperidin according to the GTs used (in mg · $l^{-1}$)

| | Hesperetin | Hesperetin 7-O-glucoside | Hesperidin |
|---|---|---|---|
| medium | 90 ± 8.1 | N/D | N/D |
| Control - | 84.2 ± 4.6 | N/D | N/D |
| FL 545 - GT SEQ ID No 92 | 59.2 ± 1.1 | 7.1 ± 0.2 | 70.4 ± 2.2 |
| FL 546 - GT SEQ ID No 94 | 85.1 ± 1.4 | N/D | 22.2 ± 1.2 |
| FL 547 - GT SEQ ID No 96 | N/D | 6 ± 0.5 | 109.9 ± 4.8 |
| FL 548 - GT SEQ ID No 98 | 46.7 ± 2.4 | N/D | 71.9 ± 2.1 |
| FL 554 - GT SEQ ID No 114 | 46.7 ± 1.7 | // | 70.4 ± 5.0 |
| FL 556 - GT SEQ ID No 116 | 107.0 ± 3.0 | // | 11.3 ± 1.1 |

// amount not determined

TABLE 25

Concentration of diosmetin, diosmetin 7-O-glucoside and diosmin according to the GTs used (in mg · $l^{-1}$)

| | Diosmetin | Diosmetin 7-O-glucoside | Diosmin |
|---|---|---|---|
| medium | 82.1 ± 3.9 | N/D | N/D |
| Control - | 75.3 ± 6.1 | N/D | N/D |
| FL 545 - GT SEQ ID No 92 | 67.1 ± 2.6 | N/D | 21.8 ± 0.4 |
| FL 546 - GT SEQ ID No 94 | 61.9 ± 3.3 | N/D | 23.2 ± 3.2 |
| FL 547 - GT SEQ ID No 96 | 2.4 ± 0.4 | 7.1 ± 0.5 | 122.8 ± 8.5 |
| FL 548 - GT SEQ ID No 98 | 17.7 ± 0.7 | N/D | 76 ± 4.1 |
| FL 554 - GT SEQ ID No 114 | 61.4 ± 4.2 | 7.1 ± 1.1 | 108.5 ± 8.3 |
| FL 556 - GT SEQ ID No 116 | 138.6 ± 3.5 | N/D | N/D |

The various strains are indeed capable of producing hesperidin and/or diosmin from hesperetin and diosmetin, in different concentrations according to the GT used.

RHM

TABLE 26

Concentration of hesperetin, hesperetin 7-O-glucoside and hesperidin according to the RHMs used (in mg · $l^{-1}$)

| | Hesperetin | Hesperetin 7-O-glucoside | Hesperidin |
|---|---|---|---|
| medium | 90 ± 8.1 | N/D | N/D |
| Control - | 84.2 ± 4.6 | N/D | N/D |
| FL 545 - RHM SEQ ID No 108 | 59.2 ± 1.1 | 7.1 ± 0.3 | 70.4 ± 2.2 |
| FL 512 - RHM SEQ ID No 110 | 45.6 ± 2.4 | N/D | 82.2 ± 5.2 |

TABLE 27

Concentration of diosmetin, diosmetin 7-O-glucoside and diosmin according to the RHMs used (in mg · $l^{-1}$)

| | Diosmetin | Diosmetin 7-O-glucoside | Diosmin |
|---|---|---|---|
| medium | 82.1 ± 3.9 | N/D | N/D |
| Control - | 75.3 ± 6.1 | N/D | N/D |
| FL 545 - RHM SEQ ID No 108 | 67.1 ± 2.6 | N/D | 21.8 ± 0.4 |
| FL 512 - RHM SEQ ID No 110 | 61.4 ± 3.6 | N/D | 23.7 ± 1 |

The various strains are indeed capable of producing hesperidin and diosmin from hesperetin and diosmetin, in different concentrations according to the RHMs used.

TABLE 28

Concentration of hesperetin, hesperetin 7-O-glucoside and hesperidin according to the RHATs used (in mg · $l^{-1}$)

| | Hesperetin | Hesperetin 7-O-glucoside | Hesperidin |
|---|---|---|---|
| medium | 90 ± 8.1 | N/D | N/D |
| Control - | 84.2 ± 4.6 | N/D | N/D |
| FL 512 - RHAT SEQ ID No 104 | 45.6 ± 2.4 | N/D | 82.2 ± 5.2 |
| FL 165 - RHAT SEQ ID No 106 | 46 ± 1.5 | 8.1 ± 0.2 | 69.8 ± 1.4 |

TABLE 29

Concentration of diosmetin, diosmetin 7-O-glucoside and diosmin according to the RHATs used (in mg · $l^{-1}$)

| | Diosmetin | Diosmetin 7-O-glucoside | Diosmin |
|---|---|---|---|
| medium | 82.1 ± 3.9 | N/D | N/D |
| Control - | 75.3 ± 6.1 | N/D | N/D |
| FL 512 - RHAT SEQ ID No 104 | 61.4 ± 3.6 | N/D | 23.7 ± 1 |
| FL 165 - RHAT SEQ ID No 106 | 66.7 ± 2.5 | N/D | 23 ± 1.5 |

The various strains are indeed capable of producing hesperidin and diosmin from hesperetin and diosmetin, in different concentrations according to the GTs, the RHMs and the RHATs used.

The results for the production of hesperidin and diosmin from hesperetin and diosmetin by the strain FL 547 are presented, respectively, in FIGS. 14 and 15.

The yeasts tested with the various constructs are indeed capable of producing hesperidin and diosmin.

*E. coli* Up to Hesperidin/Diosmin

The results for the production of hesperidin from hesperetin by the strains EC38, EC45 and EC47 are presented in FIG. 16.

These strains are indeed capable of producing hesperidin from hesperetin.

The results for the production of diosmin from diosmetin by the strains EC38, EC45 and EC47 are presented in FIG. 17.

These strains are indeed capable of producing diosmin from diosmetin.

Yeast Up to Hesperidin/Diosmin

The results for the production of hesperidin and diosmin from glucose by the strains SC1509, SC1530, SC1529, SC1568 and SC2410 are presented in FIG. 18. The results for the production of hesperidin from diosmin by the strains SC1579, SC1584, SC1621 and SC1626 are presented in FIG. 28.

All the strains containing all the enzymes of the pathway are capable of producing hesperidin and/or diosmin.

The invention claimed is:

1. A method for producing diosmin and/or hesperidin, comprising culturing a recombinant microorganism in a culture medium and harvesting diosmin and/or hesperidin produced by said recombinant microorganism, wherein the recombinant microorganism comprises a heterologous nucleic acid sequence coding for a flavanone 7-O-beta-D-glucosyltransferase (UGT) belonging to EC 2.4.1.185, which is capable of adding a glucose in position 7 of hesperetin and/or diosmetin; and a heterologous nucleic acid sequence coding for a 6"-O-rhamnosyltransferase (RhaT) belonging to EC 2.4.1.B53, which is capable of transferring a rhamnose into position 6 of the glucose of hesperetin-7-O-glucoside and/or diosmetin-7-O-glucoside; and a heterologous nucleic acid sequence coding for a UDP-glucose 4,6-dehydratase/UDP-4-keto-6-deoxy-D-glucose 3,5-epimerase/UDP-4-keto-L-rhamnose-reductase (RHM) belonging to EC 4.2.1.76, which is capable of producing UDP-rhamnose.

2. The method of claim 1, wherein the culture medium does not comprise naringenin, apigenin, eriodictyol, luteolin, hesperetin and/or diosmetin.

3. The method of claim 1, wherein the culture is performed in a bioreactor in batch, fed-batch, chemostat or continuous cultivation mode.

4. The method of claim 1, wherein the flavanone 7-O-beta-D-glucosyltransferase is selected from the group consisting of SEQ ID NOs: 113, 115, 91, 93, 95, 97, 99 and 101 and polypeptides comprising a sequence having at least 60% sequence identity with one of these sequences and having flavanone 7-O-beta-D-glucosyltransferase activity.

5. The method of claim 1, wherein the 6"-O-rhamnosyltransferase is selected from the group consisting of SEQ ID NOs: 103 and 105 and polypeptides comprising a sequence having at least 60% sequence identity with one of these sequences and having 6"-O-rhamnosyltransferase activity.

6. The method of claim 1, wherein the UDP-glucose 4,6-dehydratase/UDP-4-keto-6-deoxy-D-glucose 3,5-epimerase/UDP-4-keto-L-rhamnose-reductase is selected from the group consisting of SEQ ID NOs: 107, 109 and 111 and polypeptides comprising a sequence having at least 60% sequence identity with one of these sequences and having UDP-glucose 4,6-dehydratase/UDP-4-keto-6-deoxy-D-glucose 3,5-epimerase/UDP-4-keto-L-rhamnose-reductase activity.

7. The method of claim 1, wherein the flavanone 7-O-beta-D-glucosyltransferase is selected from the group consisting of SEQ ID NOs: 113 and 95 and polypeptides comprising a sequence having at least 60% sequence identity with one of these sequences and having flavanone 7-O-beta-D-glucosyltransferase activity; and the 6"-O-rhamnosyltransferase is selected from the group consisting of SEQ ID NO: 103 and polypeptides comprising a sequence having at least 60% sequence identity with this sequence and having 6"-O-rhamnosyltransferase activity; and the UDP-glucose 4,6-dehydratase/UDP-4-keto-6-deoxy-D-glucose 3,5-epimerase/UDP-4-keto-L-rhamnose-reductase is selected from the group consisting of SEQ ID NO: 107 and polypeptides comprising a sequence having at least 60% sequence identity with this sequence and having UDP-glucose 4,6-dehydratase/UDP-4-keto-6-deoxy-D-glucose 3,5-epimerase/UDP-4-keto-L-rhamnose-reductase activity.

8. The method of claim 1, wherein the recombinant microorganism also comprises:

a heterologous nucleic acid sequence coding for a tyrosine ammonia lyase (TAL);

a heterologous nucleic acid sequence coding for a 4-coumarin-CoA ligase (4CL);

a heterologous nucleic acid sequence coding for a naringenin-chalcone synthase (CHS); and a heterologous nucleic acid sequence coding for a chalcone isomerase (CHI).

9. The method of claim 8, wherein the recombinant microorganism comprises:

a heterologous nucleic acid sequence coding for a tyrosine ammonia lyase (TAL) comprising a sequence selected from the group consisting of SEQ ID NOs: 41 and 39 and polypeptides comprising a sequence having at least 60% sequence identity with one of these sequences and having tyrosine ammonia lyase activity;

a heterologous nucleic acid sequence coding for a 4-coumaroyl-CoA ligase (4CL) comprising a sequence selected from the group consisting of SEQ ID NOs: 123, 125, 43, 45, 47 and 49 and polypeptides comprising a sequence having at least 60% sequence identity with one of these sequences and having 4-coumarate-CoA ligase activity;

a heterologous nucleic acid sequence coding for a chalcone synthase (CHS) comprising a sequence selected from the group consisting of SEQ ID NOs: 53, 51, 55 and 57 and polypeptides comprising a sequence having at least 60% sequence identity with one of these sequences and having chalcone synthase activity; and a heterologous nucleic acid sequence coding for a chalcone isomerase (CHI) comprising a sequence selected from the group consisting of SEQ ID NOs: 61 and 59 and polypeptides comprising a sequence having at least 60% sequence identity with one of these sequences and having chalcone isomerase activity.

10. The method of claim 1, wherein the recombinant microorganism also comprises a heterologous nucleic acid sequence coding for a flavonoid 3'-monooxygenase (F3'H).

11. The method of claim 10, wherein the recombinant microorganism comprises a heterologous nucleic acid sequence coding for a flavonoid 3'-monooxygenase (F3'H) comprising a sequence selected from the group consisting of SEQ ID NOs: 7, 1, 3, 5, 9, 11, 13, 15, 17, 19, 21 and 121 and polypeptides comprising a sequence having at least 60% sequence identity with one of these sequences and having flavonoid 3'-monooxygenase activity.

12. The method of claim 1, wherein the recombinant microorganism also comprises a heterologous nucleic acid sequence coding for an O-methyltransferase (OMT).

13. The method of claim 12, wherein the recombinant microorganism comprises a heterologous nucleic acid sequence coding for an O-methyltransferase (OMT) comprising a sequence selected from the group consisting of SEQ ID NOs: 119, 117, 87 and 89 and polypeptides comprising a sequence having at least 60% sequence identity with one of these sequences and having O-methyltransferase activity.

14. The method of claim 1, wherein the recombinant microorganism also comprises:

a heterologous nucleic acid sequence coding for a phenylalanine ammonia lyase (PAL) comprising a sequence selected from the group consisting of SEQ ID NOs: 63, 65 and 77 and polypeptides comprising a sequence having at least 60% sequence identity with one of these sequences and having phenylalanine ammonia lyase activity; and a heterologous nucleic acid sequence coding for a cinnamate 4-hydroxylase (C4H) comprising a sequence selected from the group consisting of SEQ ID NOs: 67, 69 and 79 and polypeptides comprising a sequence having at least 60% sequence identity with one of these sequences and having cinnamate 4-hydroxylase activity.

15. The method of claim 1, wherein the recombinant microorganism also comprises a heterologous or endogenous nucleic acid sequence coding for a flavone synthase (FNS).

16. The method of claim 15, wherein the recombinant microorganism comprises a heterologous nucleic acid sequence coding for a flavone synthase (FNS) comprising a sequence selected from the group consisting of SEQ ID NOs: 33, 35, 37, 127, 129, 131, 133, 135, 137, 139, 141, 143, 145, 147, 149, 151, 153, 155, 157 and 159 and polypeptides comprising a sequence having at least 60% sequence identity with one of these sequences and having flavone synthase activity.

17. The method of claim 1, wherein the recombinant microorganism also comprises:

a heterologous nucleic acid sequence coding for a cytochrome P450 reductase (CPR); and/or a heterologous or endogenous nucleic acid sequence coding for an S-adenosylmethionine synthetase (SAMT).

18. The method of claim 17, wherein the recombinant microorganism comprises a heterologous nucleic acid sequence coding for a cytochrome P450 reductase (CPR) comprising a sequence selected from the group consisting of SEQ ID NOs: 25, 23, 27, 29 and 31 and polypeptides comprising a sequence having at least 60% sequence identity with one of these sequences and having cytochrome P450 reductase activity.

19. The method of claim 1, wherein the recombinant microorganism comprises:

a heterologous nucleic acid sequence coding for a phenylalanine ammonia lyase (PAL) comprising SEQ ID NO: 65 or a polypeptide comprising a sequence having at least 60% sequence identity with this sequence and having phenylalanine ammonia lyase activity;

a heterologous nucleic acid sequence coding for a cinnamate 4-hydroxylase (C4H) comprising SEQ ID NO: 79 or a polypeptide comprising a sequence having at least 60% sequence identity with this sequence and having cinnamate 4-hydroxylase activity;

a heterologous nucleic acid sequence coding for a tyrosine ammonia lyase (TAL) comprising SEQ ID NO: 41 or a polypeptide comprising a sequence having at least 60% sequence identity with this sequence and having tyrosine ammonia lyase activity;

a heterologous nucleic acid sequence coding for a 4-coumaroyl-CoA ligase (4CL) comprising SEQ ID NO: 45, 123 or a polypeptide comprising a sequence having at least 60% sequence identity with one of these sequences and having 4-coumarate-CoA ligase activity;

a heterologous nucleic acid sequence coding for a chalcone synthase (CHS) comprising SEQ ID NO: 53 or a polypeptide comprising a sequence having at least 60% sequence identity with this sequence and having chalcone synthase activity;

a heterologous nucleic acid sequence coding for a chalcone isomerase (CHI) comprising SEQ ID NO: 61 or a polypeptide comprising a sequence having at least 60% sequence identity with this sequence and having chalcone isomerase activity;

a heterologous nucleic acid sequence coding for a flavonoid 3'-monooxygenase (F3'H) comprising SEQ ID NOs: 7, 17, 121 or a polypeptide comprising a sequence having at least 60% sequence identity with one of these sequences and having flavonoid 3'-monooxygenase activity;

a heterologous nucleic acid sequence coding for a flavone synthase (FNS) comprising SEQ ID NO: 37 or a polypeptide comprising a sequence having at least 60% sequence identity with this sequence and having flavone synthase activity;

a heterologous nucleic acid sequence coding for a cytochrome P450 reductase (CPR) comprising SEQ ID NO: 25 or a polypeptide comprising a sequence having at least 60% sequence identity with this sequence and having cytochrome P450 reductase activity;

a heterologous nucleic acid sequence coding for an O-methyltransferase (OMT) comprising SEQ ID NOs: 117, 119 or a polypeptide comprising a sequence having at least 60% identity with one of these sequences and having O-methyltransferase activity;

a heterologous nucleic acid sequence coding for a flavanone 7-O-beta-D-glucosyltransferase comprising SEQ ID NOs: 113, 95 or a polypeptide comprising a sequence having at least 60% sequence identity with one of these sequences and having flavanone 7-O-beta-D-glucosyltransferase activity;

a heterologous nucleic acid sequence coding for a 6"-O-rhamnosyltransferase comprising SEQ ID NO: 103 or a polypeptide comprising a sequence having at least 60% sequence identity with this sequence and having 6"-O-rhamnosyltransferase activity; and a heterologous nucleic acid sequence coding for a UDP-glucose 4,6-dehydratase/UDP-4-keto-6-deoxy-D-glucose 3,5-epimerase/UDP-4-keto-L-rhamnose-reductase comprising SEQ ID NO: 107 or a polypeptide comprising a sequence having at least 60% sequence identity with this sequence and having UDP-glucose 4,6-dehydratase/UDP-4-keto-6-deoxy-D-glucose 3,5-epimerase/UDP-4-keto-L-rhamnose-reductase activity.

20. The method of claim 1, wherein the recombinant microorganism is a yeast or a bacterium.

* * * * *